US011517591B2

(12) United States Patent
Bae et al.

(10) Patent No.: US 11,517,591 B2
(45) Date of Patent: Dec. 6, 2022

(54) IMMUNOGENIC PEPTIDES SPECIFIC TO BCMA AND TACI ANTIGENS

(71) Applicant: Dana-Farber Cancer Institute, Inc., Boston, MA (US)

(72) Inventors: Jooeun Bae, West Roxbury, MA (US); Nikhil C. Munshi, Needham, MA (US); Kenneth C. Anderson, Wellesley, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 169 days.

(21) Appl. No.: 16/641,722

(22) PCT Filed: Aug. 31, 2018

(86) PCT No.: PCT/US2018/049260
§ 371 (c)(1),
(2) Date: Feb. 25, 2020

(87) PCT Pub. No.: WO2019/046818
PCT Pub. Date: Mar. 7, 2019

(65) Prior Publication Data
US 2020/0352995 A1 Nov. 12, 2020

Related U.S. Application Data

(60) Provisional application No. 62/553,669, filed on Sep. 1, 2017.

(51) Int. Cl.
| | | |
|---|---|---|
| A61K 35/17 | (2015.01) | |
| A61P 35/00 | (2006.01) | |
| A61K 38/19 | (2006.01) | |
| A61K 38/21 | (2006.01) | |
| A61K 39/39 | (2006.01) | |
| A61K 39/395 | (2006.01) | |
| C07K 7/06 | (2006.01) | |
| A61K 39/00 | (2006.01) | |

(52) U.S. Cl.
CPC ............ *A61K 35/17* (2013.01); *A61K 38/193* (2013.01); *A61K 38/212* (2013.01); *A61K 38/217* (2013.01); *A61K 39/39* (2013.01); *A61K 39/3955* (2013.01); *A61P 35/00* (2018.01); *C07K 7/06* (2013.01); *A61K 2039/55544* (2013.01); *A61K 2039/55566* (2013.01)

(58) Field of Classification Search
CPC ........ C07K 7/06; A61K 35/17; A61K 38/212; A61K 38/193; A61K 38/217
See application file for complete search history.

(56) References Cited

U.S. PATENT DOCUMENTS

| | | |
|---|---|---|
| 4,407,957 A | 10/1983 | Lim |
| 4,522,811 A | 6/1985 | Eppstein et al. |
| 4,638,045 A | 1/1987 | Kohn et al. |
| 4,806,621 A | 2/1989 | Kobn et al. |
| 4,879,231 A | 11/1989 | Stroman et al. |
| 4,929,555 A | 5/1990 | Cregg et al. |
| 4,946,929 A | 8/1990 | D'Amore et al. |
| 5,010,167 A | 4/1991 | Ron et al. |
| 5,019,379 A | 5/1991 | Domb et al. |
| 5,328,470 A | 7/1994 | Nabel et al. |
| 5,399,665 A | 3/1995 | Barrera et al. |
| 5,512,600 A | 4/1996 | Mikos et al. |
| 5,514,378 A | 5/1996 | Mikos et al. |
| 5,543,158 A | 8/1996 | Gref et al. |
| 5,643,786 A | 7/1997 | Cohen et al. |
| 5,696,175 A | 12/1997 | Mikos et al. |
| 5,716,404 A | 2/1998 | Vacanti et al. |
| 5,736,372 A | 4/1998 | Vacanti et al. |
| 5,770,417 A | 6/1998 | Vacanti et al. |
| 5,798,113 A | 8/1998 | Dionne et al. |
| 5,800,828 A | 9/1998 | Dionne et al. |
| 5,804,178 A | 9/1998 | Vacanti et al. |
| 5,827,516 A | 10/1998 | Urban et al. |
| 5,837,752 A | 11/1998 | Shastri et al. |
| 5,902,599 A | 5/1999 | Anseth et al. |
| 6,095,148 A | 8/2000 | Shastri et al. |
| 6,123,727 A | 9/2000 | Vacanti et al. |
| 6,506,577 B1 | 1/2003 | Deming et al. |
| 6,534,633 B1 | 3/2003 | Weidanz et al. |
| 6,632,922 B1 | 10/2003 | Deming et al. |
| 6,686,446 B2 | 2/2004 | Deming et al. |
| 6,818,732 B2 | 11/2004 | Deming et al. |
| 7,026,443 B1 | 4/2006 | Sette et al. |
| 9,487,573 B2 | 11/2016 | Parkhurst et al. |
| 9,822,162 B2 | 11/2017 | Hinrichs et al. |
| 9,872,900 B2 | 1/2018 | Ciaramella et al. |
| 10,377,808 B2 | 8/2019 | Blankenstein et al. |

(Continued)

FOREIGN PATENT DOCUMENTS

| | | |
|---|---|---|
| WO | WO 1997/32603 | 9/1997 |
| WO | WO 1998/39482 | 9/1998 |

(Continued)

OTHER PUBLICATIONS

Aguado et al., "Controlled-release vaccines—biodegradable polylactide/polyglycolide (PL/PG) microspheres as antigen vehicles," Immunobiology, Feb. 1992, 184(2-3):113-25.

Akagi et al, "Biodegradable Nanoparticles as Vaccine Adjuvants and Delivery Systems: Regulation of Immune Responses by Nanoparticle-Based Vaccine," Adv Polym Sci., Oct. 2011, 247:31-64.

Aleksic et al., "Different affinity windows for virus and cancer-specific T-cell receptors: Implications for therapeutic strategies," European Journal of Immunology, 2012, 3174-79.

(Continued)

*Primary Examiner* — Elly-Gerald Stoica
(74) *Attorney, Agent, or Firm* — Fish & Richardson P.C.

(57) ABSTRACT

This disclosure relates to immunogenic peptides that are specific to B-cell maturation antigen (BCMA) and Transmembrane activator and CAML interactor (TACI), and methods of use thereof.

38 Claims, 82 Drawing Sheets
Specification includes a Sequence Listing.

(56) References Cited

U.S. PATENT DOCUMENTS

| | | | |
|---|---|---|---|
| 10,450,372 | B2 | 10/2019 | Hanada et al. |
| 10,526,407 | B2 | 1/2020 | Alten et al. |
| 2004/0072246 | A1 | 4/2004 | Martin et al. |
| 2007/0020297 | A1 | 1/2007 | Wheeler et al. |
| 2007/0116718 | A1 | 5/2007 | Weidanz et al. |
| 2007/0269451 | A1 | 11/2007 | Crowe et al. |
| 2010/0129439 | A1 | 5/2010 | Alexis et al. |
| 2016/0008451 | A1 | 1/2016 | Stary et al. |
| 2016/0317647 | A1 | 11/2016 | Ciaramella et al. |
| 2017/0002984 | A1 | 1/2017 | Beausoleil |
| 2018/0021258 | A1 | 1/2018 | Graham et al. |
| 2018/0245242 | A1 | 8/2018 | Schendel et al. |
| 2022/0118018 | A1 | 4/2022 | Bae et al. |

FOREIGN PATENT DOCUMENTS

| | | |
|---|---|---|
| WO | WO 1999/18129 | 4/1999 |
| WO | WO 1999/45954 | 9/1999 |
| WO | WO 2000/23087 | 4/2000 |
| WO | WO 2002/066516 | 8/2002 |
| WO | WO 2002/070003 | 9/2002 |
| WO | WO 2005/037995 | 4/2005 |
| WO | WO 2009/051837 | 4/2009 |
| WO | WO 2011/119484 | 9/2011 |
| WO | WO 2015/059690 | 4/2015 |
| WO | WO 2015/158671 | 10/2015 |
| WO | WO 2017/031104 | 2/2017 |
| WO | WO 2017/173349 | 10/2017 |
| WO | WO 2018/102795 | 6/2018 |
| WO | WO 2018/151836 | 8/2018 |
| WO | WO 2020/181142 | 9/2020 |

OTHER PUBLICATIONS

Alexander et al., "Derivation of HLA-A11/Kb transgenic mice: functional CTL repertoire and recognition of human A11-restricted CTL epitopes," J. Immunol., Nov. 1997, 159(10): 4753-4761.

Altman et al., "Formation of functional peptide complexes of class II major histocompatibility complex proteins from subunits produced in Escherichia coli," Proc. Natl. Acad. Sci. USA, Nov. 1993, 90:10330-34.

Altman et al., "Phenotypic Analysis of Antigen-Specific T Lymphocytes," Mar. 1996, Science 274:94-96.

Anderson et al., "Use of gene-modified T-cells as antigen presenting cells (T-APC) for vaccination against myeloma antigens," Database Accession No. XP002787229, Nov. 2007, 3 pages.

Bae et al., "BCMA peptide-engineered nanoparticles enhance induction and function of antigen-specific CD8cytotoxic T lymphocytes against multiple myeloma: clinical applications," Leukemia, 2019, 34(1):210-223.

Bae et al., "Histone deacetylase (HDAC) inhibitor ACY241 enhances anti-tumor activities of antigen-specific central memory cytotoxic T lymphocytes against multiple myeloma and solid tumors," Leukemia, 2018, 41 pages.

Bae et al., "Identification of novel myeloma-specific XBP1 peptides able to generate cytotoxic T lymphocytes: a potential therapeutic application in multiple myeloma," Leukemia, 2011, 1610-1619.

Bae et al., "Selective targeting of multiple myeloma by B cell maturation antigen (BCMA)—specific central memory CD8+ cytotoxic T lymphocytes: immunotherapeutic application in vaccination and adoptive immunotherapy," Leukemia, 2019, 33(9):2208-26.

Barrera et al., "Synthesis and RGD Peptide Modification of a New Biodegradable Copolymer: Poly (lactic acid-colysine)," J. Am. Chem. Soc, 1993, 115:11010-11.

Borras et al., "Findings on T cell specificity revealed by synthetic combinatorial libraries," J. Immunol. Methods, 2002, 267(1):79-97.

Boussif et al., "A versatile vector for gene and oligonucleotide transfer into cells in culture and in vivo: Polyethylenimine," Proc. Natl. Acad. Sci., USA, 1995, 92:7297-7301.

Bramwell et al., "Particulate delivery systems for biodefense subunit vaccines," Adv. Drug Deliv. Rev., 2005, 57(9):1247-65.

Bullock et al., "Antigen Density Presented by Dendritic Cells in Vivo Differentially Affects the Number and Avidity of Primary, Memory, and Recall CD8 + T Cells," J. Immunol., 2003, 170:1822-1829.

Celis et al., "Induction of anti-tumor cytotoxic T lymphocytes in normal humans using primary cultures and synthetic peptide epitopes," Proc. Natl. Acad. Sci. USA, 1994, 91:2105-09.

Chen et al., "Gene therapy forbrain tumors: Regression of experimental gliomas by adenovirus-mediated gene transfer in vivo," Proc. Natl. Acad. Sci. USA, Apr. 1994, 91:3054-3057.

Collins et al., Altered peptide ligand design: altering immune responses to class I MHC/peptide complexes, Immunological Reviews, 1998, 163:151-160.

Conlon et al., "A Mutation in the TRPC6 Cation Channel Causes Familial Focal Segmental Glomerulosclerosis," Science, 2005, 308:1801-1804.

Database Accession No. XP002787228, "Immunogenic peptide having a human leukocyte antigen binding motif #1924," EBI Accession No. GSP:AAY47313. Dec. 1999, 1 page.

Database Accession No. XP002787227, "WO2011119484. 2734100," Iogenetics LLC, Sep. 2011, 1 page.

Deming et al., "Facile synthesis of block copolypeptides of defined architecture," Nature, 1997, 390:386-89.

Dimopoulos et al., "International myeloma working group consensus statement and guidelines regarding the current role of imaging techniques in the diagnosis and monitoring of multiple Myeloma," Leukemia, 2009, 23(9):1545-56.

Falk et al., "Allele-specific motifs revealed by sequencing of self-peptides eluted from MHC molecules," Nature, May 1991, 351:290-296.

Falk et al., "Identification of Naturally Processed Viral Nonapeptides Allows Their Quantification in Infected Cells and Suggests an Allele-specific T Cell Epitope Forecast," J. Exp. Med., Aug. 1991, 174:425-434.

Freudenthal et al., "The distinct surface of human blood dendritic cells, as observed after an improved isolation method," Proc. Nat. Acad. Sci. USA, Oct. 1990, 57:7698-7702.

Getts et al., "Synthetic T cell receptor-based lymphocytes for cancer therapy," Advanced Drug Delivery Reviews, 2019, 141:47-54.

Gonzalez et al., "T cell receptor binding kinetics required for T cell activation depend on the density of cognate ligand on the antigen-presenting cell," Proc. Natl. Acad. Sci. USA, Feb. 2005, 102(3):4824-4829.

Haensler et al., "Polyamidoamine Cascade Polymers Mediate Efficient Transfection of Cells in Culture," Bioconjugate Chem., 1993, 4:372-379.

Hinnen et al., "Transformation of yeast," Proc. Nat. Acad. Sci. USA. Apr. 1978, 75(4):1929-33.

Hobo et al., "Immunogenicity of dendritic cells pulsed with MAGE3 Survivin and B-cell maturation antigen mRNA for vaccination of multiple myeloma patients," Cancer Immunol Immunother, 2013, 62(8): 1381-1392.

Ito et al., "Transformation of Intact Yeast Cells Treated with Alkali Cations," J. Bacteriol., Jan. 1983, 153:163-68.

Jiang et al., "Biodegradable poly(lactic-co-glycolic acid) microparticles for injectable delivery of vaccine antigens," Adv. Drug Deliv. Rev., 2005, 57(3):391-410.

Kabanov et al., "DNA Complexes with Polycations for the Delivery of Genetic Material into Cells," Bioconjugate Chem., 1995, 6:7-20.

Kalergis et al., "Altered Peptide Ligand-Mediated TCR Antagonism Can Be Modulated by a Change in a Single Amino Acid Residue Within the CDR3 β of an MHC Class I-Restricted TCR," J Immunol., 2000, 165(1): 280-285.

Kawashima et al., "The Multi-epitope Approach for Immunotherapy for Cancer: Identification of Several CTL Epitopes from Various Tumor-Associated Antigens Expressed on Solid Epithelial Tumors," Human Immunol., 1998, 59:1-14.

Kukowska-Latallo et al., "Efficient transfer of genetic material into mammalian cells using Starburst polyamidoamine dendrimers," Proc. Natl. Acad. Sci., USA, May 1996, 93:4897-4902.

(56) References Cited

OTHER PUBLICATIONS

Kwon et al., "Pseudopoly (amino acids): a study of the synthesis and characterization of poly(trans-4-hydroxy-N-acyl-L-proline esters)," Macromolecules, 1989, 22:3250-3255.
Kyle et al., "Criteria for diagnosis, staging, risk stratification and response assessment of multiple myeloma," Leukemia, 2009, 23:3-9.
Kyle et al., "Multiple Myeloma," Blood Journal, 2008, 111:2962-72.
Kyle et al., "Multiple Myeloma," N. Engl. J. Med., 2004, 351: 1860-73.
Langer, "Biomaterials in Drag Delivery and Tissue Engineering: One Laboratory's Experience," Acc. Chem. Res., 2000, 33:94-101.
Langer, "Selected advances in drug delivery and tissue engineering," J. Control. Release, 1999, 62:7-11.
Legut et al., "Designer T-cells and T-cell receptors for customized cancer immunotherapies," Current Opinion in Pharmacology, 2018, 41:96-103.
Lemmel et al., "Differential quantitative analysis of MHC ligands by mass spectrometry using stable isotope labeling," Nat. Biotechnol., 2004, 22:450-454.
Lim et al., "A Self-Destroying Polycationic Polymer: Biodegradable Poly(4-hydroxy-L-proline ester)," J. Am. Chem. Soc, 1999, 121:5633-5639.
Lim et al., "Cationic Hyperbranched Poly(amino ester): A Novel Class of DNA Condensing Molecule with Cationic Surface, Biodegradable Three-Dimensional Structure, and Tertiary Amine Groups in the Interior," J. Am. Chem. Soc, 2001, 123:2460-61.
Lundegaard et al., "Prediction of epitopes using neural network based methods," Journal of Immunological Methods, 2011, 374(1-2):26-34.
Lustgarten et al., "Identification of Cross-Reactive Peptides Using Combinatorial Libraries Circumvents Tolerance against Her-2/neu-Immunodominant Epitope," J. Immun., 2006, 176:1796-1805.
Macatonia et al., "Suppression of immune responses by dendritic cells infected with HIV," Immunol., 1989, 67:285-289.
Mancebo et al., "Structure and Expression of the *Drosophila melanogaster* Gene for the U1 Small Nuclear Ribonucleoprotein Particle 70K Protein," Mol. Cell. Biol., 1990, 10(6):2492-2502.
Markowicz et al., "Granulocyte-macrophage colony-stimulating factor promotes differentiation and survival of human peripheral blood dendritic cells in vitro," J. Clin. Invest., 1990, 85:955-961.
Mehta-Damani et al., "Generation of antigen-specific CD8+ CTLs from naive precursors," J. Immunol., 1994, 153: 996-1003.
Niesvizky, et al. "ACY-241, a novel, HDAC6 selective inhibitor: synergy with immunomodulatory (IMiD®) drugs in multiple myeloma (MM) cells and early clinical results (ACE-MM-200 Study)," Weill Cornell Medical College, New York City, NY, 2015, 3040:1 page.
O'Doherty et al., "Dendritic Cells Freshly Isolated from Human Blood Express CD4 and Mature into Typical Immunostimulatory Dendritic Cells after Culture in Monocyte-conditioned Medium," J. Exp. Med., 1993, 178:1067-1078.
Ogg et al., "Quantitation of HIV-1-Specific Cytotoxic T Lymphocytes and Plasma Load of Viral RNA," Science, 1998, 279: 2103-2106.
Papisov, "Acyclic Polyacetals from Polysaccharides: Biomimetic Biomedical "Stealth" Polymers," ACS Symposium Series, 2001, 786:301-314.
PCT International Preliminary Report on Patentability in International Appln. No. PCT/US2018/049260, dated Mar. 3, 2020, 13 pages.
PCT International Search Report and Written Opinion in International Appln. No. PCT/US2018/049260, dated Feb. 11, 2019, 24 pages.
PCT International Search Report and Written Opinion in International Appln. No. PCT/US2020/021273, dated Jun. 4, 2020, 17 pages.
Pinilla et al., "Rapid Identification of High Affinity Peptide Ligands Using Positional Scanning Synthetic Peptide Combinatorial Libraries," Biotechniques, 1992, 13(6): 901-5.
Purcell et al., "Immunoproteomics," Mol. Cell. Proteomics, 2004, 3:193-208.
Putnam et al., "Poly(4-hydroxy-L-proline ester): Low-Temperature Polycondensation and Plasmid DNA Complexation," Macromolecules, 1999, 32:3658-62.
Rajkumar et al., "International Myeloma Working Group updated criteria for the diagnosis of multiple myeloma," Lancet Oncology, 2014, 15(12):538-48.
Rotzxhke et al., "Isolation and analysis of naturally processed viral peptides as recognized by cytotoxic T cells," Nature, 1990, 348: 252-254.
Sreekrishna et al., "Invertase gene (SUC2) of *Saccharomyces cerevisiae* as a dominant marker for transformation of Pichia pastoris," Gene, 1987, 59:115-125.
Storkus et al., "Identification of human melanoma peptides recognized by class I restricted tumor infiltrating T lymphocytes," J. Immunol., 1993, 151:3719-27.
Storkus et al., "Identification of T-cell Epitopes: Rapid Isolation of Class I-Presented Peptides from Viable Cells by Mild Acid Elution," J. Immunother., 1993,14:94-103.
Tang et al., "In Vitro Gene Delivery by Degraded Polyamidoamine Dendrimers," Bioconjugate Chem., 1996, 7:703-14.
Thomas et al., "Comparative accessory cell function of human peripheral blood dendritic cells and monocytes," J. Immunol., 1993, 151:6840-6852.
Tommaso et al., "Induction of Antigen-Specific Antibodies in Vaginal Secretions by Using a Nontoxic Mutant of Heat-Labile Enterotoxin as a Mucosal Adjuvant," Infect. Immunity, Mar. 1996, 64(3): 974-979.
Tsai al., "Identification of subdominant CTL epitopes of the GP100 melanoma-associated tumor antigen by primary in vitro immunization with peptide-pulsed dendritic cells," J. Immunol., 1997, 158: 1796-1802.
Uhrich et al, "Polymeric Systems for Controlled Drug Release," Chem. Rev., 1999, 99:3181-3198.
Wang et al., "A Novel Biodegradable Gene Carrier Based on Polyphosphoester," J. Am. Chem. Soc, 2001, 123:9480-81.
Wentworth et al., "Differences and similarities in the A2.1—restricted cytotoxic T cell repertoire in humans and human leukocyte antigen-transgenic mice," J. Immunol., 1996, 26: 97-101.
Wentworth et al., "Identification of A2-restricted hepatitis C virus-specific cytotoxic T lymphocyte epitopes from conserved regions of the viral genome," Int. Immunol. 1996, 8: 651-59.
Wentworth et al., "In Vitro Introduction of Primary, Antigen-Specific CTL From Human Peripheral Blood Mononuclear Cells Stimulated With Synthetic Peptides," Mol. Immunol., 1995, 32:603-612.
Yamamoto et al., "Mutants in the ADP-ribosyltransferase Cleft of Cholera Toxin Lack Diarrheagenicity but Retain Adjuvanticity," J. Exp. Med., 1997, 185:1203-1210.
Young et al., "Dendritic Cells Stimulate Primary Human Cytolytic Lymphocyte Responses in the Absence of CD4+ Helper T Cells," J. Exp, Med., 1990, 171: 1315-1332.
Zauner et al., "Polylysine-based transfection systems utilizing receptor-mediated delivery," Adv. Drug Del. Rev., 1998, 30:97-113.
Zhou et al., "Preparation of Poly (L-serine ester): A Structural Analogue of Conventional Poly(L-serine)," Macromolecules, 1990, 23:3399-3406.
Aggen et al., "Single-chain V$\alpha$V$\beta$ T-cell receptors function without mispairing with endogenous TCR chains," Gene therapy, Apr. 2012, 19(4):365-74.
Cohen et al., "Enhanced antitumor activity of murine-human hybrid T-cell receptor (TCR) in human lymphocytes is associated with improved pairing and TCR/CD3 stability," Cancer research, Sep. 1, 2006, 66(17):8878-86.
International Preliminary Report on Patentability in International Appln. No. PCT/US2020/021273, dated Sep. 16, 2021, 9 pages.
Knies et al., "An optimized single chain TCR scaffold relying on the assembly with the native CD3-complex prevents residual mispairing with endogenous TCRs in human T-cells," Oncotarget, Apr. 19, 2016, 7(16):21199.

(56) References Cited

OTHER PUBLICATIONS

Kochenderfer et al., "Chemotherapy-refractory diffuse large B-cell lymphoma and indolent B-cell malignancies can be effectively treated with autologous T cells expressing an anti-CD19 chimeric antigen receptor," Journal of clinical oncology, Feb. 20, 2015, 33(6):540.

Lee et al., "T cells expressing CD 19 chimeric antigen receptors for acute lymphoblastic leukaemia in children and young adults: a phase 1 dose-escalation trial," The Lancet, Feb. 7, 2015, 385(9967):517-28.

Li et al., "RNase H-dependent PCR-enabled T-cell receptor sequencing for highly specific and efficient targeted sequencing of T-cell receptor mRNA for single-cell and repertoire analysis," Nature protocols, Aug. 2019, 14(8):2571-94.

Monod et al., "IMGT/Junction Analysis: the first tool for the analysis of the immunoglobulin and T cell receptor complex V-J and V-D-J Junctions," Bioinformatics, Aug. 4, 2004, 20(suppl_1):i379-85.

Moss et al., "Sequence analysis of the human αβ T-cell receptor CDR3 region," Immunogenetics, May 1995, 42(1):10-8.

Robins et al., "Comprehensive assessment of T-cell receptor β-chain diversity in αβ T cells," Blood, The Journal of the American Society of Hematology, Nov. 5, 2009, 114(19):4099-107.

Stevanović et al., "Complete regression of metastatic cervical cancer after treatment with human papillomavirus—targeted tumor-infiltrating T cells," Journal of Clinical Oncology, May 10, 2015 33(14):1543.

Tran et al., "Cancer immunotherapy based on mutation-specific CD4+ T cells in a patient with epithelial cancer," Science, May 9, 2014, 344(6184):641-5.

Turtle et al., "CD19 CAR-T cells of defined CD4+: CD8+ composition in adult B cell ALL patients," The Journal of clinical investigation, Jun. 1, 2016, 126(6):2123-38.

Wong et al., "Comparative analysis of the CDR loops of antigen receptors," Frontiers in immunology, Oct. 15, 2019, 10:2454, 27 pages.

Wong et al., "Novel antibody-like single-chain TCR antibody Fc fusion protein," The Journal of Immunology, May 1, 2017, 198 (1 Supplement) 120.9, 5 pages (Abstract Only).

Carter et al., "Single T cell sequencing demonstrates the functional role of αβ TCR pairing in cell lineage and antigen specificity," Frontiers in immunology, 2019:1516, 13 pages.

GenBank Accession No. AB052772.1, "*Homo sapiens* gene for BCMA, complete cds," Sep. 25, 2002, 2 pages.

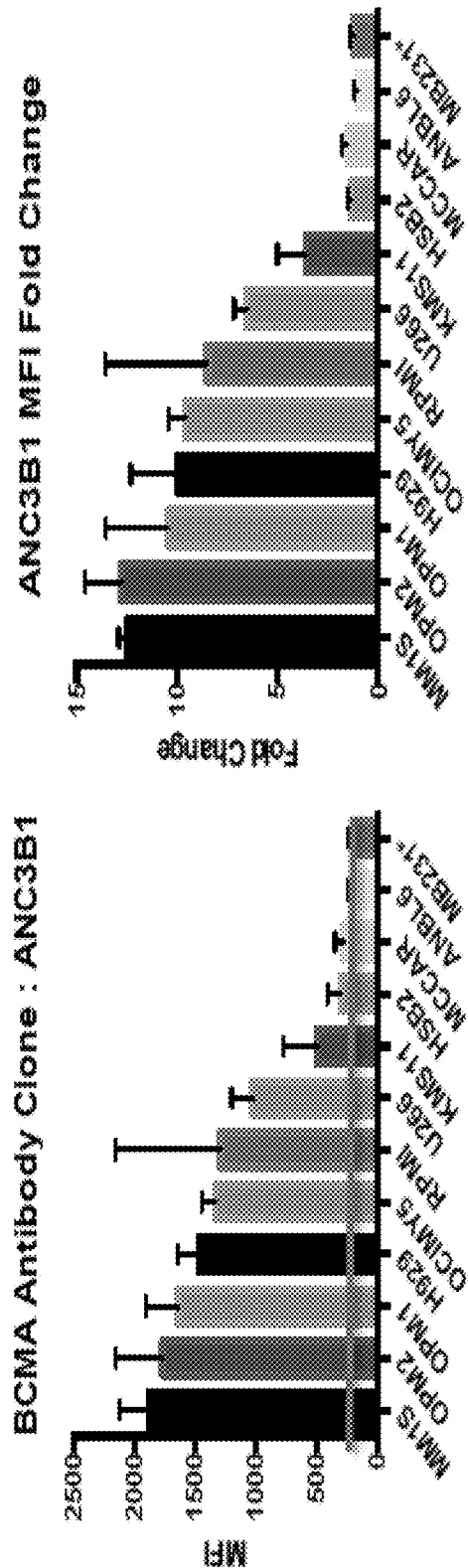
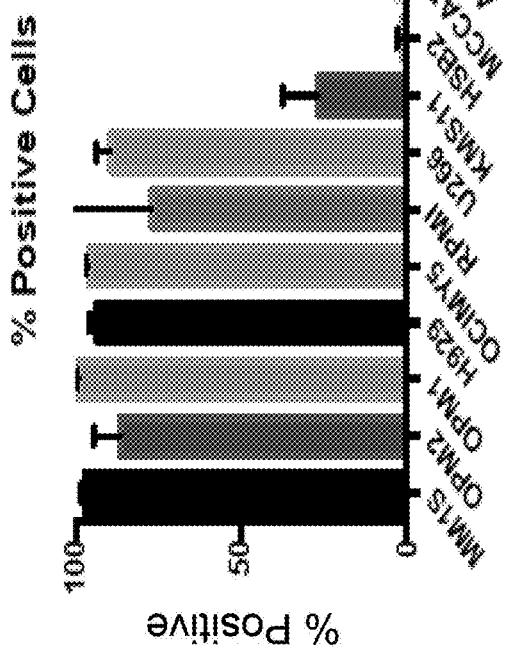
FIG. 1A
FIG. 1B
FIG. 1C

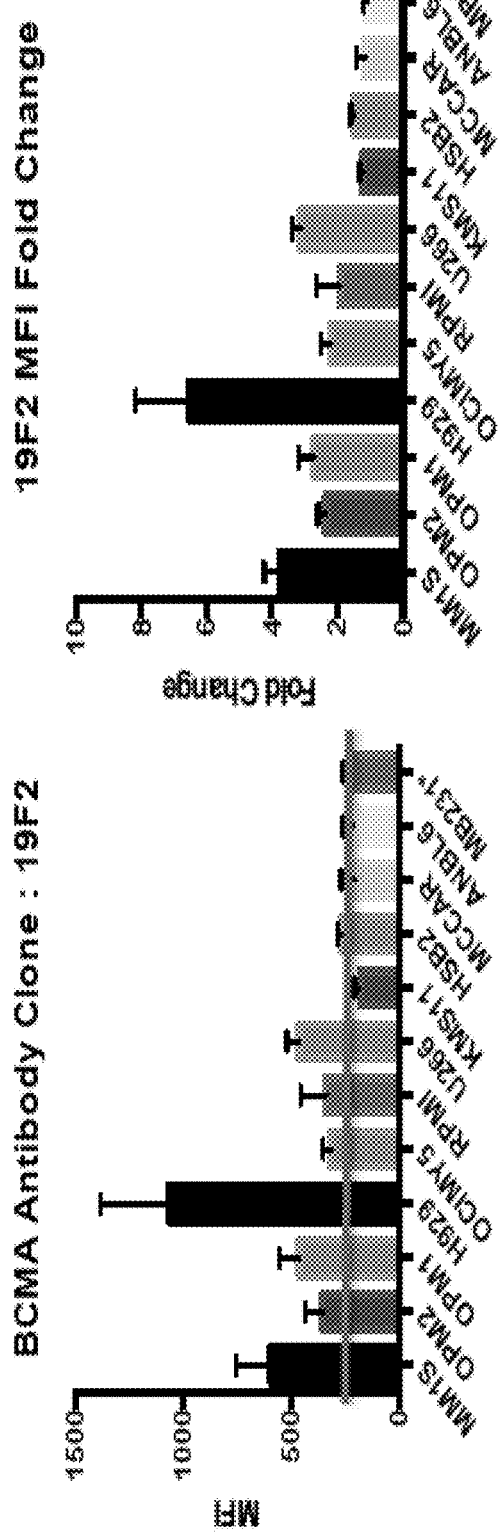
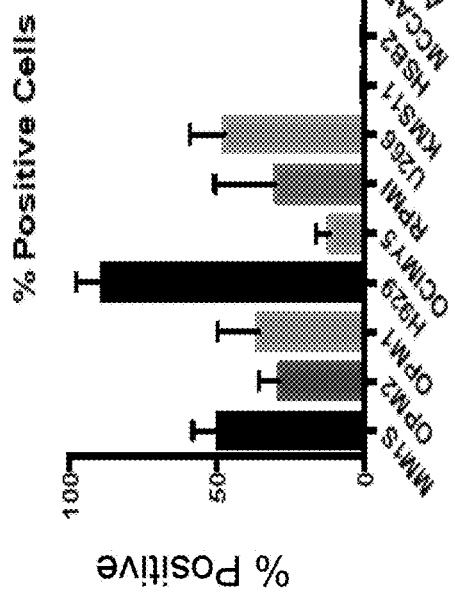
FIG. 1G
FIG. 1H
FIG. 1I

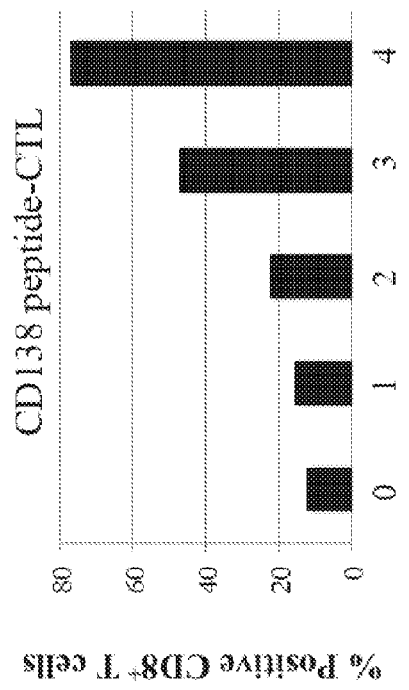
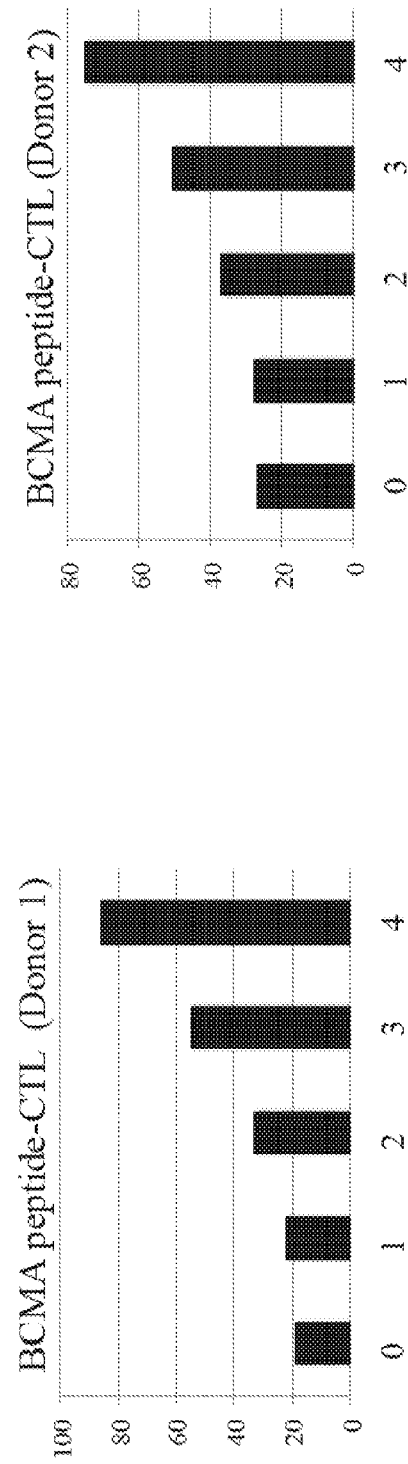
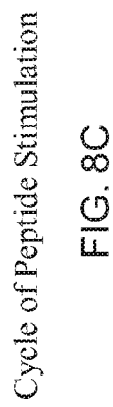
FIG. 8A
FIG. 8B
FIG. 8C

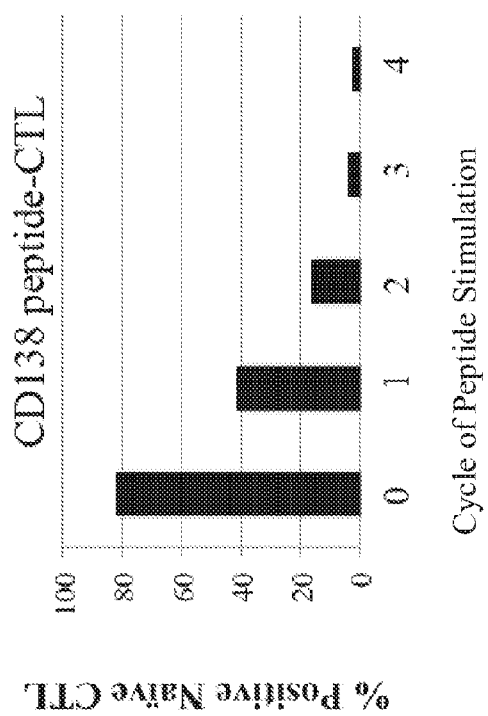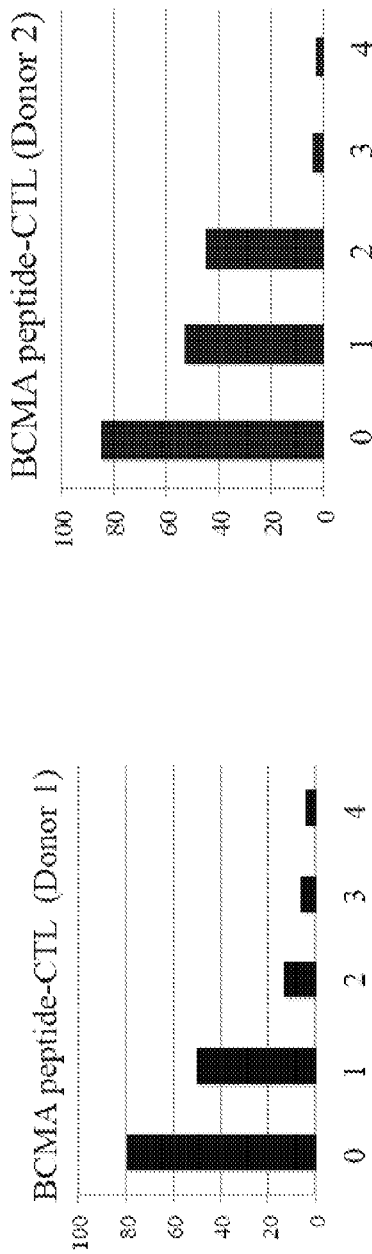
FIG. 9A
FIG. 9B
FIG. 9C

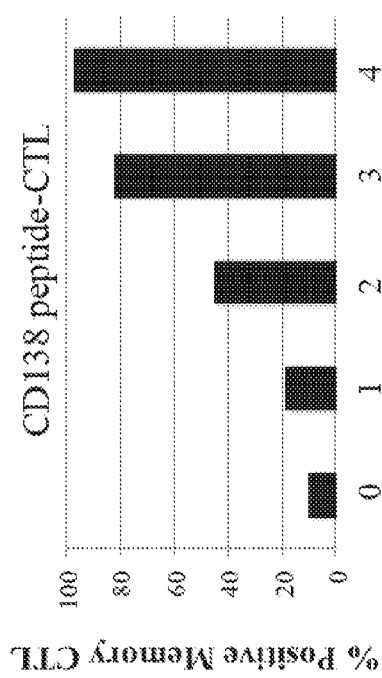
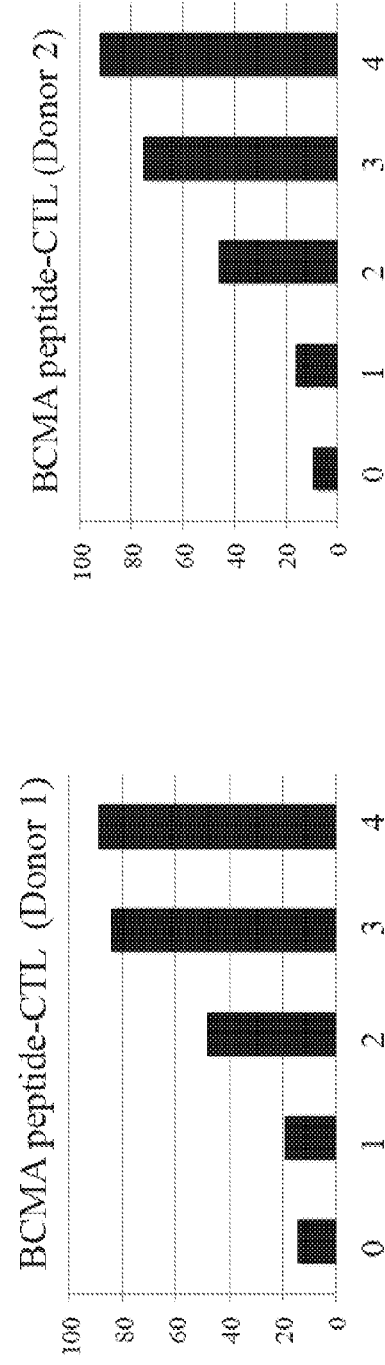
FIG. 10A, FIG. 10B, FIG. 10C

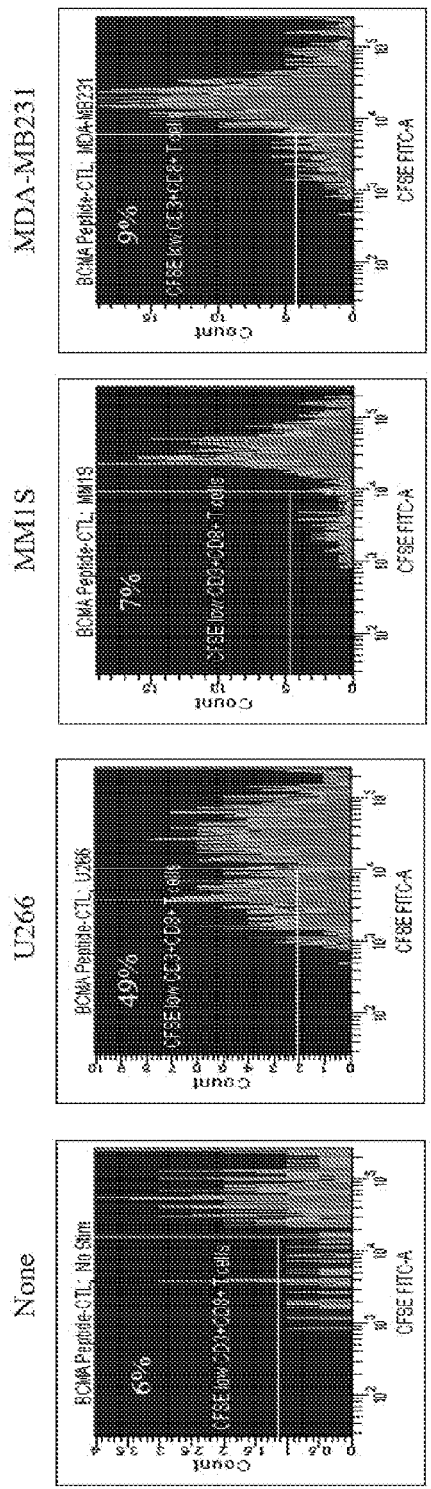
FIG. 19A
FIG. 19B
FIG. 19C
FIG. 19D
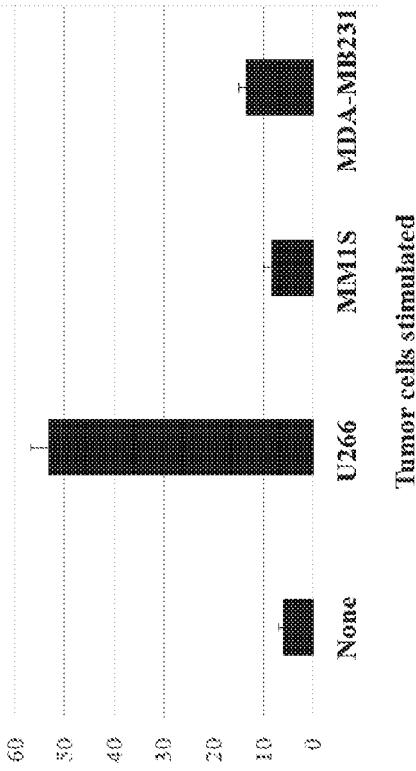
FIG. 19E

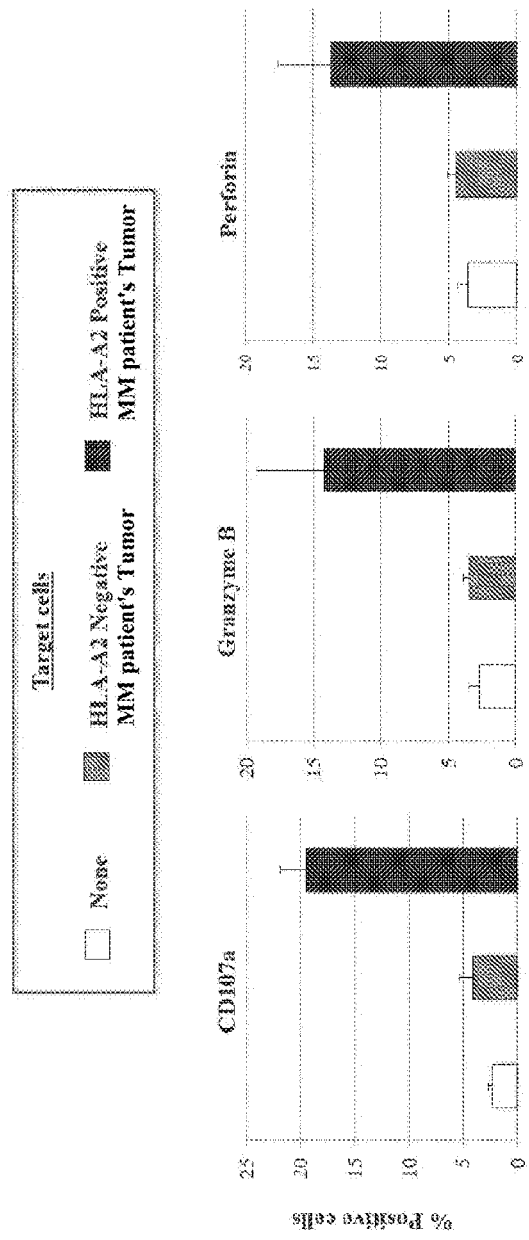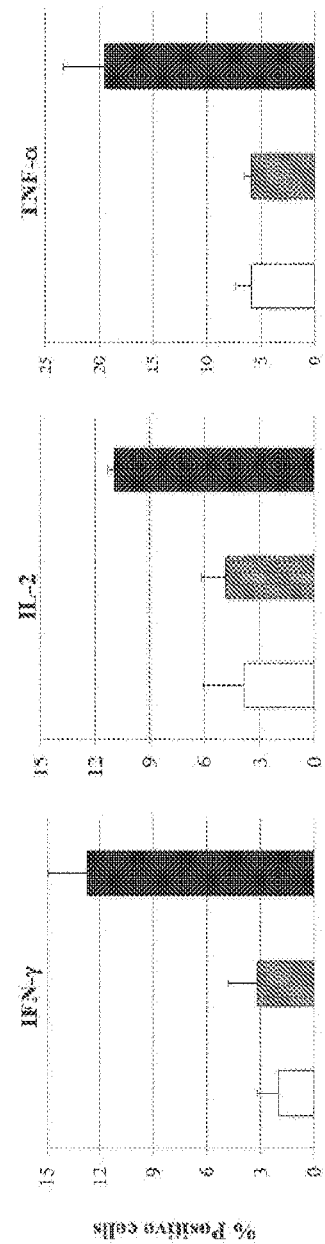
FIG. 20C, FIG. 20D, FIG. 20E, FIG. 20F, FIG. 20G, FIG. 20H

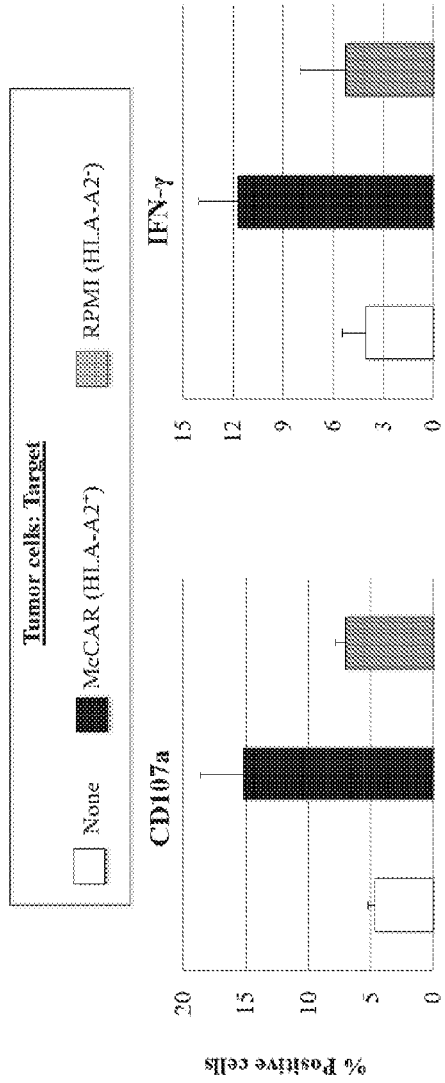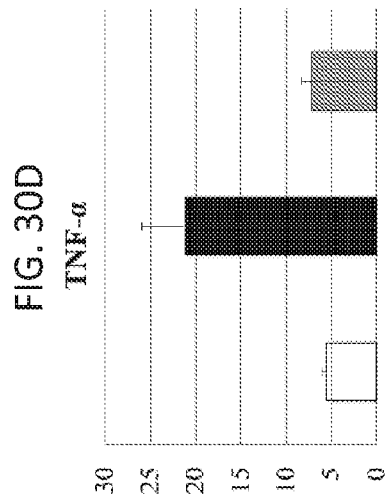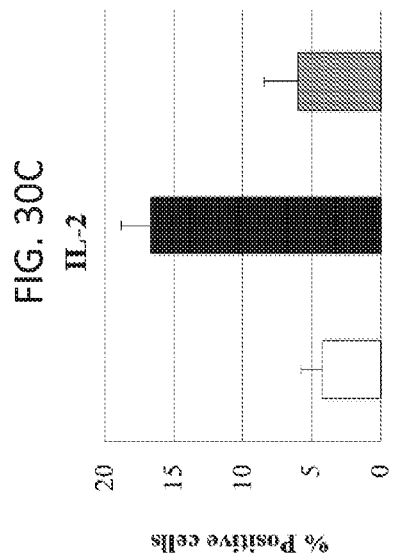

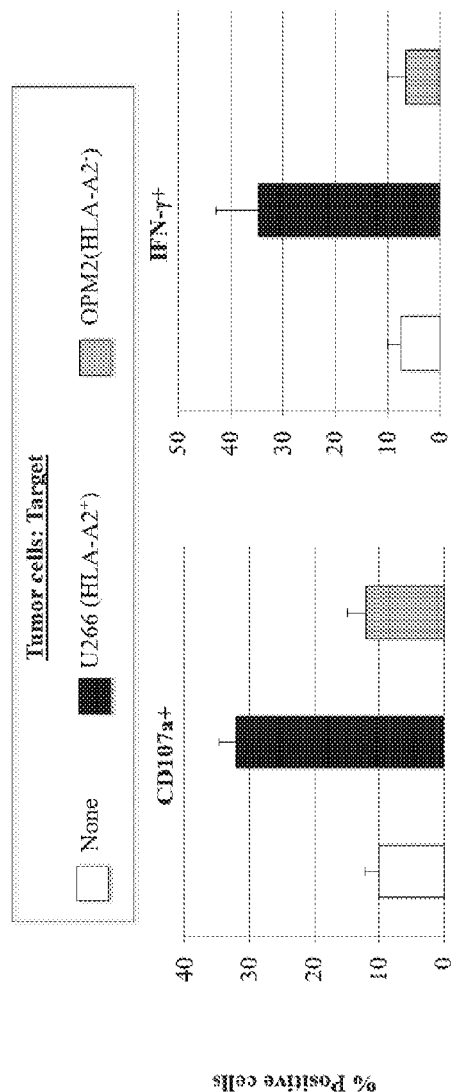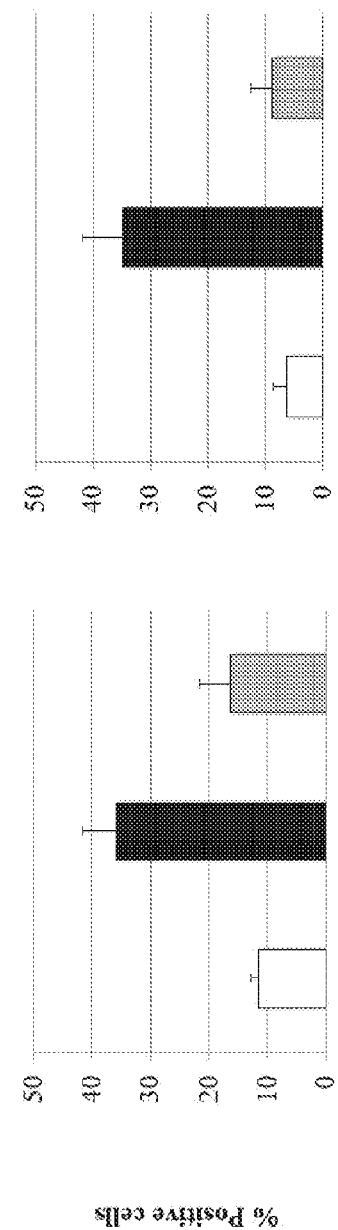
FIG. 31B  FIG. 31C  FIG. 31D  FIG. 31E

IMMUNOGENIC PEPTIDES SPECIFIC TO BCMA AND TACI ANTIGENS

CROSS-REFERENCE TO RELATED APPLICATIONS

This application is a U.S. National Stage application of International Application No. PCT/US2018/049260, filed Aug. 31, 2018, which claims the benefit of U.S. Provisional Application No. 62/553,669, filed on Sep. 1, 2017. The entire contents of each of the foregoing applications are incorporated herein by reference.

STATEMENT REGARDING FEDERALLY SPONSORED RESEARCH

This invention was made with government support under Grant Nos. P50 CA100707, P01 CA078378, and R01 CA050947 awarded by the National Institutes of Health. The Government has certain rights in the invention.

TECHNICAL FIELD

This disclosure relates to immunogenic peptides that are specific to B-cell maturation antigen (BCMA) and Transmembrane activator and CAML interactor (TACI), and methods of use thereof.

BACKGROUND

Cancer is currently one of the diseases that have the highest human mortality. According to the World Health Organization statistical data, in 2012 the number of global cancer incidence and death cases reached 14 million and 8.2 million, respectively. In the United States, cancer is responsible for at least 25% of all deaths.

In recent years, new therapies have been developed for treating various types of cancers. Patients afflicted with cancers are often treated by using, e.g., surgeries, chemotherapies and/or immune therapies. The prognosis for these patients sometimes is still unsatisfactory. Efficacious therapies and/or prophylactic regimens for treating the cancer are therefore urgently needed.

SUMMARY

This disclosure relates, in part to, to immunogenic peptides, T cells (e.g., CD8$^+$ cytotoxic T cells (CTL) and/or CD4$^+$ helper T cells), and nanoparticles (e.g., polymeric nanocarriers or liposomal nanoparticles) encapsulating peptides that are specific to B-cell maturation antigen (BCMA) or Transmembrane activator and CAML interactor (TACI), and methods of use thereof.

In one aspect, the disclosure relates to a peptide comprising, consisting essentially of, or consisting of, an amino acid sequence that is identical to the amino acid sequence set forth in any one of SEQ ID NO: 13-17, or differs by 1 to 6 amino acid residues. In some embodiments, the amino acid at position 1 of SEQ ID NOs: 13-17 is unaltered. In some embodiments, the amino acid(s) at one or more of positions 1, 2, or 9 of SEQ ID NOs: 13-17 is substituted with another amino acid. For example, position 1, 2, or 9 is substituted; positions 1 and 2 are substituted; positions 2 and 9 are substituted; positions 1 and 9 are substituted; or positions 1, 2, and 9 are substituted. In certain embodiments, the peptide is 9 to 30 amino acids in length (i.e., 9, 10, 11, 12, 13, 14, 15, 16, 17, 18, 19, 20, 21, 22, 23, 24, 25, 26, 27, 28, 29, 30).

In some embodiments, the amino acid sequence is SEQ ID NO: 13, SEQ ID NO: 14, SEQ ID NO: 15, SEQ ID NO: 16, or SEQ ID NO: 17.

In some embodiments, the peptide comprises an amino acid sequence set forth in any one of SEQ ID NO: 13-17 wherein the peptide includes 1 to 15 (i.e., 1, 2, 3, 4, 5, 6, 7, 8, 9, 10, 11, 12, 13, 14, 15) amino acids at the N- and/or C-terminus of the amino acid sequence.

In another aspect, the disclosure relates to a peptide comprising, consisting essential of, or consisting of, a first amino acid sequence consisting of an amino acid sequence that is at least 40%, at least 45%, at least 50%, at least 55%, at least 60%, at least 65%, at least 70%, at least 75%, at least 80%, at least 85%, at least 90%, or at least 95% identical to any one of SEQ ID NOs: 1-17; and a second amino acid sequence that is heterologous to the first amino acid sequence. In some embodiments, the amino acid(s) at one or more of positions 1, 2, or 9 of SEQ ID NOs: 1-17 is substituted with another amino acid. For example, position 1, 2, or 9 is substituted; positions 1 and 2 are substituted; positions 2 and 9 are substituted; positions 1 and 9 are substituted; or positions 1, 2, and 9 are substituted. In certain embodiments, the peptide is 9 to 30 amino acids in length (i.e., 9, 10, 11, 12, 13, 14, 15, 16, 17, 18, 19, 20, 21, 22, 23, 24, 25, 26, 27, 28, 29, 30).

In another aspect, the disclosure relates to a peptide comprising, consisting essentially of, or consisting of an amino acid sequence that is at least 40%, at least 45%, at least 50%, at least 55%, at least 60%, at least 65%, at least 70%, at least 75%, at least 80%, at least 85%, at least 90%, or at least 95% identical to any one of SEQ ID NOs: 1-17. In some embodiments, the amino acid(s) at one or more of positions 3, 4, 5, 6, 7, or 8 of SEQ ID NOs: 1-17 is substituted with another amino acid. For example, position 3, 4, 5, 6, 7, or 8 is substituted; positions 3 and 4 are substituted; positions 3 and 5 are substituted; positions 3 and 6 are substituted; positions 3 and 7 are substituted; positions 3 and 8 are substituted; positions 4 and 5 are substituted; positions 4 and 6 are substituted; positions 4 and 7 are substituted; positions 4 and 8 are substituted; positions 5 and 6 are substituted; positions 5 and 7 are substituted; positions 5 and 8 are substituted; positions 6 and 7 are substituted; positions 6 and 8 are substituted; positions 7 and 8 are substituted; or any combination of three different, 4 different, 5 different, or 6 different positions from the group of positions 3, 4, 5, 6, 7, and 8 are substituted.

In some embodiments, the peptide binds to a major histocompatibility complex (MHC) molecule. In some embodiments, wherein the peptide, in association with a MEW molecule, is recognized by an antigen specific T cell receptor on a T cell. In some embodiments, the MEW molecule is an MEW class I molecule or an MEW class II molecule. In some embodiments, the MEW class I molecule is HLA-A (e.g., HLA-A2, HLA-A24, HLA-A1, HLA-A3, HLA-A30, HLA-A26, HLA-A68, or HLA-A11), HLA-B or HLA-C. In some embodiments, the MEW molecule is an HLA-A2 molecule or a HLA-A24 molecule.

The disclosure also provides a composition comprising the peptide as described herein and a second agent. In some embodiments, the second agent is selected from the group consisting of compounds to enhance the BCMA and TACI-specific responses such as (1) Cytokines and Chemokines; (2) checkpoint inhibitors including anti-PD1, anti-PDL1, anti-CTLA4, anti-LAG3, and anti-TIM3; (2) immune agonists including anti-CD28, anti-CD40L (CD154), anti-41BB (CD137), anti-OX40 and anti-GITR, (3) immune modulators including lenalidomide, pomalidomide, a Thalidomide analogue, IMiDS compound, and/or HDAC inhibitors (e.g., ACY241) as a single agent and/or in combination with Dexamethasone; (4) adjuvant; (5) therapeutics which increase the BCMA and TACI-specific responses including with vaccine, cell therapies and/or antibodies; (6) therapeutics which alternate the BCMA and TACI-specific responses including peptide-based vaccine, different types of vaccine (RNA vaccine, DNA vaccine), cell therapies, specific modulators and/or specific inhibitors; and (7) therapeutics that have an independent approach from the BCMA and TACI-targeting therapy to widely cover immune responses to the disease including biological and non-biological approaches. In some embodiments, the second agent is an immune stimulatory agent (e.g., a cytokine or a T helper epitope). In some embodiments, the second agent is a T helper epitope. In some embodiments, the T helper epitope is a PADRE sequence or a universal Tetanus Toxoid T helper (TT Th) epitope. In some embodiments, the second agent is an adjuvant. The adjuvant can be selected from the group consisting of Freund's complete adjuvant, Freund's incomplete adjuvant, alum, a ligand for a Toll receptor, QS21, RIBI, cholera toxin (CT), E. coli heat labile toxin (LT), mutant CT (MCT), and mutant E. coli heat labile toxin (MLT). In some embodiments, the second agent is a toll like receptor-3 ligand (e.g., Poly ICLC), interferon alpha (IFNα), interferon gamma (IFNγ), Granulocyte-macrophage colony-stimulating factor (GM-CSF), anti-interleukin 6 (IL-6), IL-6 inhibitor, an anti-OX40 antibody, an anti-GITR antibody. In some embodiments, the second agent is a checkpoint inhibitor (e.g., anti-LAG3 antibody). In some embodiments, the second agent is an immune modulator including lenalidomide, pomalidomide, a Thalidomide analogue, IMiDS compound, and/or HDAC inhibitors (e.g., ACY241) as a single agent and/or in combination with Dexamethasone.

In one aspect, the disclosure also relates to a pharmaceutical composition comprising the peptide as described herein and a pharmaceutically acceptable carrier. In some embodiments, the pharmaceutical composition comprises an agent selected from the group consisting of compounds to enhance the BCMA and TACI-specific responses such as (1) Cytokines and Chemokines; (2) checkpoint inhibitors including anti-PD1, anti-PDL1, anti-CTLA4, anti-LAG3, and anti-TIM3; (2) immune agonists including anti-CD28, anti-CD40L (CD154), anti-41BB (CD137), anti-OX40 and anti-GITR, (3) immune modulators including lenalidomide, pomalidomide, a Thalidomide analogue, IMiDS compound, and/or HDAC inhibitors (e.g., ACY241) as a single agent and/or in combination with Dexamethasone; (4) adjuvant; (5) therapeutics which increase the BCMA and TACI-specific responses including with vaccine, cell therapies and/or antibodies; and (6) therapeutics that have an independent approach from the BCMA and TACI-targeting therapy to widely cover immune responses to the disease. In some instances, the pharmaceutical composition includes one or more of: an adjuvant (e.g., Freund's complete adjuvant, Freund's incomplete adjuvant, alum, a ligand for a Toll receptor, QS21, RIBI, cholera toxin (CT), E. coli heat labile toxin (LT), mutant CT (MCT), and mutant E. coli heat labile toxin (MLT)); an immune agonist (e.g., an anti-OX40 antibody, an anti-GITR antibody); a checkpoint inhibitor (e.g., anti-LAG3 antibody); or an immune modulator (e.g., lenalidomide, pomalidomide, a Thalidomide analogue, IMiDS compound, and/or HDAC inhibitors (e.g., ACY241) as a single agent and/or in combination with Dexamethasone).

In some embodiments, the pharmaceutical composition further comprises a checkpoint inhibitor. In one embodiment, the checkpoint inhibitor is an anti-LAG3 antibody. In some embodiments, the pharmaceutical composition further comprises lenalidomide. In some embodiments, the pharmaceutical composition further comprises lenalidomide, pomalidomide, a Thalidomide analogue, IMiDS compound and/or HDAC inhibitors (e.g., ACY241) as a single agent and/or in combination with Dexamethasone.

In some embodiments, the pharmaceutical composition further comprises a T cell (e.g., a CTL) specific for BCMA. In some embodiments, the pharmaceutical composition further comprises a T cell (e.g., a CTL) specific for TACI. In certain instances, the CTL is a CTL obtained by exposure to a peptide comprising or consisting of one or more of SEQ ID NO: 13 or 14. In other instances, the CTL is a CTL obtained by exposure to a peptide comprising or consisting of any one or more of SEQ ID NOs: 15-17. In some instances, the CTL is a memory $CD8^+$ CTL. In some instances, the CTL is a memory $CD8^+$ $CD45RO^+$ CTL. In some instances, the CTL is a non-memory $CD8^+$ CTL. In some instances, the CTL is an effector $CD8^+$ CTL. In some instances, the CTL is activated $CD8^+$ CTL. In some instances, the CTL is a Tetramer-positive $CD8^+$ CTL. In some instances, the CTL is a $CD8^+$ CTL that has upregulated a costimulatory molecule expression. In some instances, the CTL is a $CD8^+$ CTL that has upregulated a checkpoint molecule expression. In some instances, the CTL is a $CD8^+$ CTL that produce cytokine(s) and/or that has upregulated critical cytolytic marker(s) (e.g. CD107, Granzyme, Perforin) expression and/or production. In some instances, the CTL is a $CD8^+$ CTL that has activities against tumor or other targets.

In one aspect, the disclosure relates to a nucleic acid encoding a peptide as described herein. In certain instances, the nucleic acid is a RNA (e.g., mRNA). In other embodiments, the nucleic acid is a DNA. In some instances, the RNA or DNA is encapsulated in a nanocarrier (e.g., polymeric such as PLGA or liposomal). The RNA and DNA may comprises other regulatory sequences (e.g., start codon, stop codon, polyA tail).

In one aspect, the disclosure also relates to a vector comprising a nucleic acid encoding the peptide as described herein. In some embodiments, the nucleic acid sequence is operably linked to a promoter, a regulatory element, or an expression control sequence.

In another aspect, the disclosure also relates to a cultured cell comprising the vector as described herein. In some embodiments, the cell is a mammalian cell, a human cell, or an immune cell.

In another aspect, the disclosure provides a virus comprising a nucleic acid encoding the peptide as described herein. In some embodiments, the virus is a lentivirus, an adenovirus, an adeno-associated virus, a human foamy virus, parvovirus, myxoma virus, Newcastle disease virus, a reovirus, Seneca valley virus, measles virus, poliovirus, vaccinia virus, herpes simplex virus, or vesicular stomatitis virus.

In one aspect, the disclosure relates to a combination of at least two different peptides, wherein the at least two different peptides are selected from the group of peptides having an amino acid sequence set forth in SEQ ID NOs: 13-17. The combination can include peptides with 1 to 4 substitutions in one or more of SEQ ID NOs: 13-17. In some instances, the substitutions are at one or more of positions 1, 2, or 9. In some instances, position 1 is not altered. In some instances, the peptides are 9 to 30 amino acids in length. In some embodiments, the combination comprises at least 2, 3, 4, or all 5 peptides having an amino acid sequence set forth in SEQ ID NOs: 13-17. In some instances, the combination comprises two or more peptides set forth in SEQ ID NOs: 13-17, wherein the two or more peptides have 1 to 15 (i.e., 1, 2, 3, 4, 5, 6, 7, 8, 9, 10, 11, 12, 13, 14, 15) amino acids at the N- and/or C-terminus of the amino acid sequence.

In one aspect, the disclosure also relates to a pharmaceutical composition comprising the combination of peptides as described herein; and a pharmaceutically acceptable carrier. In some embodiments, the pharmaceutical composition comprises an agent selected from the group consisting of compounds to enhance the BCMA and TACI-specific responses such as (1) Cytokines and Chemokines; (2) checkpoint inhibitors including anti-PD1, anti-PDL1, anti-CTLA4, anti-LAG3, and anti-TIM3; (2) immune agonists including anti-OX40 and anti-GITR, (3) immune modulators including lenalidomide, pomalidomide, a Thalidomide analogue, IMiDS compound, and/or HDAC inhibitors (e.g., ACY241) as a single agent and/or in combination with Dexamethasone; (4) adjuvant; (5) therapeutics which increase the BCMA and TACI-specific responses including with vaccine, cell therapies and/or antibodies; and (6) therapeutics that have an independent approach from the BCMA and TACI-targeting therapy to widely cover immune responses to the disease. In some instances, the pharmaceutical composition includes one or more of: an adjuvant (e.g., Freund's complete adjuvant, Freund's incomplete adjuvant, alum, a ligand for a Toll receptor, QS21, RIBI, cholera toxin (CT), *E. coli* heat labile toxin (LT), mutant CT (MCT), and mutant *E. coli* heat labile toxin (MLT)); an immune agonist (e.g., an anti-OX40 antibody, an anti-GITR antibody); a checkpoint inhibitor (e.g., anti-LAG3 antibody); and/or lenalidomide, pomalidomide, a Thalidomide analogue, IMiDS compound, and/or HDAC inhibitors (e.g., ACY241) as a single agent and/or in combination with Dexamethasone.

In some embodiments, the pharmaceutical composition further comprises an immune agonist. In some instances, the immune agonist can be an anti-OX40 antibody or an anti-GITR antibody. In some embodiments, the pharmaceutical composition further comprises a checkpoint inhibitor. In one instance, the checkpoint inhibitor is an anti-LAG3 antibody. In some embodiments, the pharmaceutical composition further comprises lenalidomide, pomalidomide, a Thalidomide analogue, IMiDS compound, and/or HDAC inhibitors (e.g., ACY241) as a single agent and/or in combination with Dexamethasone. In one aspect, the disclosure also provides a composition comprising an isolated dendritic cell, wherein the dendritic cell presents a peptide sequence on its surface, wherein the peptide sequence comprises at least one major histocompatibility complex (MHC) class I peptide epitope of one or both of BCMA antigen (SEQ ID NO: 18) and TACI antigen (SEQ ID NO: 19).

In some embodiments, the MHC class I peptide epitope is an HLA-A2 peptide epitope.

In some embodiments, the MHC class I peptide epitope is an HLA-A24 peptide epitope.

In some embodiments, the dendritic cell acquires the peptide sequence in vitro by exposure to a peptide comprising the peptide sequence.

In some embodiments, the peptide sequence is a synthetic peptide sequence. In some embodiments, the peptide sequence is a sequence set forth in any one of SEQ ID NO: 1-12 and SEQ ID NO: 13-17. In some instances, the peptide sequence is a sequence set forth in SEQ ID NO: 13-17 but having 1 to 4 amino acid substitutions. In certain cases, the substitution is at one or more of position 1, 2, or 9. In one particular embodiment, the peptide sequence is SEQ ID NO: 13. In another embodiment, the peptide is SEQ ID NO:13 but having 1 to 4 amino acid substitutions. In certain cases, the substitution is at one or more of position 1, 2, or 9. In another particular embodiment, the peptide sequence is SEQ ID NO: 16. In another embodiment, the peptide is SEQ ID NO:16 but having 1 to 4 amino acid substitutions. In certain cases, the substitution is at one or more of position 1, 2, or 9.

In some embodiments, the composition comprises between $10^5$ and $10^8$ dendritic cells.

In some embodiments, the composition further comprises a peptide set forth in any one of SEQ ID NO: 1-12 and SEQ ID NO: 13-17. In one particular embodiment, the peptide sequence is SEQ ID NO: 13. In another particular embodiment, the peptide sequence is SEQ ID NO: 16. In some embodiments, the composition comprises an agent selected from the group consisting of compounds to enhance the BCMA and TACT-specific responses such as (1) Cytokines and Chemokines; (2) checkpoint inhibitors including anti-PD1, anti-PDL1, anti-CTLA4, anti-LAG3, and anti-TIM3; (2) immune agonists including anti-CD28, anti-CD40L (CD154), anti-41BB (CD137), anti-OX40 and anti-GITR, (3) immune modulators including lenalidomide, pomalidomide, a Thalidomide analogue, IMiDS compound, and/or HDAC inhibitors (e.g., ACY241) as a single agent and/or in combination with Dexamethasone; (4) adjuvant; (5) therapeutics which increase the BCMA and TACI-specific responses including with vaccine, cell therapies and/or antibodies; (6) therapeutics which alternate the BCMA and TACT-specific responses including peptide-based vaccine, different types of vaccine (RNA vaccine, DNA vaccine), cell therapies, specific modulators and/or specific inhibitors; and (7) therapeutics that have an independent approach from the BCMA and TACI-targeting therapy to widely cover immune responses to the disease including biological and non-biological approaches. In some embodiments, the composition further comprises an immune agonist (e.g., anti-OX40 antibody, anti-GITR antibody). In some embodiments, the composition further comprises a checkpoint inhibitor (e.g., anti-LAG3 antibody).

In one aspect, the disclosure relates to a method of inducing an immune response against BCMA- and/or TACI-expressing cell (e.g., cancer cells) in a human subject in need thereof, the method comprising administering to the human subject a peptide as described herein (e.g., a peptide comprising or consisting of SEQ ID NOs: 13-17), or a composition (e.g., a pharmaceutical composition) as described herein. In another embodiment, the peptide is SEQ ID NO:13 but having 1 to 4 amino acid substitutions. In certain cases, the substitution is at one or more of position 1, 2, or 9 In another particular embodiment, the peptide sequence is SEQ ID NO: 16. In another embodiment, the peptide is SEQ ID NO:16 but having 1 to 4 amino acid substitutions. In certain cases, the substitution is at one or more of position 1, 2, or 9.

In some embodiments, the subject has a cancer that expresses BCMA and/or TACI, and the immune response is against such a cancer cell.

In some embodiments, the subject has a non-cancer cell that expresses BCMA and/or TACI, and the immune response is against such a non-cancer cell.

In some embodiments, the cancer is a hematological cancer (e.g., multiple myeloma). In some embodiments, the cancer cell is a plasma cell (e.g., cancerous plasma cells). In some embodiments, the human subject has refractory multiple myeloma. In some embodiments, the human subject has refractory multiple myeloma relapsing after allotransplantation.

In some embodiments, the cancer cell expresses BCMA, and the level of BCMA in the cancer cell is at least 5%, at least 10%, at least 15%, at least 20%, at least 25%, at least 30%, at least 40%, or at least 50% more than a plasma cell in a healthy human subject.

In some embodiments, the cancer cell expresses TACI, and the level of TACI in the cancer cell is at least 5%, at least 10%, at least 15%, at least 20%, at least 25%, at least 30%, at least 40%, or at least 50% more than a plasma cell in a healthy human subject.

In some embodiments, the method further comprises administering to the human subject a CTL specific for BCMA. In some embodiments, the method further comprises administering to the human subject a CTL specific for TACI. In certain instances, the CTL is a CTL obtained by exposure to a peptide comprising or consisting of one or more of SEQ ID NO: 13 or 14. In some cases, the CTL is exposed to a peptide of SEQ ID NO: 13 or 14, but with 1 to 4 substitutions. In some cases, the substitutions are at one or more of positions 1, 2, or 9. In some cases, the peptide is 9 to 30 amino acids in length. In other instances, the CTL is a CTL obtained by exposure to a peptide comprising or consisting of any one or more of SEQ ID NOs: 15-17. In some cases, the CTL is exposed to a peptide of SEQ ID NO: 15, 16, or 17, but with 1 to 4 substitutions. In some cases, the substitutions are at one or more of positions 1, 2, or 9. In some cases, the peptide is 9 to 30 amino acids in length. In some instances, the CTL is a memory $CD8^+$ CTL. In some instances, the CTL is a memory $CD8^+$ $CD45RO^+$ CTL. In some instances, the CTL is an effector $CD8^+$ CTL. In some instances, the CTL is an activated $CD8^+$ CTL. In some instances, the CTL is a Tetramer-positive $CD8^+$ CTL. In some instances, the $CD8^+$ CTL is a CTL that when stimulated with a peptide described herein upregulates a costimulatory molecule expression. In some instances, the $CD8^+$ CTL is a CTL that when stimulated with a peptide described herein upregulates a checkpoint molecule expression. In some instances, the CTL is a $CD8^+$ CTL that produce cytokine(s) and/or that has upregulated critical cytolytic marker(s) (e.g. CD107, Granzyme, Perforin) expression and/or production. In some instances, the CTL is a $CD8^+$ CTL that has activities against tumor or other targets.

In some embodiments, the method further comprises administering to the human subject an immune agonist. In some embodiments, the immune agonist is anti-CD28, anti-CD40L (CD154), anti-41BB (CD137), anti-OX40 and anti-GITR.

In some embodiments, the method further comprises administering to the human subject a checkpoint inhibitor (e.g., anti-LAG3 antibody). In certain embodiments, the method further comprises administering to the human subject lenalidomide. In some embodiments, the method further comprises administering to the human subject one or more of: an immune agonist (e.g., anti-OX40 antibody, anti-GITR antibody), a checkpoint inhibitor (e.g., anti-LAG3 antibody), or an immune modulator.

In some embodiments, the method further comprises, after administering to the human subject the peptide or the composition, determining whether an immune response against BCMA and/or TACI-expressing cancers occurred in the human subject.

In one aspect, the disclosure relates to a method of treating a human subject having a cancer or a pre-malignant disease, the method comprising administering to the human subject a peptide as described herein, or a composition as described herein.

In some embodiments, the cancer is a hematologic cancer. In some embodiments, the cancer is multiple myeloma, leukemia, lymphoma or any B-cell or plasma cell malignancy.

In some embodiments, the pre-malignant disease is monoclonal gammopathy of undermined significance (MGUS) or smoldering multiple myeloma.

In some embodiments, the method further comprises detecting that one or more cancer cells in the human subject expresses or overexpress BCMA and/or TACI.

In some embodiments, the human subject has one or more cancer cells that overexpress BCMA and/or TACI, wherein the level of BCMA and/or TACI in the cancer cell is at least 20% more than a normal cell (e.g., a plasma cell in a healthy subject).

In some embodiments, the subject has one or more cancer cells that express a WIC molecule.

In some embodiments, the method further comprises administering to the human subject a CTL specific for BCMA. In some embodiments, the method further comprises administering to the human subject a CTL specific for TACI. In certain instances, the CTL is a CTL obtained by exposure to a peptide comprising or consisting of one or more of SEQ ID NO: 13 or 14. In some cases, the CTL is exposed to a peptide of SEQ ID NO: 13 or 14, but with 1 to 4 substitutions. In some cases, the substitutions are at one or more of positions 1, 2, or 9. In some cases, the peptide is 9 to 30 amino acids in length. In other instances, the CTL is a CTL obtained by exposure to a peptide comprising or consisting of any one or more of SEQ ID NOs: 15-17. In some cases, the CTL is exposed to a peptide of SEQ ID NO: 15, 16, or 17, but with 1 to 4 substitutions. In some cases, the substitutions are at one or more of positions 1, 2, or 9. In some cases, the peptide is 9 to 30 amino acids in length. In some instances, the CTL is a memory CD8+ CTL. In some instances, the CTL is a memory CD8+CD45RO+ CTL. In some instances, the CTL is an effector CD8+ CTL. In some instances, the CTL is activated CD8+ CTL. In some instances, the CTL is a Tetramer-positive CD8+ CTL. In some instances, the CTL is a CD8+ CTL that has upregulated a costimulatory molecule expression. In some instances, the CTL is a CD8+ CTL that has upregulated a checkpoint molecule expression.

In some embodiments, the method comprises administering to the human subject an agent selected from the group consisting of compounds to enhance the BCMA and TACI-specific responses such as (1) Cytokines and Chemokines; (2) checkpoint inhibitors including anti-PD1, anti-PDL1, anti-CTLA4, anti-LAG3, and anti-TIM3; (2) immune agonists including anti-OX40 and anti-GITR, (3) immune modulators including lenalidomide, pomalidomide, HDAC inhibitors (e.g., ACY241); (4) adjuvant; (5) therapeutics which increase the BCMA and TACI-specific responses including with vaccine, cell therapies and/or antibodies; and (6) therapeutics that have an independent approach from the BCMA and TACI-targeting therapy to widely cover immune responses to the disease. In some embodiments, the method further comprises administering to the human subject an immune agonist. In some embodiments, the immune agonist is an anti-OX40 antibody or an anti-GITR antibody.

In some embodiments, the method further comprises administering to the human subject a checkpoint inhibitor (e.g., anti-LAG3 antibody). In certain embodiments, the method further comprises administering to the human subject lenalidomide. In some embodiments, the method further comprises administering to the human subject one or more of: an immune agonist (e.g., anti-OX40 antibody, anti-GITR antibody), a checkpoint inhibitor (e.g., anti-LAG3 antibody), or an immune modulator.

In some embodiments, the method further comprises administering a chemotherapy or a radiotherapy to the human subject.

In one aspect, the disclosure relates to a method of generating and/or proliferating BCMA-specific cytotoxic T cells, the method comprising contacting one or more cytotoxic T cells with one or more antigen presenting cells pulsed with a peptide comprising an amino acid sequence selected from SEQ ID NO: 13 and SEQ ID NO: 14. In some cases, the CTL is exposed to a peptide of SEQ ID NO: 13 or 14, but with 1 to 4 substitutions. In some cases, the substitutions are at one or more of positions 1, 2, or 9. In some cases, the peptide is 9 to 30 amino acids in length.

In some embodiments, the cytotoxic T cells are memory cytotoxic T cells. In some embodiments, the cytotoxic T cells are effector cytotoxic T cells. In some instances, the CD8+ CTL is a CTL that when stimulated with a peptide described herein upregulates a costimulatory molecule expression. In some instances, the CD8+ CTL is a CTL that when stimulated with a peptide described herein upregulates a checkpoint molecule expression. In some instances, the CTL is a CD8+ CTL that produce cytokine(s) and/or that has upregulated critical cytolytic marker(s) (e.g. CD107, Granzyme, Perforin) expression and/or production. In some instances, the CTL is a CD8+ CTL that has activities against tumor or other targets.

In some embodiments, the antigen presenting cells are dendritic cells (DCs). In one particular embodiment, the peptide comprises or consists of SEQ ID NO: 13. In another aspect, the disclosure relates to a method of generating TACI-specific cytotoxic T cells, the method comprising contacting one or more cytotoxic T cells with one or more antigen presenting cells pulsed with a peptide comprising an amino acid sequence selected from SEQ ID NO: 15-17. In some cases, the CTL is exposed to a peptide of SEQ ID NO: 15, 16, or 17, but with 1 to 4 substitutions. In some cases, the substitutions are at one or more of positions 1, 2, or 9. In some cases, the peptide is 9 to 30 amino acids in length.

In one particular embodiment, the peptide comprises or consists of SEQ ID NO: 16.

In one aspect, the disclosure also relates to a method of killing a target cell, the method comprising contacting the target cell with one or more BCMA-specific cytotoxic T cells, wherein the target cell expresses or overexpresses BCMA. In some embodiments, the target cell expresses HLA-A.

In some embodiments, the method further comprises contacting the one or more BCMA-specific cytotoxic T cells with an agent selected from the group consisting of compounds to enhance the BCMA and TACI-specific responses such as (1) Cytokines and Chemokines; (2) checkpoint inhibitors including anti-PD1, anti-PDL1, anti-CTLA4, anti-LAG3, and anti-TIM3; (2) immune agonists including anti-OX40 and anti-GITR, (3) immune modulators including lenalidomide, pomalidomide, a Thalidomide analogue, IMiDS compound, and/or HDAC inhibitors (e.g., ACY241) as a single agent and/or in combination with Dexamethasone; (4) adjuvant; (5) therapeutics which increase the BCMA and TACI-specific responses including with vaccine, cell therapies and/or antibodies; and (6) therapeutics that have an independent approach from the BCMA and TACI-targeting therapy to widely cover immune responses to the disease.

In some embodiments, the method further comprises contacting the one or more BCMA-specific cytotoxic T cells with an immune agonist.

In some embodiments, the method comprises further administering a peptide comprising or consisting of an amino acid sequence set forth in SEQ ID NOs: 13 or 14. In some cases, the peptide may have 1 to 15 (i.e., 1, 2, 3, 4, 5, 6, 7, 8, 9, 10, 11, 12, 13, 14, 15) amino acids added at the N- and/or C-terminus of the amino acid sequence of SEQ ID NO.: 13 or 14.

In some embodiments, the immune agonist is an OX40 agonist or an GITR agonist. In some embodiments, the immune agonist is an anti-OX40 antibody or an anti-GITR antibody.

In some embodiments, the method further comprises administering to the human subject a checkpoint inhibitor (e.g., anti-LAG3 antibody). In certain embodiments, the method further comprises administering to the human subject lenalidomide. In some embodiments, the method further comprises administering to the human subject one or more of: an immune agonist (e.g., anti-OX40 antibody, anti-GITR antibody), a checkpoint inhibitor (e.g., anti-LAG3 antibody), or lenalidomide.

In another aspect, the disclosure relates to a method of killing a target cell, the method comprising contacting the target cell with one or more TACI-specific cytotoxic T cells, wherein the target cell expresses or overexpresses TACI. In some embodiments, the target cell expresses HLA-A.

In some embodiments, the method comprises further administering a peptide comprising or consisting of an amino acid sequence set forth in any one of SEQ ID NOs: 15-17. In some cases, the peptide may have 1 to 15 (i.e., 1, 2, 3, 4, 5, 6, 7, 8, 9, 10, 11, 12, 13, 14, 15) amino acids added at the N- and/or C-terminus of the amino acid sequence of SEQ ID NO.: 15-17.

In some embodiments, the method further comprises contacting the one or more TACI-specific cytotoxic T cells with an agent selected from the group consisting of compounds to enhance the BCMA and TACI-specific responses such as (1) Cytokines and Chemokines; (2) checkpoint inhibitors including anti-PD1, anti-PDL1, anti-CTLA4, anti-LAG3, and anti-TIM3; (2) immune agonists including anti-OX40 and anti-GITR, (3) immune modulators including lenalidomide, pomalidomide, HDAC inhibitors (e.g., ACY241); (4) adjuvant; (5) therapeutics which increase the BCMA and TACI-specific responses including with vaccine, cell therapies and/or antibodies; and (6) therapeutics that have an independent approach from the BCMA and TACI-targeting therapy to widely cover immune responses to the disease.

In some embodiments, the method further comprises contacting the one or more TACI-specific cytotoxic T cells with an immune agonist.

In some embodiments, the immune agonist is an OX40 agonist or an GITR agonist.

In some embodiments, the immune agonist is an anti-OX40 antibody or an anti-GITR antibody. In some embodiments, the method further comprises administering to the human subject a checkpoint inhibitor (e.g., anti-LAG3 antibody). In certain embodiments, the method further comprises administering to the human subject lenalidomide. In some embodiments, the method further comprises administering to the human subject one or more of: an immune agonist (e.g., anti-OX40 antibody, anti-GITR antibody), a checkpoint inhibitor (e.g., anti-LAG3 antibody), or lenalidomide.

In one aspect, the disclosure relates to a method of treating a human subject having a BCMA or TACI-expressing disease or cancer, the method comprising administering a plurality of BCMA-specific cytotoxic T cells or TACI-specific cytotoxic T cells to the human subject.

In some embodiments, the method further comprises administering to the human subject a peptide comprising or consisting of a sequence set forth in any one of SEQ ID NOs: 13-17. In some instances, the peptide has a sequence set forth in one of SEQ ID NO: 13-17 except that it has 1 to 4 substitutions. In some cases, the substitutions may be at one or more of positions 1, 2, or 9. In some instances, the peptide is 9 to 30 amino acids in length.

In some embodiments, the method further comprises administering to the human subject an agent selected from the group consisting of compounds to enhance the BCMA and TACI-specific responses such as (1) Cytokines and Chemokines; (2) checkpoint inhibitors including anti-PD1, anti-PDL1, anti-CTLA4, anti-LAG3, and anti-TIM3; (2) immune agonists including anti-OX40 and anti-GITR, (3) immune modulators including lenalidomide, pomalidomide, HDAC inhibitors (e.g., ACY241); (4) adjuvant; (5) therapeutics which increase the BCMA and TACI-specific responses including with vaccine, cell therapies and/or antibodies; and (6) therapeutics that have an independent approach from the BCMA and TACI-targeting therapy to widely cover immune responses to the disease.

In some embodiments, the method further comprises administering to the subject an immune agonist. In some embodiments, the immune agonist is an OX40 agonist or an GITR agonist. In some embodiments, the immune agonist is an anti-OX40 antibody or an anti-GITR antibody.

In some embodiments, the method further comprises administering to the human subject a checkpoint inhibitor (e.g., anti-LAG3 antibody). In certain embodiments, the method further comprises administering to the human subject lenalidomide. In some embodiments, the method further comprises administering to the human subject one or more of: an immune agonist (e.g., anti-OX40 antibody, anti-GITR antibody), a checkpoint inhibitor (e.g., anti-LAG3 antibody), or lenalidomide.

In some embodiments, the cytotoxic T cells are derived from the cells of the human subject. In some embodiments, the cytotoxic T cells are derived from induced pluripotent stem cells.

In some embodiments, the cancer expresses BCMA and/or TACI. In some embodiments, the human subject has multiple myeloma.

In one aspect, the disclosure relates to a process comprising,
(a) obtaining bone marrow derived mononuclear cells from a subject;
(b) culturing the mononuclear cells in vitro under a condition in which mononuclear cells become adherent to a culture vessel;
(c) selecting adherent mononuclear cells;
(d) culturing the adherent mononuclear cells in the presence of one or more cytokines under a condition in which the cells differentiate into antigen present cells; and (e) contacting the antigen presenting cells with a peptide as described herein (e.g., SEQ ID NOs: 13-17), thereby generating antigen presenting cells that present the peptide on a major histocompatibility complex (MHC) molecule.

In some embodiments, the major histocompatibility complex molecule is a MHC class I molecule.

In some embodiments, the one or more cytokines comprise granulocyte macrophage colony stimulating factor (GM-CSF) and interleukin-4 (IL-4).

In some embodiments, the one or more cytokines comprise tumor necrosis factor-α (TNF-α).

In some embodiments, the bone marrow derived cells are obtained from a subject diagnosed with multiple myeloma.

In one aspect, the discourse relates to a method of identifying a T cell antigen receptor sequence for BCMA, the method comprising
(a) generating and/or proliferating BCMA-specific cytotoxic T cells by the method as described herein;
(b) determining the T cell antigen receptor sequence for BCMA in the BCMA-specific cytotoxic T cells.

In another aspect, the disclosure relates to a method for treating a human subject having a BCMA-expressing disease or cancer, comprising: administering to the human subject a composition comprising a chimeric antigen receptor T cell (CAR-T cell), wherein the CAR-T cell expresses a chimeric antigen receptor, wherein the chimeric antigen receptor binds to BCMA.

In some embodiments, the cancer expresses BCMA. In some embodiments, the human subject has multiple myeloma.

In some embodiments, the method further comprises administering to the human subject a peptide comprising or consisting of a sequence set forth in any one of SEQ ID NO.: 13 or 14. In some cases, the peptide has the sequence set forth in SEQ ID NO:13 or 14, except that it has 1 to 4 amino acid substitutions. In some instances, the substitutions are at one or more of positions 1, 2, or 9. In some instances, the peptide is 9 to 30 amino acids in length. In some embodiments, the method further comprises administering to the human subject an agent selected from the group consisting of compounds to enhance the BCMA and TACI-specific responses such as (1) Cytokines and Chemokines; (2) checkpoint inhibitors including anti-PD1, anti-PDL1, anti-CTLA4, anti-LAG3, and anti-TIM3; (2) immune agonists including anti-OX40 and anti-GITR, (3) immune modulators including lenalidomide, pomalidomide, HDAC inhibitors (e.g., ACY241); (4) adjuvant; (5) therapeutics which increase the BCMA and TACI-specific responses including with vaccine, cell therapies and/or antibodies; and (6) therapeutics that have an independent approach from the BCMA and TACI-targeting therapy to widely cover immune responses to the disease.

In some embodiments, the method further comprises administering to the subject an immune agonist. In some embodiments, the immune agonist is an OX40 agonist or an GITR agonist. In some embodiments, the immune agonist is an anti-OX40 antibody or an anti-GITR antibody.

In some embodiments, the method further comprises administering to the human subject a checkpoint inhibitor (e.g., anti-LAG3 antibody). In certain embodiments, the method further comprises administering to the human subject lenalidomide. In some embodiments, the method further comprises administering to the human subject one or more of: an immune agonist (e.g., anti-OX40 antibody, anti-GITR antibody), a checkpoint inhibitor (e.g., anti-LAG3 antibody), or lenalidomide.

In one aspect, the discourse relates to a method of identifying a T cell antigen receptor sequence for TACI, the method comprising
(a) generating and/or proliferating TACI-specific cytotoxic T cells by the method as described herein;
(b) determining the T cell antigen receptor sequence for TACI in the TACT-specific cytotoxic T cells.

In another aspect, the disclosure relates to a method for treating a human subject having a TACI-expressing disease or cancer, comprising: administering to the human subject a composition comprising a chimeric antigen receptor T cell (CAR-T cell), wherein the CAR-T cell expresses a chimeric antigen receptor, wherein the chimeric antigen receptor binds to TACI.

In some embodiments, the cancer expresses TACI. In some embodiments, the human subject has multiple myeloma.

In some embodiments, the method further comprises administering to the human subject a peptide comprising or consisting of a sequence set forth in any one of SEQ ID NOs: 15-17.

In some embodiments, the method further comprises administering to the human subject an agent selected from the group consisting of compounds to enhance the BCMA and TACI-specific responses such as (1) Cytokines and Chemokines; (2) checkpoint inhibitors including anti-PD1, anti-PDL1, anti-CTLA4, anti-LAG3, and anti-TIM3; (2) immune agonists including anti-OX40 and anti-GITR, (3) immune modulators including lenalidomide, pomalidomide, HDAC inhibitors (e.g., ACY241); (4) adjuvant; (5) therapeutics which increase the BCMA and TACI-specific responses including with vaccine, cell therapies and/or antibodies; and (6) therapeutics that have an independent approach from the BCMA and TACI-targeting therapy to widely cover immune responses to the disease.

In some embodiments, the method further comprises administering to the subject an immune agonist. In some embodiments, the immune agonist is an OX40 agonist or an GITR agonist. In some embodiments, the immune agonist is an anti-OX40 antibody or an anti-GITR antibody.

In some embodiments, the method further comprises administering to the human subject a checkpoint inhibitor (e.g., anti-LAG3 antibody). In certain embodiments, the method further comprises administering to the human subject lenalidomide. In some embodiments, the method further comprises administering to the human subject one or more of: an immune agonist (e.g., anti-OX40 antibody, anti-GITR antibody), a checkpoint inhibitor (e.g., anti-LAG3 antibody), or lenalidomide.

In one aspect, the disclosure provides a composition comprising a nanoparticle, and a peptide comprising a sequence that is at least 60% identical to any one of SEQ ID NOs: 1-17. In some embodiments, the peptide comprises or consists of the sequence of SEQ ID NO: 13. In certain instances, the peptide has the sequence of SEQ ID NO:13 but with 1 to 4 amino acid substitutions. In some cases, the substitutions are at one or more of positions 1, 2, or 9. The peptide can be 9 to 30 amino acids in length. In other embodiments, the sequence comprises or consists of the sequence of SEQ ID NO: 16. In certain instances, the peptide has the sequence of SEQ ID NO:16 but with 1 to 4 amino acid substitutions. In some cases, the substitutions are at one or more of positions 1, 2, or 9. The peptide can be 9 to 30 amino acids in length.

In some embodiments, the peptide is encapsulated in the nanoparticle. In some embodiments, the nanoparticle is a liposome.

In some embodiments, the nanoparticle comprises a biodegradable polymer. In some embodiments, the nanoparticle comprises poly(D,L-lactide-co-glycolide) (PLGA). In some embodiments, the nanoparticle comprises poly(lactic-co-glycolic acid)-poly(ethylene glycol) (PLGA-PEG) copolymer.

In some embodiments, the amino acid sequence is SEQ ID NO: 13. In some embodiments, the amino acid sequence is SEQ ID NO: 14. In some embodiments, the amino acid sequence is SEQ ID NO: 15. In some embodiments, the amino acid sequence is SEQ ID NO: 16. In some embodiments, the amino acid sequence is SEQ ID NO: 17. In certain instances, the peptide has the sequence of any one of SEQ ID NO:13 to 17 but with 1 to 4 amino acid substitutions. In some cases, the substitutions are at one or more of positions 1, 2, or 9. The peptide can be 9 to 30 amino acids in length.

In some embodiments, the nanoparticle comprises an adjuvant. In some embodiments, the nanoparticle comprises a Toll-like receptor agonist (e.g., R848 or unmethylated CpG oligodeoxynucleotide).

In one aspect, the disclosure provides methods for treating a human subject having a cancer. The methods involve administering to the human subject the composition as described herein (e.g., nanoparticles). In some embodiments, the human subject has multiple myeloma.

In some embodiments, the cancer expresses BCMA. In other embodiments, the cancer expresses TACI.

In some embodiments, the method further comprises administering to the human subject a peptide comprising or consisting of a sequence set forth in any one of SEQ ID NOs: 15-17. In some embodiments, the peptide has a sequence set forth in one of SEQ ID NOs.: 15-17 except having 1 to 4 amino acid substitutions. The substitutions may be at one or more of positions 1, 2, or 9. The peptide can be 9 to 30 amino acids in length.

In some embodiments, the method further comprises administering to the human subject a CTL specific for BCMA. In some embodiments, the method further comprises administering to the human subject a CTL specific for TACI. In certain instances, the CTL is a CTL obtained by exposure to a peptide comprising or consisting of one or more of SEQ ID NO: 13 or 14. In other instances, the CTL is a CTL obtained by exposure to a peptide comprising or consisting of any one or more of SEQ ID NOs: 15-17. In some instances, the CTL is a memory CD8+ CTL. In some instances, the CTL is a memory CD8+CD45R0+ CTL. In some instances, the CTL is an effector CD8+ CTL. In some instances, the CTL is activated CD8+ CTL. In some instances, the CTL is a Tetramer-positive CD8+ CTL. In some instances, the CTL is a CD8+ CTL that has upregulated a costimulatory molecule expression. In some instances, the CTL is a CD8+ CTL that has upregulated a checkpoint molecule expression. In some embodiments, the method further comprises administering to the subject an immune agonist. In some embodiments, the immune agonist is an OX40 agonist or an GITR agonist. In some embodiments, the immune agonist is an anti-OX40 antibody or an anti-GITR antibody.

In some embodiments, the method further comprises administering to the human subject a checkpoint inhibitor (e.g., anti-LAG3 antibody). In certain embodiments, the method further comprises administering to the human subject lenalidomide. In some embodiments, the method further comprises administering to the human subject one or more of: an immune agonist (e.g., anti-OX40 antibody, anti-GITR antibody), a checkpoint inhibitor (e.g., anti-LAG3 antibody), or lenalidomide.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-1I show BCMA expression on multiple myeloma cell lines.

FIGS. 8A-8C show increased CD8$^+$ cytotoxic T cell (CTL) with heteroclitic BCMA #4 peptide stimulation.

FIGS. 9A-9C show decreased naïve CTL with heteroclitic BCMA #4 peptide stimulation.

FIGS. 10A-10C show increased memory CTL with heteroclitic BCMA #4 peptide stimulation.

FIGS. 19A-19F show HLA-A2 restricted and antigen-specific immune responses by heteroclitic BCMA$_{72-80}$-specific CTL to HLA-A2$^+$ MM cell lines.

FIGS. 20A-20H show anti-tumor activities of heteroclitic BCMA$_{54-62}$-specific CTL or heteroclitic BCMA$_{72-80}$ specific CTL against patients' MM cells.

FIGS. 30A-30F show anti-tumor activities of heteroclitic TACI$_{154-162}$ specific CTL against HLA-A2+ multiple myeloma cells (McCAR).

FIGS. 31A-31E show anti-tumor activities of heteroclitic TACI$_{154-162}$ specific CTL against HLA-A2+ multiple myeloma cells.

DETAILED DESCRIPTION

Figures 1D, 1E, 1F:
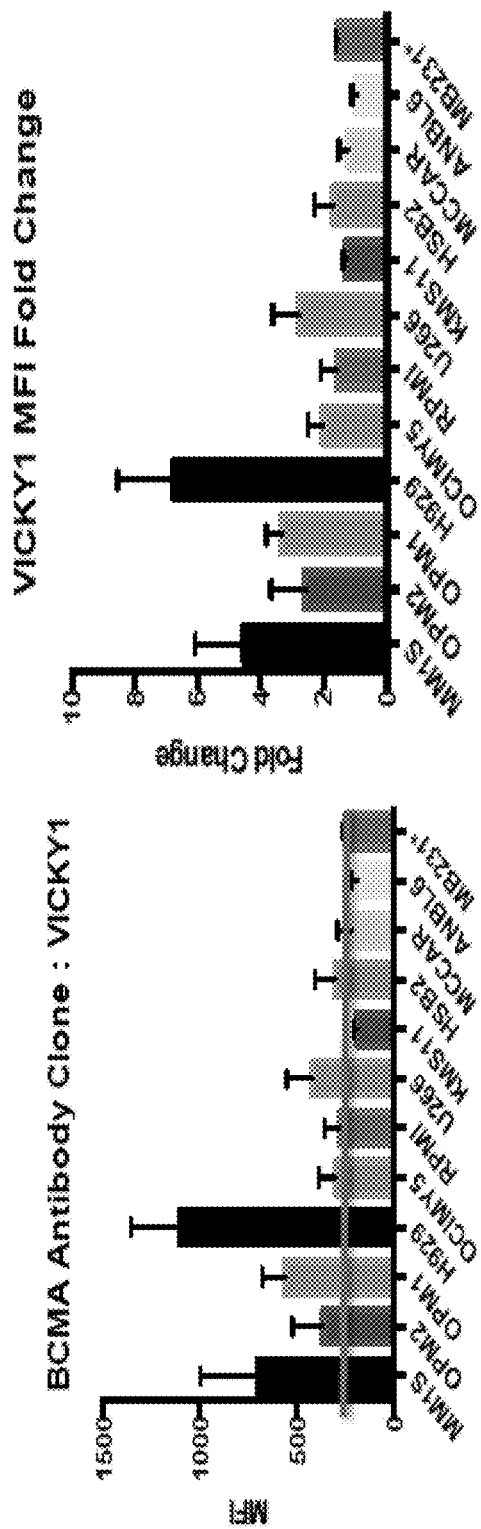

B-cell maturation antigen (BCMA) and Transmembrane activator and CAML interactor (TACT) are critical antigens specific to many cancers, including, e.g., multiple myeloma and other hematological malignancies. This disclosure is based at least, in part, on the identification of HLA-A2-specific immunogenic peptides derived from BCMA and TACI antigens, which can be used to generate, e.g., multiple myeloma (MM)-specific T cells immune response. Thus, the disclosure relates to BCMA-derived peptides and TACI-derived peptides (and pharmaceutical compositions thereof), which can be used to, e.g., induce an immune response (e.g., stimulate a cytotoxic T cell (CTL) response) against tumor cells, or stimulate the production of cytokines or antibodies, in a subject. The peptides can be used in a variety of applications such as methods for inducing an immune response, methods for producing an antibody, methods for producing cytokines involved in anti-tumor immune responses, and methods for treating a cancer (e.g., such as multiple myeloma). The peptides can also be included in MHC molecule multimer compositions and used in, e.g., methods for detecting a T cell (e.g., the antigen-specific T cell) in a population of cells.

The present disclosure also provides information for various types of therapeutic applications including peptide-based vaccination, peptide composing various approaches of vaccine (including nanoparticle-based and virus-based), adoptive transfer of ex vivo generated BCMA-specific T cells or TACI-specific T cells and the antigen-specific T cells with engineered technology (including CAR-TCR therapy-based and induced pluripotent stem cell-based) or infusion of peptide-pulsed dendritic cells, as a single or combination therapy described herein, in cancer patients including multiple myeloma, their pre-malignant diseases or other cancers, or any diseases which uniquely-express and/or overexpress the BCMA and TACI antigens.

BCMA-Derived Peptides and TACI-Derived Peptides B-cell maturation antigen (BCMA) (NM_001192.2→NP_001183.2), also known as tumor necrosis factor receptor superfamily member 17 (TNFRSF17), is a protein that in humans is encoded by the TNFRSF17 gene. BCMA is a cell surface receptor of the TNF receptor superfamily which recognizes B-cell activating factor (BAFF). BCMA is expressed in mature B lymphocytes. This receptor has been shown to specifically bind to the tumor necrosis factor (ligand) superfamily, member 13b (TNFSF13B/TALL-1/BAFF), and to lead to NF-kappaB and MAPK8/JNK activation. This receptor also binds to various TRAF family members, and thus may transduce signals for cell survival and proliferation. BCMA is often overexpressed in various cancer cells, e.g., in a subject with leukemia, lymphomas, and multiple myeloma.

Transmembrane activator and CAML interactor (TACI) (NM_012452.2→NP_036584.1), also known as tumor necrosis factor receptor superfamily member 13B (TNFRSF13B) is a protein that in humans is encoded by the TNFRSF13B gene. TACI is a transmembrane protein of the TNF receptor superfamily found predominantly on the surface of B cells. TACI recognizes three ligands: APRIL, BAFF and CAML. TACI is also often overexpressed in various cancer cells as well, e.g., in a subject with leukemia, lymphomas, and multiple myeloma.

The amino acid sequences of human BCMA and human TACI are shown below.

```
Human BCMA (NP_001183.2; SEQ ID NO: 18)
  1 mlqmagqcsq neyfdsllha cipcqlrcss
    ntppltcqry cnasvtnsvk gtnailwtcl 61 glsliislav fvlmfllrki nseplkdefk
    ntgsgllgma nidleksrtg deiilprgle
```

-continued 121 ytveectced cikskpkvds dhcfplpame
    egatilvttk tndyckslpa alsateieks 181 isar Human TACI (NP_036584.1; SEQ ID NO: 19)
  1 msglgrsrrg grsrvdqeer fpqglwtgva
    mrscpeeqyw dpllgtcmsc kticnhqsqr 61 tcaafcrsls crkeqgkfyd hllrdcisca
    sicgqhpkqc ayfcenklrs pvnlppelrr 121 qrsgevenns dnsgryqgle hrgseaspal
    pglklsadqv alvystlglc lcavlccflv 181 avacflkkrg dpcscqprsr prqspakssq
    dhameagspv stspepvetc sfcfpecrap 241 tqesavtpgt pdptcagrwg chtrttvlqp
    cphipdsglg ivcvpaqegg pga The disclosure provides peptides (e.g., naïve peptides) that are derived from BCMA or TACI antigen and heteroclitic peptide that are derived from the peptides (naïve peptides). These peptides can be any portion or fragment of the BCMA or TACI peptide. In some embodiments, these peptides have a length of greater than 5, 6, 7, 8, 9, 10, 11, 12, 13, 14, 15, 16, 17, 18, 19, 20, 21, 22, 23, 24, 25, 26, 27, 28, 29, or 30 amino acid residues. In some embodiments, these peptides have a length of less than 6, 7, 8, 9, 10, 11, 12, 13, 14, 15, 16, 17, 18, 19, 20, 21, 22, 23, 24, 25, 26, 27, 28, 29, or 30 amino acid residues. In some embodiments, these peptides have a length of 8 to 12 amino acid residues, 8 to 15 amino acid residues, 9 to 13 amino acid residues, 9 to 12 amino acid residues, or 11 to 30 amino acid residues. In some embodiments, the length of the peptide is 9, 10, 11, or 12 amino acid residues (e.g., 9 amino acid residues).

In some embodiments, peptides that are derived from BCMA or TACI include the following:

```
#1. BCMA₆₄₋₇₂ (LIISLAVFV)       (SEQ ID NO: 1)

#2. BCMA₆₉₋₇₇ (AVFVLMFLL)       (SEQ ID NO: 2)

#3. BCMA₉₋₁₇ (SQNEYFDSL)        (SEQ ID NO: 3)

#4. BCMA₇₂₋₈₀ (VLMFLLRKI)       (SEQ ID NO: 4)

#5. BCMA₅₄₋₆₂ (AILWTCLGL)       (SEQ ID NO: 5)

#6. BCMA₁₁₄₋₁₂₂ (ILPRGLEYT)     (SEQ ID NO: 6)

#1. TACI₁₇₈₋₁₈₆ (FLVAVACFL)     (SEQ ID NO: 7)

#2. TACI₁₇₄₋₁₈₂ (VLCCFLVAV)     (SEQ ID NO: 8)

#3. TACI₁₅₄₋₁₆₂ (KLSADQVAL)     (SEQ ID NO: 9)

#4. TACI₁₆₆₋₁₇₄ (TLGLCLCAV)     (SEQ ID NO: 10)

#5. TACI₁₆₁₋₁₆₉ (ALVYSTLGL)     (SEQ ID NO: 11)

#6. TACI₁₅₅₋₁₆₃ (LSADQVALV)     (SEQ ID NO: 12)
```

These peptides can bind to Major Histocompatibility Complex (MHC) molecules. MHC is a large gene family with an important role in the immune system, autoimmunity, and reproduction. MHC molecules assume roles in the presentation of peptides, including self and non-self (antigenic) on their surface to T-cells. MHC class I molecules bind short peptides, whose N- and C-terminal ends are anchored into the pockets located at the ends of the peptide binding groove. While many of these peptides are of length 9, longer peptides can be accommodated by the bulging of their central portion, resulting in binding peptides of length, e.g., 8 to 15. Peptides binding to class II proteins are not constrained in size and can vary, e.g., from 11 to 30 amino acids long. The peptide binding groove in the MHC class II molecules is open at both ends, which enables binding of peptides with relatively longer length. Though the "core" nine residues long segment contributes the most to the recognition of the peptide, the flanking regions are also important for the specificity of the peptide to the class II allele.

Thus, the disclosure also provides a peptide that has a sequence that comprises, consists of, or consists essentially of any sequences that are described in the present disclosure. In some embodiments, the peptides can bind to MHC class I molecules and/or MHC class II molecules. In some embodiments, the MHC class I molecule is HLA-A (e.g., HLA-A2, HLA-A24, HLA-A1, HLA-A3, HLA-A30, HLA-A26, HLA-A68, or HLA-A11), HLA-B or HLA-C.

In order to improve the stability of the peptide binding to MHC molecules (e.g., MHC class I molecules, HLA-A2) molecules, increase immunogenicity, and/or increase immune response, various modifications can be made to the peptides. For example, in order to increase immunogenicity, amino acid residues can be modified, by enhancing affinity to the T cell receptor (TCR) by altering TCR interaction sites, e.g., in the positions 3, 4, 5, 6, 7, and/or 8 of any peptides described herein (e.g., SEQ ID NOS: 1-17).

Dibasic amino acid residues (e.g., Arg-Arg, Arg-Lys, Lys-Arg, or Lys-Lys) can also be added to the N- and C-termini of peptides. In some embodiments, amino acids are substituted either to enhance Major Histocompatibility Complex (MHC) binding by modifying anchor residues ("fixed anchor epitopes") or to enhance binding to the T cell receptor (TCR) by modifying TCR interaction sites (e.g., positions 1, 2, and/or 9 of SEQ ID NOS: 1-17). In some embodiments, the epitopes described herein can be modified at any position (e.g., at one, two, three, four, five, or six positions). The peptides can also include internal mutations that render them "superantigens" or "superagonists" for T cell stimulation. Superantigen peptides can be generated by screening T cells with a positional scanning synthetic peptide combinatorial library (PS-CSL) as described in Pinilla et al, Biotechniques, 13(6): 901-5, 1992; Borras et al, J. Immunol. Methods, 267(1): 79-97, 2002; U.S. Publication No. 2004/0072246; and Lustgarten et al., J. Immun. 176: 1796-1805, 2006. In some embodiments, a superagonist peptide is a peptide as described herein, with one, two, three, or four amino acid substitutions which render the peptide a more potent immunogen. In some embodiments, the first amino acid residues of the peptides that are derived from BCMA or TACI can be changed to Tyrosine.

Some heteroclitic peptides that are derived from BCMA or TACI include:

```
                                          (SEQ ID NO: 13)
    Heteroclitic #4. BCMA72-80(YLMFLLRKI)

(SEQ ID NO: 14)
    Heteroclitic #5. BCMA54-62(YILWTCLGL)

(SEQ ID NO: 15)
    Heteroclitic #1. TACI178-186(YLVAVACFL)

(SEQ ID NO: 16)
    Heteroclitic #3. TACI154-162(YLSADQVAL)

(SEQ ID NO: 17)
    Heteroclitic #4. TACI166-174(YLGLCLCAV)
```

As used herein, the term "heteroclitic" (e.g., a heteroclitic peptide) refers to a form of a peptide in which one or more amino acid residues have been modified from a wild-type or original sequence in order to produce a peptide that is more immunogenic than the corresponding peptide with wildtype sequence or original sequence.

The disclosure further provides variants of the peptides as described herein (e.g., SEQ ID NO: 1-17). Variants of the peptides described herein can include forms of the peptides having not more than five, not more than four, not more than three, not more than two, not more than one amino acid substitutions (e.g., 5, 4, 3, 2, or 1 amino acid substitutions). In some embodiments, variants of the peptides described herein can include forms of the peptides having at least one, at least two, at least three, or at least four substitutions.

In some embodiments, amino acids at positions 1, 2, and/or 9 of SEQ ID NOS: 1-17 contribute to HLA binding affinity, and thus can be substituted without affecting the peptide-specific T cells responses. Thus, the immunogenicity of peptides can be still maintained with substitutions at position of 1, 2 and/or 9 of SEQ ID NOS: 1-17. In some embodiments, the amino acid at position 1 of SEQ ID NOS: 1-17 (e.g., SEQ ID NO: 13 or SEQ ID NO: 16) is substituted. In some embodiments, the amino acid at position 2 of SEQ ID NOS: 1-17 (e.g., SEQ ID NO: 13 or SEQ ID NO: 16) is substituted. In some embodiments, the amino acid at position 9 of SEQ ID NOS: 1-17 (e.g., SEQ ID NO: 13 or SEQ ID NO: 16) is substituted. In some embodiments, the amino acids at positions 1 and 2, positions 1 and 9, positions 2 and 9, or positions 1, 2, and 9 of SEQ ID NOS: 1-17 are substituted. In some embodiments, the disclosure provides a peptide comprising a sequence as described herein (e.g., one of SEQ ID NOS: 1-17 with or without substitutions as described herein) and has up to 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 amino acids. Thus, in some embodiments, the length of the peptide can be between 9 and 20 amino acids, between 9 and 30 amino acids, or between 9 and 40 amino acids.

The substitutions can be any type of amino acid substitution, e.g., conservative or non-conservative. Conservative substitutions include substitutions within the following groups: (1) valine, alanine and glycine; leucine, valine, and isoleucine; (2) aspartic acid and glutamic acid; (3) asparagine and glutamine; (4) serine, cysteine, and threonine; lysine and arginine; and (5) phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics, e.g., substituting an amino acid with another amino acid within another group.

In some embodiments, one or more (e.g., one, two, three, four, or all five) of positions three, four, five, six, seven, and eight of any of the peptides are not substituted. In some embodiments, one or more (e.g., one, two, three, four, or all five) of positions three, four, five, six, seven, and eight of the peptides are identical to a sequence selected from SEQ ID NOs: 1-17. As used herein, the term position refers to a position starting from the N-terminal of a peptide. For example, position 3 of the peptide refers to the third amino acid residue starting from the N-terminal of the peptide. In some embodiments, the residues at positions three, four, five, six, seven, and eight of SEQ ID NOs: 1-17 contribute the most to the recognition of the peptide.

The disclosure further provides an amino acid sequence or a nucleotide sequence comprising, consisting of, or consisting essentially of, a sequence that is at least 50% (e.g., 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%) identical to any sequence as described in this disclosure, e.g., SEQ ID NOs: 1-17, SEQ ID NOs: 18 and 19, and a nucleotide sequence encoding SEQ ID NOs: 1-17.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blosum 62 scoring matrix with a gap penalty of 12, a gap extend penalty of 4, and a frameshift gap penalty of 5.

Also provided herein are peptides comprising or consisting of a first amino acid sequence; and a second amino acid sequence that is heterologous to the first amino acid sequence. An amino acid sequence that is "heterologous" to a first amino acid sequence, or the term "heterologous amino acid sequence," is an amino acid sequence flanking the first amino acid sequence, wherein the flanking sequence does not occur in nature (e.g., the flanking sequence is not linked to the first amino acid sequence in nature). The first amino acid sequence can comprise, consist essentially of, or consist of any sequence as described herein, e.g., SEQ ID NOs: 1-17, or any sequence derived from SEQ ID NOs: 1-17 (e.g., a sequence with no more than four substitutions of SEQ ID NOs: 1-17). The peptide with heterologous flanking amino acid sequence generally do not (and are selected such that do not) adversely affect the generation in the cell of an immunogenic peptide of SEQ ID NO: 1-17. The cellular machinery is expected to remove any additional sequences in the peptide to yield an immunogenic peptide of SEQ ID NO: 1-17, which peptide is presented by a class I or class II MHC molecule to stimulate an immune response against BCMA or TACI-expressing cancer cells.

A heterologous flanking sequence can be, for example, a sequence used for purification of the recombinant protein (e.g., FLAG, polyhistidine (e.g., hexahistidine), hemagglutinin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). In some embodiments, the peptides can contain all or part of an immunoglobulin molecule (e.g., all or part of an immunoglobulin heavy chain constant region).

In some embodiments, the heterologous sequence can comprise a therapeutic or immune-stimulating polypeptide sequence (e.g., a T helper epitope (e.g., a PADRE epitope or a Tetanus Toxoid universal T helper cell epitope) or all or part of a cytokine or chemokine) and/or a carrier (e.g., KLH) useful, e.g., in eliciting an immune response (e.g., for antibody generation). In some embodiments, the peptide can contain one or more linker peptide sequences. The peptide can also contain a targeting polypeptide. Heterologous sequences can be of varying length and in some cases can be longer sequences than the first amino acid sequences to which the heterologous amino acid sequences are attached. It is understood that a peptide containing a first amino acid sequence and a second amino acid sequence that is heterologous to the first does not correspond in sequence to a naturally occurring protein.

Targeting polypeptides, as used herein, are polypeptides that target the moiety (or moieties) they are attached to (e.g., the first amino acid sequence) to specific tissues (e.g., to a lymph node) or cells (e.g., to an antigen presenting cell or other immune cell), or where in vitro, specific isolated molecules or molecular complexes. Targeting polypeptides can be, e.g., an antibody (immunoglobulin) or antigen binding fragment thereof or a ligand for a cell surface receptor. An antibody (or antigen-binding fragment thereof) can be, e.g., a monoclonal antibody, a polyclonal antibody, a humanized antibody, a fully human antibody, a single chain antibody, a chimeric antibody, or an Fab fragment, an F(ab')2 fragment, an Fab' fragment, an Fv fragment, or an scFv fragment of an antibody. Antibody fragments that include, or are, Fc regions (with or without antigen-binding regions) can also be used to target the reagents to Fc receptor-expressing cells (e.g., antigen presenting cells such as interdigitating dendritic cells, macrophages, monocytes, or B cells). A ligand for a cell surface receptor can be, e.g., a chemokine, a cytokine (e.g., interleukins 1, 2, 3, 4, 5, 6, 7, 8, 9, 10, 11, 12, 13, 14, 15, or 16), or a death receptor ligand (e.g., FasL or TNFα).

In some embodiments, the heterologous sequence can comprise, e.g., a "transportation sequence" that aids in the delivery of the peptide to the cell or to a specific compartment of a cell (e.g., the endoplasmic reticulum or Golgi apparatus). Transportation sequences can include, e.g., membrane translocating sequence, a transportan sequence, an antennapedia sequence, a cyclic integrin-binding peptide, and a Tat-mediated peptide, or modified versions thereof.

A linker peptide can connect the first amino acid sequence to one or more heterologous amino acid sequences. For example, a linker peptide can connect the first amino acid sequence to a second amino acid sequence. In certain embodiments, a linker peptide can link/connect a peptide of any one of SEQ ID NOs: 1-17 with a second peptide selected from SEQ ID NOs: 1-17. The linker peptide can, or contain, e.g., stretches of amino acids where at least four to six amino acids are glycine. (See, e.g., Mancebo et al. (1990) Mol. Cell. Biol. 10: 2492-2502). A linker can also be, or contain, six or more (e.g., seven, eight, nine, ten, eleven, or twelve or more) histidine residues. The linker peptide can contain, or be, at least one (e.g., one, two, three, four, five, six, seven, or eight or more) protease cleavage site(s). The protease sites can be, e.g., a trypsin, a chymotrypsin, or a factor Xa cleavage site. Such protease sites can be useful, e.g., to separate a first amino acid sequence from a heterologous sequence. For example, after expression and purification of a peptide containing a first amino acid sequence joined to a polyhistidine sequence (e.g., for purification) by a trypsin protease cleavage site, the polyhistidine sequence can be removed from first amino acid sequence by contacting the peptide with trypsin.

In some embodiments, the disclosure provides a peptide (e.g., any one of SEQ ID NOs: 1-17) that can have at the amino-terminal end and/or carboxy-terminal end up to 200 (e.g., one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, or 200) amino acids that are heterologous or are present in the native protein.

In some embodiments, the peptide can include a sequence that is at least 40%, at least 50%, at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical to any sequence as described herein (e.g., any one of SEQ ID NOs: 1-17). In some embodiments, the sequence can have equal to or at least one, two, three, four, five, six, seven, eight, nine, 10, 11, 12, 13, 14, 15, 16, 17, 18, 19, or 20 amino acids selected from any sequence as described herein (e.g., any one of SEQ ID NOs: 1-17). In some embodiments, the sequence is SEQ ID NO: 13. In some embodiments, the sequence is SEQ ID NO: 14. In some embodiments, the sequence is SEQ ID NO: 16.

In some embodiments, the peptide can have an additional sequence. The additional sequence can be located at the amino-terminal end or the carboxy-terminal of the peptide. In some embodiments, the additional sequence can have at least one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, or 200 amino acids. In some embodiments, the additional sequence can have up to one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, or 200 amino acids.

In certain instances, the disclosure encompasses any combination of 2 or more peptides selected from SEQ ID NOs: 13-17.

The peptides described herein can bind to a major histocompatibility complex (MHC) molecule (e.g., an MHC class I molecule or an MHC class II molecule). In humans, the MHC is known as the HLA complex. An "HLA supertype or family," as used herein, refers to sets of HLA molecules grouped on the basis of shared peptide-binding specificities. HLA class I molecules that share somewhat similar binding affinity for peptides bearing certain amino acid motifs are grouped into HLA supertypes. The terms HLA superfamily, HLA supertype family, HLA family, and HLA xx-like molecules (where xx denotes a particular HLA type), are synonyms. Types of HLA class I molecules include, e.g., HLA-A1, HLA-A2, HLA-A3, HLA-A24, HLA-B7, HLA-B27, HLA-B44, HLA-B58, or HLA-B62. Such HLA molecules are described in detail in U.S. Pat. No. 7,026,443, the entire disclosure of which is incorporated by reference in its entirety.

A peptide can bind to an MHC molecule with high affinity or intermediate affinity. As used herein, "high affinity" binding of a peptide to an HLA class I molecule is defined as a binding with a dissociation constant (KD) of less than 50 (e.g., 45, 40, 35, 30, 25, 20, 15, 10, 5, 1, 0.5, 0.1, or less than 0.05) nM. "Intermediate affinity" is a binding of a peptide to an HLA class I molecule with a KD of between about 50 nM and about 500 nM (e.g., 55, 60, 65, 70, 75, 80, 85, 90, 95, 100, 110, 115, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 nM). "High affinity" binding of a peptide to HLA class II molecules is defined as binding with a KD of less than 100 (e.g., 95, 90, 85, 80, 75, 70, 65, 60, 55, 50, 45, 40, 35, 30, 25, 20, 15, 10, 5, 1, 0.5, 0.1, or less than 0.05) nM. "Intermediate affinity" of a peptide for an HLA class II molecule is binding with a KD of between about 100 and about 1000 nM (e.g., 100, 110, 115, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nM). Methods for determining the binding affinity of a peptide and an MHC molecule are known in the art. Suitable methods are also described in, e.g., U.S. Pat. No. 7,026,443.

The peptides described herein can also be, in association with an MHC molecule, recognized by an antigen specific T cell receptor on a T cell. A variety of suitable methods can be used to determine whether a peptide, in association with an MHC molecule, is recognized by a T cell receptor on a T cell. For example, peripheral blood lymphocytes (PBL) from normal subjects can be cultured with a test peptide in the presence of antigen presenting cells in vitro over a period of several weeks. T cells specific for the peptide become activated during this time and can be detected using, e.g., proliferation assays (carboxyfluorescein succinimidyl ester (CFSE) assays of H-thymidine assays), limiting dilution assays, cytotoxicity assays (e.g., calcein-release assays), or cytokine- (e.g., IFNγ), lymphokine-, or 51Cr-release assays (see, e.g., Wentworth, P. A. et al., Mol. Immunol. 32: 603, 1995; Celis, E. et al, Proc. Natl. Acad. Sci. USA 91: 2105, 1994; Tsai, V. et al., J. Immunol. 158: 1796, 1997; Kawashima, I. et al., Human Immunol. 59: 1, 1998, the disclosures of each of which are incorporated by reference in their entirety). A suitable in vivo method involves immunizing HLA transgenic mice, wherein peptides in adjuvant are administered subcutaneously to HLA transgenic mice and several weeks following immunization, splenocytes are removed and cultured in vitro in the presence of test peptide for approximately one week, peptide-specific T cells are detected using, e.g., a 51Cr-release assay (see, e.g., Wentworth, P. A. et al., J. Immunol. 26: 97, 1996; Wentworth, P. A. et al., Int. Immunol. 8: 651, 1996; Alexander, J. et al., J. Immunol. 159: 4753, 1997, the disclosures of each of which are incorporated by reference in their entirety).

Additionally, direct quantification of antigen-specific T cells can be performed by staining T cells with detectably-labeled MHC complexes such as any of the MHC molecule multimer compositions described herein or HLA-I tetramers (e.g., as described in Altman, J. D. et al., Proc. Natl. Acad. Sci. USA 90: 10330, 1993 and Altman, J. D. et al., Science 274: 94, 1996, the disclosures of each of which are incorporated by reference in their entirety).

In some embodiments, the peptides can be further modified (e.g., amino acids of the peptides can be substituted) in order to modulate (e.g., increase or decrease) one of more properties of the peptides. For example, one or more (e.g., two, three, or four) amino acids of one of the peptides described herein can be substituted in order to increase the affinity of the peptide for an WIC molecule. In some embodiments, an amino acid of one of the peptides described herein (e.g., a T cell Receptor contacting amino acid residue of the peptide) can be modified in order to enhance a binding interaction between a T cell receptor and the peptide (in the context of an WIC molecule). Such modified peptides are often referred to as "altered peptide ligands." (See, e.g., Kalergis et al. (2000) J Immunol. 165(1): 280; Conlon et al. (2002) Science 1801; and International Publication No. WO02070003, the disclosure of each of which is incorporated by reference in their entirety). Suitable methods for modifying the peptides as well as determining the effect of the modification are described in, e.g., Collins et al. (Immunological Reviews (1998) 163: 151-160, the disclosure of which is incorporated by reference in its entirety).

The disclosure further provides a composition comprising any peptides as described herein. Furthermore, to counter the tumor's ability to evade therapies directed against it, the composition can comprise a variety of specific peptides to induce the immune response. For example, more than one epitope from the same protein can be included in the composition, e.g., the composition can contain at least one, at least two, at least three, at least four, at least five, at least six, or at least seven different peptides derived from BCMA or TACI. In addition, combinations or mixtures of at least one (e.g., at least two, three, four, five) peptides derived from BCMA and at least one (e.g., at least two, three, four, five) peptides derived from TACI can also be used. Thus, in some embodiments, the disclosure provides a composition comprising at least 2, 3, 4, 5, 6, 7, or 8 BCMA-derived peptides (e.g., at least two BCMA-derived peptides selected from, e.g., SEQ ID NOs: 1-6 and 13-14). In some embodiments, the disclosure provides a composition comprising at least 2, 3, 4, 5, 6, 7, or 8 TACI-derived peptides (e.g., at least two TACI-derived peptides selected from e.g., SEQ ID NOs: 7-12 and 16-17). In some embodiments, the disclosure provides a composition comprising at least one (e.g., at least 2, 3, 4, 5, 6, 7, or 8) BCMA-derived peptides and at least one (e.g., at least 2, 3, 4, 5, 6, 7, or 8) TACI-derived peptides.

In some embodiments, the composition further comprises an immune stimulatory agent (e.g., a cytokine or a T helper epitope). The T helper epitope can be a PADRE sequence or a universal Tetanus Toxoid T helper (TT Th) epitope. In some embodiments, the composition comprises an adjuvant, such as Freund's complete adjuvant, Freund's incomplete adjuvant, alum, a ligand for a Toll receptor, QS21, RIBI, or similar immunostimulatory agent. Adjuvants also include, e.g., cholera toxin (CT), E. coli heat labile toxin (LT), mutant CT (MCT) (Yamamoto et al. (1997) J. Exp. Med. 185: 1203-1210) and mutant E. coli heat labile toxin (MLT) (Di Tommaso et al. (1996) Infect. Immunity 64: 974-979). In some embodiments, the composition comprises a toll like receptor-3 ligand (e.g., Poly ICLC), interferon alfa (IFNα), interferon gamma (IFNγ), or Granulocyte-macrophage colony-stimulating factor (GM-CSF). In some embodiments, the composition further comprises an immune agonist, e.g., an anti-OX40 antibody or an anti-GITR antibody.

In some embodiments, the composition comprises a chemotherapeutic agent (e.g., Lenalidomide). In some embodiments, the composition comprises a histone deacetylase 6 (HDAC6) inhibitor (e.g., ACY241; See Niesvizky, et al. "ACY-241, a novel, HDAC6 selective inhibitor: synergy with immunomodulatory (IMiD®) drugs in multiple myeloma (MM) cells and early clinical results (ACE-MM-200 Study)." (2015): 3040-3040; Bae et al. "Histone deacetylase (HDAC) inhibitor ACY241 enhances anti-tumor activities of antigen-specific central memory cytotoxic T lymphocytes against multiple myeloma and solid tumors." Leukemia (2018): 1). In some embodiments, the composition comprises a checkpoint inhibitor (e.g., anti-LAG3 antibody) or an immune agonist (e.g., anti-OX40). In some embodiments, the composition comprises an antibody (e.g., human antibody) the specifically binds to PD-1, CTLA-4, LAG-3, BTLA, PD-L1, CD27, CD28, CD40, CD47, 4-1BB (CD137), CD154, TIGIT, TIM-3, GITR (CD357), OX40, CD20, EGFR, or CD319.

In some embodiments, the composition comprises a peptide comprising a sequence set forth in SEQ ID NO: 13, SEQ ID NO: 14, or SEQ ID NO: 16, and Lenalidomide. In some embodiments, the composition comprises a peptide comprising a sequence set forth in SEQ ID NO: 13, SEQ ID NO: 14, or SEQ ID NO: 16, and an anti-OX40 antibody, an anti-LAG3 antibody, and/or an anti-GITR antibody.

Nucleic Acids and Methods for Producing the Peptides

The disclosure also features nucleic acid sequences (as well as nucleic acid vectors containing nucleic acid sequences) encoding, and methods for producing, one or more (e.g., one, two, three, four, five, six, seven, eight, nine, 10, 11, 12, 13, or 14) of any of the peptides described herein. Such methods can include the steps of: optionally, providing a cell (or group of cells) comprising a nucleic acid vector containing a nucleic acid sequence encoding one of more of any of the peptides described herein, the nucleic acid sequence being operably linked to an expression control sequence, and culturing the cell under conditions that permit the expression of the peptides. The methods can also include the step of isolating the one or more peptides from the cell, or from the medium in which the cell was cultured. Thus, in one aspect, the disclosure provides RNA-based therapeutics and DNA-based therapeutics including e.g., cancer vaccines. In some embodiments, the cancer vaccines can have a polynucleotide as described herein (e.g., a polynucleotide encoding SEQ ID NOS: 1-17). In some instances, the polynucleotide encodes a peptide that is identical to one of SEQ ID NOs.: 1-17, except having 1 to 4 amino acid substitutions. In some cases, the substitution is at one or more of positions 1, 2, or 9. In some cases, the peptide is 2 to 30 amino acids in length. In some cases, the nucleic acid can include regulatory sequences (e.g., start codon, stop, codon polyA tail). In some embodiments, the RNA/DNA cancer vaccines can be formulated within a polymeric or liposomal nanocarrier (e.g., a nanoparticle).

Suitable methods for constructing nucleic acid sequences and vectors (e.g., expression vectors) for recombinant expression of one or more of the peptides described herein are well known to those skilled in the art and described in, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989, the disclosure of which is incorporated by reference in its entirety. The nucleic acids and vectors can be used, e.g., to express the peptides in a wide variety of host cells including, e.g., a bacterial, a yeast, or a mammalian cell. The nucleic acids and vectors can also be used in, e.g., in vivo and ex vivo methods as described below. The peptide-coding sequences can be operably-linked to a promoter, a regulatory element, or an expression control sequence. The promoter and/or enhancer elements can direct the expression of the peptides encoded by the nucleic acids. Enhancers provide expression specificity in terms of time, location, and level. Unlike a promoter, an enhancer can function when located at variable distances from the transcription initiation site, provided a promoter is present. An enhancer can also be located downstream of the transcription initiation site or in an exon of the relevant gene. To bring a coding sequence under the control of a promoter, it is necessary to position the translation initiation site of the translational reading frame of the peptide between one and about fifty nucleotides downstream (3') of the promoter. Promoters of interest include, but are not limited to, the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3 phosphoglycerate kinase, the promoters of acid phosphatase, and the promoters of the yeast a mating factors, the adenoviral EIb minimal promoter, or the thymidine kinase minimal promoter.

The peptide-coding sequences, or vectors containing the peptide-coding sequences, can contain a leader sequence that encodes a signal peptide. The leader sequence can be at the 5' end of the sequence encoding one or more of the peptides described herein. The signal peptide can be immediately N-terminal of a given peptides or can be separated from it by one or more (e.g., 2, 3, 4, 6, 8, 10, 15 or 20) amino acids, provided that the leader sequence is in frame with the nucleic acid sequence encoding the peptides. The signal peptide, which is generally cleaved from the peptide prior to secretion (unless of course the signal peptide directs the insertion of a transmembrane protein), directs the peptide to which it is attached into the lumen of the host cell endoplasmic reticulum (ER) during translation and the peptides are then secreted, via secretory vesicles, into the environment of the host cell. Useful signal peptides include, e.g., native leader sequences of cytokines or growth factors, KDEL (Lys-Asp-Glu-Leu), or any signal sequences described in, e.g., U.S. Pat. No. 5,827,516, the disclosure of which is incorporated herein by reference in its entirety.

In some embodiments, the 5' end of a peptide-coding sequence can include a non-native ATG "start sequence." That is, e.g., an ATG sequence can be added to a nucleic acid encoding a peptide to ensure that the peptide is properly transcribed and translated. Although a leader sequence generally includes an ATG start sequence, in embodiments where it does not, the ATG sequence can be added at the 5' end of a nucleic acid encoding the leader sequence.

Suitable methods for constructing peptide-coding sequences and expression vectors are well known to those skilled in the art and described in, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989; the disclosure of which is incorporated herein by reference in its entirety. A recombinant vector can be introduced into a cell using a variety of methods, which methods can depend, at least in part, on the type of cell into which the nucleic acid is introduced. For example, bacterial cells can be transformed using methods such as electroporation or heat shock. Methods for transfecting yeast cells include, e.g., the spheroplast technique or the whole-cell lithium chloride yeast transformation method (see, e.g., U.S. Pat. No. 4,929,555; Hinnen et al. (1978) Proc. Nat. Acad. Sci. USA 75: 1929; Ito et al. (1983) J. Bacteriol. 153: 163; U.S. Pat. No. 4,879,231; and Sreekrishna et al. (1987) Gene 59: 115, the disclosures of each of which are incorporated herein by reference in their entirety). Transfection of animal cells can feature, for example, the introduction of a vector to the cells using calcium phosphate, electroporation, heat shock, liposomes, or transfection reagents such as FUGENE® or LIPO-FECTAMINE®, or by contacting naked nucleic acid vectors with the cells in solution (see, e.g., Sambrook et al., supra).

Expression systems that can be used for small or large scale production of the peptides described herein include, but are not limited to, microorganisms such as bacteria (for example, *E. coli* and *B. subtilis*) transformed with recombinant bacteriophage DNA, plasmid DNA, or cosmid DNA expression vectors; fungus (e.g., yeast (for example, *Saccharomyces* and *Pichia*)) transformed with recombinant yeast expression vectors; insect cell systems infected with recombinant virus expression vectors (for example, baculovirus); plant cell systems infected with recombinant virus expression vectors (for example, cauliflower mosaic virus (CaMV) and tobacco mosaic virus (TMV)) or transformed with recombinant plasmid expression vectors (for example, Ti plasmid); or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter, a CMV promoter, an SV40 promoter, or the vaccinia virus 7.5K promoter). Also useful as host cells are primary or secondary cells obtained directly from a mammal, transfected with a plasmid vector or infected with a viral vector (e.g., viral vectors such as herpes viruses, retroviruses, vaccinia viruses, attenuated vaccinia viruses, canary pox viruses, adenoviruses and adeno-associated viruses, among others).

Following the expression of any of the peptides described herein, the peptides can be isolated from the cultured cells, or from the media in which the cells were cultured, using standard techniques. Methods of isolating proteins are known in the art and include, e.g., liquid chromatography (e.g., HPLC), affinity chromatography (e.g., metal chelation or immunoaffinity chromatography), ion-exchange chromatography, hydrophobic-interaction chromatography, precipitation, or differential solubilization.

Smaller peptides (e.g., peptides having less than 200 (e.g., less than 175, less than 150, less than 125, less than 100, less than 90, less than 80, less than 70, or less than 60) amino acids) can be chemically synthesized by standard chemical means such as FMOC solid-phase synthesis.

The peptides described herein can, but need not, be isolated. The term "isolated," as applied to any of the peptides described herein, refers to a peptide, a fragment thereof, (or for compositions, a macromolecular complex), that has been separated or purified from components (e.g., proteins or other naturally-occurring biological or organic molecules) which naturally accompany it. It is understood that recombinant molecules (e.g., recombinant peptides) will always be "isolated." Typically, a peptide (or fragment or macromolecular complex) is isolated when it constitutes at least 60%, 70%, 80%, or 90% by weight, of the total molecules of the same type in a preparation, e.g., at least 60%, 70%, 80%, or 90% of the total molecules of the same type in a sample. For example, a peptide described herein is considered isolated when it constitutes at least 60%, 70%, 80%, or 90% by weight, of the total protein in a preparation or sample. In some embodiments, a molecule in the preparation consists of at least 75%, at least 90%, or at least 99%, by weight, of the total molecules of the same type in a preparation.

Similarly, the peptide-coding sequences or vectors containing the peptide-coding sequences described herein can also be isolated. The term "isolated," as applied to any of the peptide-coding sequences or vectors described herein, refers to a peptide-coding sequence or vector, a fragment thereof that has been separated or purified from components (e.g., nucleic acids, proteins, or other naturally-occurring biological or organic molecules) which naturally accompany it. It is understood that recombinant molecules (e.g., recombinant vectors or peptide-coding sequences) will always be "isolated." Typically, a peptide-coding sequence or vector (or fragment thereof) is isolated when it constitutes at least 60%, 70%, 80%, or 90% by weight, of the total molecules of the same type in a preparation, e.g., at least 60%, 70%, 80%, or 90% of the total molecules of the same type in a sample. For example, a peptide-coding sequence or vector described herein is considered isolated when it constitutes at least 60%, 70%, 80%, or 90% by weight, of the total nucleic acid in a preparation or sample. In some embodiments, a molecule in the preparation consists of at least 75%, at least 90%, or at least 99%, by weight, of the total molecules of the same type in a preparation.

In some embodiments, the isolated peptides, peptide-coding sequences, or vectors can be frozen, lyophilized, or immobilized and stored under appropriate conditions, which allow the molecules to retain activity (e.g., the ability of a peptide to bind to an WIC molecule such as an WIC class I molecule or an WIC class II molecule, or the ability of a vector to support expression of a peptide in a cell).

Processing of the Peptides

Following the expression or synthesis of any of the peptides described herein, the peptides can be further processed. The further processing can include chemical or enzymatic modifications to peptides or, in cases where the peptides are modified, the processing can include enzymatic or chemical alterations of existing modifications, or both. The additional processing of the peptides can include the addition (covalent or non-covalent joining) of a heterologous amino acid sequence such as, but not limited to, any of the heterologous amino acid sequences described herein. Enzymatic treatment can involve contacting a peptide with, e.g., one or more proteases, phosphatases, or kinases under conditions that allow the peptide to be modified. Enzymatic treatment can involve contacting a peptide with one or more enzymes (e.g., an oligosaccharyltransferase or a mannosidase) capable of glycosylating, or modifying the glycosylation of, the peptide.

The processing can include the addition of, e.g., a detectable label to a peptide. For example, a peptide can be detectably labeled with an enzyme (e.g., horseradish peroxidase, alkaline phosphatase, β-galactosidase, or acetylcholinesterase), a fluorescent material (e.g., umbelliferone, fluorescein, fluorescein isothiocyanate, rhodamine, dichlorotriazinylamine, fluorescein, dansyl chloride, allophycocyanin (APC), or phycoerythrin), a luminescent material (e.g., a lanthanide or chelate thereof), a bioluminescent material (e.g., luciferase, luciferin, or aequorin), or a radionuclide (e.g., $^{3}H$, $^{32}P$, $^{33}P$, $^{125}I$ or $^{35}S$).

The processing can also involve the coupling of the peptide to a polymer (e.g., a polyalkylene glycol moiety such as a polyethylene glycol moiety), or a nanoparticle. In some embodiments, the polymer is coupled to the polypeptide at a site on the peptide that is an N terminus. In some embodiments, a peptide can contain one or more internal amino acid insertions that provide an internal polymer conjugation site to which a polymer can be conjugated.

Methods for Inducing an Immune Response

The disclosure also provides a variety of methods for inducing an immune response in a subject (e.g., peptide based vaccination, nanoparticle-based immunotherapy, APC-based immunotherapy, T cell-based immunotherapy, CAR T cell-based immunotherapy, or induced pluripotent stem cell-approaches). The methods for inducing an immune response in a subject can include, e.g., the step of administering to a subject one or more of the compositions described herein (e.g., any of peptides (or expression vectors containing nucleic acid sequences encoding the peptides) described herein (or any of the pharmaceutical compositions containing one or more peptides (or vectors) described herein)). In some embodiments, the composition described herein is used as a vaccine.

Any of the peptides described herein can be used to stimulate an immune response by use of a nucleic acid expression system that encodes one or more of the peptides described herein. That is, methods for inducing an immune response in a subject can include the step of administering to a subject an expression vector containing nucleic acid sequences encoding one or more of the peptides described herein (or a pharmaceutical composition containing the expression vector). The immune response can be a CD8+ T cell, a CD4+ T cell, a cytotoxic T lymphocyte (CTL), a TH1 response, a TH2 response, or a combination of both types of responses.

Any of the above methods can also be, e.g., methods for treating or preventing (prophylaxis against) a cancer (e.g., plasma cell disorder such as multiple myeloma, or any other cancer expressing BCMA and/or TACI) in a subject. When the terms "prevent," "preventing," or "prevention" are used herein in connection with a given treatment for a given condition, they mean that the treated subject either does not develop a clinically observable level of the condition at all (e.g., the subject does not exhibit one or more symptoms of the condition or, in the case of a cancer, the subject does not develop a detectable level of the cancer), or the condition develops more slowly and/or to a lesser degree (e.g., fewer symptoms or lower numbers of cancer cells in the subject) in the subject than it would have absent the treatment. These terms are not limited solely to a situation in which the subject experiences no aspect of the condition whatsoever. For example, a treatment will be said to have "prevented" the condition if it is given during, e.g., during an early diagnosis of a cancer (e.g., the detection of a few cancer cells in a sample from the subject) that would have been expected to produce a given manifestation of the condition (an advanced cancer), and results in the subject's experiencing fewer and/or milder symptoms of the condition than otherwise expected. A treatment can "prevent" a cancer (e.g., a plasma cell disorder such as multiple myeloma) when the subject displays only mild overt symptoms of the cancer. "Prevention" does not imply that there must have been no development of even a single cancer cell by a subject so treated.

Generally, a peptide delivered to the subject will be suspended in a pharmaceutically-acceptable carrier (e.g., physiological saline) and administered orally, rectally, or parenterally, e.g., injected intravenously, subcutaneously, intramuscularly, intrathecally, intraperitoneally, intrarectally, intravaginally, intranasally, intragastrically, intratracheally, or intrapulmonarily.

Administration can be by periodic injections of a bolus of the pharmaceutical composition or can be uninterrupted or continuous by intravenous or intraperitoneal administration from a reservoir which is external (e.g., an IV bag) or internal (e.g., a bioerodable implant, a bioartificial organ, or a colony of implanted reagent production cells). See, e.g., U.S. Pat. Nos. 4,407,957, 5,798,113 and 5,800,828, each incorporated herein by reference in its entirety.

Conventional and pharmaceutically acceptable routes of administration of a therapeutic nucleic acid include, but are not necessarily limited to, intramuscular, subcutaneous, intradermal, transdermal, intravenous, rectal (e.g., enema, suppository), oral, intragastric, intranasal and other routes of effective inhalation routes, and other parenteral routes of administration. Routes of administration may be combined, if desired, or adjusted depending upon the nucleic acid molecule and/or the desired effect on the immune response. Methods for administering a nucleic acid to a subject can include a variety of well-known techniques such as vector-mediated gene transfer (e.g., viral infection/transfection, or various other protein-based or lipid-based gene delivery complexes) as well as techniques facilitating the delivery of "naked" polynucleotides (such as electroporation, "gene gun" delivery, and various other techniques used for the introduction of polynucleotides to a subject or a cell of a subject).

In general, the dosage of a peptide or a nucleic acid required depends on the choice of the route of administration; the nature of the formulation; the nature or severity of the subject's illness; the immune status of the subject; the subject's size, weight, surface area, age, and sex; other drugs being administered; and the judgment of the attending medical professional.

Suitable dosages of peptide for inducing an immune response are in the range of 0.000001 to 10 mg of the reagent or antigenic/immunogenic composition per kg of the subject. Wide variations in the needed dosage are to be expected in view of the variety of reagents and the differing efficiencies of various routes of administration. For example, nasal or rectal administration may require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). For example, a peptide can be administered as an initial immunization and then administered one or more times subsequently as a booster immunization.

The dose of nucleic acid administrated to a subject, in the context of the methods described herein, should be sufficient to effect a beneficial therapeutic response in the subject over time, or to alleviate symptoms. Although the dosage used will vary depending on, e.g., the subject or the clinical goals to be achieved. A suitable dosage range is one which provides up to about 1 to about 1,000 to about 5,000 to about 10,000 to about 25,000 µg or about 50,000 µg of nucleic acid per ml of carrier in a single dosage.

In order to optimize therapeutic efficacy (e.g., the efficacy of the one or more peptides or the nucleic acids encoding the peptides to induce an immune response in a subject), compositions containing the peptides or nucleic acids can be first administered at different dosing regimens. The unit dose and regimen depend on factors that include, e.g., the species of mammal, its immune status, the body weight of the mammal. The frequency of dosing for a pharmaceutical composition (e.g., a pharmaceutical composition containing one or more peptides or one or more nucleic acid sequences encoding one or more of the peptides described herein) is within the skills and clinical judgement of medical practitioners (e.g., doctors or nurses). Typically, the administration regime is established by clinical trials which may establish optimal administration parameters. However, the practitioner may vary such administration regimes according to the subject's age, health, weight, sex and medical status.

In some embodiments, a pharmaceutical composition can be administered to a subject at least two (e.g., three, four, five, six, seven, eight, nine, 10, 11, 12, 15, or 20 or more) times. For example, a pharmaceutical composition can be administered to a subject once a month for three months; once a week for a month; once a year for three years, once a year for five years; once every five years; once every ten years; or once every three years for a lifetime.

As defined herein, a "therapeutically effective amount" of a peptide or a nucleic acid encoding a peptide is an amount of the peptide or nucleic acid that is capable of producing an immune response in a treated subject. A therapeutically effective amount of a peptide (i.e., an effective dosage) includes milligram, microgram, nanogram, or picogram amounts of the agent per kilogram of subject or sample weight (e.g., about 1 nanogram per kilogram to about 500 micrograms per kilogram, about 1 microgram per kilogram to about 500 milligrams per kilogram, about 100 micrograms per kilogram to about 5 milligrams per kilogram, or about 1 microgram per kilogram to about 50 micrograms per kilogram). A therapeutically effective amount of a nucleic acid also includes microgram, nanogram, or picogram amounts of the agent per kilogram of subject or sample weight (e.g., about 1 nanogram per kilogram to about 500 micrograms per kilogram, about 1 microgram per kilogram to about 500 micrograms per kilogram, about 100 micrograms per kilogram to about 500 micrograms per kilogram, or about 1 microgram per kilogram to about 50 micrograms per kilogram).

As defined herein, a "prophylactically effective amount" of a peptide or nucleic acid encoding a peptide is an amount of the peptide or nucleic acid that is capable of producing an immune response against a cancer cell (e.g., a multiple myeloma) in a treated subject, which immune response is capable of preventing the development of a cancer in a subject or is able to substantially reduce the chance of a subject developing or continue developing a cancer. A prophylactically effective amount of a peptide (i.e., an effective dosage) includes milligram, microgram, nanogram, or picogram amounts of the agent per kilogram of subject or sample weight (e.g., about 1 nanogram per kilogram to about 500 micrograms per kilogram, about 1 microgram per kilogram to about 500 milligrams per kilogram, about 100 micrograms per kilogram to about 5 milligrams per kilogram, or about 1 microgram per kilogram to about 50 micrograms per kilogram). A prophylactically effective amount of a nucleic acid also includes microgram, nanogram, or picogram amounts of the agent per kilogram of subject or sample weight (e.g., about 1 nanogram per kilogram to about 500 micrograms per kilogram, about 1 microgram per kilogram to about 500 micrograms per kilogram, about 100 micrograms per kilogram to about 500 micrograms per kilogram, or about 1 microgram per kilogram to about 50 micrograms per kilogram).

In some embodiments, the methods can also include determining if an immune response occurred in a subject after administering the compositions to the subject. Suitable methods for determining whether an immune response occurred in a subject include use of immunoassays to detect, e.g., the presence of antibodies specific for a peptide in a biological sample from the subject. For example, after the administration of the peptide to the subject, a biological sample (e.g., a blood sample) can be obtained from the subject and tested for the presence of antibodies specific for the peptide(s). An immune response can also be detected by assaying for the presence or amount of activated T cells in a sample. Such assays include, e.g., proliferation assays, limiting dilution assays, cytotoxicity assays (e.g., lymphokine- or 51Cr-release assays).

In some embodiments, the methods described herein (e.g., therapeutics that increase the BCMA and TACI-specific responses, vaccines, cell therapies, antibodies, and/or therapeutic approach targeting some targets other than BCMA and TACI) can also include administering to a subject various types of compounds to enhance the BCMA and TACI-specific responses (e.g. cytokines and chemokines), checkpoint inhibitors (e.g., an anti-PD1, anti-PDL1, anti-CTLA4, anti-LAG3, and/or anti-TIM3 antibody), immune agonists (e.g., an anti-OX40 or anti-GITR antibody), immune modulators (e.g., Lenalidomide, Pomalidomide, HDAC inhibitors such as ACY241), and/or adjuvants.

The methods can also include the step of administering to the subject one or more chemotherapeutic agents, one or more forms of ionizing radiation, or one or more immunomodulatory agents. The one or more forms of ionizing radiation can be gamma-irradiation, X-irradiation, or beta-irradiation. The one or more chemotherapeutic agents can be selected from the group consisting of cisplatin, carboplatin, procarbazine, mechlorethamine, cyclophosphamide, camptothecin, adriamycin, ifosfamide, melphalan, chlorambucil, busulfan, nitrosourea, dactinomycin, daunorubicin, doxorubicin, bleomycin, lincomycin, mitomycin, etoposide, verapamil, podophyllotoxin, tamoxifen, taxol, thalidomide, lenalidomide, a proteasome inhibitor (e.g., bortezomib), an hsp90 inhibitor (e.g., tanespimycin), transplatinum, 5-fluorouracil, vincristine, vinblastine, methotrexate, or an analog of any of the aforementioned. Immunomodulatory agents include, e.g., a variety of chemokines and cytokines such as Interleukin 2 (IL-2), granulocyte/macrophage-colony stimulating factor (GM-C SF), and Interleukin 12 (IL-12). In some embodiments, the peptide or a nucleic acid encoding the peptide can be administered with an immune modulator such as a Toll Receptor ligand or an adjuvant.

In some embodiments, the additional therapeutic agent is a histone deacetylase 6 (HDAC6) inhibitor (e.g., ACY241).

In some embodiments, the one or more additional therapeutic agents can be an immunomodulatory agent, a checkpoint inhibitor (e.g., anti-LAG3 antibody) or an immune agonist (e.g., anti-OX40 antibody, anti-GITR antibody).

In some embodiments, the additional therapeutic agent can comprise one or more inhibitors selected from the group consisting of an inhibitor of B-Raf, an EGFR inhibitor, an inhibitor of a MEK, an inhibitor of ERK, an inhibitor of K-Ras, an inhibitor of c-Met, an inhibitor of anaplastic lymphoma kinase (ALK), an inhibitor of a phosphatidylinositol 3-kinase (PI3K), an inhibitor of an Akt, an inhibitor of mTOR, a dual PI3K/mTOR inhibitor, an inhibitor of Bruton's tyrosine kinase (BTK), and an inhibitor of Isocitrate dehydrogenase 1 (IDH1) and/or Isocitrate dehydrogenase 2 (IDH2). In some embodiments, the additional therapeutic agent is an inhibitor of indoleamine 2,3-dioxygenase-1) (IDO1) (e.g., epacadostat).

In some embodiments, the additional therapeutic agent can comprise one or more inhibitors selected from the group consisting of an inhibitor of HERS, an inhibitor of LSD1, an inhibitor of MDM2, an inhibitor of BCL2, an inhibitor of CHK1, an inhibitor of activated hedgehog signaling pathway, and an agent that selectively degrades the estrogen receptor.

In some embodiments, the combination therapy includes one or more of the following:

(A) compounds that can enhance the BCMA and TACI-specific responses such as (1) cytokines and chemokines, (2) checkpoint inhibitors including e.g., an anti-PD1, anti-PDL1, anti-CTLA4, anti-LAG3, and/or anti-TIM3 antibody, (2) immune agonists including e.g., an anti-OX40 and/or anti-GITR antibody, (3) immune modulators including e.g., Lenalidomide, Pomalidomide, HDAC inhibitors such as ACY241, (4) adjuvant;

(B) therapeutics which can increase the BCMA and TACI-specific responses, including any therapeutics as described herein (e.g., vaccine, cell therapies and/or antibodies) or independent approach that target other targets (e.g., non-BCMA or non-TACI-targeting therapy); and (C) additional compounds such as one or more inhibitors selected from the group consisting of an inhibitor of B-Raf, an EGFR inhibitor, an inhibitor of a MEK, an inhibitor of ERK, an inhibitor of K-Ras, an inhibitor of c-Met, an inhibitor of anaplastic lymphoma kinase (ALK), an inhibitor of a phosphatidylinositol 3-kinase (PI3K), an inhibitor of an Akt, an inhibitor of mTOR, a dual PI3K/mTOR inhibitor, an inhibitor of Bruton's tyrosine kinase (BTK), and an inhibitor of Isocitrate dehydrogenase 1 (IDH1) and Isocitrate dehydrogenase 2 (IDH2), and/or inhibitor of indoleamine 2,3-dioxygenase-1) (IDO1) (e.g., epacadostat).

In some embodiments, the additional therapeutic agent can comprise one or more therapeutic agents selected from the group consisting of Trabectedin, nab-paclitaxel, Trebananib, Pazopanib, Cediranib, Palbociclib, everolimus, fluoropyrimidine, IFL, regorafenib, Reolysin, Alimta, Zykadia, Sutent, temsirolimus, axitinib, everolimus, sorafenib, Votrient, Pazopanib, IMA-901, AGS-003, cabozantinib, Vinflunine, an Hsp90 inhibitor, Ad-GM-CSF, Temozolomide, IL-2, IFNa, vinblastine, Thalomid, dacarbazine, cyclophosphamide, lenalidomide, azacytidine, lenalidomide, bortezomib, amrubicin, carfilzomib, pralatrexate, and enzastaurin.

In some embodiments, the additional therapeutic agent can comprise one or more therapeutic agents selected from the group consisting of an adjuvant, a TLR agonist, tumor necrosis factor (TNF) alpha, IL-1, HMGB1, an IL-10 antagonist, an IL-4 antagonist, an IL-13 antagonist, an IL-17 antagonist, an HVEM antagonist, an ICOS agonist, a treatment targeting CX3CL1, a treatment targeting CXCL9, a treatment targeting CXCL10, a treatment targeting CCL5, an LFA-1 agonist, an ICAM1 agonist, and a Selectin agonist.

In some embodiments, carboplatin, nab-paclitaxel, paclitaxel, cisplatin, pemetrexed, gemcitabine, FOLFOX, or FOLFIRI are administered to the subject.

In some embodiments, the additional therapeutic agent is an antibody (e.g., human antibody) the specifically binds to PD-1, CTLA-4, LAG-3, BTLA, PD-L1, CD27, CD28, CD40, CD47, 4-1BB (CD137), CD154, TIGIT, TIM-3, GITR (CD357), OX40, CD20, EGFR, or CD319. In some embodiments, the additional therapeutic agent is an anti-OX40 antibody, an anti-PD-L1 antibody, an anti-PD-L2 antibody, an anti-LAG-3 antibody, an anti-TIGIT antibody, an anti-BTLA antibody, an anti-CTLA-4 antibody, or an anti-GITR antibody.

The disclosure also provides a virus comprising nucleic acids encoding one or more peptides as described herein or a virus particle comprising one or more peptides as described herein. Various viruses can be used, e.g., retrovirus, lentivirus, adenovirus, adeno-associated virus, alphavirus and the like. These viruses can be used to deliver the peptide or nucleic acids encoding the peptides thereof to a subject to induce immune response. Similarly, liposomes that comprise one or more peptides as described herein and/or nucleic acids encoding the peptides thereof can also be used to deliver the peptides or the nucleic acids to a subject in need thereof to induce immune response.

In some embodiments, the methods described herein can increase immune response, activity (e.g., producing cytokines, IFN-γ, IL-2, or TNF-α), or number of immune cells (e.g., T cells, CD8+ T cells, cytotoxic T cells, and/or CD4+ T cells) by at least 10%, 20%, 30%, 40%, 50%, 60%, 70%, 80%, 90%, 100%, 2 folds, 3 folds, 5 folds, 10 folds, 20 folds, or 50 folds. In some embodiments, the methods described herein can increase CD107a degranulation by at least 10%, 20%, 30%, 40%, 50%, 60%, 70%, 80%, 90%, 100%, 2 folds, 3 folds, 5 folds, 10 folds, 20 folds, or 50 folds. In some embodiments, the methods as described herein can increase number of CD8+ effector T cells (e.g., total number of CD8+ effector T cells, or e.g., percentage of CD8+ in CD45+ cells) that specifically target the cancer cell or recognize the peptides described herein by at least 50%, 60%, 70%, 80%, 90%, 100%, 2 folds, 3 folds, 5 folds, 10 folds, 20 folds, or 50 folds.

Nanoparticles

The disclosure further provides nanoparticles or nanocarriers comprising one or more peptides as described herein (e.g., SEQ ID NO: 1-17) or one or more polynucleotides as described herein (e.g., a sequence encoding SEQ ID NO: 1-17). In some cases, the nanocarriers comprise a peptide that is identical to an amino acid sequence of SEQ ID NO: 1-17 but having 1 to 4 amino acid substitutions. In some instances, the substitutions are at one or more of positions 1, 2, and 9. Polynucleotides (e.g., mRNA, DNA) encoding such peptides can also be encapsulated in a nanocarrier. The nanoparticles or nanocarriers can be administered to a subject in need thereof to induce immune response.

The peptides can be attached to the nanoparticles or nanocarriers via various attachment mechanisms. This attachment mechanism can be an electrostatic attraction, covalent coupling, or a hydrophobic interaction. In some embodiments, the nanoparticles can be loaded with adjuvants. The adjuvants can be a dendritic cell targeting molecule, for example, a Toll-like receptor agonist, e.g., R-848, which is recognized as a potent synthetic agonist of TLR7/TLR8, or an unmethylated CpG oligodeoxynucleotide, which is immunostimulatory agonist of TLR-9, or monophosphoryl lipid A, which is immunostimulatory agonist of TLR-4, or an endosomal membrane targeting agent, e.g., the Endo-Porter peptide.

The polymer that forms the nanoparticles can be any biodegradable or non-biodegradable synthetic or natural polymer. Preferably, the polymer is a biodegradable polymer. Examples of useful biodegradable polymers include polylactic acid (PLA), poly(glycolic acid) (PGA), or poly (lactic-co-glycolic acid) (PLGA). These polymers have an established safety record and can be used in human subjects (Jiang, et al., Adv. Drug Deliv. Rev., 57(3): 391-410, 2005; Aguado and Lambert, Immunobiology, 184(2-3): 113-25, 1992; Bramwell, et al., Adv. Drug Deliv. Rev., 57(9): 1247-65, 2005). Other amphiphilic poly(amino acid) nanoparticles, amphiphilic polysaccharide nanoparticles, or polyion nanoparticles can be used in the vaccine composition disclosed herein (see, Akagi et al., Adv Polym Sci. 247: 31-64, 2012). The foregoing polymers can be used alone, as physical mixtures, or by forming copolymers. In certain embodiments, the nanoparticles are formed by a mixture of poly(lactic-co-glycolic acid)-block-poly(L-histidine)-block-poly(ethylene glycol) (PLGA-PLH-PEG) triblock copolymer; PLGA-PEG diblock copolymer, and PLA. These copolymers can be synthesized using standard techniques. For example, the copolymer PLGA-PLH-PEG can be synthesized using a block end-grafting strategy.

As used herein, a "nanoparticle" is a particle in the range of between 500 nm to 0.5 nm, e.g., having a diameter that is between 50 and 500 nm, having a diameter that is between 100 and 400 nm, or having a diameter that is between 200 and 400 nm.

Nanoparticles and how to make and use nanoparticles are known in the art, and are described, e.g., in US 2016/0008451, US 2010/0129439, US2018/0021258, each of which is incorporated herein by reference in its entirety. In some embodiments, the nanoparticle is a liposome. In some embodiments, the nanoparticle is a polymeric particle.

The polymer that forms the nanoparticles can be any biodegradable or non-biodegradable synthetic or natural polymer. In some embodiments, the polymer is a biodegradable polymer. Examples of useful biodegradable polymers include polylactic acid (PLA), poly(glycolic acid) (PGA), or poly(lactic-co-glycolic acid) (PLGA). These polymers have an established safety record and can be used in human subjects (Jiang, et al, Adv. Drug Deliv. Rev., 57(3):391-410, 2005; Aguado and Lambert, Immunobiology, 184(2-3): 113-25, 1992; Bramwell, et al., Adv. Drug Deliv. Rev., 57(9): 1247-65, 2005). Other amphiphilic poly(amino acid) nanoparticles, amphiphilic polysaccharide nanoparticles, or polyion nanoparticles can be used in the composition disclosed herein (see, Akagi et al, Adv Polym Sci. 247:31-64, 2012).

The polymers can be used alone, as physical mixtures, or by forming copolymers. In some embodiments, the nanoparticles are formed by a mixture of poly(lactic-co-glycolic acid)-block-poly(L-histidine)-block-poly(ethylene glycol) (PLGA-PLH-PEG) triblock copolymer; PLGA-PEG diblock copolymer, and PLA. These copolymers can be synthesized using standard techniques. For example, the copolymer PLGA-PLH-PEG can be synthesized using a block end-grafting strategy. A linear structure (e.g., PLGA-PLH-PEG) can provide the nanoparticles several characteristics compatible with extended circulation and charge-mediated targeting.

In some embodiments, natural polymers can be used. Examples of natural polymers include alginate and other polysaccharides, collagen, albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Other suitable biodegradable polymers include, but are not limited to, poly(hydroxy acids), such as polymers and copolymers of lactic acid and glycolic acid, polyanhydrides, poly(ortho)esters, polyesters, polyurethanes, poly(butyric acid), poly(valeric acid), poly(caprolactone), poly(hydroxyalkanoates), and poly(lactide-co-caprolactone).

The polymer can be a bioadhesive polymer that is hydrophilic or hydrophobic. Hydrophilic polymers include CARBOPOL™ (a high molecular weight, crosslinked, acrylic acid-based polymers manufactured by Noveon), polycarbophil, cellulose esters, and dextran.

These polymers can be obtained from sources such as Sigma Chemical Co., St. Louis, Mo.; Polysciences, Warrenton, Pa.; Aldrich, Milwaukee, Wis.; Fluka, Ronkonkoma, N.Y.; and BioRad, Richmond, Calif., or can be synthesized from monomers obtained from these or other suppliers using standard techniques.

A wide variety of polymers and methods for forming polymeric matrices therefrom are known conventionally. In general, a polymeric matrix comprises one or more polymers. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers in accordance with the present invention are organic polymers.

Examples of polymers suitable for use in the composition described herein include, but are not limited to polyethylenes, polycarbonates (e.g. poly(1,3-dioxan-2one)), polyanhydrides (e.g. poly(sebacic anhydride)), polypropylfumarates, polyamides (e.g., polycaprolactam), polyacetals, polyethers, polyesters (e.g., polylactide, polyglycolide, polylactide-co-glycolide, polycaprolactone, polyhydroxyacid (e.g. poly(-hydroxyalkanoate))), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly(ethylene imine)-PEG copolymers.

In some embodiments, polymers in accordance with the present invention include polymers that have been approved for use in humans by the U.S. Food and Drug Administration (FDA) under 21 C.F.R. § 177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers can comprise anionic groups (e.g., phosphate group, sulfate group, carboxylate group); cationic groups (e.g., quaternary amine group); or polar groups (e.g., hydroxyl group, thiol group, amine group). In some embodiments, polymers can be hydrophobic. Selection of the hydrophilicity or hydrophobicity of the polymer can have an impact on the nature of materials that are incorporated (e.g., coupled) within the synthetic nanoparticle.

In some embodiments, polymers can be modified with one or more moieties and/or functional groups. A variety of moieties or functional groups can be used in accordance with the present invention. In some embodiments, polymers can be modified with polyethylene glycol (PEG), with a carbohydrate, and/or with acyclic polyacetals derived from polysaccharides (Papisov, 2001, ACS Symposium Series, 786:301). Certain embodiments can be made using the general teachings of U.S. Pat. No. 5,543,158 to Gref et al, or WO publication WO2009/051837 by Von Andrian et al.

In some embodiments, polymers can be modified with a lipid or fatty acid group. In some embodiments, a fatty acid group can be one or more of butyric, caproic, caprylic, capric, lauric, myristic, palmitic, stearic, arachidic, behenic, or lignoceric acid. In some embodiments, a fatty acid group can be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers can be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, poly(caprolactone), poly(caprolactone)-PEG copolymers, poly(L-lactide-co-L-lysine), poly(serine ester), poly(4-hydroxy-L-proline ester), poly[a-(4-aminobutyl)-L-glycolic acid], and derivatives thereof. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers can be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer can comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g., DNA, or derivatives thereof). Amine-containing polymers such as poly(lysine) (Zauner et al., 1998, Adv. Drug Del. Rev., 30:97; and Kabanov et al, 1995, Bioconjugate Chem., 6:7), poly(ethylene imine) (PEI; Boussif et al, 1995, Proc. Natl. Acad. Sci., USA, 1995, 92:7297), and poly (amidoamine) dendrimers (Kukowska-Latallo et al., 1996, Proc. Natl. Acad. Sci., USA, 93:4897; Tang et al., 1996, Bioconjugate Chem., 7:703; and Haensler et al, 1993, Bioconjugate Chem., 4:372) are positively-charged at physiological pH, form ion pairs with nucleic acids, and mediate transfection in a variety of cell lines.

In some embodiments, polymers can be degradable polyesters bearing cationic side chains (Putnam et al, 1999, Macromolecules, 32:3658; Barrera et al, 1993, J. Am. Chem. Soc, 115: 11010; Kwon et al, 1989, Macromolecules, 22:3250; Lim et al, 1999, J. Am. Chem. Soc, 121:5633; and Zhou et al., 1990, Macromolecules, 23:3399). Examples of these polyesters include poly(L-lactide-co-L-lysine) (Barrera et al, 1993, J. Am. Chem. Soc, 115: 11010), poly(serine ester) (Zhou et al, 1990, Macromolecules, 23:3399), poly (4-hydroxy-L-proline ester) (Putnam et al, 1999, Macromolecules, 32:3658; and Lim et al, 1999, J. Am. Chem. Soc, 121:5633), and poly(4-hydroxy-L-proline ester) (Putnam et al, 1999, Macromolecules, 32:3658; and Lim et al, 1999, J. Am. Chem. Soc, 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al, 2001, J. Am. Chem. Soc, 123:9480; Lim et al, 2001, J. Am. Chem. Soc, 123:2460; Langer, 2000, Acc. Chem. Res., 33:94; Langer, 1999, J. Control. Release, 62:7; and Uhrich et al, 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al, Prentice-Hall, 1981; Deming et al., 1997, Nature, 390:386; and in U.S. Pat. Nos. 6,506,577, 6,632,922, 6,686,446, and 6,818,732. Each of the forgoing is incorporated herein by reference in its entirety.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step. It is further to be understood that inventive synthetic nanoparticles can comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

In some embodiments, synthetic nanoparticles can optionally comprise one or more amphiphilic entities. In some embodiments, an amphiphilic entity can promote the production of synthetic nanoparticles with increased stability, improved uniformity, or increased viscosity. In some embodiments, amphiphilic entities can be associated with the interior surface of a lipid membrane (e.g., lipid bilayer, lipid monolayer, etc.). Many amphiphilic entities known in the art are suitable for use in making synthetic nanoparticles in accordance with the present invention. Such amphiphilic entities include, but are not limited to, phosphoglycerides; phosphatidylcholines; dipalmitoyl phosphatidylcholine (DPPC); dioleoylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxamer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl stearate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component can be a mixture of different amphiphilic entities. Those skilled in the art will recognize that this is an exemplary, not comprehensive, list of substances with surfactant activity. Any amphiphilic entity can be used in the production of synthetic nanoparticles to be used in accordance with the present invention.

In some embodiments, synthetic nanoparticles can optionally comprise one or more carbohydrates. Carbohydrates can be natural or synthetic. A carbohydrate can be a derivatized natural carbohydrate. In certain embodiments, a carbohydrate comprises monosaccharide or disaccharide, including but not limited to glucose, fructose, galactose, ribose, lactose, sucrose, maltose, trehalose, cellobiose, mannose, xylose, arabinose, glucuronic acid, galactoronic acid, mannuronic acid, glucosamine, galactosamine, and neuraminic acid. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextrin, glycogen, hydroxyethylstarch, carrageenan, glycon, amylose, chitosan, N,O-carboxymethylchitosan, algin and alginic acid, starch, chitin, inulin, konjac, glucomannan, pustulan, heparin, hyaluronic acid, curdlan, and xanthan. In embodiments, the inventive synthetic nanoparticles do not comprise (or specifically exclude) carbohydrates, such as a polysaccharide. In certain embodiments, the carbohydrate can comprise a carbohydrate derivative such as a sugar alcohol, including but not limited to mannitol, sorbitol, xylitol, erythritol, maltitol, and lactitol.

In some embodiments, the nanoparticle comprises a peptide comprising a sequence set forth in SEQ ID NO: 13, SEQ ID NO: 14, or SEQ ID NO: 16 (e.g., SEQ ID NO: 13). In certain instances, the nanoparticles disclosed herein can be administered in combination with another therapy described below (e.g., APC-based therapy, CTL-based therapy, peptide vaccine therapy). In some instances, the nanoparticles disclosed herein can be administered to a human subject in combination with an immune agonist (e.g., anti-OX40 antibody; anti-GITR antibody), a checkpoint inhibitor (e.g., anti-LAG3 antibody), and/or lenalidomide.

Antigen Presenting Cell (APC)-Based Immunotherapy

An ex vivo strategy for inducing an immune response in a subject can involve contacting suitable antigen presenting cells (e.g., dendritic cells, monocytes, or macrophages) obtained from the subject with any of the peptides described herein. Alternatively, the cells can be transfected with a nucleic acid (e.g., an expression vector) encoding one or more of the peptides and optionally cultured for a period of time and under conditions that permit the expression of the peptides. The transfection method will depend on the type of cell and nucleic acid being transfected into the cell. Following the contacting or transfection, the cells are then returned to the subject.

The cells can be any of a wide range of types expressing MHC class I or II molecules. For example, the cells can include bone marrow cells, macrophages, monocytes, dendritic cells, T cells (e.g., T helper cells, CD4+ cells, CD8+ cells, or cytotoxic T cells), or B cells.

Thus, the disclosure provides a composition comprising an APC (e.g., dendritic cell), wherein the APC presents a peptide sequence on its surface, wherein the peptide sequence comprises at least one major histocompatibility complex (MHC) class I or class II peptide epitope of one or both of BCMA antigen (SEQ ID NO: 18) and TACI antigen (SEQ ID NO: 19). In some embodiments, the APC is a dendritic cell. In some embodiments, the MHC peptide epitope is MHC class I peptide epitope (e.g., HLA-A2 or HLA-A24 peptide epitope). In some embodiments, the APC acquires the peptide sequence in vitro by exposure to a synthetic peptide comprising the peptide sequence.

In some embodiments of any of the ex vivo methods, cells that are obtained from the subject, or from a subject of the same species other than the subject (allogeneic) can be contacted with the reagents (or immunogenic/antigenic compositions) and administered to the subject.

In some embodiments, the composition comprises at least $10^4$, $10^5$, $10^6$, $10^7$, $10^8$, or $10^9$ APCs (e.g., dendritic cells). In some embodiments, the composition comprises less than $10^5$, $10^6$, $10^7$, $10^8$, $10^9$, or $10^{10}$ APCs (e.g., dendritic cells).

a. Preparation of Antigen Presenting Cells

Antigen presenting cells (APC), such as dendritic cells (DC), suitable for administration to subjects (e.g., multiple myeloma patients) can be isolated or obtained from any tissue in which such cells are found, or can be otherwise cultured and provided. APC (e.g., DC) can be found, by way of example, in the bone marrow or peripheral blood mononuclear cells (PBMC) of a mammal, in the spleen of a mammal or in the skin of a mammal (i.e., Langerhan's cells, which possess certain qualities similar to that of DC, can be found in the skin). For instance, bone marrow can be harvested from a mammal and cultured in a medium that promotes the growth of DC. GM-CSF, IL-4 and/or other cytokines (e.g., TNF-α), growth factors and supplements can be included in this medium. After a suitable amount of time in culture in medium containing appropriate cytokines (e.g., suitable to expand and differentiate the DCs into mature DCs, e.g., 4, 6, 8, 10, 12, or 14 days), clusters of DC cultured in the presence of antigens of interest (e.g., in the presence of one or more peptide epitopes of BCMA or TACI, or a combination of at least two peptides of SEQ ID NOs: 13-17) and harvested for use in a cancer vaccine using standard techniques. Antigens (e.g., isolated or purified peptides, or synthetic peptides) can be added to cultures at a concentration of 1 μg/ml-50 μg/ml per antigen, e.g., 2, 5, 10, 20, 30, or 40 μg/ml per antigen.

In some embodiments, APC are isolated from a subject (e.g., a human). Mononuclear cells are isolated from blood using leukapheresis (e.g., using a COBE Spectra Apheresis System). The mononuclear cells are allowed to become adherent by incubation in tissue culture flasks for 2 hours at 37° C. Non-adherent cells are removed by washing. Adherent cells are cultured in medium supplemented with granulocyte macrophage colony stimulating factor (GM-CSF) (800 units/ml, clinical grade, Immunex, Seattle, Wash.) and interleukin-4 (IL-4)(500 units/ml, R&D Systems, Minneapolis, Minn.) for five days. On day five, TNF-α is added to the culture medium for another 3-4 days. On day 8 or 9, cells are harvested and washed, and incubated with peptide antigens for 16-20 hours on a tissue rotator. Peptide antigens are added to the cultures at a concentration of ~10 µg/ml (per antigen).

Various other methods can be used to isolate the APCs, as would be recognized by one of skill in the art. DCs occur in low numbers in all tissues in which they reside, making isolation and enrichment of DCs a requirement. Any of a number of procedures entailing repetitive density gradient separation, fluorescence activated cell sorting techniques, positive selection, negative selection, or a combination thereof are routinely used to obtain enriched populations of isolated DCs. Guidance on such methods for isolating DCs can be found in O'Doherty, U. et al., J. Exp. Med., 178: 1067-1078, 1993; Young and Steinman, J. Exp. Med., 171: 1315-1332, 1990; Freudenthal and Steinman, Proc. Nat. Acad. Sci. USA, 57: 7698-7702, 1990; Macatonia et al., Immunol., 67: 285-289, 1989; Markowicz and Engleman, J. Clin. Invest., 85: 955-961, 1990; Mehta-Damani et al., J. Immunol., 153: 996-1003, 1994; and Thomas et al., J. Immunol., 151: 6840-6852, 1993. One method for isolating DCs from human peripheral blood is described in U.S. Pat. No. 5,643,786.

The dendritic cells prepared according to methods described herein present epitopes corresponding to the antigens at a higher average density than epitopes present on dendritic cells exposed to a tumor lysate (e.g., a neural tumor lysate). The relative density of one or more antigens on antigen presenting cells can be determined by both indirect and direct means. Primary immune response of naïve animals is roughly proportional to antigen density of antigen presenting cells (Bullock et al., J. Immunol., 170: 1822-1829, 2003). Relative antigen density between two populations of antigen presenting cells can therefore be estimated by immunizing an animal with each population, isolating B or T cells, and monitoring the specific immune response against the specific antigen by, e.g., tetramer assays, ELISPOT, or quantitative PCR.

Relative antigen density can also be measured directly. In one method, the antigen presenting cells are stained with an antibody that binds specifically to the MHC-antigen complex, and the cells are then analyzed to determine the relative amount of antibody binding to each cell (see, e.g., Gonzalez et al., Proc. Natl. Acad. Sci. USA, 102: 4824-4829, 2005). Exemplary methods to analyze antibody binding include flow cytometry and fluorescence activated cell sorting. The results of the analysis can be reported e.g., as the proportion of cells that are positive for staining for an individual MHC-antigen complex or the average relative amount of staining per cell. In some embodiments, a histogram of relative amount of staining per cell can be created.

In some embodiments, antigen density can be measured directly by direct analysis of the peptides bound to MHC, e.g., by mass spectrometry (see, e.g., Purcell and Gorman, Mol. Cell. Proteomics, 3: 193-208, 2004). Typically, MHC-bound peptides are isolated by one of several methods. In one method, cell lysates of antigen presenting cells are analyzed, often following ultrafiltration to enrich for small peptides (see, e.g., Falk et al., J. Exp. Med., 174: 425-434, 1991; Rotzxhke et al., Nature, 348: 252-254, 1990). In another method, MHC-bound peptides are isolated directly from the cell surface, e.g., by acid elution (see, e.g., Storkus et al., J. Immunother., 14: 94-103, 1993; Storkus et al., J. Immunol., 151: 3719-27, 1993). In another method, MHC-peptide complexes are immunoaffinity purified from antigen presenting cell lysates, and the MHC-bound peptides are then eluted by acid treatment (see, e.g., Falk et al., Nature, 351: 290-296). Following isolation of MHC-bound peptides, the peptides are then analyzed by mass spectrometry, often following a separation step (e.g., liquid chromatography, capillary gel electrophoresis, or two-dimensional gel electrophoresis). The individual peptide antigens can be both identified and quantified using mass spectrometry to determine the relative average proportion of each antigen in a population of antigen presenting cells. In some methods, the relative amounts of a peptide in two populations of antigen presenting cells are compared using stable isotope labeling of one population, followed by mass spectrometry (see Lemmel et al., Nat. Biotechnol., 22: 450-454, 2004).

b. Administration of Antigen Presenting Cells

The APC-based cancer vaccine may be delivered to a patient or test animal by any suitable delivery route, which can include injection, infusion, inoculation, direct surgical delivery, or any combination thereof. In some embodiments, the cancer vaccine is administered to a human in the deltoid region or axillary region. For example, the vaccine is administered into the axillary region as an intradermal injection. In some embodiments, the vaccine is administered intravenously.

An appropriate carrier for administering the cells may be selected by one of skill in the art by routine techniques. For example, the pharmaceutical carrier can be a buffered saline solution, e.g., cell culture media, and can include DMSO for preserving cell viability.

The quantity of APC appropriate for administration to a patient as a cancer vaccine to effect the methods of the present invention and the most convenient route of such administration may be based upon a variety of factors, as may the formulation of the vaccine itself. Some of these factors include the physical characteristics of the patient (e.g., age, weight, and sex), the physical characteristics of the tumor (e.g., location, size, rate of growth, and accessibility), and the extent to which other therapeutic methodologies (e.g., chemotherapy, and beam radiation therapy) are being implemented in connection with an overall treatment regimen. Notwithstanding the variety of factors one should consider in implementing the methods of the present invention to treat a disease condition, a mammal can be administered with from about $10^5$ to about $10^8$ APC (e.g., $10^7$ APC) in from about 0.05 mL to about 2 mL solution (e.g., saline) in a single administration. Additional administrations can be carried out, depending upon the above-described and other factors, such as the severity of tumor pathology. In one embodiment, from about one to about five administrations of about $10^6$ APC is performed at two-week intervals.

DC vaccination can be accompanied by other treatments. For example, a patient receiving DC vaccination may also be receiving chemotherapy, radiation, and/or surgical therapy concurrently. Methods of treating cancer using DC vaccination in conjunction with chemotherapy are described in Wheeler et al., US Pat. Pub. No. 2007/0020297. In some embodiments, a patient receiving DC vaccination has already received chemotherapy, radiation, and/or surgical treatment for the cancer. In one embodiment, a patient receiving DC vaccination is treated with a COX-2 inhibitor, as described in Yu and Akasaki, WO 2005/037995.

T Cell-Based Immunotherapy

Ex vivo methods for stimulating an immune response can also include contacting in vitro a T cell (e.g., in a population of lymphocytes obtained from a subject) with an antigen-presenting cell (APC) expressing an MEW molecule bound to one of the peptides described herein for an amount of time (and under conditions) that is sufficient to activate the T cell (e.g., cytotoxic T cells and/or CD4+ helper T cells). Thus, the disclosure provides methods of generating and/or proliferating BCMA-specific and/or TACI-specific T cells (e.g., cytotoxic T cells and/or CD4+ helper T cells). The methods involve contacting one or more T cells (e.g., cytotoxic T cells and/or CD4+ helper T cells) with one or more antigen presenting cells pulsed with a peptide as described herein. These T cells can be cytotoxic T cells, e.g., memory cytotoxic T cells, effector cytotoxic T cells, or CD4+ helper T cells.

The activated T cells can be used kill a target cell. In some embodiments, the methods involve contacting the target cell with one or more BCMA-specific cytotoxic T cells, wherein the target cell expresses or overexpresses BCMA, and expresses HLA-A. In some embodiments, the methods involve contacting the target cell with one or more TACI-specific cytotoxic T cells, wherein the target cell expresses or overexpresses TACI, and expresses HLA-A.

In some embodiments, the BCMA- or TACI-specific T cells (e.g., cytotoxic T cells and/or CD4+ helper T cells) are administered in combination with a peptide disclosed herein (e.g., one or more of SEQ ID NOs: 13-17), an APC that presents a BCMA (e.g., SEQ ID NO: 13 or 14) or TACI (SEQ ID NO: 16) peptide, lenalidomide, an immunomodulatory agent, a checkpoint inhibitor (e.g., anti-LAG3 antibody) or an immune agonist (e.g., anti-OX40, anti-GITR). In some embodiments, the additional therapeutic agent administered with the BCMA- or TACI-specific CTL T cells is an antibody (e.g., human antibody) the specifically binds to PD-1, CTLA-4, LAG-3, BTLA, PD-L1, CD27, CD28, CD40, CD47, 4-1BB (CD137), CD154, TIGIT, TIM-3, GITR (CD357), OX40, CD20, EGFR, or CD319. In some embodiments, the additional therapeutic agent is an anti-OX40 antibody, an anti-PD-L1 antibody, an anti-PD-L2 antibody, an anti-LAG-3 antibody, an anti-TIGIT antibody, an anti-BTLA antibody, an anti-CTLA-4 antibody, or an anti-GITR antibody. In some embodiments, the T cells are administered in combination with an immune agonist, e.g., an anti-OX40 or anti-GITR antibody.

The activated T cell(s) can also be reintroduced into the subject from which the cells were obtained. In some embodiments, T cells can be obtained from a subject of the same species other than the subject (allogeneic) can be contacted with the reagents (or immunogenic/antigenic compositions) and administered to the subject.

In some embodiments, T cells are derived from in vitro induction in patient-derived peripheral blood mononuclear cells (PBMC). The following protocol can be used to produce antigen specific CTL in vitro from patient derived PBMC. To generate dendritic cells, the plastic adherent cells from PBMCs are cultured in AIM-V medium supplemented with recombinant human GM-CSF and recombinant human IL-4 at 37° C. in a humidified $CO_2$ (5%) incubator. Six days later, the immature dendritic cells in the cultures are stimulated with recombinant human TNF-α for maturation. Mature dendritic cells are then harvested on day 8, resuspended in PBS at $1\times10^6$ per mL with peptide (2 µg/mL), and incubated for 2 hours at 37° C. Autologous CD8+ T cells are enriched from PBMCs using magnetic microbeads (Miltenyi Biotec, Auburn, Calif.). CD8+ T cells ($2\times10^6$ per well) are cocultured with $2\times10^5$ per well peptide-pulsed dendritic cells in 2 mL/well of AIM-V medium supplemented with 5% human AB serum and 10 units/mL rhIL-7 (Cell Sciences) in each well of 24-well tissue culture plates. About 20 U/ml of IL-2 is added 24 h later at regular intervals, 2 days after each restimulation. On day 7, lymphocytes are restimulated with autologous dendritic cells pulsed with peptide in AIM-V medium supplemented with 5% human AB serum, rhIL-2, and rhIL-7 (10 units/mL each). About 20 U/ml of IL-2 is added 24 h later at regular intervals, 2 days after each restimulation. On the seventh day, after the three rounds of restimulation, cells are harvested and tested the activity of CTL. The stimulated CD8+ cultured cells (CTL) are co-cultured with T2 cells (a human TAP-deficient cell line) pulsed with 2 µg/ml Her-2, gp100, AIM-2, MAGE-1, or IL13 receptor α2 peptides. After 24 hours incubation, IFN-γ in the medium is measured by ELISA assay.

Chimeric Antigen Receptor (CAR) T-Cell Based Immunotherapy

The present disclosure further provides methods for adoptive transfer of T cells expressing chimeric antigen receptors for treating a cancer. CAR-modified T cells can be engineered to target virtually any tumor associated antigen (e.g., BCMA and/or TACI). Usually, T cells are genetically engineered to express CARs specifically directed towards antigens on the patient's tumor cells, then infused back into the patient.

The common form of CARs are fusions of single-chain variable fragments (scFv), fused to CD3-zeta transmembrane- and endodomain. The scFV can be derived from the antigen-specific receptor of T cells (e.g., BCMA-specific cytotoxic T cells, or TACI-specific cytotoxic T cells), or antibodies that specifically bind to the antigen.

In some embodiments, the sequence of the T cell receptors in BCMA-specific cytotoxic T cells or TACI-specific cytotoxic T cells is determined, e.g., by sequencing. The sequence of the T cell receptors in BCMA-specific cytotoxic T cells and/or TACI-specific cytotoxic T cells can be used to generate a CAR.

In some embodiments, these T cells are collected from the patient. In some embodiments, these T cells are obtained from induced pluripotent stem cell (iPSC).

Viral vectors such as retrovirus, lentivirus or transposon, are often used to integrate the transgene (e.g., CAR) into the host cell genome. Alternatively, non-integrating vectors such as plasmids or mRNA can be used to transfer the CAR gene to the T cells, and make T cells to express CAR under appropriate conditions.

Induced Pluripotent Stem Cell-Approaches

Adoptive T-cell therapy with the administration of a large number of ex vivo expanded activated antigen-specific cytotoxic T lymphocytes (CTL) targeting tumor specific-antigens has induced durable remissions in selected malignancies. Although utilizing TCR which recognize mainly intracellular antigens that have already been processed and presented as peptide complexes with MHC molecules (Johnson et al. 2009; Morgan et al. 2006) may further enhance tumor selectivity, introduction of exogenous TCR genes can result in mismatching of transferred and endogenous α and β chains, resulting in serious autoimmune adverse events (Bendle et al. 2010, Hinrichs et al. 2013). In contrast, CAR-T recognize antigens expressed on the cell surface in a non-MHC-restricted manner. To date, the most successful CAR-T therapy targeting the B-cell antigen CD19 has achieved minimal residual disease negative complete responses in patients with relapsed and chemo-refractory B-cell malignancies (Kochenderfer et al. 2010, Grupp et al. 2013). Nonetheless ongoing efforts are directed to minimize adverse effects, including cytokine release syndrome, and improve durability of response (Brentjens et al. 2011, Kalos et al. 2011, Kochenderfer et al. 2012, Porter et al. 2011). Importantly, CTL continuously exposed to tumor antigens during long-term expansion to be used for TCR-based or CAR-based therapy, may lose their proliferative capacity ("exhausted") and their functional activity with terminal differentiation.

To overcome these limitations, a technique currently being developed is exploitation of fully rejuvenated CTL from "induced pluripotent stem cells (iPSC)". These iPSC are a special type of pluripotent cell that are derived from adult somatic cells upon ectopic expression of a set of defined transcription factors. Importantly, tumor antigen-specific CTL can be reprogrammed by iPSC technology from antigen-specific CTL (Vizcardo et al. 2013, Ando et al. 2015, Timmermans et al. 2009, Kennedy et al. 2012). These iPSC-CTL are functionally rejuvenated and demonstrate longer telomeres (1.5 fold increase) and a higher proliferative capacity (5-50 fold increase) than the original CTL from which they were derived (Nishimura et al. 2013). This powerful reprogramming therapeutic approach has the potential to markedly increase the efficacy and durability of antigen-specific cancer immunotherapy. Thus, the disclosure provides methods of rejuvenating cytotoxic T cells. In some embodiments, the methods can increase the proliferative capacity by at least 5, 6, 7, 8, 9, 10, 20, 30, 40, 50, 60, 70, 80, 90, or 100 folds.

Activation of tumor-specific CTLs is the main goal of many cancer immunotherapies. The isolation of tumor-specific T-cells from a cancer patient, in vitro preparation (activation and expansion), and transfusion of these T-cells to the patient are basic steps of adaptive immunotherapy with T-cell. iPSC technology can be used to improve the efficacy of adoptive cell transfer immunotherapy (ACT).

The iPSC can be obtained from differentiated cells (e.g., fibroblasts, immune cells, T cells, B cells) induced through retroviral transfection of Yamanaka factors (a combination of Oct3/4, Sox2, Klf4, and c-Myc), and differentiated into T-cell lineages by culturing it on monolayer OP9-DL1 cell system in addition to Flt-3 ligand and IL-7.

In some embodiments, iPSCs can be generated from T-cells. After the expansion, these cells are differentiated again into T-cells. Human T lymphocyte can act as cell source for iPSC generation. Peripheral blood mononuclear cells (PBMCs) can be separated from whole blood by leukapheresis or venipuncture and then CD3+ T-cells can be expanded by stimulation with IL-2 and anti-CD3 antibody. T-cell-derived iPSCs (TIPS) can be generated from activated T-cell when exposed to retroviral transduction of the reprogramming factors. These T-iPSCs preserve their original T-cell receptor (TCR) gene rearrangements, so they can be used as an unlimited source of hematopoietic stem cells bearing endogenous tumor-specific TCR gene for cancer ACT therapy.

Thus, in some embodiments, iPSCs are generated from antigen-specific cytotoxic T cells. These antigen-specific T cells are generated by the methods as described herein, e.g., by contacting one or more T cells with one or more antigen presenting cells pulsed with a peptide comprising an amino acid sequence as described herein (e.g., SEQ ID NOs: 1-17). As the T-iPSCs preserve their original T-cell receptor (TCR) gene rearrangements, after these T-iPSCs differentiates into T cells, these T cells can recognize BCMA and/or TACI on a cancer cell.

In some embodiments, a nucleic acid that encodes CAR that specifically recognizes BCMA and/or TACI can be introduced into T-iPSCs. Once after these T-iPSCs differentiates into T cells, these T cells can recognize BCMA and/or TACI on a cancer cell.

In some embodiments, the differentiated T cells are administered to a subject. In some embodiments, T-iPSCs are administered to a subject, and then these cells are differentiated into cytotoxic T cells in the body of the subject.

Subjects

The subject can be any animal capable of an immune response to an antigen. The terms "subject" and "patient" are used interchangeably throughout the specification and describe an animal, human or non-human, to whom treatment according to the methods of the present disclosure is provided. Veterinary and non-veterinary applications are contemplated by the present invention. Human patients can be adult humans or juvenile humans (e.g., humans below the age of 18 years old). In addition to humans, subjects include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

The subject can be one having, suspected of having, or at risk of developing a cancer. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. In some embodiments, the subject has a hematological cancer, e.g., multiple myeloma, leukemia, non-Hodgkin lymphoma, or Hodgkin lymphoma.

In some embodiments, the subject has a BCMA-expressing/overexpressing disease or a TACI-expressing/overexpressing disease, including e.g., multiple myeloma, B cell-related malignancies, plasma cell-related malignancies, a pre-malignant disease (e.g., a pre-malignant disease of MM, such as SMM or MGUS).

In some embodiments, the subject can be one having, suspected of having, or at risk of developing a plasma cell disorder. As used herein, the term "plasma cell disorders" refer to a group of diseases or disorders characterized by clonal plasma cell (PC) proliferation and hyper-secretion of paraproteins (e.g., monoclonal immunoglobulin and/or free light chain (FLC)).

Non-limiting examples of plasma cell disorders include monoclonal gammopathy of undermined significance (MGUS), multiple myeloma (MM), Waldenström macroglobulinemia (WM), light chain amyloidosis (AL), solitary plasmacytoma (e.g., solitary plasmacytoma of bone, or extramedullary plasmacytoma), polyneuropathy, organomegaly, endocrinopathy monoclonal gammopathy and skin changes syndrome (POEMS), and heavy-chain disease. Other plasm cell disorders include, e.g., Monoclonal Gammopathy of Renal Significance (MGRS), MGUS-associated neuropathy, and other paraproteinemic neuropathy.

MGUS, smoldering MM (SMM), and symptomatic MM represent a spectrum of the same disease. Symptomatic or active multiple myeloma is characterized by more than 10% BM infiltration by clonal plasma cells and/or biopsy proven plasmacytoma in addition to any level of monoclonal protein and the presence of end-organ damage that consists of a myeloma defining event in the form of any of the CRAB criteria (hypercalcemia, renal insufficiency, anemia, or bone lesions which are deemed related to the plasma cell clone) or any of the new biomarker of malignancy (BM involvement by equal or greater than 60% clonal plasma cell; a ratio of involved versus uninvolved FLC equal or exceeding 100; and/or the presence of more than one bone lesion on MRI (Kyle R. A. et al., Leukemia, 23: 3-9 (2009); Rajkumar V. S. et al, Lancet Oncology, 15: 12, 2014). MM is a plasma cell malignancy that characteristically involves extensive infiltration of bone marrow (BM), and occasionally the formation of plasmacytoma, as discrete clusters of malignant plasma cells inside or outside of the BM space (Kyle R. A. et al., N. Engl. J. Med., 351: 1860-73 (2004)). Consequences of this disease are numerous and involve multiple organ systems. Disruption of BM and normal plasma cell function leads to anemia, leukopenia, hypogammaglobulinemia, and thrombocytopenia, which variously result in fatigue, increased susceptibility to infection, and, less commonly, increased tendency to bleed. Disease involvement in bone creates osteolytic lesions, produces bone pain, and may be associated with hypercalcemia (Kyle R. A. et al., Blood, 111: 2962-72 (2008)).

Smoldering MM (SMM) is characterized by having a serum immunoglobulin (Ig) G or IgA monoclonal protein of 30 g/L or higher and/or 10% or more plasma cells in the bone marrow but no evidence of end-organ damage or malignancy-defining biomarkers (Rajkumar et al, Lancet, 2014). A study of the natural history of SMM suggests that there are 2 different types: evolving smoldering MM and non-evolving Smoldering MM (Dimopoulos M. et al., Leukemia, 23(9): 1545-56 (2009)). Evolving SMM is characterized by a progressive increase in M protein and a shorter median time to progression (TTP) to active multiple myeloma of 1.3 years. Non-evolving SMM has a more stable M protein that may then change abruptly at the time of progression to active multiple myeloma, with a median TTP of 3.9 years.

Monoclonal gammopathy of undetermined significance (MGUS), is a condition in which an abnormal immunoglobin protein (known as a paraprotein) is found in the blood during standard laboratory blood tests. MGUS resembles multiple myeloma and similar diseases, but the levels of antibody are lower, the number of plasma cells (white blood cells that secrete antibodies) in the bone marrow is lower, and it has no symptoms or major problems.

In some embodiments, the subject has multiple myeloma, SMM, or MGUS. In some embodiments, the subject can be one in remission from multiple myeloma. In some embodiments, the subject has a pre-malignant disease (e.g., a pre-malignant disease of MM, such as SMM or MGUS).

In some embodiments, the subject can have a type of cancer that expresses or overexpress BCMA or TACI. Thus, the methods can also include the step of, prior to administering the one or more peptides (or nucleic acids) to the subject, determining whether one or more cancer cells of the subject's cancer (e.g., multiple myeloma) express or overexpress BCMA or TACI. Expression of these proteins includes both mRNA and protein expression. Methods for detecting protein and mRNA expression in a cell are known in the art and include, e.g., enzyme-linked immunosorbent assay (ELISA), western and dot-blotting techniques, or immunohistochemistry techniques for detecting protein and reverse transcription-polymerase chain reaction (RT-PCR) or northern-blotting techniques for detecting mRNA. In some embodiments, the average level of expression of BCMA or TACI in the cancer cell is at least 20%, 30%, 40%, 50%, 60%, 70%, 80%, 90%, 100% higher than the average level of expression of BCMA or TACI in a normal cell (e.g., a normal tissue cell in the same subject, a normal plasma cell in the same subject, or a tissue cell or a plasma cell in a healthy subject). In some embodiments, the average level of expression of BCMA or TACI in the cancer cell is at least 2 fold, 3 fold, 5 fold, 10 fold, 20 fold, or 50 fold higher than the average level of expression of BCMA or TACI in a normal cell (e.g., a normal tissue cell in the same subject, a normal plasma cell in the same subject, or a tissue cell or a plasma cell in a healthy subject).

The subject can have, be suspected of having, or be at risk of developing a cancer (e.g., multiple myeloma). A subject "suspected of having a cancer" is one having one or more symptoms of a cancer. Symptoms of cancer are well-known to those of skill in the art and generally include, without limitation, pain, weight loss, weakness, excessive fatigue, difficulty eating, loss of appetite, chronic cough, worsening breathlessness, coughing up blood, blood in the urine, blood in stool, nausea, vomiting, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, difficulty swallowing, and the like. Symptoms of multiple myeloma specifically include, e.g., bone pain (e.g., in the back or ribs), high levels of calcium in the blood, excessive thirst or urination, constipation, nausea, loss of appetite, confusion, weakness or numbness in the legs, weight loss, or repeated infections.

As used herein, a subject "at risk of developing a cancer" is a subject that has a predisposition to develop a cancer, i.e., a genetic predisposition to develop cancer such as a mutation in a tumor suppressor gene (e.g., mutation in BRCA1, p53, RB, or APC), has been exposed to conditions, or is presently affected by conditions, that can result in cancer. Thus, a subject can also be one "at risk of developing a cancer" when the subject has been exposed to mutagenic or carcinogenic levels of certain compounds (e.g., carcinogenic compounds in cigarette smoke such as acrolein, 4-aminobiphenyl, aromatic amines, benzene, benzo{a}anthracene, benzo{a}pyrene, formaldehyde, hydrazine, Polonium-210 (Radon), urethane, or vinyl chloride). The subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. In addition, a subject can be "at risk of developing a cancer" when the subject suffers from an inflammation (e.g., chronic inflammation). A subject can be at risk of developing multiple myeloma if, e.g., the subject has monoclonal gammopathy of undetermined significance (MGUS). Thus, it is understood that subjects "suspected of having a cancer" or "at risk of developing a cancer" are not all the subjects within a species of interest.

In some embodiments, the methods can also include the step of determining whether a subject has a cancer. Suitable methods for such a determination depend on the type of cancer to be detected in the subject, but are known in the art. Such methods can be qualitative or quantitative. For example, a medical practitioner can diagnose a subject as having multiple myeloma when the subject exhibits two or more (e.g., three, four, five, or six or more) symptoms of multiple myeloma such as any of those described herein. A subject can also be determined to have multiple myeloma by measuring the blood calcium level, the white or red blood cell count, or the amount of protein in the urine of a subject.

MHC Molecule Multimer

The disclosure also features compositions comprising: (i) one or more of any of the peptides described herein and (ii) a major histocompatibility complex (MHC) molecule multimer. The multimer contains two or more (e.g., three, four, five, six, seven, eight, nine, ten or more) entire MHC molecules or peptide-binding regions of an MHC molecule. The one or more peptides can be associated with (e.g., covalently or non-covalently bound to) the MHC molecule multimer.

An MHC molecule of the multimer can be an MHC class I molecule (e.g., an HLA-A2 molecule) or an MHC class II molecule. The MHC molecule can be a mammalian (e.g., a rodent, a non-human primate, a human, or any other mammal described herein) MHC molecule.

The two or more MHC molecules (or the peptide-binding regions of the MHC molecules) in the multimer can be from the same MHC molecule or from different MHC molecules. For example, an MHC molecule multimer can contain five MHC molecules, three of which are the same MHC molecules and two of which are different from the first three. In another example, each MHC molecule of the multimer is different. At least one of the MHC molecules can bind to at least one of the peptides.

In some embodiments, the above compositions can contain at least two (e.g., two, three, four, five, six, seven, eight, nine, 10, 11, or 15 or more) of any of the peptides described herein.

The compositions can also be associated with a detectable label. For example, one or more of the MHC molecules of the multimer can be covalently or non-covalently bound to a detectable label. Suitable detectable labels (e.g., enzymes, fluorescent materials, luminescent materials, bioluminescent materials, or radionuclides) as well as methods for joining detectable labels to a peptide or an MHC molecule are also provided.

An MHC multimer composition can be generated using a peptide described herein as follows: a peptide that binds to an HLA molecule is refolded in the presence of the corresponding HLA heavy chain and β2-microglobulin to generate a trimolecular complex. The complex is then biotinylated at the carboxyl terminal end of the heavy chain at a site that was previously engineered into the heavy chain. Multimer formation is then induced by the addition of streptavidin.

As T cell receptors are capable of recognizing a specific peptide-MHC complex on a target cell among a wide variety of other peptide-MHC complexes, the MHC multimer compositions described herein can be used to, e.g., detect antigen-specific T cells in a population of unrelated T cells. For such assays, the multimers will generally be detectably labeled.

For example, a multimeric MHC molecule/peptide complex can be used in an assay to assess peripheral blood mononuclear cells for the presence of antigen-specific CTL following exposure to an immunogen. The MHC multimer complex can be used to directly visualize antigen-specific CTL (see, e.g., Ogg et al., Science 279: 2103-2106, 1998; and Altman et al., Science 174: 94-96, 1996) and determine the frequency of the antigen-specific CTL population in a sample of peripheral blood mononuclear cells. In some embodiments, a detectably-labeled streptavidin used to multimerize the MHC multimer can be used to label T cells that bind to the MHC molecule/peptide complexes of the multimer. To do this, cells treated with the multimer are exposed, e.g., to a label (e.g., a fluorophore conjugated to biotin). The cells can then be readily isolated or detected, e.g., using flow cytometry.

The peptides (and pharmaceutical compositions thereof), MHC multimer containing compositions, kits, and articles of manufacture described herein can be used in a variety of methods. For example, the peptides can be used to: (i) induce an immune response in a subject (e.g., a subject with a cancer); (ii) activate a T cell in culture; and/or (iii) treat or event prevent a cancer such as multiple myeloma. As described herein, the MHC multimer containing compositions can be used to, e.g., detect antigen-specific T cells in a population of unrelated T cells.

Methods for Producing an Antibody in a Subject

Methods of producing an antibody specific for an immunogen (e.g., one or more of any of the peptides described herein) are known in the art. For example, antibodies or antibody fragments specific for a peptide described herein can be generated by immunization, e.g., using an animal, or by in vitro methods such as phage display. All or part of a peptide described herein can be used to generate an antibody or antibody fragment.

A peptide can be used to prepare antibodies by immunizing a suitable subject, (e.g., rabbit, goat, mouse, or other mammal such as a human) with the peptide. An appropriate immunogenic preparation can contain, for example, any of the composition described herein. The preparation can further include an adjuvant, such as Freund's complete or incomplete adjuvant, alum, RIBI, or similar immunostimulatory agent. Adjuvants also include, e.g., cholera toxin (CT), E. coli heat labile toxin (LT), mutant CT (MCT) (Yamamoto et al. (1997) J. Exp. Med. 185: 1203-1210) and mutant E. coli heat labile toxin (MLT) (Di Tommaso et al. (1996) Infect. Immunity 64: 974-979). MCT and MLT contain point mutations that substantially diminish toxicity without substantially compromising adjuvant activity relative to that of the parent molecules. Immunization of a suitable subject with an immunogenic peptide preparation (e.g., any of the compositions described herein) induces a polyclonal anti-peptide antibody response. In some embodiments, a toll like receptor-3 ligand (e.g., Poly ICLC), interferon alfa (IFNα), interferon gamma (IFNγ), or Granulocyte-macrophage colony-stimulating factor (GM-CSF) can be administered to the subject, e.g., to boost the immune response.

The term antibody as used herein refers to immunoglobulin molecules and immunologically active portions of immunoglobulin molecules (i.e., molecules that contain an antigen binding site that specifically binds to the peptide (e.g., a peptide described herein)). An antibody that specifically binds to a peptide described herein is an antibody that binds the peptide, but does not substantially bind other molecules in a sample. Examples of immunologically active portions of immunoglobulin molecules include, e.g., F(ab) fragments, F(ab')2 fragments, or any other antibody fragments described herein.

An isolated antibody or antigen-binding fragment thereof produced by the methods described herein can selectively bind to an epitope within or overlapping the amino acid sequence of any of SEQ ID NOs: 1-17. The antibody can also be one that cross-blocks the binding of antibody that binds to an epitope within or overlapping the amino acid sequence of any of SEQ ID NOs: 1-17. Typically, binding of an antibody to an epitope is considered selective when the antibody binds with a KD of less than $10^{-6}$ M. If necessary, nonspecific binding can be reduced without substantially affecting selective binding by varying the binding conditions. An antibody that "crossblocks" or a "crossblocking antibody" refers to a first antibody that, when bound to an epitope (e.g., one contained within or overlapping any of SEQ ID NOs: 1-17), reduces or eliminates the ability of a second antibody to bind to the peptide (relative to binding of the second antibody to the peptide that occurs in the absence of the first antibody). It is understood that an antibody produced by a method described herein (e.g., an antibody specific for one or more of the peptides described herein) can be used to, e.g., detect a cancer cell expressing BCMA or TACI and thus is useful in many exemplary methods described herein.

Immunological Testing

The antigen-specific cellular immune responses of vaccinated subjects can be monitored by a number of different assays, such as tetramer assays, ELISPOT, and quantitative PCR. These methods and protocols are described, e.g., in Current Protocols in Immunology, Coligan, J. et al., Eds., (John Wiley & Sons, Inc.; New York, N.Y.).

A tetramer assay can be used to detect and quantify T-cells that are specific for a given antigen within a blood sample. Tetramers comprised of recombinant MHC molecules complexed with peptide can be used to identify populations of antigen-specific T cells. To detect T cells specific for antigens, fluorochrome labeled specific peptide tetramer complexes (e.g., phycoerythrin (PE)-tHLA) containing peptides from these antigens are synthesized and provided by Beckman Coulter (San Diego, Calif.). Specific CTL clone CD8 cells are resuspended at $10^5$ cells/50 µl FACS buffer (phosphate buffer plus 1% inactivated FCS buffer). Cells are incubated with 1 µl tHLA for 30 minutes at room temperature and incubation is continued for 30 minutes at 4° C. with 10 µl anti-CD8 mAb (Becton Dickinson, San Jose, Calif.). Cells are washed twice in 2 ml cold FACS buffer before analysis by FACS (Becton Dickinson).

ELISPOT assays can be used to detect cytokine secreting cells, e.g., to determine whether cells in a vaccinated patient secrete cytokine in response to antigen, thereby demonstrating whether antigen-specific responses have been elicited. ELISPOT assay kits are supplied from R & D Systems (Minneapolis, Minn.) and performed as described by the manufacturer's instructions. Responder (R) $1×10^5$ patients' PBMC cells from before and after vaccination are plated in 96-well plates with nitrocellulose membrane inserts coated with capture Ab. Stimulator (S) cells (TAP-deficient T2 cells pulsed with antigen) are added at the R:S ratio of 1:1. After a 24-hour incubation, cells are removed by washing the plates 4 times. The detection Ab is added to each well. The plates are incubated at 4° C. overnight and the washing steps will be repeated. After a 2-hour incubation with streptavidin-AP, the plates are washed. Aliquots (100 µl) of BCIP/NBT chromogen are added to each well to develop the spots. The reaction is stopped after 60 min by washing with water. The spots are scanned and counted with computer-assisted image analysis (Cellular Technology Ltd, Cleveland, Ohio). When experimental values are significantly different from the mean number of spots against non-pulsed T2 cells (background values), as determined by a two-tailed Wilcoxon rank sum test, the background values are subtracted from the experimental values.

Quantitative PCR is another means for evaluating immune responses. To examine IFN-γ production in patients by quantitative PCR, cryopreserved PBMCs from patients' pre-vaccination and post-vaccinations samples and autologous dendritic cells are thawed in RPMI DC culture medium with 10% patient serum, washed and counted. PBMC are plated at $3×10^6$ PBMCs in 2 ml of medium in 24-well plate; dendritic cells are plated at $1×10^6$/ml and are pulsed 24 hour with 10 µg/ml tumor peptide in 2 ml in each well in 24 well plate. Dendritic cells are collected, washed, and counted, and diluted to $1×10^6$/ml, and $3×10^5$ (i.e., 300 µl solution) added to wells with PBMC (DC:PBMC=1:10). 2.3 µl IL-2 (300 IU/mL) is added every 3-4 days, and the cells are harvested between day 10 and day 13 after initiation of the culture. The harvested cells are then stimulated with tumor cells or autologous PBMC pulsed with 10 µg/ml tumor peptide for 4 hours at 37° C. On days 11-13, cultures are harvested, washed twice, then divided into four different wells, two wells using for control (without target); and another two wells CTL cocultured with tumor cells (1:1) if tumor cells are available. If tumor cells are not available, 10 µg/ml tumor lysate is added to CTL. After 4 hours of stimulation, the cells are collected, RNA extracted, and IFN-γ and CD8 mRNA expression evaluated with a thermocycler/fluorescence camera system. PCR amplification efficiency follows natural log progression, with linear regression analyses demonstrating correlation co-efficients in excess of 0.99. Based on empirical analysis, a one-cycle difference is interpreted to be a two-fold difference in mRNA quantity, and CD8-normalized IFN-γ quantities are determined. An increase of >1.5-fold in post-vaccine relative to pre-vaccine IFN-γ is the established standard for positive type I vaccine responsiveness.

Methods for Selecting a Therapy

Methods for selecting a therapy for a subject with a cancer (e.g., a plasma cell disorder such as multiple myeloma or any cancer in which BCMA or TACI are expressed or overexpressed) include the steps of: optionally, determining whether one or more cancer cells of the subject express or over express BCMA or TACI; and if one or more cells express BCMA or TACI, selecting as a therapy for the subject a composition containing at least one peptide as described herein (a peptide comprising the amino acid sequence of any one of SEQ ID NOs: 1-17, a peptide comprising the amino acid sequence that is at least 50%, 60%, 70%, 80%, or 90% identical to SEQ ID NOs: 1-17, or have no more than 4 substitutions of, the amino acid sequence of any of SEQ ID NOS: 1-17), provided that the amino acid sequence is capable of: (i) inducing in the subject an immune response; (ii) binding to an MHC molecule; and (iii) being recognized, in the context of an MHC molecule, by a T cell receptor on a T cell.

In some embodiments, the methods further include the steps of determine whether one or more cancer cells of the subject express a MHC molecule, e.g., an MHC class I molecule (e.g., HLA-A2), or an MHC class II molecule.

It is understood that where one or more cells (e.g., plasma cells) of a subject's cancer express or overexpress both BCMA and TACI, a combination of suitable peptides can be delivered to the subject. For example, where one or more cells (e.g., plasma cells) of a subject's cancer are determined to express or overexpress both BCMA and TACI, the methods for selecting a therapy can include selecting as a therapy for the subject: a combination of a composition containing at least one peptide comprising the amino acid sequence of any one of SEQ ID NOs: 1-6 and 13-14, and a composition containing at least one peptide comprising the amino acid sequence of any one of SEQ ID NOs: 7-12 and 15-17.

Methods for determining whether one or more cells express BCMA, TACI, and/or a WIC molecule are known in the art. For example, a biological sample (e.g., a blood sample or lymph node tissue sample) obtained from a subject can be tested using an BCMA and/or TACI-specific antibody made by a method described herein to detect the presence or amount of an BCMA and TACI polypeptide expressed by a cell (or cell lysate). Methods for assaying a biological sample for the presence or amount of a polypeptide include, e.g., ELISA, immunohistochemistry, flow cytometry, western-blotting, or dot-blotting assays. In some embodiments, any of the methods described herein can also include the step of providing a biological sample from a subject and/or obtaining a biological sample from a subject. Suitable biological samples for the methods described herein include any biological fluid, cell, tissue, or fraction thereof, which includes analyte proteins of interest. A biological sample can be, for example, a specimen obtained from a subject or can be derived from such a subject. For example, a sample can be a tissue section obtained by biopsy, or cells that are placed in or adapted to tissue culture. A biological sample can also be a cell-containing biological fluid such as urine, blood, plasma, serum, saliva, semen, sputum, cerebral spinal fluid, tears, mucus or an aspirate (e.g., a lung or breast nipple aspirate), or such a sample absorbed onto a paper or polymer substrate. A biological sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of sample types from a subject such as a combination of a tissue and biological fluid.

The biological samples can be obtained from a subject, e.g., a subject having, suspected of having, or at risk of developing, a cancer (e.g., multiple myeloma). Any suitable methods for obtaining the biological samples can be employed, although exemplary methods include, e.g., phlebotomy, swab (e.g., buccal swab), aspiration, or fine needle aspirate biopsy procedure. Non-limiting examples of tissues susceptible to fine needle aspiration include lymph node, lung, thyroid, breast, and liver. Samples can also be collected, e.g., by microdissection (e.g., laser capture microdissection (LCM) or laser microdissection (LIVID)), bladder wash, smear (PAP smear), or ductal lavage.

A medical practitioner can also select, prescribe and/or administer one or more additional therapeutic agents to treat a cancer or one or more medicaments to treat side-effects of an anti-cancer agent. Suitable chemotherapeutic agents for treating multiple myeloma include, e.g., melphalan, cyclophosphamide, vincristine, doxorubicin, prednisone, dexamethasone, proteasome inhibitors (e.g., bortezomib), thalidomide, or lenalidomide. Side effects of anti-cancer agents include, e.g., anemia, gastrointestinal symptoms (e.g., nausea, vomiting, diarrhea), leukopenia (decreased number of white blood cells, which may cause infection), temporary hair loss, or thrombocytopenia (decreased number of platelets, which may cause bleeding). Thus, a medical practitioner can prescribe or administer to a subject a chemotherapeutic agent such as vincristine along with an anti-anemia medicament such as epoetin alpha (e.g., Procrit® or Epogen®).

Nucleic Acid Vaccines

The present disclosure provides Nucleic Acid Vaccines (NAVs) comprising one or more polynucleotides, e.g., polynucleotide constructs, which encode one or more polypeptides as described herein. Exemplary polynucleotides include e.g., polynucleotide constructs, include DNA, RNA, antigen-encoding RNA polynucleotides, e.g., mRNAs. In some embodiments, the polynucleotides, e.g., antigen-encoding RNA polynucleotides, can include at least one chemical modification. In some embodiments, the nucleic acid vaccines can be formulated within a polymeric or liposomal nanocarrier (e.g., a nanoparticle).

In some embodiments, adjuvants or immune potentiators can also be administered with or in combination with one or more NAVs. In some embodiments, an adjuvant acts as a co-signal to prime T-cells and/or B-cells and/or NK cells.

NAVs can vary in their valency. Valency refers to the number of antigenic components in the NAV or NAV polynucleotide (e.g., RNA polynucleotide) or polypeptide. In some embodiments, the NAVs are monovalent. In some embodiments, the NAVs are divalent. In some embodiments, the NAVs are trivalent. In some embodiments the NAVs are multi-valent. Multivalent vaccines can comprise 2, 3, 4, 5, 6, 7, 8, 9, 10, 11, 12, 13, 14, 15, 16, 17, 18, 19, 20, or more antigens or antigenic moieties (e.g., antigenic peptides, etc.). The antigenic components of the NAVs can be on a single polynucleotide or on separate polynucleotides.

The NAVs can be used as therapeutic or prophylactic agents. They are provided for use in medicine and/or for the priming of immune effector cells, e.g., stimulate/transfect peripheral blood mononuclear cells (PBMCs) ex vivo and re-infuse the activated cells. For example, a NAV described herein can be administered to a subject, wherein the polynucleotides is translated in vivo to produce an antigen. Provided are compositions, methods, kits, and reagents for diagnosis, treatment or prevention of a disease or condition in humans and other mammals. The active therapeutic agents can include NAVs, cells containing NAVs or polypeptides translated from the polynucleotides contained in said NAVs.

Provided herein are methods of inducing translation of a polypeptide (e.g., antigen or immunogen) in a cell, tissue or organism using the polynucleotides of the NAVs described herein. Such translation can be in vivo, ex vivo, in culture, or in vitro. The cell, tissue or organism is contacted with an effective amount of a composition containing a NAV which contains a polynucleotide that has at least one a translatable region encoding the polypeptide of interested (e.g., antigen or immunogen).

An "effective amount" of the NAV composition is provided based, at least in part, on the target tissue, target cell type, means of administration, physical characteristics of the polynucleotide (e.g., size, and extent of modified nucleosides) and other components of the NAV, and other determinants. In general, an effective amount of the NAV composition provides an induced or boosted immune response as a function of antigen production in the cell, preferably more efficient than a composition containing a corresponding unmodified polynucleotide encoding the same antigen. Increased antigen production can be demonstrated by increased cell transfection (i.e., the percentage of cells transfected with the NAV), increased protein translation from the polynucleotide, decreased nucleic acid degradation (as demonstrated, e.g., by increased duration of protein translation from a modified polynucleotide), or altered innate immune response of the host cell.

The present disclosure also provides methods of inducing in vivo translation of a polypeptide antigen in a mammalian subject in need thereof. Therein, an effective amount of a NAV composition containing a polynucleotide that has at least one structural or chemical modification and a translatable region encoding the polypeptide (e.g., antigen or immunogen) is administered to the subject using the delivery methods described herein. The polynucleotide is provided in an amount and under other conditions such that the polynucleotide is translated in the cell. The cell in which the polynucleotide is localized, or the tissue in which the cell is present, can be targeted with one or more than one rounds of NAV administration.

The proteins described herein can be engineered for localization within the cell, potentially within a specific compartment such as the cytoplasms or nucleus, or are engineered for secretion from the cell or translocation to the plasma membrane of the cell.

In some embodiments, the nucleic acid (e.g., DNA, RNA) can have one or more modifications. In some embodiments, the nucleic acid molecule (e.g., an RNA molecule) as defined herein can contain nucleotide analogues/modifications, e.g. backbone modifications, sugar modifications or base modifications. A backbone modification in connection with the present invention is a modification, in which phosphates of the backbone of the nucleotides contained in a nucleic acid molecule as defined herein are chemically modified. A sugar modification in connection with the present invention is a chemical modification of the sugar of the nucleotides of the nucleic acid molecule as defined herein. Furthermore, a base modification in connection with the present invention is a chemical modification of the base moiety of the nucleotides of the nucleic acid molecule of the nucleic acid molecule. In this context, nucleotide analogues or modifications are preferably selected from nucleotide analogues which are applicable for transcription and/or translation.

The modified nucleosides and nucleotides, which can be incorporated into the nucleic acid molecule can be modified in the sugar moiety. For example, the 2' hydroxyl group (OH) of an RNA molecule can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O(CH$_2$CH$_2$O)nCH$_2$CH$_2$OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

The sugar group can also contain one or more carbons that possess the opposite stereochemical configuration than that of the corresponding carbon in ribose. Thus, a modified nucleic acid molecule can include nucleotides containing, for instance, arabinose as the sugar.

The phosphate backbone can further be modified in the modified nucleosides and nucleotides, which can be incorporated into the nucleic acid molecule (e.g., an RNA) as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenoates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

The modified nucleosides and nucleotides, which can be incorporated into the nucleic acid molecule (e.g., an RNA molecule) as described herein, can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In some embodiments, the nucleotide analogues/modifications are selected from base modifications, which can be selected, e.g., from 2-amino-6-chloropurineriboside-5'-triphosphate, 2-Aminopurine-riboside-5 '-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5 triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5 '-triphosphate.

In some embodiments, the nucleic acid molecule can be modified by the addition of a so-called "5'-CAP" structure. A 5'-cap is an entity, typically a modified nucleotide entity, which generally "caps" the 5'-end of a mature mRNA. A 5'-cap can typically be formed by a modified nucleotide, particularly by a derivative of a guanine nucleotide. Preferably, the 5'-cap is linked to the 5'-terminus via a 5'-5'-triphosphate linkage. A 5'-cap can be methylated, e.g. m7GpppN, wherein N is the terminal 5' nucleotide of the nucleic acid carrying the 5'-cap, typically the 5'-end of an RNA. m7GpppN is the 5'-CAP structure which naturally occurs in mRNA transcribed by polymerase II and is therefore not considered as modification comprised in the modified RNA according to the invention.

How to make and use nucleic acid vaccines are described, e.g., in US20070269451, US20160317647, U.S. Pat. No. 9,872,900, and US2017002984 each of which is incorporated herein by reference in its entirety.

Pharmaceutical Compositions

Any of the peptides, nucleic acids encoding the peptides, nanoparticles, and cells described herein can be incorporated into pharmaceutical compositions. The compositions can include one or more of the peptides (and/or nucleic acids encoding the peptides) and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. One or more peptides can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Supplementary active compounds (e.g., one or more chemotherapeutic agents) can also be incorporated into the compositions.

A pharmaceutical composition is generally formulated to be compatible with its intended route of administration. Examples of routes of administration include oral, rectal, and parenteral, e.g., intravenous, intramuscular, intradermal, subcutaneous, inhalation, transdermal, or transmucosal. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The compositions can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the pharmaceutical composition must be sterile and should be fluid to the extent that easy syringability exists. It should be stable under the conditions of manufacture and storage and must be preserved against any contamination by microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of contamination by microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as mannitol, sorbitol, sodium chloride in the composition. Prolonged absorption of the injectable compositions can be facilitated by including in the composition an agent that delays absorption, for example, aluminum monostearate and gelatin.

Sterile injectable solutions can be prepared by incorporating one or more of the peptides (or one or more the nucleic acids encoding the peptides) in the required amount in an appropriate solvent with one or a combination of ingredients, as required, followed by filtered sterilization. Generally, dispersions are prepared by incorporating the peptide(s) (or nucleic acid(s) encoding the peptide(s)) into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the one or more peptides can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

The powders and tablets can contain from 1% to 95% (w/w) of an individual peptide or a mixture of two or more peptides. In certain embodiments, the peptide can range from about 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the peptide (or nucleic acid) with encapsulating material as a carrier providing a capsule in which the peptide with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

For administration by inhalation, the peptides or nucleic acids can be delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the peptides or nucleic acids can be formulated into ointments, salves, gels, or creams as generally known in the art.

The peptides or nucleic acids can also be prepared in the form of suppositories (e.g., with conventional suppository bases such as cocoa butter and other glycerides) or retention enemas for rectal delivery.

In some embodiments, the peptides or nucleic acids can be prepared with carriers that will protect the peptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to, e.g., APCs with monoclonal antibodies to APC-specific antigens) can also be used as pharmaceutically acceptable carriers. These can be prepared according to methods known to those skilled in the art, for example, as described in U.S. Pat. No. 4,522,811.

It can be advantageous to formulate oral or parenteral compositions in dosage unit form for ease of administration and uniformity of dosage. Dosage unit form, as used herein, refers to physically discrete units suited as unitary dosages for the subject to be treated; each unit containing a predetermined quantity of the peptides (or nucleic acids) calculated to produce the desired therapeutic effect in association with the required pharmaceutical carrier. Dosage units can also be accompanied by instructions for use.

The nucleic acid molecules encoding the peptides can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al. (1994) Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Additional examples of gene delivery vehicles include, but are not limited to, liposomes, biocompatible polymers, including natural polymers and synthetic polymers; lipoproteins; polypeptides; polysaccharides; lipopolysaccharides; artificial viral envelopes; metal particles; bacteria; viruses such as baculovirus, adenovirus, and retrovirus; bacteriophage; cosmids; plasmids; fungal vectors and other recombination vehicles typically used in the art which have been described for expression in a variety of eukaryotic and prokaryotic hosts, and may be used for gene therapy as well as for simple protein expression.

Examples of viral vectors include retroviral vectors, lentivirus vectors, adenovirus vectors, adeno-associated virus vectors, alphavirus vectors and the like. Liposomes that comprise a targeting moiety such as an antibody or fragment thereof can also be used to prepare pharmaceutical compositions of nucleic acids for delivery to a subject.

Any of the pharmaceutical compositions described herein can be included in a container, pack, or dispenser together with instructions for administration as described below.

Kits and Articles of Manufacture

The disclosure also features a variety of kits. The kits can include, e.g., one or more (e.g., one, two, three, four, five, six, seven, eight, nine, or 10 or more) of any of the peptides (or expression vectors containing nucleic acid sequences encoding one or more peptides) described herein; and instructions for administering the peptide to a subject. The kit can include one or more pharmaceutically acceptable carriers and/or one or more immune stimulating agents. The immune stimulating agents can be, e.g., a T helper epitope, an altered peptide ligand, or an adjuvant. The kits can also contain one or more therapeutic agents, diagnostic agents, or prophylactic agents. The one or more therapeutic, diagnostic, or prophylactic agents include, but are not limited to: (i) an agent that modulates inflammatory responses (e.g., aspirin, indomethacin, ibuprofen, naproxen, steroids, cromolyn sodium, or theophylline); (ii) an agent that affects renal and/or cardiovascular function (e.g., furosemide, thiazide, amiloride, spironolactone, captopril, enalapril, lisinopril, diltiazem, nifedipine, verapamil, digoxin, isordil, dobutamine, lidocaine, quinidine, adenosine, *digitalis*, mevastatin, lovastatin, simvastatin, or mevalonate); (iii) drugs that affect gastrointestinal function (e.g., omeprazole or sucralfate); (iv) antibiotics (e.g., tetracycline, clindamycin, amphotericin B, quinine, methicillin, vancomycin, penicillin G, amoxicillin, gentamicin, erythromycin, ciprofloxacin, doxycycline, streptomycin, gentamicin, tobramycin, chloramphenicol, isoniazid, fluconazole, or amantadine); (v) anticancer agents (e.g., cyclophosphamide, methotrexate, fluorouracil, cytarabine, mercaptopurine, vinblastine, vincristine, doxorubicin, bleomycin, mitomycin C, hydroxyurea, prednisone, tamoxifen, cisplatin, or dacarbazine); (vi) immunomodulatory agents (e.g., interleukins, interferons (e.g., interferon gamma (IFN-γ), granulocyte macrophage-colony stimulating factor (GM-CSF), tumor necrosis factor alpha (TNFα), tumor necrosis factor beta (TNFβ), cyclosporine, FK506, azathioprine, steroids); (ix) drugs acting on the blood and/or the blood-forming organs (e.g., interleukins, G-CSF, GM-CSF, erythropoietin, heparin, warfarin, or coumarin); or (vii) hormones (e.g., growth hormone (GH), prolactin, luteinizing hormone, TSH, ACTH, insulin, FSH, CG, somatostatin, estrogens, androgens, progesterone, gonadotropin-releasing hormone (GnRH), thyroxine, triiodothyronine); hormone antagonists; agents affecting calcification and bone turnover (e.g., calcium, phosphate, parathyroid hormone (PTH), vitamin D, bisphospho nates, calcitonin, fluoride).

In some embodiments, the kits can contain one or more (e.g., one, two, or three or more) of any of the BCMA and/or TACI antibodies described herein. In some embodiments, the kits can include two antibodies, each specific for a different protein. For example, a kit can contain one BCMA-specific antibody (described herein) and one TACI-specific antibody (described herein). The kits can optionally include instructions for assaying a biological sample for the presence or amount of one or more of BCMA, and/or TACI proteins. Also featured are articles of manufacture that include: a container; and a composition contained within the container, wherein the composition comprises an active ingredient for inducing an immune response in a mammal (e.g., a human), wherein the active ingredient comprises one or more (e.g., two, three, four, five, six, seven, eight, nine, or 10 or more) of any of the peptides described herein, and wherein the container has a label indicating that the composition is for use in inducing an immune response in a mammal (e.g., any of the mammals described herein). The label can further indicate that the composition is to be administered to a mammal having, suspected of having, or at risk of developing, multiple myeloma. The composition of the article of manufacture can be dried or lyophilized and can include, e.g., one or more solutions (and/or instructions) for solubilizing a dried or lyophilized composition.

The articles of manufacture can also include instructions for administering the composition to the mammal.

EXAMPLES

The invention is further described in the following examples, which do not limit the scope of the invention described in the claims.

Example 1. BCMA Expression on Multiple Myeloma Cell Lines

A total of 12 cancer cell lines including 11 MM cell lines and 1 breast cancer cell line (MDA-MB231) were evaluated for their expression levels of BCMA antigen by staining with an antibody specific to each following clone; #1. ANC3B1 (LifeSpan Biosciences, Cat #LS-C357630), #2. VICKY1 (LifeSpan Biosciences, Cat #LS-C18662), and #3. 19F2 (BioLegend, Cat #357506). Among the cell lines, H929 (MM cell line) showed the highest level of BCMA expression and MDA-MB231 (breast cancer cell line; BCMA negative) showed the minimum level of BCMA expression. (FIGS. 1A-1I).

Example 2. Selection of BCMA and TACI Native Peptides Specific to HLA-A2

Six native peptides derived from BCMA or TACI antigen, respectively, were identified as following:

```
                                        (SEQ ID NO: 1)
#1. BCMA₆₄₋₇₂ (LIISLAVFV)

(SEQ ID NO: 2)
#2. BCMA₆₉₋₇₇ (AVFVLMFLL)

(SEQ ID NO: 3)
#3. BCMA₉₋₁₇ (SQNEYFDSL)

(SEQ ID NO: 4)
#4. BCMA₇₂₋₈₀ (VLMFLLRKI)

(SEQ ID NO: 5)
#5. BCMA₅₄₋₆₂ (AILWTCLGL)

(SEQ ID NO: 6)
#6. BCMA₁₁₄₋₁₂₂ (ILPRGLEYT)

(SEQ ID NO: 7)
#1. TACI₁₇₈₋₁₈₆ (FLVAVACFL)

(SEQ ID NO: 8)
#2. TACI₁₇₄₋₁₈₂ (VLCCFLVAV)

(SEQ ID NO: 9)
#3. TACI₁₅₄₋₁₆₂ (KLSADQVAL)
```

-continued
```
                                        (SEQ ID NO: 10)
#4. TACI₁₆₆₋₁₇₄ (TLGLCLCAV)

(SEQ ID NO: 11)
#5. TACI₁₆₁₋₁₆₉ (ALVYSTLGL)

(SEQ ID NO: 12)
#6. TACI₁₅₅₋₁₆₃ (LSADQVALV)
```

Figure 2:
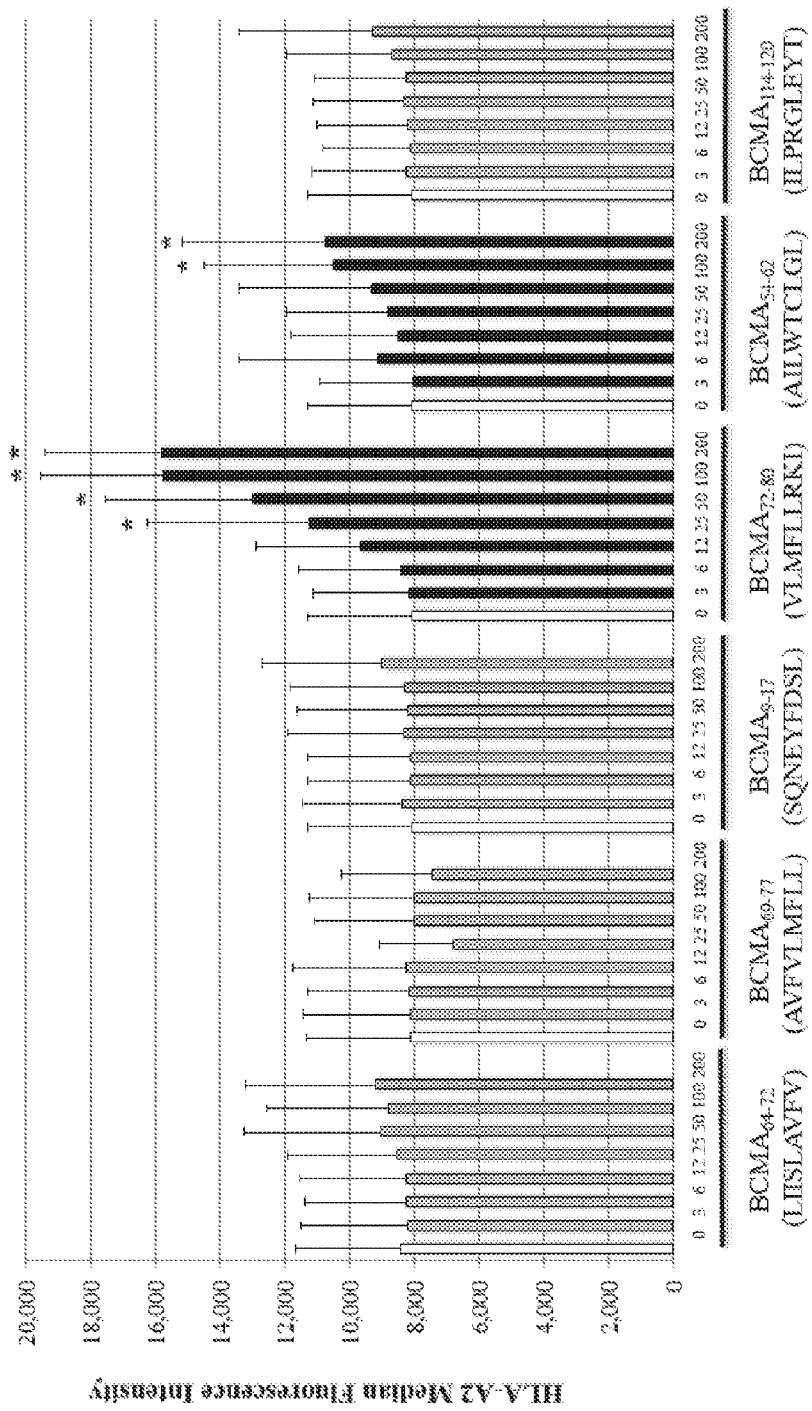
FIG. 2 shows binding affinity of native BCMA peptides to HLA-A2.

Example 3. Binding Affinity of BCMA or TACI Native Peptides to HLA-A2 Molecule The listed BCMA peptides were evaluated for HLA-A2-specific binding capacity using the T2 cell line. In the assay, T2 cells were washed, resuspended in serum-free AIM-V medium to a final concentration of $1 \times 10^6$ cells/ml and transferred into wells of a 24-well tissue culture plate. The cells were pulsed with different concentrations of respective BCMA peptide (0-200 μg/ml) plus 3 μg/ml human β2-microglobulin (Sigma) and incubated at 37° C., 5% $CO_2$ in humidified air. Following overnight incubation, the cells were washed, stained with mouse anti-human HLA-A2-FITC mAb for 15 minutes at 4° C., washed and analyzed using a FACSort™ flow cytometer with CellQuest™ v2.1 software (Becton Dickinson, San Jose, Calif.). Peptide binding to HLA-A2 was determined by the up-regulation of HLA-A2 molecules on T2 cells caused by HLA-A2 specific peptide binding and demonstrated by measuring mean fluorescence intensity (MFI) by flow cytometric analyses. Among the BCMA peptides evaluated, "#4. BCMA₇₂₋₈₀ (VLMFLLRKI (SEQ ID NO: 4))" showed the highest level of HLA-A2 specificity and "#5. BCMA₅₄-62 (AILWTCLGL (SEQ ID NO: 5))" showed the second highest level of the specificity. (FIG. 2). Among the TACI peptides evaluated, all peptides expect for TACI #5 showed HLA-A2 specificity, but the highest level was measured by #4.

TACI₁₆₆₋₁₇₄ (TLGLCLCAV (SEQ ID NO: 10)) (FIG. 3).

Example 4. Stability of BCMA or TACI Native Peptides to HLA-A2 Molecule

In order to improve the stability of the peptide binding to HLA-A2 molecules, the following heteroclitic BCMA or TACI peptides were designed:

```
                                        (SEQ ID NO: 13)
Heteroclitic #4. BCMA₇₂₋₈₀ (YLMFLLRKI)

(SEQ ID NO: 14)
Heteroclitic #5. BCMA₅₄₋₆₂ (YILWTCLGL)

(SEQ ID NO: 15)
Heteroclitic #1. TACI₁₇₈₋₁₈₆ (YLVAVACFL)

(SEQ ID NO: 16)
Heteroclitic #3. TACI₁₅₄₋₁₆₂ (YLSADQVAL)

(SEQ ID NO: 17)
Heteroclitic #4. TACI₁₆₆₋₁₇₄ (YLGLCLCAV)
```

Figure 4:
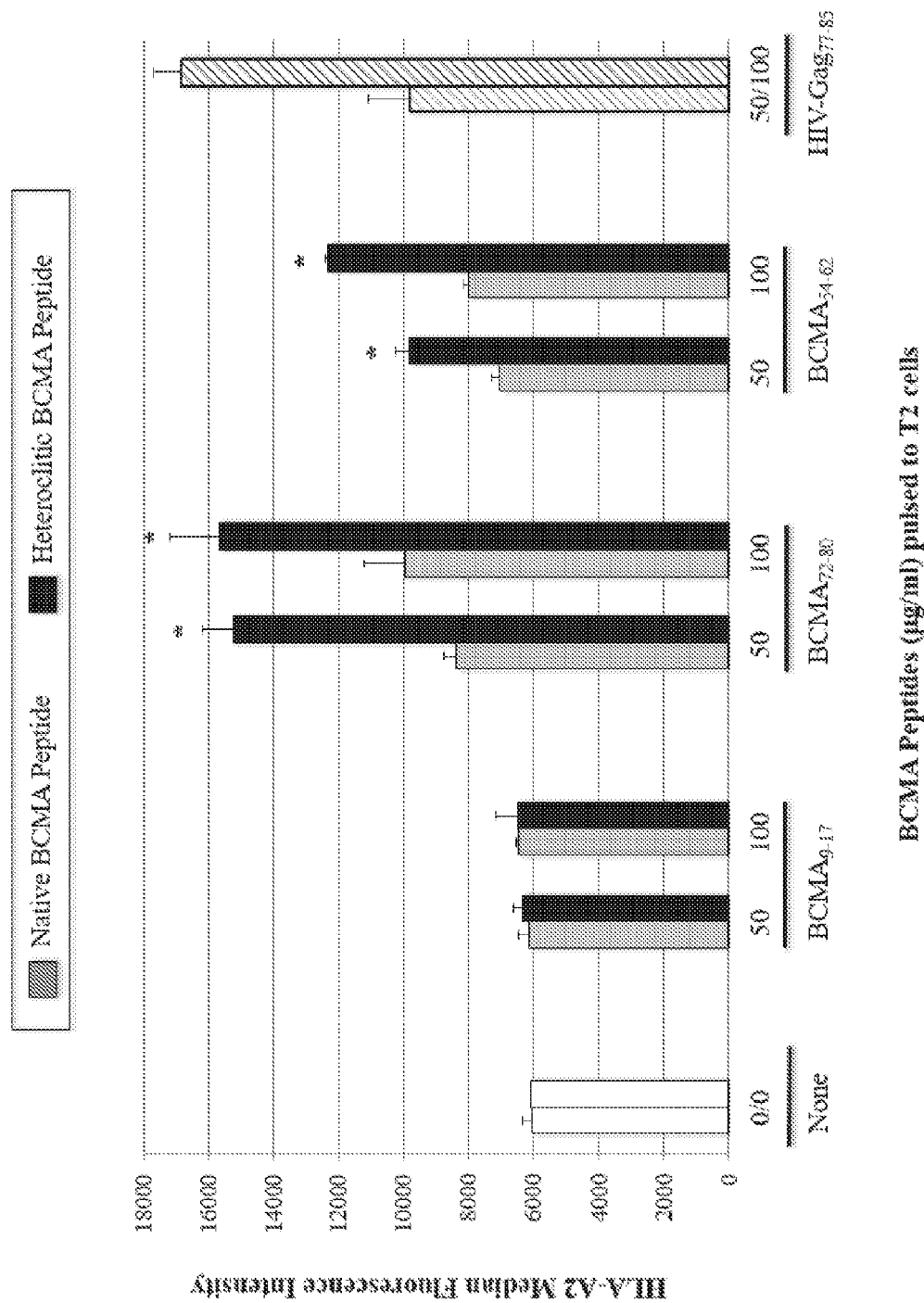
FIG. 4 shows binding affinity of BCMA peptides to HLA-A2: native peptide vs. heteroclitic peptide.
Figure 5:
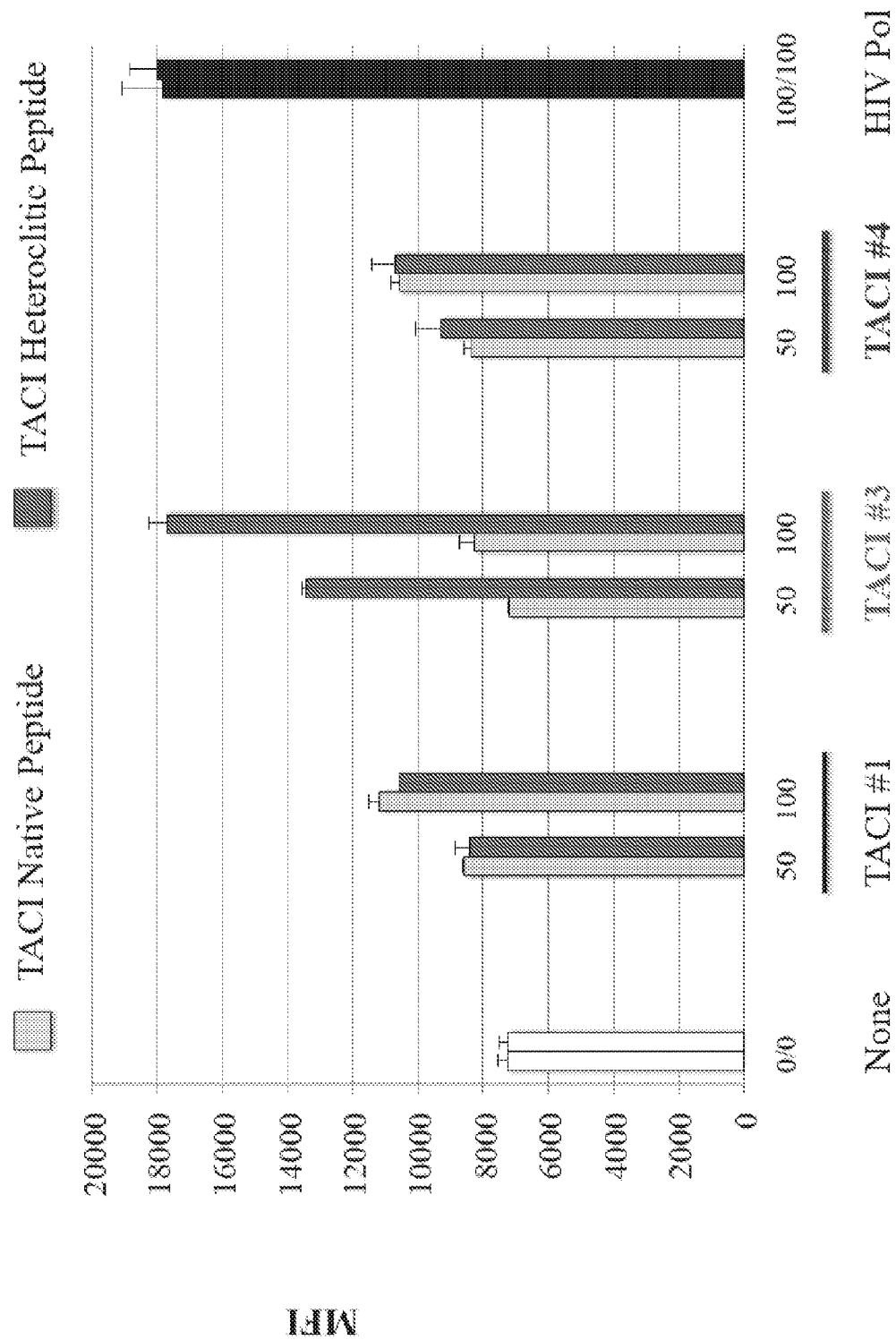
FIG. 5 shows binding affinity of TACI peptides to HLA-A2: native peptide vs. heteroclitic peptide.
Figure 6:
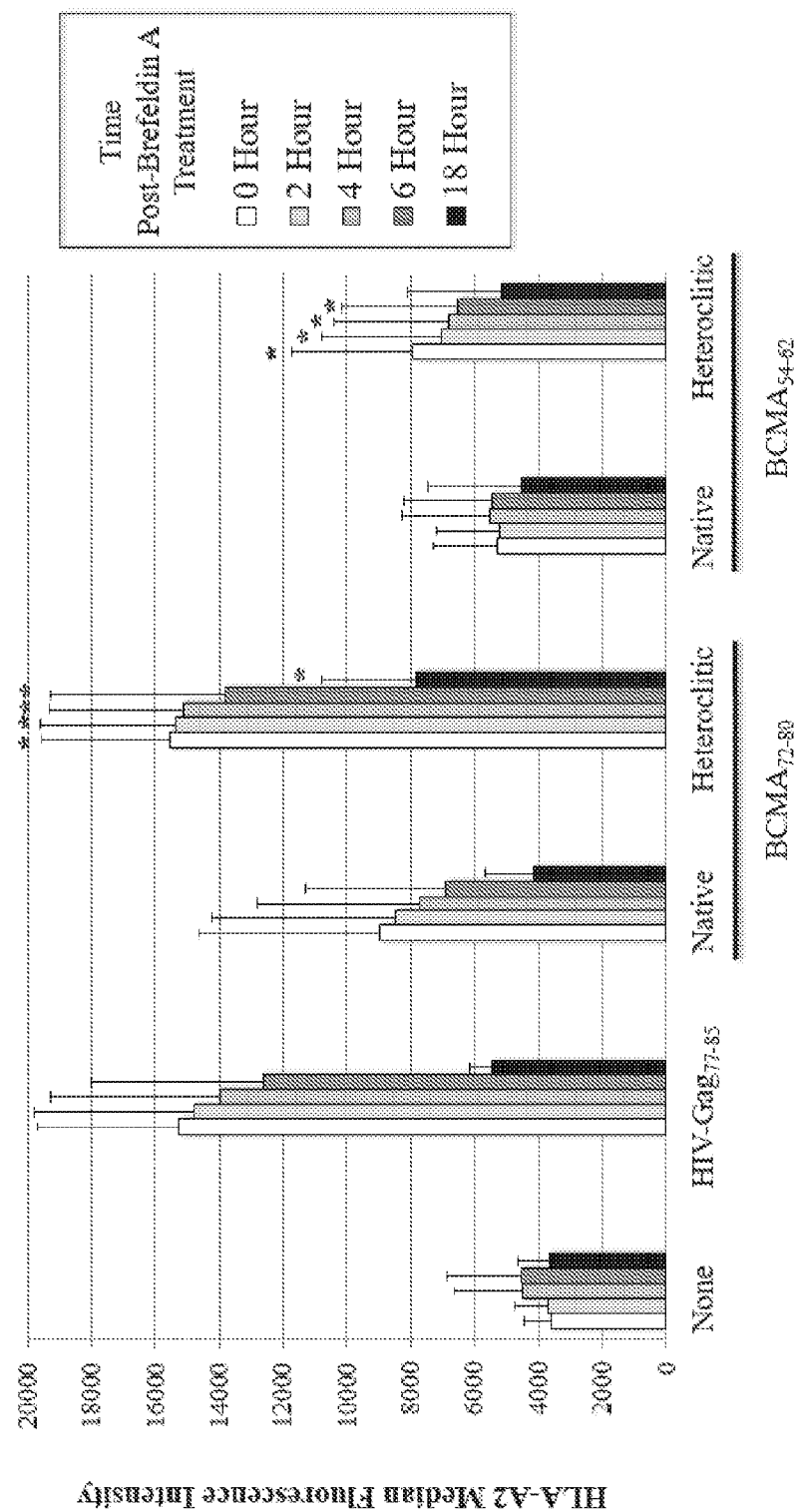
FIG. 6 shows HLA-A2 stability of BCMA #4 and #5 peptides: native peptide vs. heteroclitic peptide (50 ug/ml).
Figure 7:
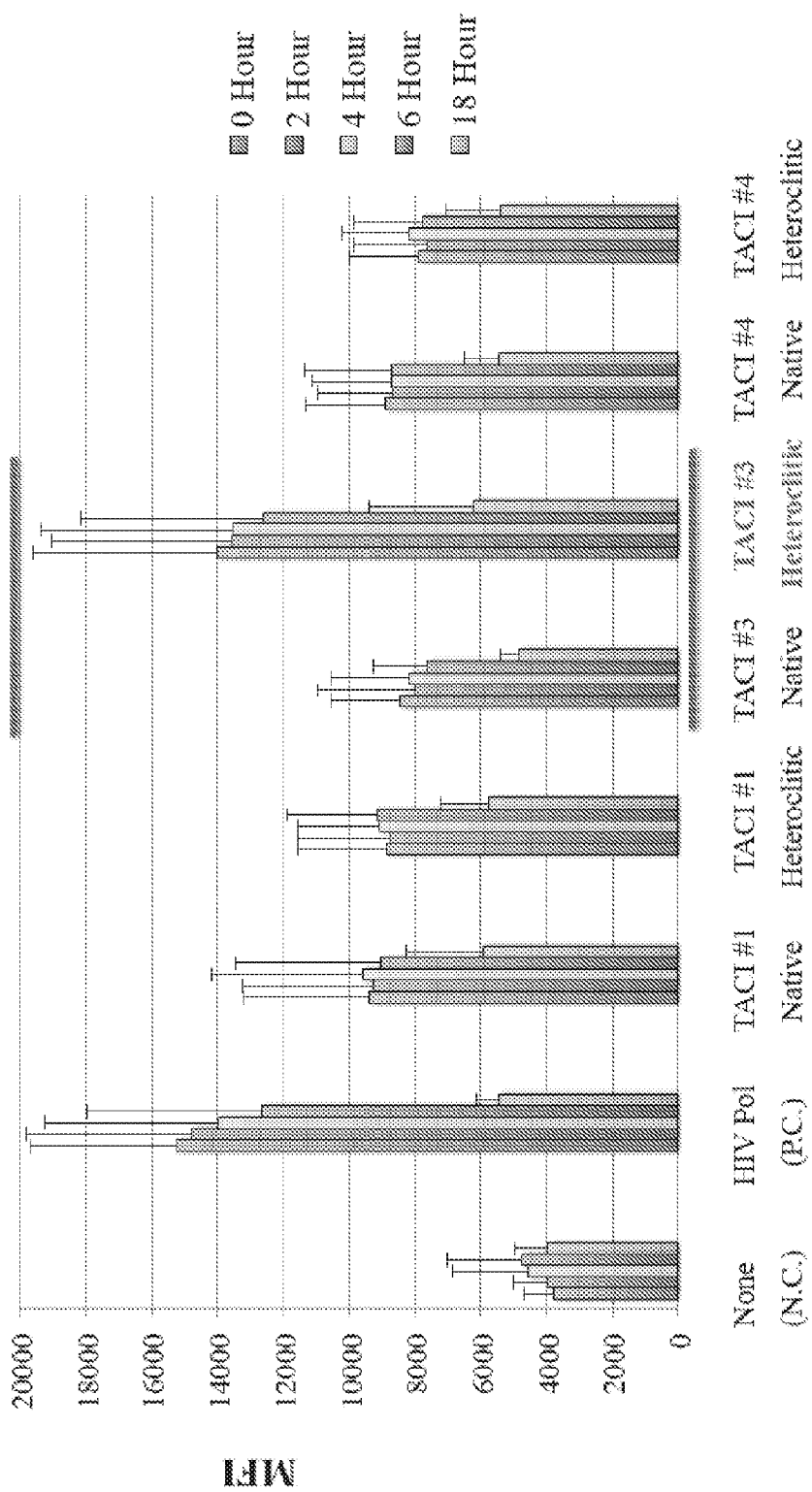
FIG. 7 shows HLA-A2 stability of TACI #1, #3 and #4 peptides: native peptide vs. heteroclitic peptide (50 ug/ml).

The native and heteroclitic BCMA and TACI peptides were examined for HLA-A2 binding stability using the T2 cell line. T2 cells were pulsed with the respective peptide. After overnight incubation, the cells were washed to remove unbound peptide; they were evaluated for binding affinity as shown above and stability as following. The cells were incubated with 10 µg/ml Brefeldin A (Sigma) at 37° C. and 5% $CO_2$ for 1 hour to block cell surface expression of newly synthesized HLA-A2 molecules. Peptide/HLA-A2 binding stability was evaluated at 0, 2, 4, 6 and 18 hours post-Brefeldin A treatment. Following the incubation period, the cells were harvested, washed, stained with mouse anti-human HLA-A2-FITC mAb and analyzed by flow cytometry. The HLA-A2 binding affinity of the "Heteroclitic #4 $BCMA_{72-80}$ (YLMFLLRKI (SEQ ID NO: 13))", "Heteroclitic #5 $BCMA_{54-62}$ (YILWTCLGL (SEQ ID NO: 14))" and "Heteroclitic #3 $TACI_{154-162}$ (YLSADQVAL (SEQ ID NO: 16))" was increased from their native peptide (FIGS. 4 and 5). In terms of the binding stability, "Heteroclitic #4 $BCMA_{72-80}$ (YLMFLLRKI (SEQ ID NO: 13))" and "Heteroclitic #3 $TACI_{154-162}$ (YLSADQVAL (SEQ ID NO: 16))" peptides showed a significant improvement in their HLA-A2 affinity at all the time points evaluated including 0, 2, 4, 6 and 18 hours compared to the native peptide (FIGS. 6 and 7). Therefore, the Heteroclitic #4 $BCMA_{72-80}$ (YLMFLLRKI (SEQ ID NO: 13)) and Heteroclitic #3. $TACI_{154-162}$ (YLSADQVAL (SEQ ID NO: 16) peptides were selected for further evaluation of their immunogenic potential to generate MM-specific cytotoxic T cells (CTLs).

Example 5. Induction of BCMA or TACI Peptide-Specific $CD3^+CD8^+$ CTL

The peptide-specific CTL were generated from different $HLA-A2^+$ normal donors for the evaluation of the functional activities targeting MM cell lines. To generate the peptide-specific CTL, mature dendritic cells (mDC) generated from the same donor were resuspended in serum-free AIM-V media and pulsed with 50 µg/ml of the Heteroclitic #4 $BCMA_{72-80}$ (YLMFLLRKI (SEQ ID NO: 13)) peptide or "Heteroclitic #3 $TACI_{154-162}$ (YLSADQVAL (SEQ ID NO: 16))" peptide, overnight at 37° C., 5% $CO_2$ in humidified air. The peptide-pulsed mDC were washed, counted, irradiated at 10 Gy and used to prime $CD3^+$ T cells at a 1:20 antigen-presenting cells/peptide-to-$CD3^+$ T cell ratio in AIM-V media supplemented with 10% human AB serum. The cultures were restimulated every seven days with irradiated T2 cells pulsed with peptide for a total of 4 cycles. To maintain the T cells ex vivo, IL-2 (50 U/ml) was added to the cultures two days after the second stimulation. Control T cell cultures were maintained under the same culture conditions in the presence of IL-2 (50 U/ml), but without peptide stimulation. Phenotype of the resulting CTL was evaluated one week after each cycle of peptide stimulation. Flow cytometric analysis showed a distinct change in the phenotype of the $CD3^+CD8^+$ T cell subsets stimulated with the Heteroclitic #4 $BCMA_{72-80}$ (YLMFLLRKI (SEQ ID NO: 13)) with a gradual increase in the population. The $CD3^+ CD8^+$ T cell increases by the heteroclitic BCMA peptide was similar to those with the immunogenic $CD138_{260-268}$ (GLVGLIFAV (SEQ ID NO: 20)), which was previously identified as immunogenic peptide, suggesting the potential immunogenicity of the BCMA peptide. The BCMA peptide-specific CTL cultures contained a higher percentage of $CD8^+$ T cells (~80%) upon 4 cycle of peptide stimulation compared to non-peptide stimulated control T cells (~20%) (FIGS. 8A-8C).

Example 6. Decreased Naïve and Increased Memory $CD3^+CD8^+$ CTL by Heteroclitic $BCMA_{72-80}$ Peptide Stimulation Antigen-specific CTL can be phenotypically identified as activated/memory T cells from naïve T cells by their expression of distinct cell surface antigens. The phenotype of the BCMA-CTL were examined as potential effector cells by analyzing the phenotype of naïve and memory cells. BCMA peptide-specific CTL were generated by repeated stimulation of $HLA-A2^+$ normal donor's $CD3^+$ T cells weekly with antigen-presenting cells pulsed with 50 µg/ml heteroclitic $BCMA_{72-80}$ (YLMFLLRKI (SEQ ID NO: 13)). One week after each peptide stimulation, the resulting CTL were evaluated for their phenotypic profile by flow cytometry. The BCMA-CTL showed a decreased frequency of naive $CD3^+CD8^+$ T cells as compared to the control T cells (Donor 1: 80% unstimulated to 2% upon 4 cycles of stimulation; Donor 2: 83% unstimulated to 2% upon 4 cycles of stimulation). A corresponding increase was observed in the frequency of the memory $CD3^+CD8^+$ T cells (Donor 1: 18% unstimulated to 86% upon 4 cycles of stimulation; Donor 2: 10% unstimulated to 92% upon 4 cycles of stimulation) with the heteroclitic $BCMA_{72-80}$ (YLMFLLRKI (SEQ ID NO: 13)) peptide. These phenotypic changes demonstrate that repeated stimulation of $CD3^+$ T cells with heteroclitic $BCMA_{72-80}$ (YLMFLLRKI (SEQ ID NO: 13)) resulted in an expansion of $CD8^+$ CTL with a phenotype of memory cells, indicating the immunogenicity of the BCMA peptide (FIGS. 9 and 10).

Figures 11A, 11B, 11C:
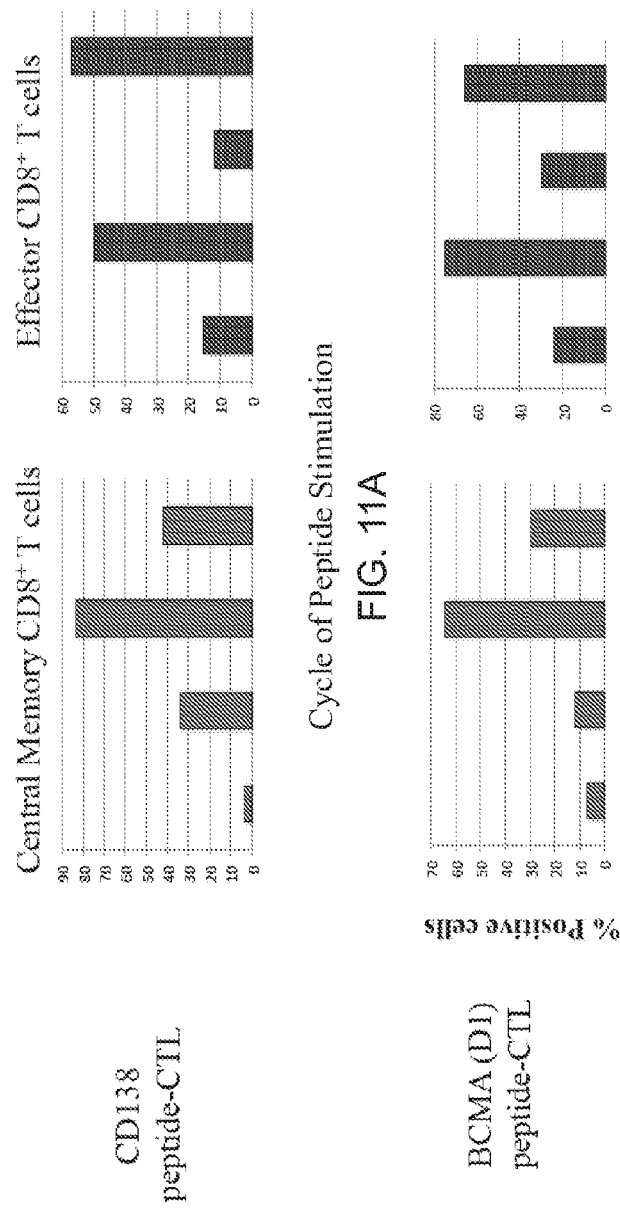
FIGS. 11A-11C show kinetics of CM vs. effector cells with heteroclitic BCMA #4 peptide stimulation.

Example 7. Changes in Frequency of Central Memory and Effector $CD3^+CD8^+$ CTL by Heteroclitic $BCMA_{72-80}$ Peptide Stimulation Further evaluation of central memory and effector cells was performed, upon the stimulation of T cells with heteroclitic $BCMA_{72-80}$ (YLMFLLRKI (SEQ ID NO: 13)) peptide. The expansion of central memory CTL by the BCMA peptide was detected after 3 cycle of stimulation, which was aligned with a decrease of effector CTL. Upon 4 cycle of the peptide stimulation, a decrease in central memory CTL and increase in effector CTL including effector memory cells were also detected. The pattern of this phenotype change in the CD8+ T cells with the heteroclitic $BCMA_{72-80}$ (YLMFLLRKI (SEQ ID NO: 13)) peptide was similar to the cells stimulated with $CD138_{260-268}$ (GLVGLIFAV (SEQ ID NO: 20)) (FIGS. 11A-11C).

Figure 12:
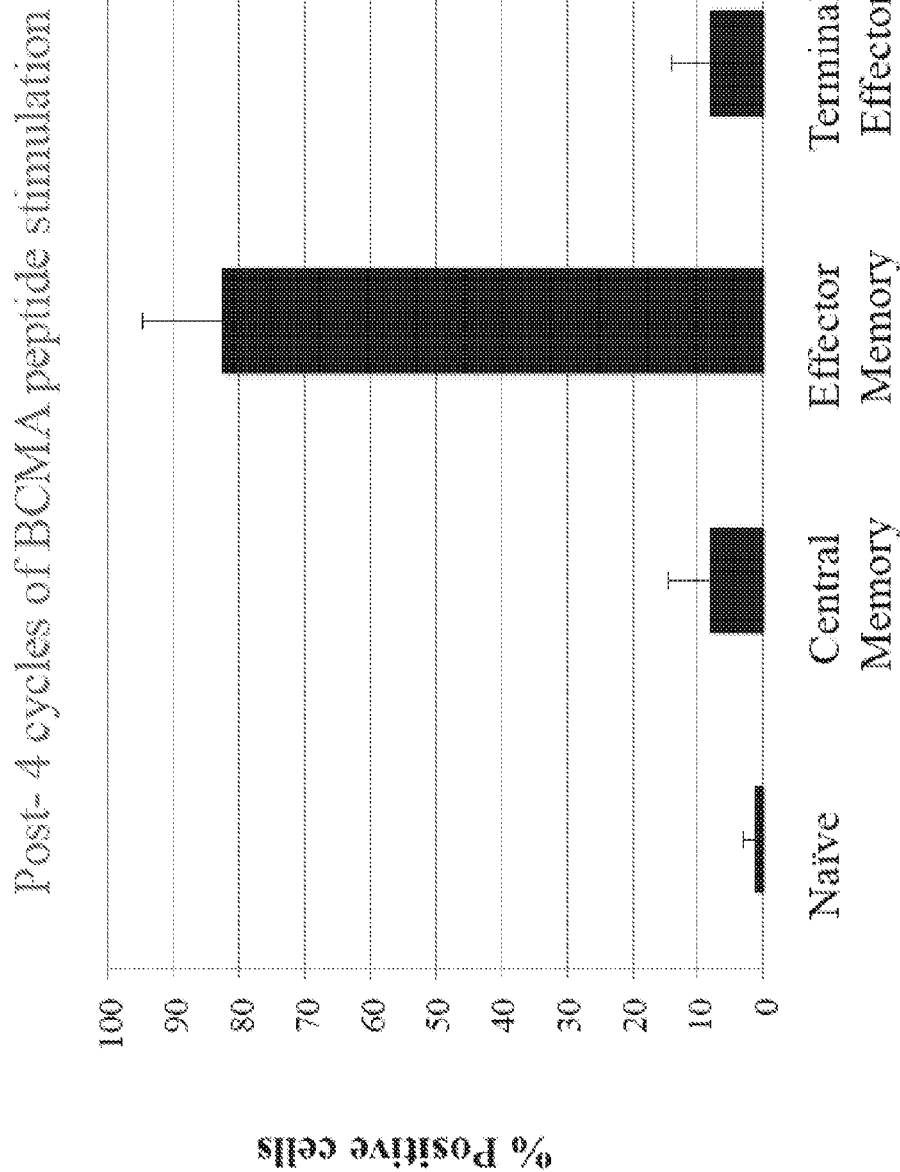
FIG. 12 shows induction of memory CD8+ CTL by heteroclitic BCMA #4 peptide.
Figure 13:
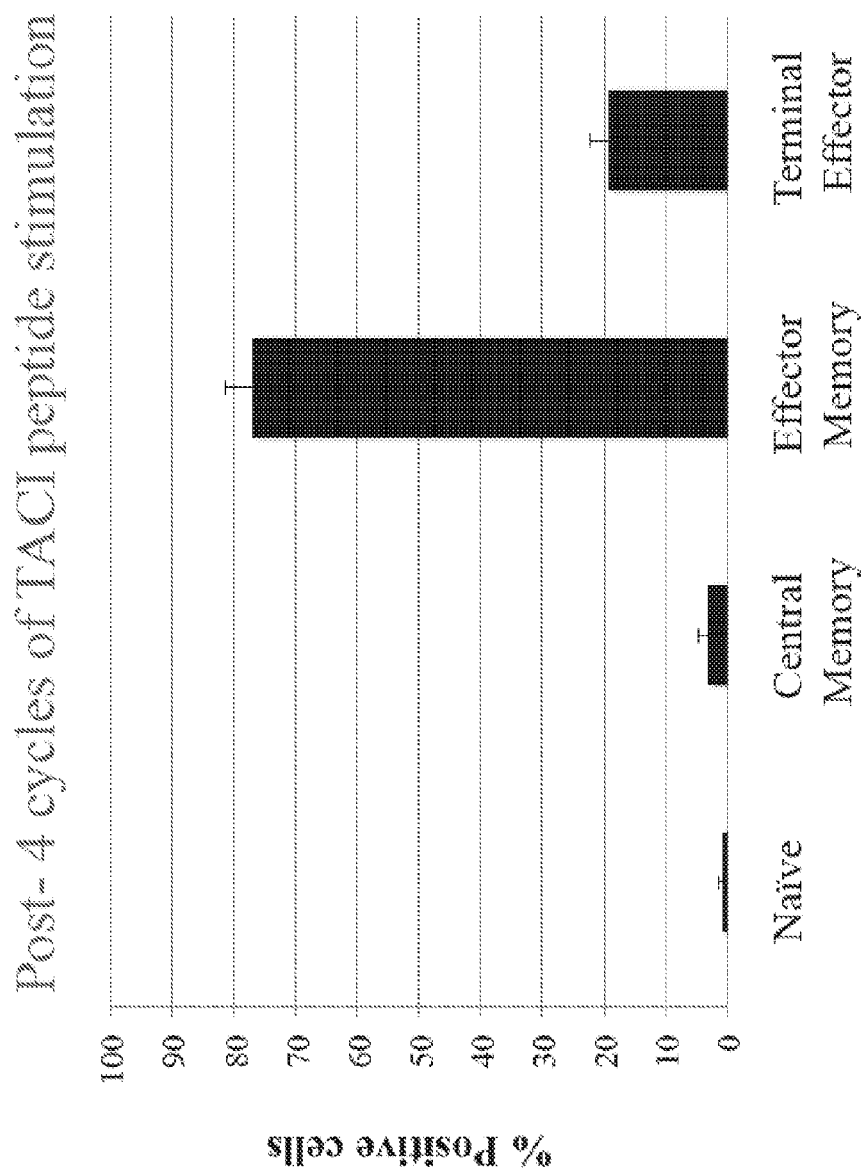
FIG. 13 shows induction of memory CD8+ CTL by heteroclitic TACI #3 peptide.

Example 8. The Specific CTL Stimulated with Heteroclitic $BCMA_{72-80}$ (YLMFLLRKI—SEQ ID NO: 13) Peptide or Heteroclitic $TACI_{154-162}$ (YLSADQVAL SEQ ID NO: 16) Peptide Display a Distinct Phenotype Representing Specific T Cell Subtypes We also observed distinct phenotypic changes in the $CD3^+CD8^+$ T cell subset within the CTL stimulated with heteroclitic $BCMA_{72-80}$ (YLMFLLRKI (SEQ ID NO: 13)) peptide or heteroclitic $TACI_{154-162}$ (YLSADQVAL SEQ ID NO: 16)) peptide in frequency of naïve ($CD45RO^-/CCR7^+$), central memory ($CD45RO^+/CCR7^+$), effector memory ($CD45RO^+/CCR7^-$) and terminal effector ($CD45RO^-/CCR7^-$) cells within the $CD8^+$ T cell subsets in the $CD3^+$ T cell cultures stimulated with the peptide. After 4 cycles of peptide stimulation, the frequency of effector memory $CD3^+CD8^+$ T cells was increased, associated with a corresponding decrease in naïve T cells ($CD45RO^-CCR7^+/CD3^+CD8^+$) and central memory T cells ($CD45RO^+CCR7^+/CD3^+CD8^+$). Thus, these results demonstrate that repeated stimulation of $CD3^+$ T cells with the selected heteroclitic BCMA or TACI peptide results in distinct phenotypic changes and expansion of CD3+CD8+ T cell subsets characteristic of antigen-specific CTL. (FIG. 12 and FIG. 13).

Figure 14:
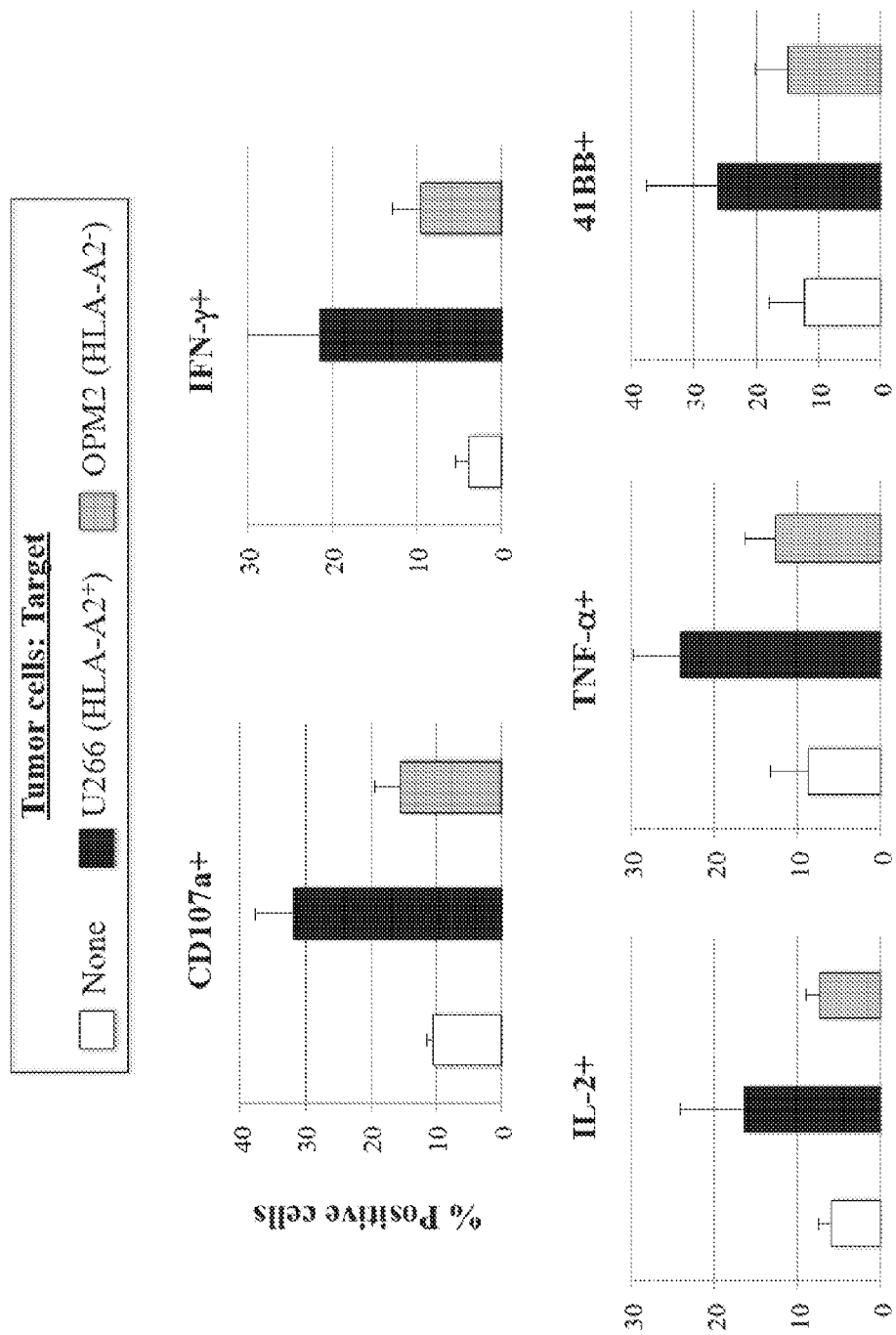
FIG. 14 shows anti-tumor activities of heteroclitic BCMA #4 peptide-CTL (N=5).
Figure 15:
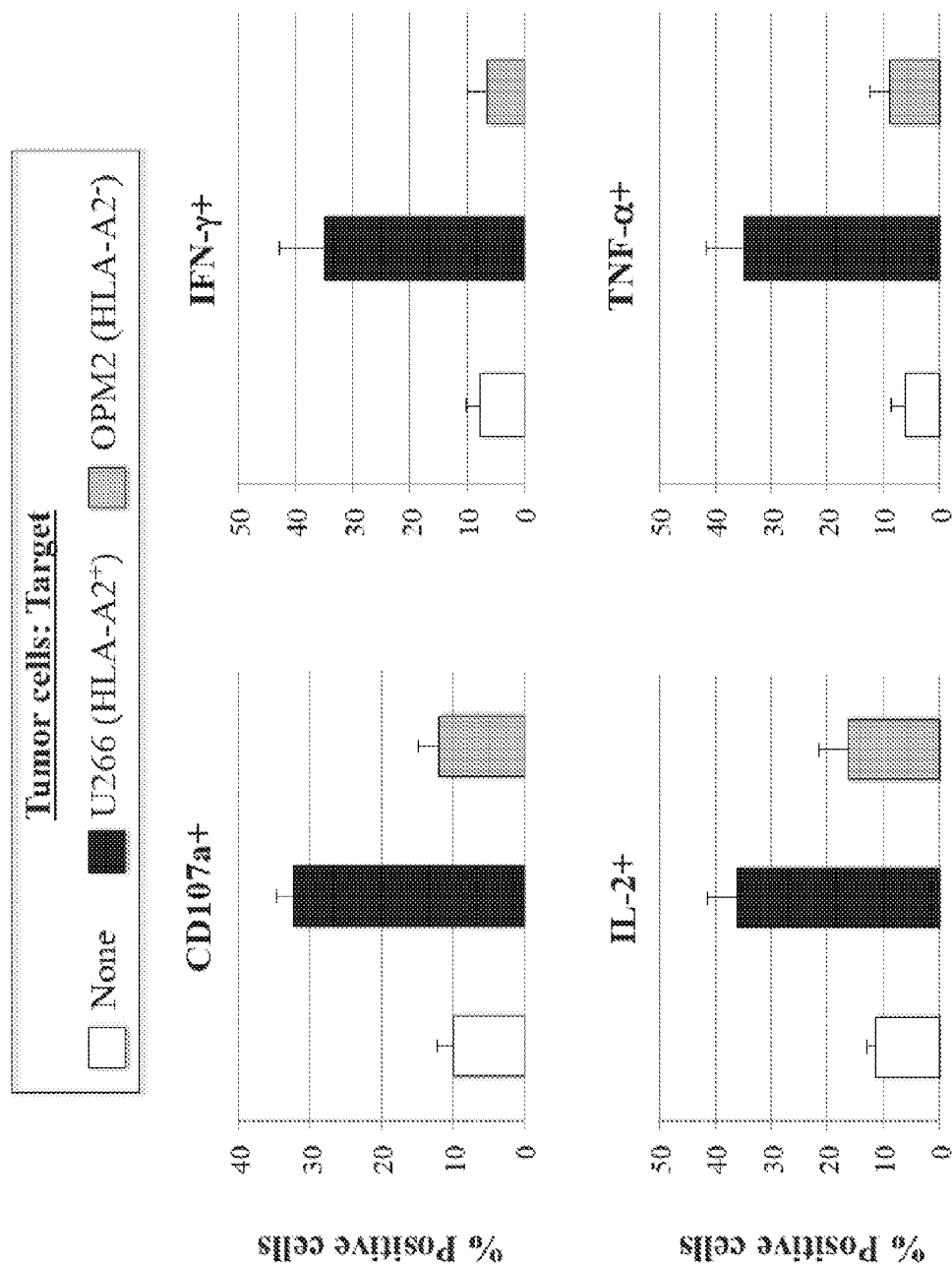
FIG. 15 shows anti-tumor activities of heteroclitic TACI #3 peptide-CTL (n=4).

Example 9. BCMA-Specific CTL and TACI-Specific CTL Induce Cytotoxic Activity, Produce Th1-Type of Cytokines (IFN-γ, IL-2, TNF-α) and Upregulate 41BB Expression to MM Cells, in an HLA-A2-Restricted Manner The peptide-specific CTL stimulated with heteroclitic BCMA$_{72-80}$ (YLMFLLRKI (SEQ ID NO: 13)) peptide or heteroclitic TACI$_{154-162}$ (YLSADQVAL (SEQ ID NO: 16)) were analyzed by flow cytometry for their ability to lyse myeloma cells and produce critical cytokines, which are involved in anti-tumor activities. The BCMA-CTL and TACI-specific CTL demonstrated a significant increase in the frequency of cells expressing CD107a degranulation marker, a measure of cytotoxic activity, upon recognition of HLA-A2+ U266 cells, which was higher than HLA-A2− OPM2 cells. An increased level of IFN-γ, IL-2, and TNF-α production was detected in BCMA-specific CTL and TACI-specific CTL to HLA-A2+ MM cells, but not to HLA-A2− MM cells, demonstrating the immune responses are in an HLA-A2 restricted manner (FIG. 14 and FIG. 15).

Figure 16:
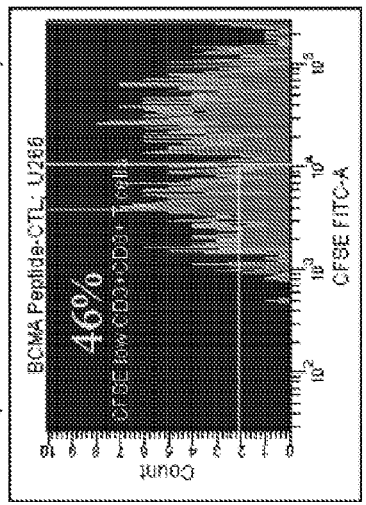
FIG. 16 shows HLA-A2 specific proliferation of heteroclitic BCMA #4 peptide-CTL.
Figure 16:
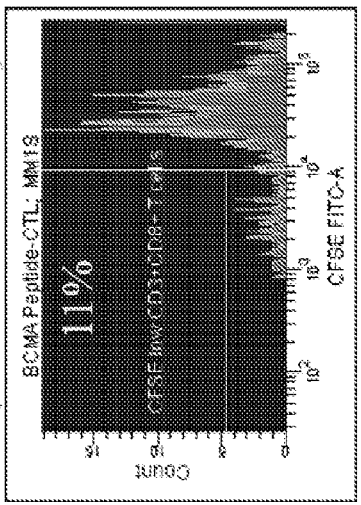
Figure 16:
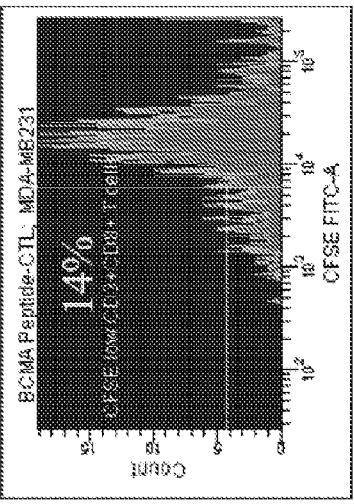

Example 10. BCMA-Specific CTL Proliferate in Response to MM Cells in HLA-A2 Restricted and Antigen-Specific Manner Functional activities of the peptide-specific CTL stimulated with heteroclitic BCMA$_{72-80}$ (YLMFLLRKI (SEQ ID NO: 13)) were further analyzed using a CFSE-proliferation assay. The proliferation of CD8+ T cells in the BCMA peptide-specific CTL was measured on day 4, evidenced by a decrease in fluorescence of the CFSE-labeled CTL (gated CFSE low) following stimulation with HLA-A2+ MM (U266), HLA-A2+ breast cancer (MDA-MB231) or HLA-A2− MM (MM1S) cells. The BCMA-CTL induced a significant CD8+ T cell proliferation in response to HLA-A2+ U266 MM cell line (proliferating cells: 46%). However, the CD8+ T cells proliferation was not induced in response to MDA-MB231 or MM1S and stayed at a low level (11%-14%) as the cells cultured in media alone (10%). Taken together, these results suggest that the BCMA-CTL respond to myeloma cells specifically and their CD8+ T cells proliferation is HLA-A2-restricted and antigen-specific (FIG. 16).

Figure 17:
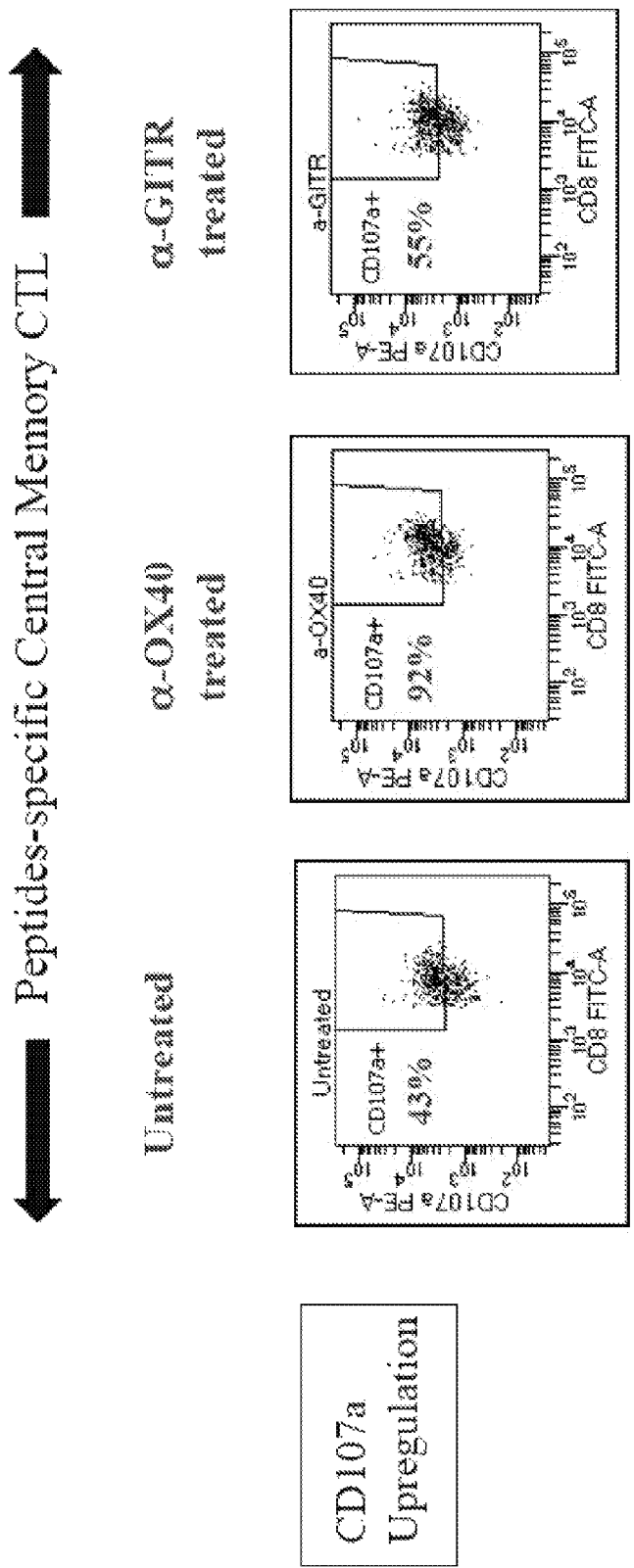
FIG. 17 shows enhanced α-tumor activities by central memory cells of BCMA-specific CTL treated w. α-OX40 or α-GITR.

Example 11. Higher Level of Cytotoxicity by BCMA-Specific CTL in Combination with Immune Agonist The activity of peptide-specific CTL stimulated with heteroclitic BCMA$_{72-80}$ (YLMFLLRKI (SEQ ID NO: 13)) was measured in treatment of the cells with anti-OX40 or anti-GITR for 48 hrs. The level of cytotoxicity was measured by CD107a degranulation in the CD3+CD8+ T cells gated. It was observed that the CD107a degranulation was increased upon the treatment of BCMA peptide-specific CTL with anti-OX40 (92%) or anti-GITR (55%) compared to untreated group (43%), suggesting that the combination treatment with immune agonists is helpful for inducing anti-tumor activity of BCMA-CTL (FIG. 17).

Example 12. Selective Targeting of Multiple Myeloma by BCMA-Specific Central Memory CD8+ Cytotoxic T Lymphocytes Despite recent advances in treatment of multiple myeloma (MM) incorporating novel therapies into the stem cell transplantation paradigm, ongoing DNA damage and genomic evolution underlie relapse in many patients. Novel therapeutic approaches with distinct mechanisms of action are therefore needed. The constitutive or evolving genetic complexity, coupled with immune responsiveness of B cell malignancies, has stimulated the development of immunotherapeutic options in MM including monoclonal antibodies, bispecific antibodies, immunotoxins, and CAR T cells. Although MM patient-specific CAR T cell therapy has achieved remarkable deep responses, durability of responses is not establishes and they are labor-intensive, time-consuming, and expensive. To overcome these limitations, this example provides immunogenic peptides-based cancer vaccines as an off-the-shelf immunotherapy for treating patients more widely and efficiently. The peptide-based therapeutic approach does not have limitations of recombinant proteins, mRNA, or DNA-based vaccines, which require the processes of internalization, degradation of protein into optimal immunogenic peptides to HLA, along with additional steps required for suitable translation (for mRNA) or transcription (for DNA). To overcome MHC restriction and treat a more diverse patient population using the immunogenic epitope vaccine approach, peptide cocktails were pooled to include major HLA subtypes. Moreover, lenalidomide can augment peptide vaccine specific immune responses and memory cytotoxic T cell (CTL) activities, setting the stage for combination approaches with checkpoint inhibitors and/or immune agonists. In addition, anti-tumor efficacy triggered by immunogenic peptides can be enhanced by their ability to induce "epitope spreading" upon the generation of effector cells, whereby targeted lysed cancer cells release new antigenic epitopes which are subsequently taken up, processed, and presented by antigen-presenting cells to a new repertoire of CTLs.

B cell maturation antigen (BCMA) is a member of the TNF receptor superfamily 17 (TNFRSF17) and is characterized as a type III trans-membrane protein containing cysteine-rich extracellular domains with a central role in regulating B-cell maturation and differentiation into plasma cells. As a receptor for the MM cell growth and survival factors B cell activating factor (BAFF) and a proliferation-inducing ligand (APRIL), BCMA is required for the survival of MM cells, making it a promising therapeutic target. Nearly all MM tumor cells express BCMA, and it has been proposed as a marker for identification of tumor cells. Its selective expression on a subset of mature B and long lived plasma cells further suggest a favorable therapeutic index for BCMA directed treatment approaches. At present BCMA is being targeted by several immunotherapeutic strategies including antibodies (naked antibodies, antibodies-drug conjugates, and bispecific antibodies) and cellular therapies (chimeric antigen receptor T-cells), with promising clinical results even in relapsed refractory MM. In addition, serum soluble BCMA is elevated among patients with MM and chronic lymphocytic leukemia and can serve as a prognostic marker and monitor of response. Finally, most recent studies indicate that BCMA is expressed in non-hemopoietic tissue: BCMA is abnormally expressed in non-small cell lung cancer cell lines and may play a role in the tumors through the ERK1/2 signaling pathway. These data support targeting BCMA in immunotherapeutic strategies in MM and potentially BCMA expressing solid tumors as well.

This example provides a peptide-based immunotherapeutic approach targeting BCMA by generating antigen-specific CD8+ CTL with effective and long-lasting immunity against MM cells. Novel immunogenic native and heteroclitic HLA-A2-specific BCMA peptides capable of eliciting MM-specific responses with highly effective anti-tumor activities were identified. Importantly, the heteroclitic BCMA$_{72-80}$ (YLMFLLRKI (SEQ ID NO: 13)) peptide demonstrated the highest level of immunogenicity, with the greatest affinity/stability to HLA-A2 molecule and robust induction of BCMA-specific memory CTL with poly-functional activities against HLA-A2$^+$ patients' MM cells and MM cell lines. The experiments show the framework for clinical application of this novel engineered immunogenic BCMA$_{72-80}$ peptide in cancer vaccine and adoptive immunotherapeutic protocols, and provide long lasting memory anti-tumor immunity in patients with MM or BCMA expressing cancers.

Particularly, this results show that tumor-associated antigens on CD138$^+$ tumor cells obtained from newly diagnosed MM patients (N=616) can be used to expand the breadth and extent of current multiple myeloma (MM)-specific immunotherapy. These experiments are designed to target B-cell Maturation Antigen (BCMA), which promotes MM cell growth and survival, by generating BCMA-specific memory CD8$^+$ CTL which mediate effective and long-lasting immune response against MM cells. Here, the experiment shows novel engineered peptides specific to BCMA, BCMA$_{72-80}$ (YLMFLLRKI (SEQ ID NO: 13)) and BCMA$_{54-62}$ (YILWTCLGL (SEQ ID NO: 14)) display improved affinity/stability to HLA-A2 compared to their native peptides and induce BCMA-specific CTL with increased activation (CD38, CD69) and co-stimulatory (CD40L, OX40, GITR) molecule expression. Importantly, the heteroclitic BCMA$_{72-80}$ specific CTL demonstrated poly-functional Th1-specific immune activities [IFN-γ/IL-2/TNF-α production, proliferation, cytotoxicity] against MM, which were directly correlated with expansion of Tetramer$^+$ and memory CD8$^+$ CTL populations. When combined with anti-OX40 or anti-LAG3, the heteroclitic BCMA$_{72-80}$ specific CTL displayed increased cytotoxicity against MM, especially by central memory CTL. These results provide the framework for clinical application of heteroclitic BCMA$_{72-80}$ peptide, alone and in combination with anti-LAG3 and/or anti-OX40, in vaccination and adoptive immunotherapeutic strategies to generate long-lasting autologous anti-tumor immunity in patients with MM and other BCMA expressing tumors.

The following materials and methods were used in this example.
Materials and Methods
Cell Lines The MM cell lines, MM1S, OPM2, OPM1, H929, OCIMY5, RPMI, U266, KMS1, HSB2, McCAR and ANBL6, and a breast cancer cell line MDA-MB-231 were obtained from ATCC (Manassas, Va.). The T2 cell line, a human B and T cell hybrid expressing HLA-A2 molecules, was provided by Dr. J. Molldrem (University of Texas M. D. Anderson Cancer Center, Houston, Tex.). The cell lines were cultured in DMEM (for MM and T2 cells; Gibco-Life Technologies, Rockville, Md.) or Leibovitz's L-15 (for MDA-MB231; ATCC, Manassas, Va.) media supplemented with 10% fetal calf serum (FCS; BioWhittaker, Walkersville, Md.), 100 IU/ml penicillin and 100 μg/ml streptomycin (Gibco-Life Technologies).
Reagents Fluorochrome conjugated anti-human BCMA, HLA-A2, CD3, CD8, CD38, CD40L, CD69, 41BB, CCR7, CD45RO, CD107a, IFN-γ, IL-2, TNF-α, PD1, LAG3, OX40 and GITR monoclonal antibodies (mAbs) were purchased from Becton Dickinson (BD) (San Diego, Calif.), LifeSpan Bioscience (Seattle, Wash.) or BioLegend (San Diego, Calif.). Live/Dead Aqua stain kit was purchased from Molecular Probes (Grand Island, N.Y.). Recombinant human GM-CSF was obtained from Immunex (Seattle, Wash.); and human IL-2, IL-4, IFN-α, and TNF-α were purchased from R&D Systems (Minneapolis, Minn.). BCMA peptide-specific Tetramer-PE was synthesized by MBL International Corporation (Woburn, Mass.). Clinical grade mAb to LAG3 or OX40 was provided by Bristol-Myers Squibb (New York, N.Y.).
Synthetic Peptides Native BCMA peptides [BCMA$_{64-72}$ (LIISLAVFV (SEQ ID NO: 1)), BCMA$_{69-77}$ (AVFVLMFLL (SEQ ID NO: 2)), BCMA$_{9-17}$ (SQNEYFDSL (SEQ ID NO: 3)), BCMA$_{72-80}$ (VLMFLLRKI (SEQ ID NO: 4)), BCMA$_{54-62}$ (AILWTCLGL (SEQ ID NO: 5)), BCMA$_{114-120}$ (ILPRGLEYT (SEQ ID NO: 6))], heteroclitic BCMA peptides [hBCMA$_{72-80}$ (YLMFLLRKI (SEQ ID NO: 13)), hBCMA$_{54-62}$ (YILWTCLGL (SEQ ID NO: 14)), hBCMA$_{9-17}$ (YQNEYFDSL (SEQ ID NO: 22))] and HIV-Gag$_{77-85}$ (SLYNTVATL (SEQ ID NO: 21)) were synthesized by standard fmoc (9-fluorenylmethyl-oxycarbonyl) chemistry, purified to >95% using reverse-phase chromatography, and validated by mass-spectrometry for molecular weight (Biosynthesis, Lewisville, Tex.).
HLA A2 Affinity and Stability Assays T2 cells were pulsed overnight with various doses of peptide plus β2-microglobulin (3 μg/ml) (Sigma, St Louis, Mo.). Following overnight incubation, the cells were stained with HLA-A2-PE mAb and analyzed using a FACSCanto™ flow cytometer (BD). Peptide/HLA-A2 complex stability was measured on peptide loaded T2 cells at 0, 2, 4, 6 and 14 hours post-brefeldin A treatment by staining with HLA-A2-PE mAb and flow cytometric analysis.
Generation of Dendritic Cells Monocytes isolated from peripheral blood mononuclear cells (PBMC) were cultured for 7 days in the presence of 1,000 units/ml GM-CSF and 1,000 units/ml IL-4 in RPMI-1640 medium (Gibco-Life Technologies) supplemented with 10% FCS. Fresh media plus GM-CSF and IL-4 was added to the cultures every other day. Mature DC (mDC) were obtained on day 7, following 3 additional days incubation with 1,000 units/ml IFN-α plus 10 ng/ml TNF-α.
Induction of BCMA Peptide-Specific CTL BCMA peptide-specific CTL (BCMA-CTL) were generated ex vivo by repeated stimulation of CD3$^+$ T cells obtained from HLA-A2$^+$ donors with peptide-pulsed antigen-presenting cells (APC). In brief, peptide (50 μg/ml)-pulsed APC were irradiated (10 Gy) and used to stimulate T cells at a 1 APC/peptide: 20 T cell ratio. The T cell cultures were restimulated every 7 days and maintained in AIM-V medium supplemented with 10% human AB serum (BioWhittaker) in the presence of IL-2 (50 units/ml).
Phenotypic Analysis of BCMA Peptide-Specific CTL or Tumor Cells Phenotypic characterization was performed on BCMA-CTL after staining with Live/Dead Aqua stain kit and fluorochrome conjugated anti-human mAbs and Tetramer-PE. Alternatively, the MM and breast cancer cell lines were stained with fluorochrome-conjugated BCMA or HLA-A2 mAb. After staining, the cells were washed, fixed in 2% paraformaldehyde, and analyzed by flow cytometry.
Cell Proliferation by Carboxy Fluorescein Succinimidyl Ester (CFSE) Tracking BCMA-CTL were labeled with CFSE (Molecular Probes) and co-incubated with irradiated (10 Gy) tumor cells or peptide-pulsed APC in the presence of IL-2 (10 units/ml). On day 4, 5, 6 or 8 of co-culture, cells were harvested and stained with Live/Dead Aqua stain kit and CD3/CD8/CD45RO/CCR7 mAbs. The level of CD3+CD8+ CTL proliferation was determined as a reduction in CFSE fluorescence intensity, as measured by flow cytometry.

CD107a Degranulation and Intracellular IFN-γ/IL-2/TNF-α Cytokines Production

The functional cytolytic activity of BCMA-CTL was measured by CD107a degranulation and Th1 cytokine production by flow cytometry. In brief, BCMA-CTL were co-incubated with tumor cells or T2/peptide in the presence of CD107a mAb. After 1 hour incubation, CD28/CD49d mAb, brefeldin A, and Monensin (BD) were added for an additional 5 h. Cells were harvested, washed in PBS, and incubated with mAbs specific to T cell antigens. After surface staining, cells were fixed/permeabilized, stained with anti-IFN-γ/IL-2/TNF-α mAbs, washed with Perm/Wash solution (BD), fixed in 2% paraformaldehyde, and analyzed by flow cytometry.

Statistical Analysis

Results are presented as mean±SE. Groups were compared using unpaired Student's t-test. Differences were considered significant when p<0.05.

BCMA Peptides Binding Affinity and Stability to HLA-A2 Molecules.

The full length BCMA protein sequence was evaluated to predict epitopes with HLA-A2 affinity, extended half-time disassociation rates, proteasomal C terminal cleavage, and TAP transport using various search software programs including BIMAS and NetCTL. Among the six native peptides selected [BCMA$_{64-72}$ (LIISLAVFV), BCMA$_{69-77}$ (AVFVLMFLL), BCMA$_{9-17}$ (SQNEYFDSL), BCMA$_{72-80}$ (VLMFLLRKI), BCMA$_{54-62}$ (AILWTCLGL), BCMA$_{114-120}$ (ILPRGLEYT)], BCMA$_{72-80}$ (VLMFLLRKI) and BCMA$_{54-62}$ (AILWTCLGL) showed the highest HLA-A2 binding affinity in a dose-dependent manner. Among the heteroclitic peptides designed, heteroclitic BCMA$_{72-80}$ (YLMFLLRKI (SEQ ID NO: 13)) and heteroclitic hBCMA$_{54-62}$ (YILWTCLGL (SEQ ID NO: 14)) displayed the highest increase in HLA-A2 binding affinity, as compared to their native peptides (n=3, p<0.05). In contrast, replacing the anchor motif in the non-HLA-A2 specific BCMA$_{9-17}$ (SQNEYFDSL) to heteroclite BCMA$_{9-17}$ (YQNEYFDSL (SEQ ID NO: 22)) did not alter its HLA-A2 affinity status, indicating improved HLA-A2 affinity by modification only within the HLA-A2-specific peptides.

The HLA-A2 stability of BCMA$_{72-80}$ and BCMA$_{54-62}$ HLA-A2-specific peptides after brefeldin A treatment of the T2 cells pulsed with peptide was assessed. Native BCMA$_{72-80}$ and BCMA$_{54-62}$ peptides displayed extended HLA-A2 stability for greater than 6 hours, which was further enhanced by engineering into heteroclitic BCMA$_{72-80}$ (YLMFLLRKI (SEQ ID NO: 13)) and BCMA$_{54-62}$ (YILWTCLGL (SEQ ID NO: 14)). Overall, the highest level of HLA-A2 affinity and stability was detected with the BCMA$_{72-80}$ (YLMFLLRKI (SEQ ID NO: 13)) at each time point tested, which was higher than the HLA-A2 positive control HIV-Gag$_{77-85}$ peptide.

BCMA-Specific CTL Generated with Heteroclitic BCMA$_{72-80}$ (YLMFLLRKI (SEQ ID NO: 13)) or BCMA$_{54-62}$ (YILWTCLGL (SEQ ID NO: 14)) Show Increased T Cell Activation and Costimulatory Molecule Expression.

Figure 18A:
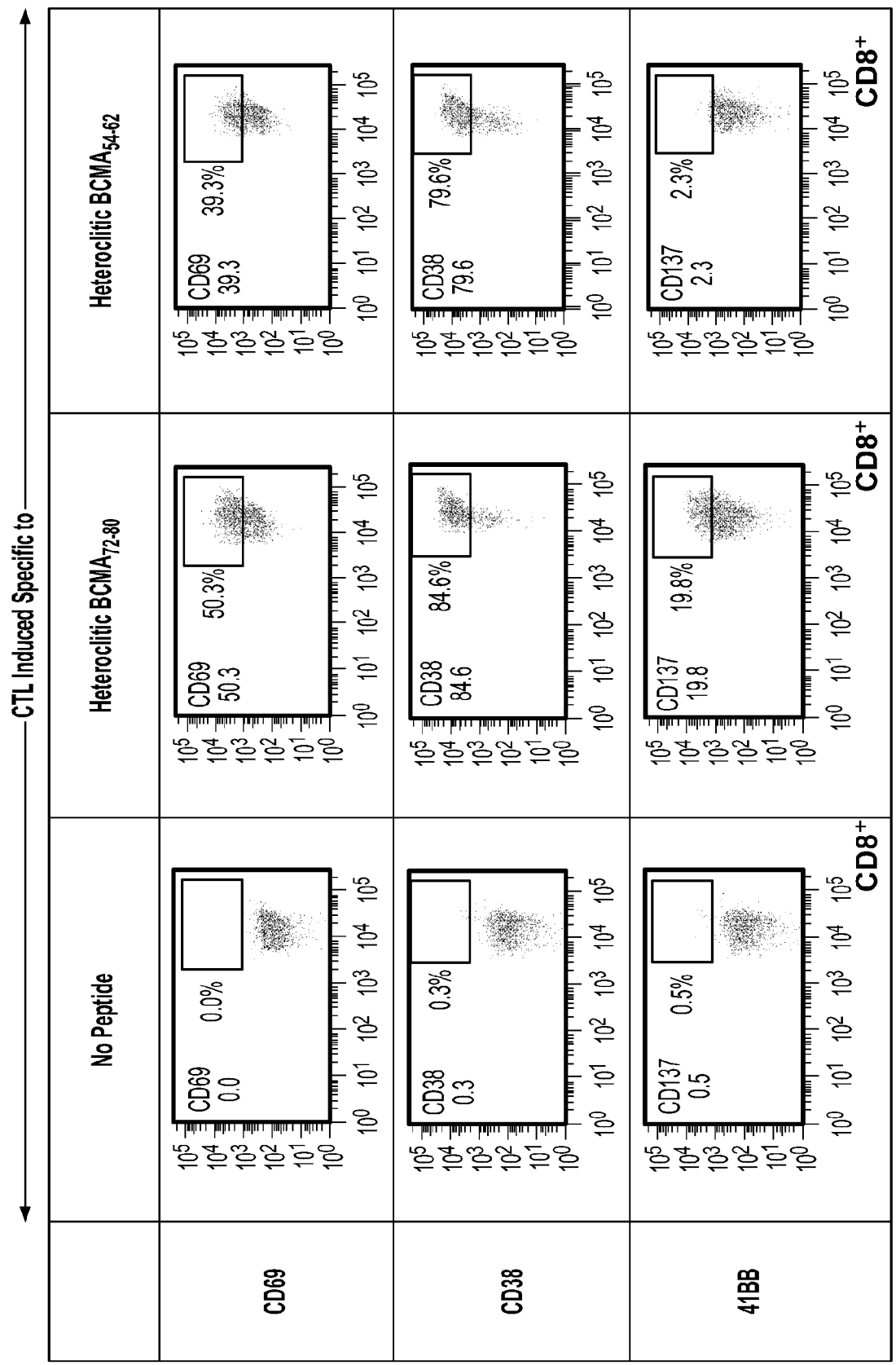
FIGS. 18A-18C show upregulation of critical T cells markers on BCMA peptide-specific CTL stimulated with heteroclitic BCMA peptides.

Phenotypic characterization of heteroclitic BCMA$_{72-80}$ peptide-specific CTL (hBCMA$_{72-80}$ CTL) or heteroclitic hBCMA$_{54-62}$ peptide-specific CTL (hBCMA$_{54-62}$ CTL) was performed after the fourth round of peptide stimulation using flow cytometry. Both CTL populations displayed increased activation marker (CD69, CD38) expression, with the highest upregulation detected on the hBCMA$_{72-80}$ CTL: CD38 increased to 80% from baseline 23%; and CD69 increased to 38% from baseline 7% (FIG. 18A). In addition, the hBCMA$_{72-80}$ CTL showed higher expression of 41BB, CD40L, OX30, and GITR co-stimulatory molecules than hBCMA$_{54-62}$ CTL (FIGS. 18B and 18C).

Figure 18B:
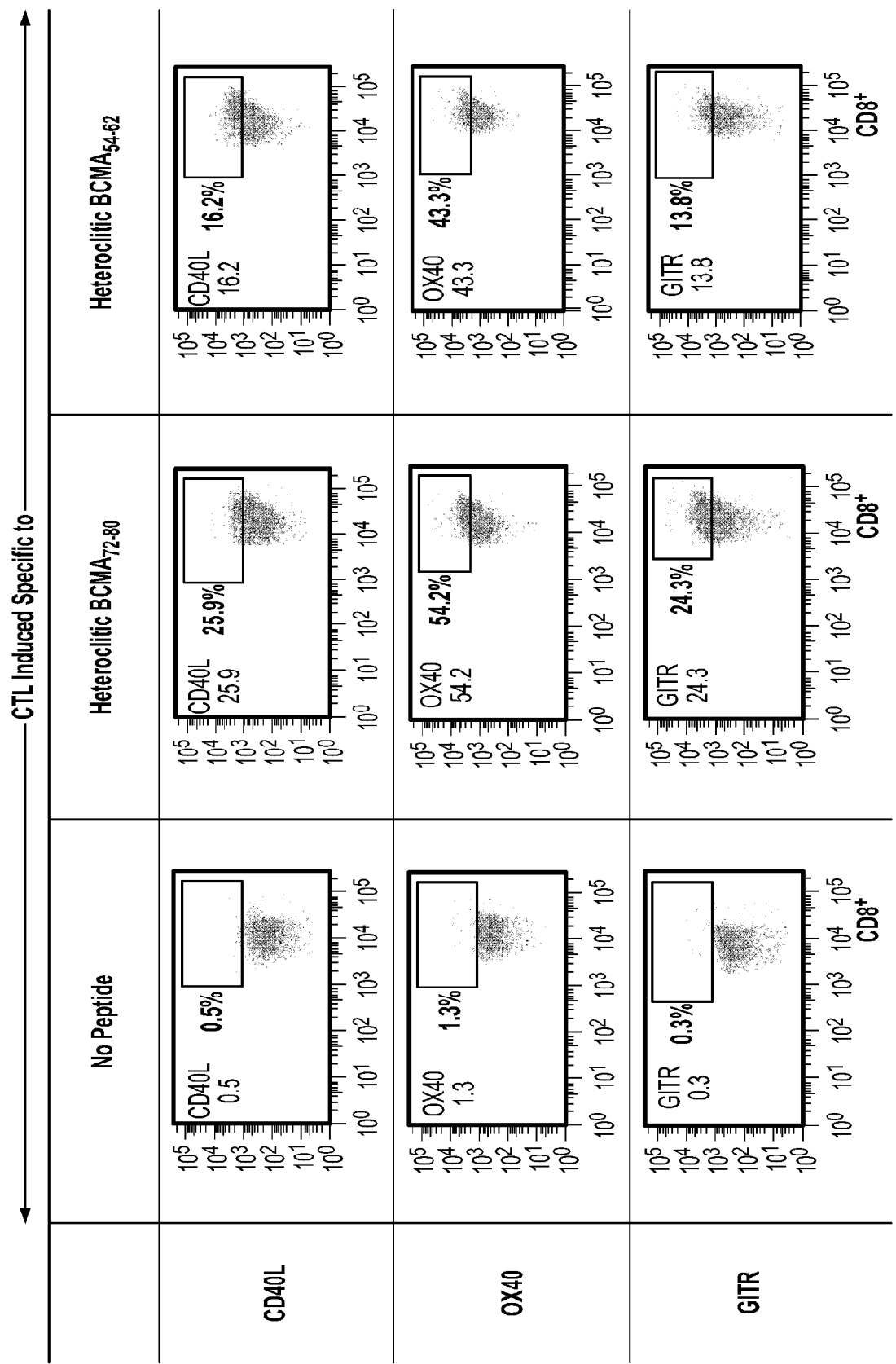
Figure 18C:
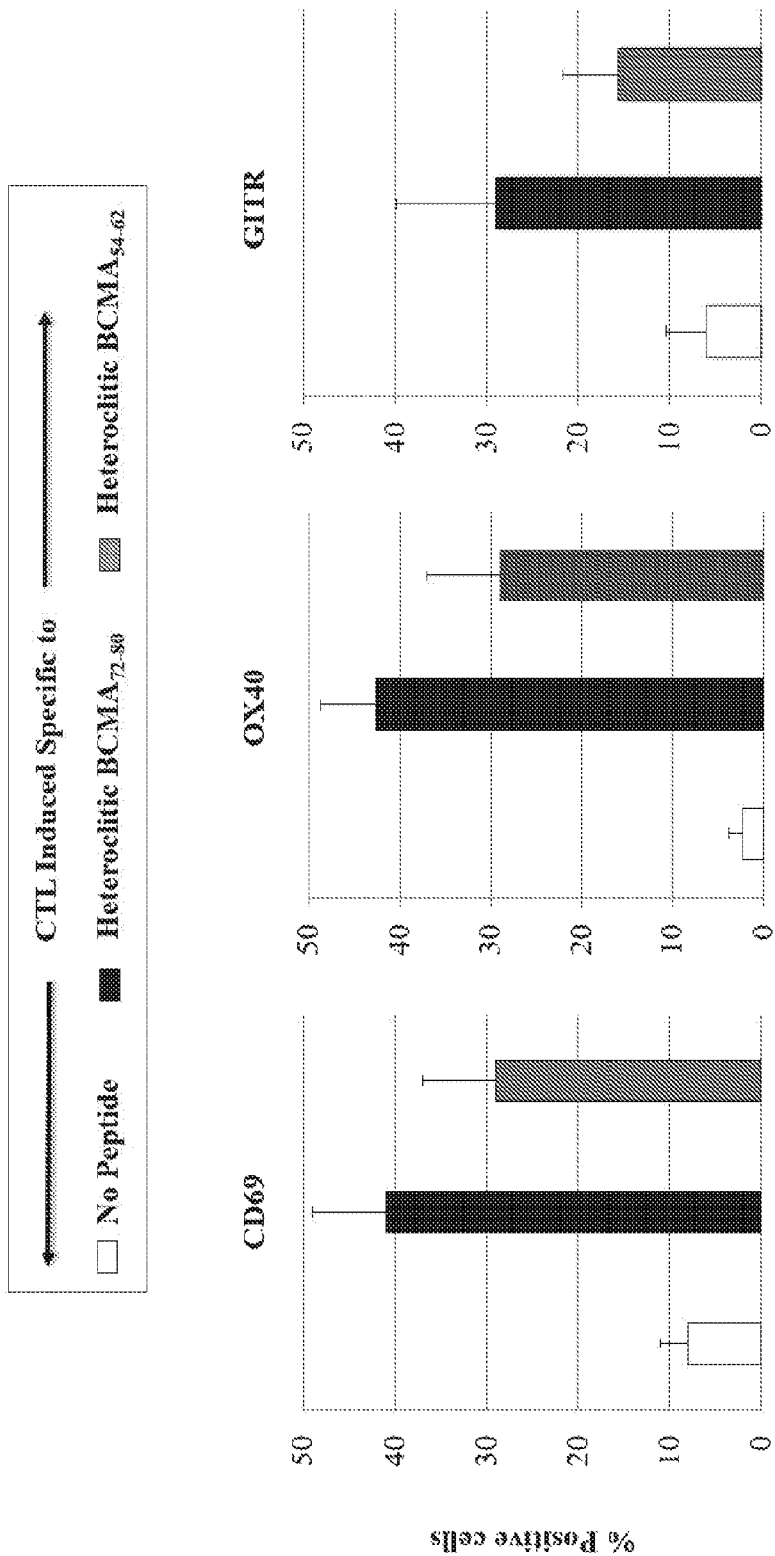

In FIGS. 18A-18C, the CD3+ T cells obtained from HLA-A2+ individuals were stimulated weekly with irradiated APC pulsed with respective heteroclitic BCMA peptide, either BCMA72-80 (YLMFLLRKI (SEQ ID NO: 13)) or BCMA54-62 (YILWTCLGL (SEQ ID NO: 14)). One week after the 4th cycle of stimulation, the CD3+CD8+ T cells were analyzed by flow cytometry. The expression of T cell activation markers (CD69, CD38) and costimulatory molecules (41BB, CD40L, OX30, GITR) were evaluated on CD8+ T cells. The results are demonstrated as a representative (FIGS. 18A and 18B) or a summary of three independent experiments using BCMA-CTL generated from different individuals (N=3) (FIG. 18C).

Heteroclitic BCMA$_{72-80}$ Specific CTL Display Antigen-Specific Anti-Tumor Activities in Response to MM Cell Lines.

Figure 19F:
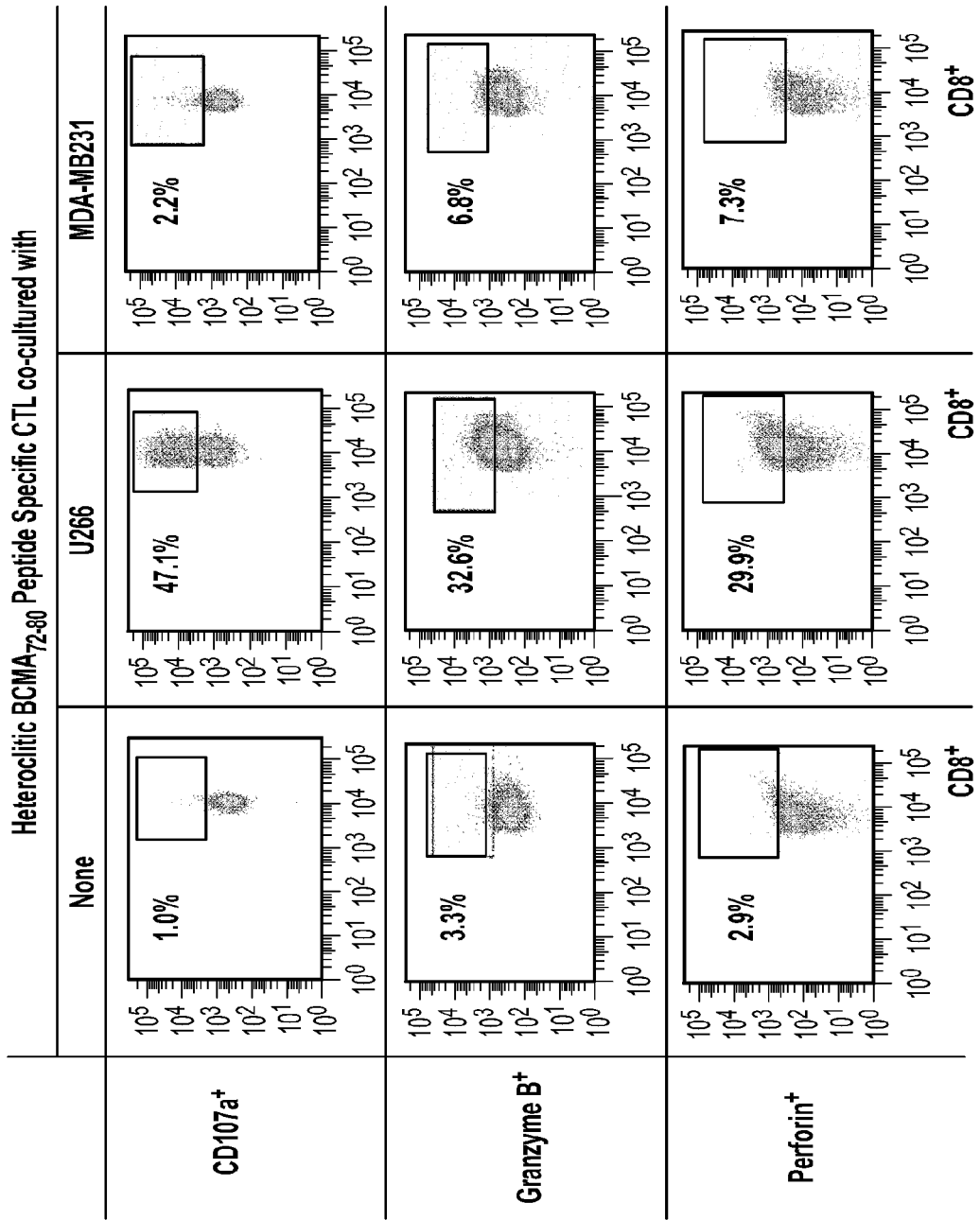
Figures 25A, 25B:
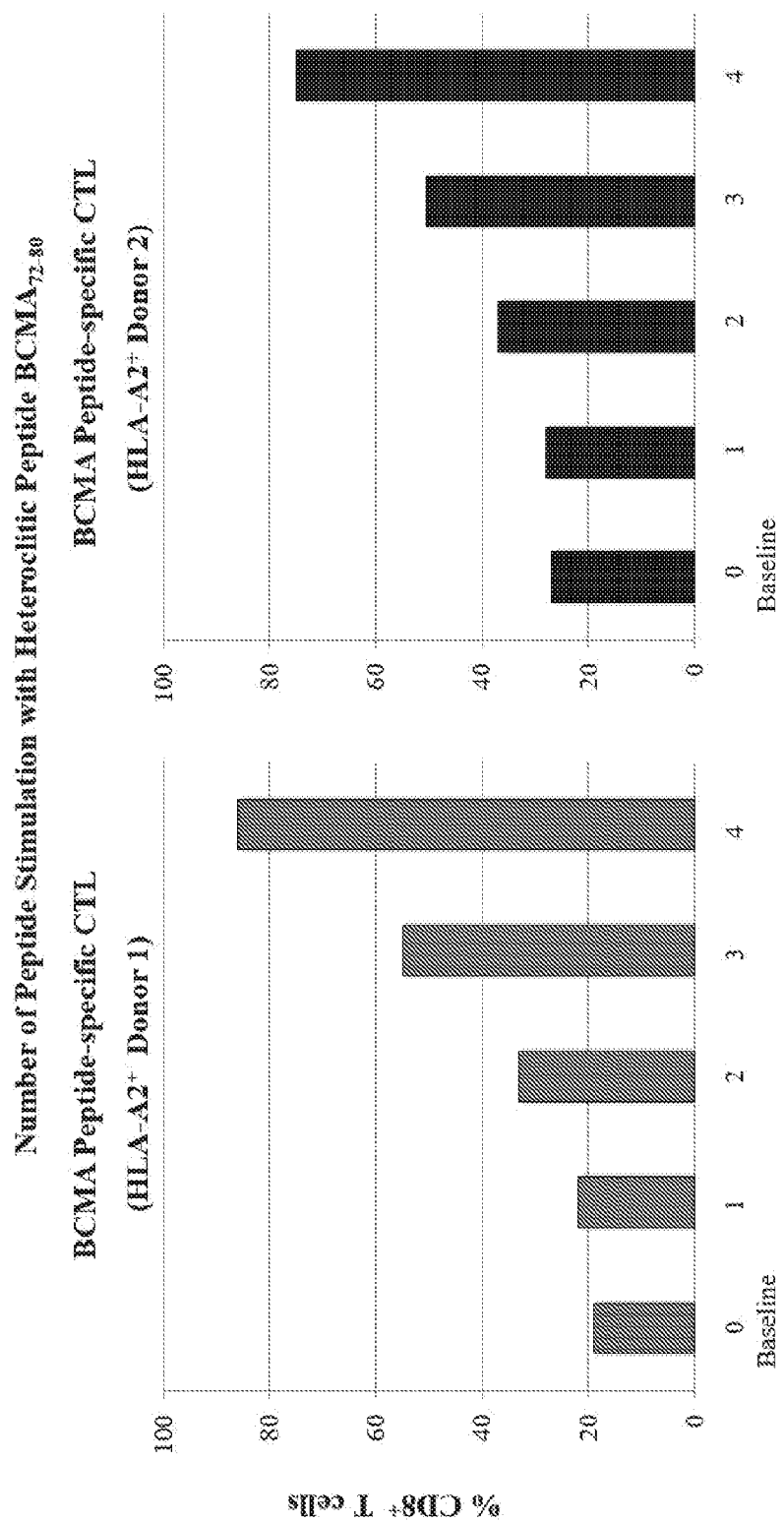
FIGS. 25A-25B. The percentage of CD3+CD8+ T cells after peptide stimulation with heteroclitic BCMA$_{72-80}$.
Figures 26A, 26B:
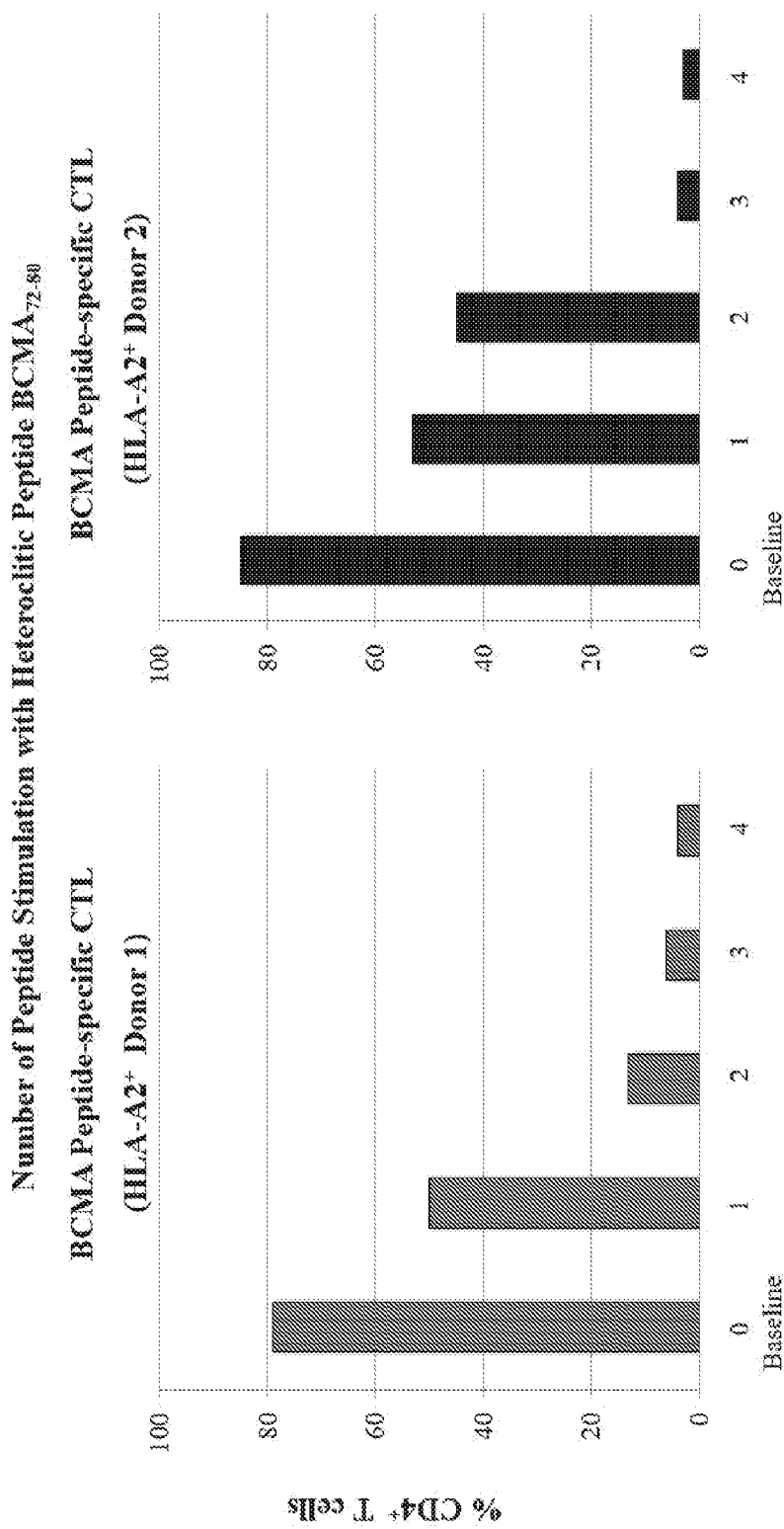
FIGS. 26A-26B. The percentage of CD3+CD4+ T cells after peptide stimulation with heteroclitic BCMA$_{72-80}$.
Figures 27A, 27B, 27C:
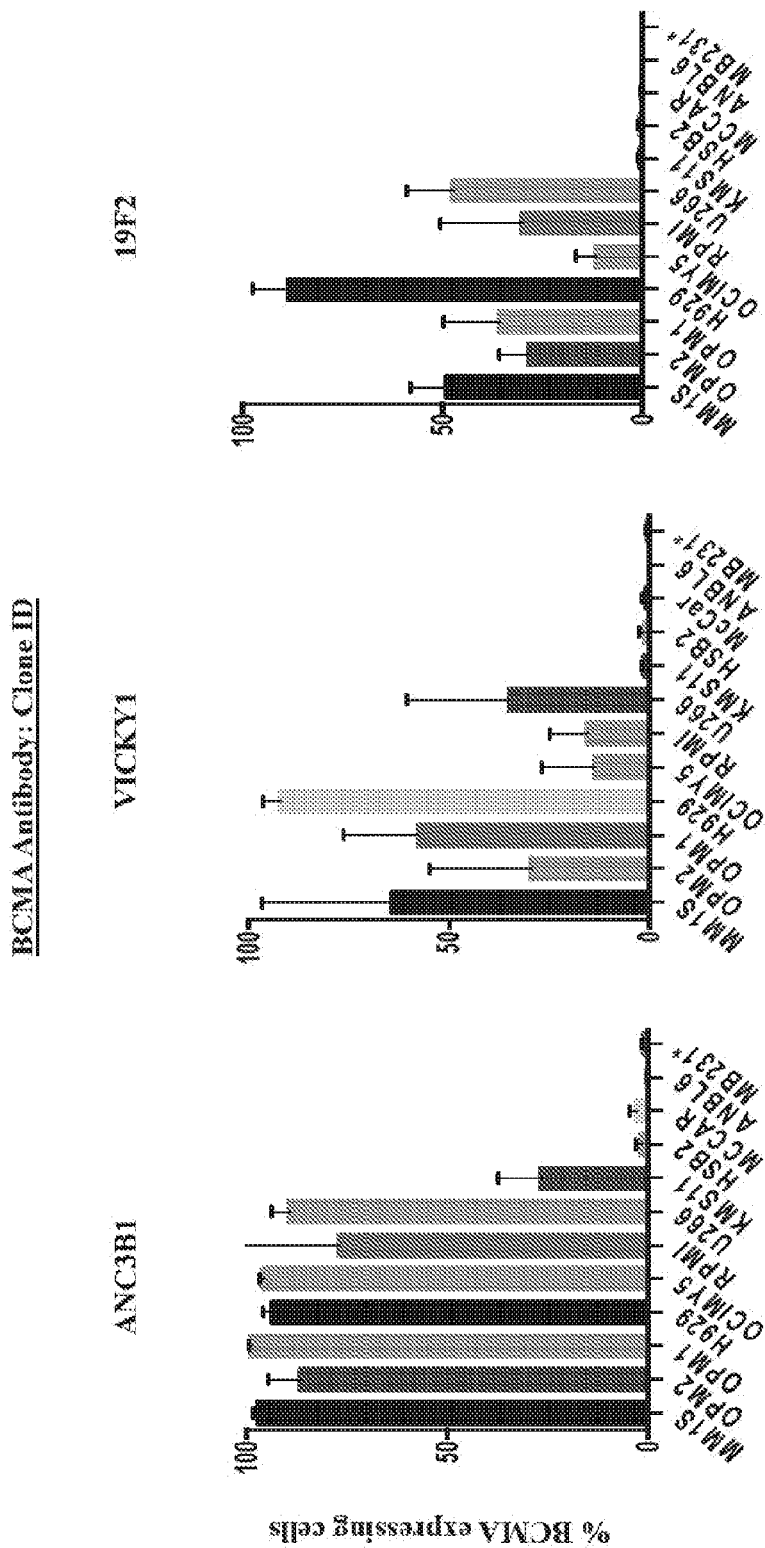
FIGS. 27A-27C show high BCMA expression on H929, MMIS, U266 and OPM1 cell lines, but not on breast cancer cell line (MDA-MB231).
Figures 28A, 28B:
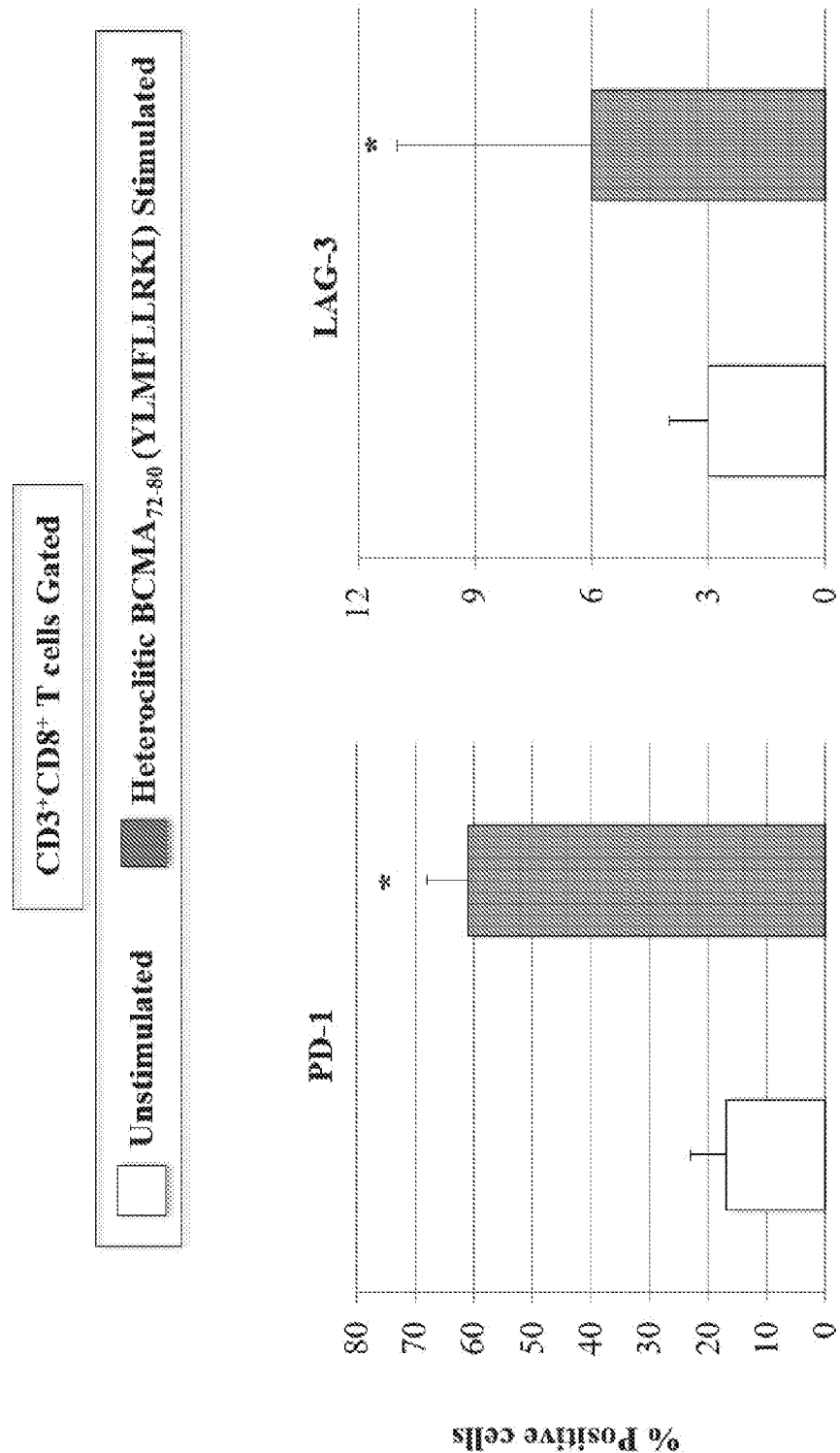
FIGS. 28A-28B show percentage of CD3+CD8+ T cells that express PD-1 and LAG-3 after peptide stimulation with heteroclitic BCMA$_{72-80}$.

The phenotype and activities of hBCMA$_{72-80}$ CTL were assessed after each round of peptide stimulation. A gradual increase in the % CD3+CD8+ T cells (FIGS. 25A-25B) and a corresponding decrease in % CD3+CD4+ T cells (FIGS. 26A-26B) was observed upon stimulation with heteroclitic BCMA$_{72-80}$ (YLMFLLRKI (SEQ ID NO: 13)) in the specific CTL (n=3) generated. In parallel, phenotype analyses of target cells stained with BCMA mAb clones (ANC3B1, VICKY1, 19F2) showed high BCMA expression on H929, MMIS, U266 and OPM1 cell lines, but not on breast cancer cell line (MDA-MB231) (FIGS. 27A-27C). In evaluation of functional activities, hBCMA$_{72-80}$ CTL showed significantly (*p<0.05) higher CD3+CD8+ T cells proliferation in response to HLA-A2+ BCMA+ U266 (49%) compared to HLA-A2− BCMA+ MM1S (7%), HLA-A2+ BCMA− MDA-MB231 (9%), or media alone (6%) (FIGS. 19A-19D; Histogram). This HLA-A2-restricted and MM-specific CD8+ CTL proliferation was consistently observed in hBCMA$_{72-80}$ CTL generated from three HLA-A2+ individuals (FIG. 19E; Bar graphs). In addition, hBCMA$_{72-80}$ CTL demonstrated increases in CD8+ T cells expressing CD107a degranulation marker (47.1%) and producing Granzyme B (32.6%) and Perforin (29.9%) in response to HLA-A2+ U266, but not to HLA-A2+ MDA-MB231 cells (FIG. 19F). Consistent results in anti-tumor activities were observed in hBCMA$_{72-80}$ CTL generated from other HLA-A2+ individuals (N=5), as measured by IFN-γ/IL-2/TNF-α production, 41BB upregulation, and CD107a degranulation against BCMA+ MM cells in an HLA-A2 restricted manner. These data further demonstrate the induction of MM-specific immune responses by heteroclitic BCMA$_{72-80}$ peptide.

In FIGS. 19A-9F, the BCMA-specific CTL generated by repeated stimulation with heteroclitic BCMA$_{72-80}$ (YLMFLLRKI (SEQ ID NO: 13)) peptide were examined for their antigen-specific and HLA-A2-restricted CD8+ T cells responses by proliferation, CD107a degranulation, Granzyme B/perforin production, IFN-γ/IL-2/TNF-α production, and 41BB upregulation in response to BCMA+ MM cells or BCMA− breast cancer cells. The results are demonstrated as a representative (FIGS. 19A-19F) or a summary of three independent experiments using BCMA-CTL generated from different individuals (N=3).

Heteroclitic BCMA$_{72-80}$ CTL Functional Immune Responses Against HLA-A2$^+$ Patient MM Cells.

Figure 20A:
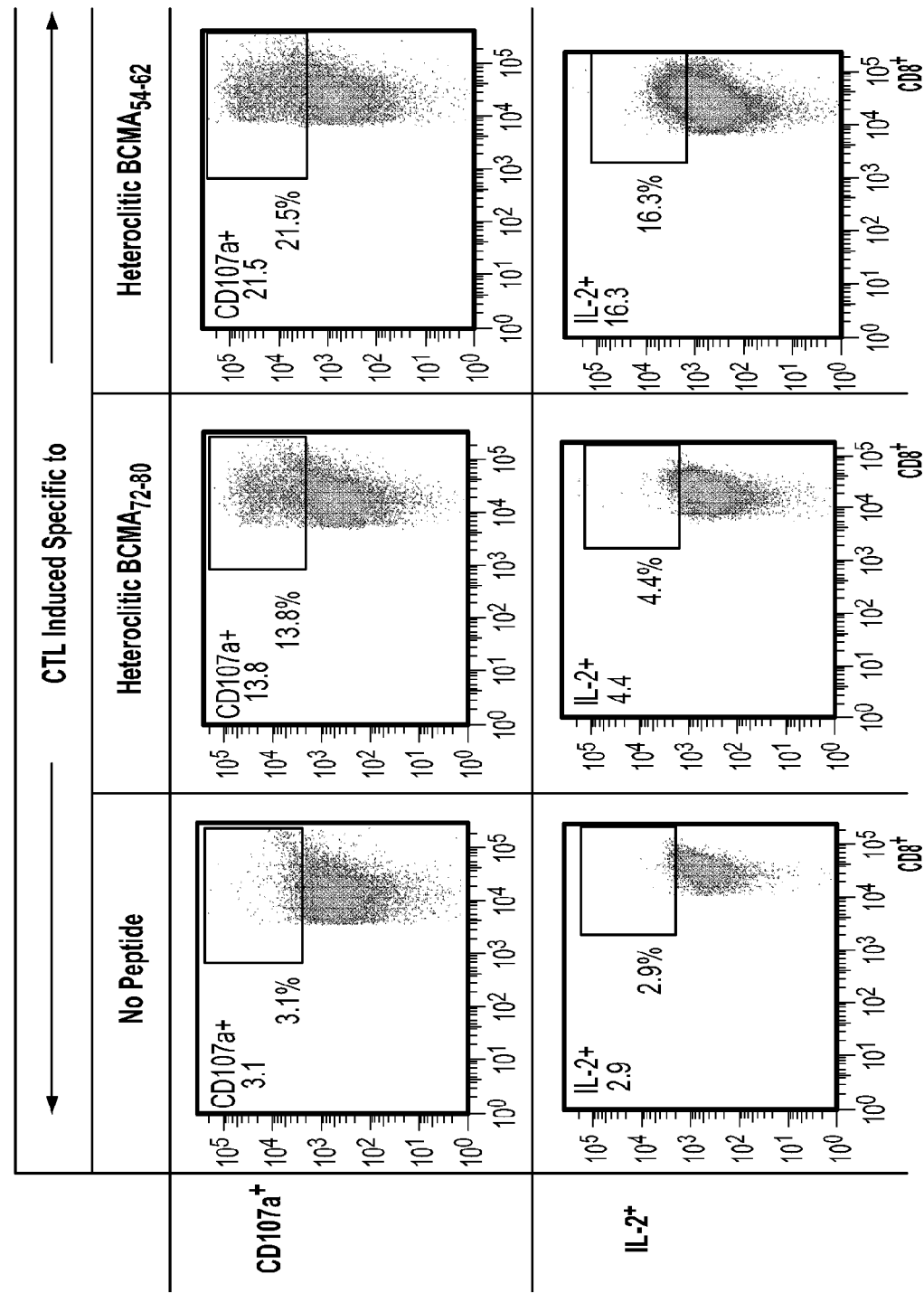
Figure 20B:
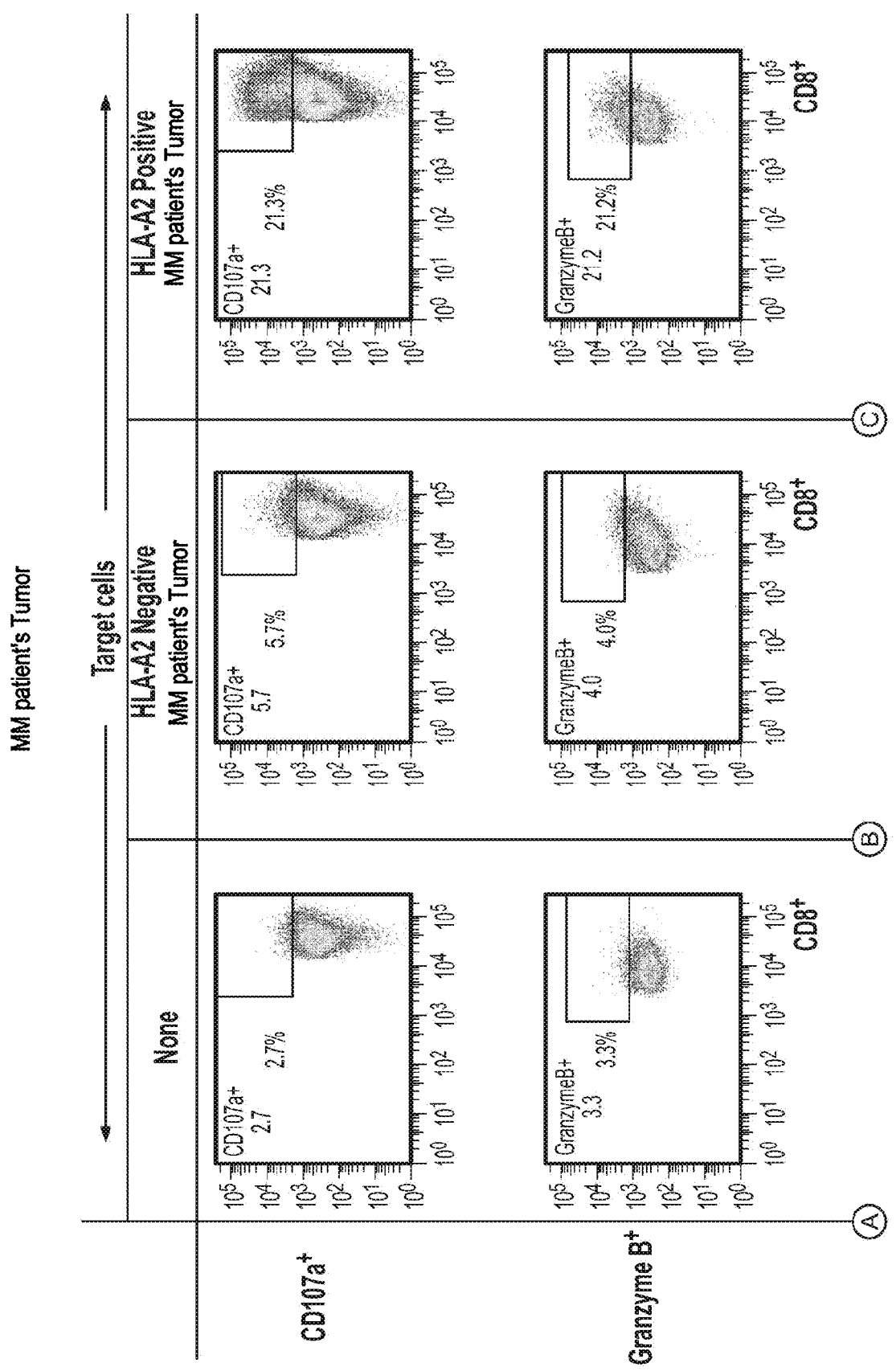

MM patients' CD138$^+$ tumor cells were utilized as target cells to evaluate BCMA-specific CTL generated with respective heteroclitic peptides. Compared to heteroclitic BCMA$_{54-62}$, BCMA$_{72-80}$ peptide evoked more robust antigen-specific CTL and anti-tumor activities against patient MM cells, as measured by CD107a degranulation (hBCMA$_{54-62}$ CTL 13.8% vs. hBCMA$_{72-80}$ CTL 21.5%) and IL-2 production (4.4% vs. 16.3%, respectively) (FIG. 20A). The hBCMA$_{72-80}$ CTL consistently demonstrated higher anti-MM activities against patient cells including CD107a degranulation, Granzyme B/IFN-γ/TNF-α upregulation (FIG. 20B), and perforin/IL-2 production (n=3) (FIGS. 20C-20H) in an HLA-A2 restricted manner. Thus, the anti-MM responses detected in the hBCMA$_{72-80}$ CTL were consistent with higher activation (CD69, CD38) and co-stimulatory molecule expression (41BB, CD40L, OX40, GITR) (FIGS. 18A-18C). These data provide additional evidence on the immunogenicity of heteroclitic BCMA$_{72-80}$ and support its potential clinical application in novel MM treatments.

In FIGS. 20A-20H, the heteroclitic BCMA peptide-specific CTL were evaluated for their functional activities against patients' MM cells. The specific activities of BCMA-CTL were measured in response to CD138$^+$ tumor cells obtained from HLA-A2 negative or HLA-A2 positive MM patients in relative to baseline response (stimulated with no tumor cells). The results are demonstrated as a representative (FIG. 20A, FIG. 20B) or a summary of three independent experiments using BCMA specific-CTL generated from different individuals (N=3) (FIGS. 20C-20H).

Heteroclitic BCMA$_{72-80}$ Specific CTL are Enriched for CD8$^+$ Tetramer$^+$ T Cells with Robust Anti-MM Activities.

Figure 21A:
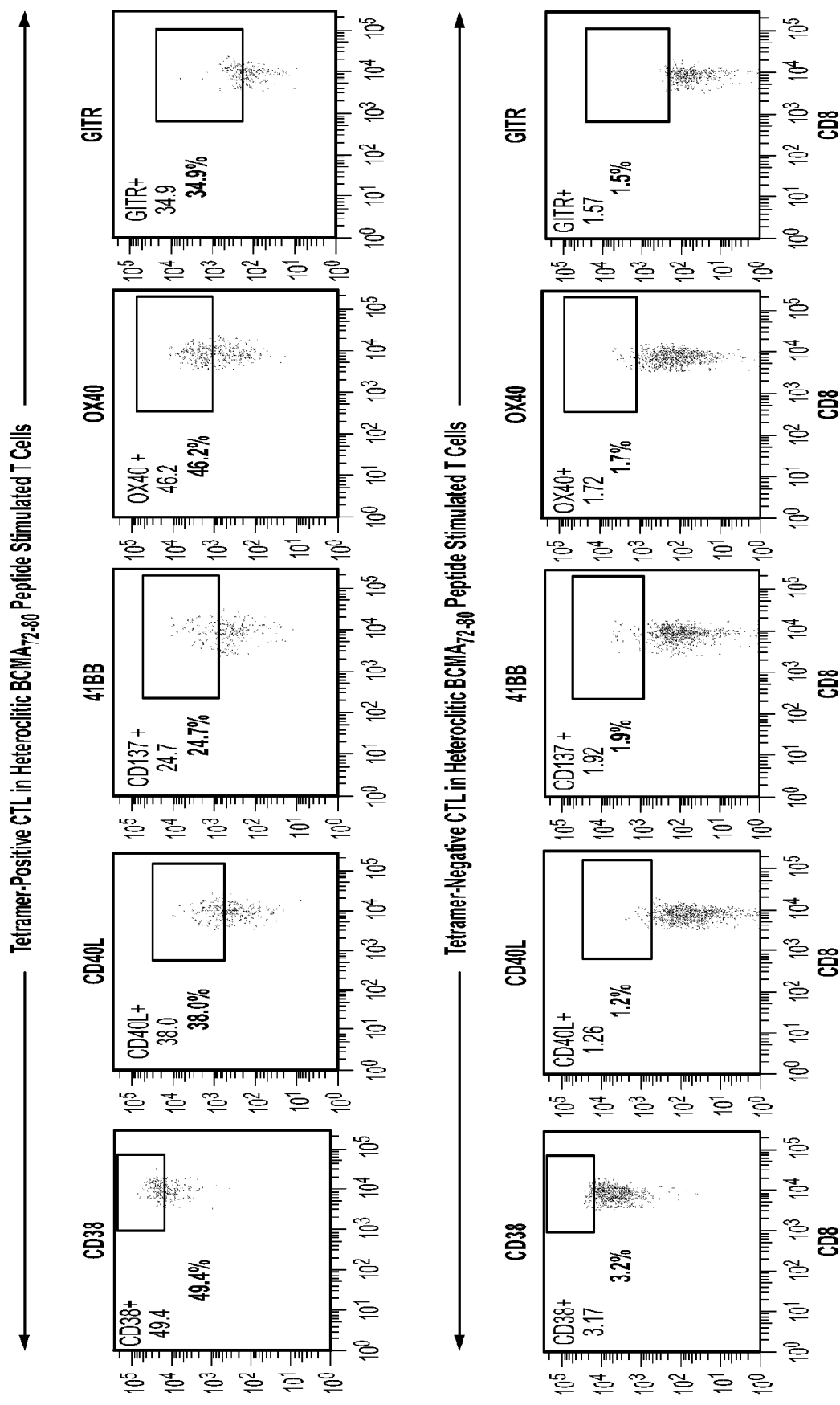
FIGS. 21A-21C. BCMA$_{72-80}$ specific Tetramer$^+$ CTL displaying distinct phenotypes and high level of anti-tumor activities against MM cells.
Figure 21B:
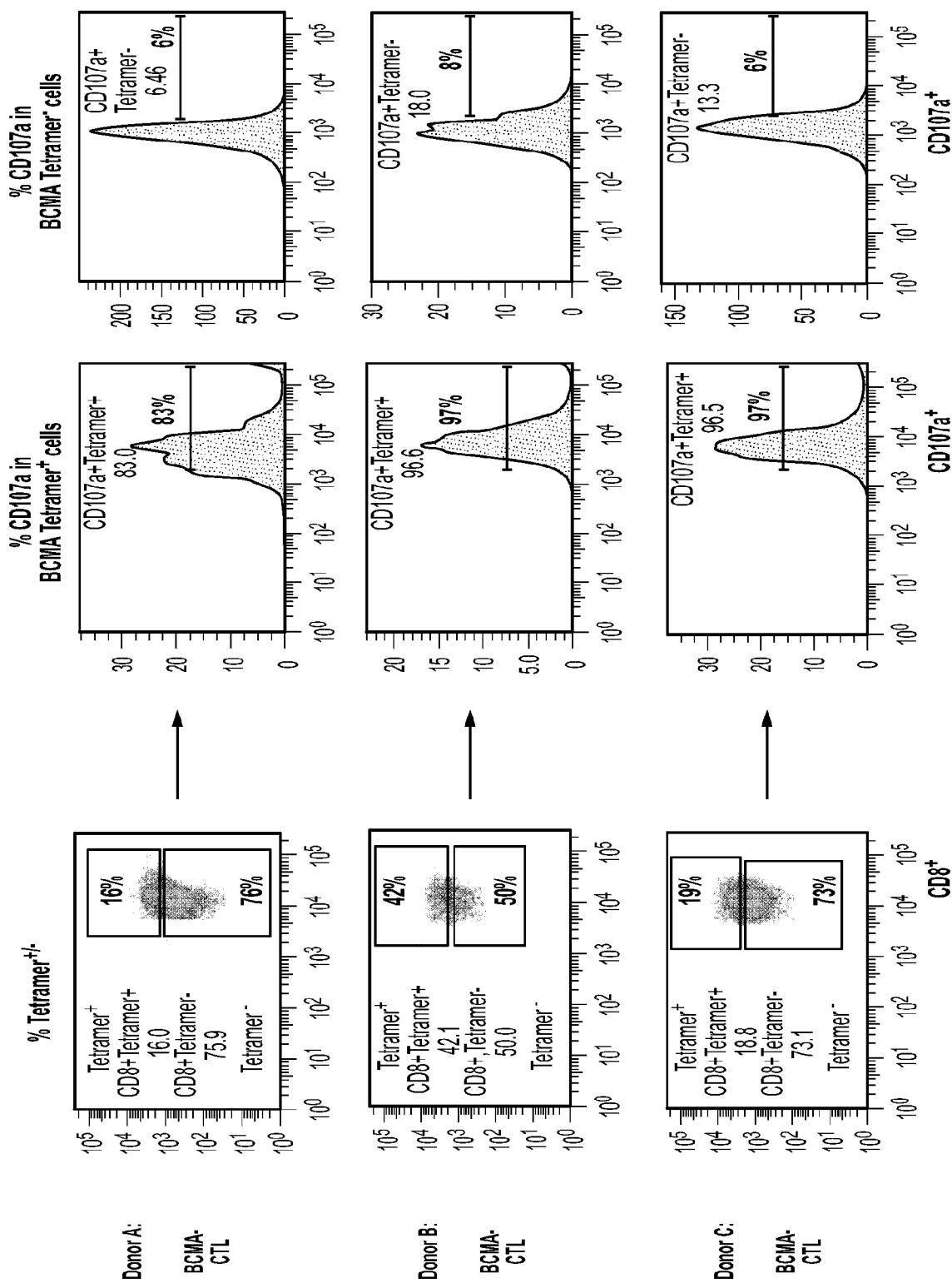
Figure 21C:
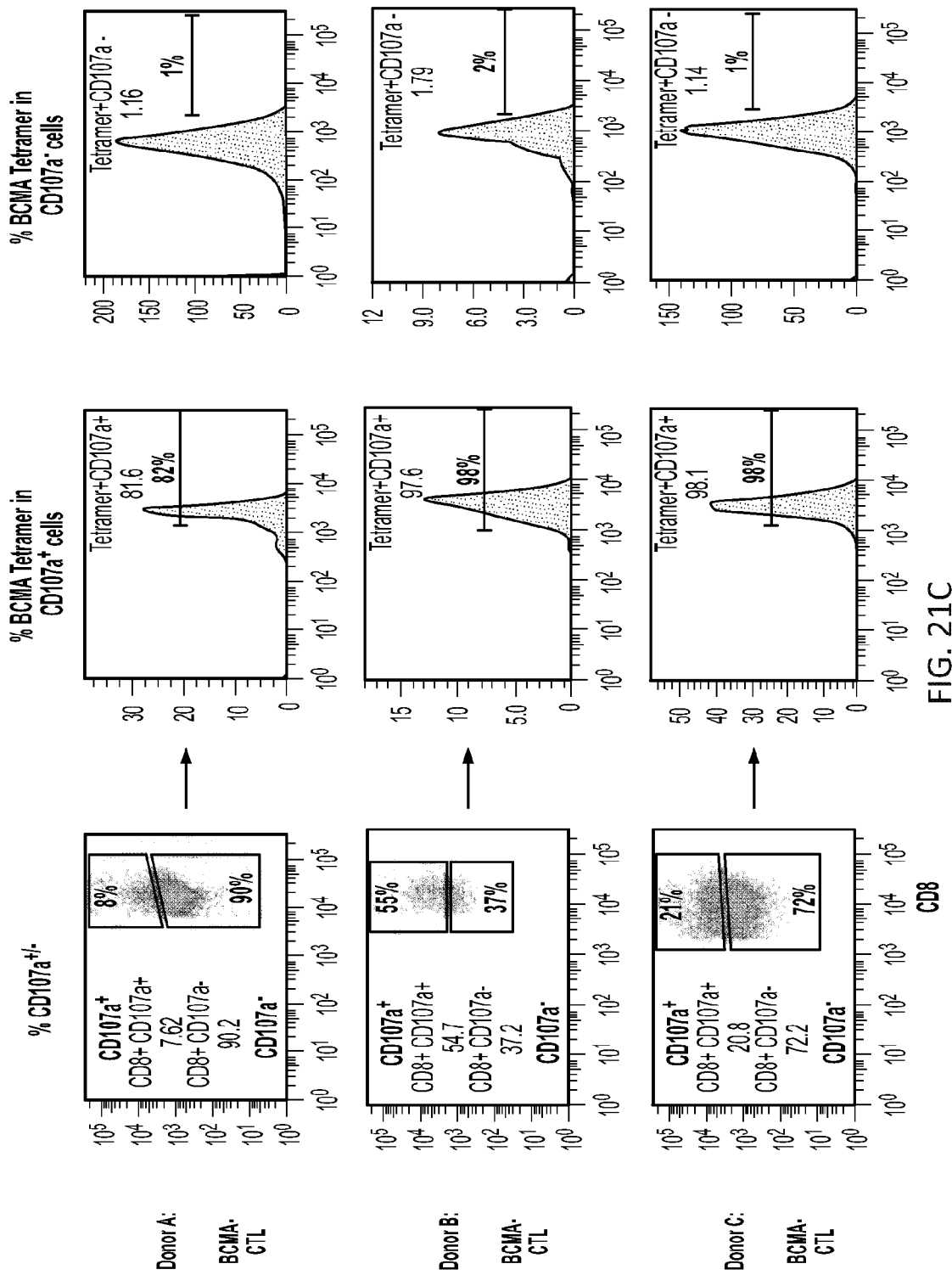

The hBCMA$_{72-80}$ CTL were further characterized for their phenotypes and anti-tumor activities within the Tetramer-positive population. The Tetramer-positive CTL displayed significantly increased the CD8$^+$ T cells with activation (CD38$^+$: Tetramer$^+$ vs. Tetramer$^-$: 49.4% vs. 3.2%) and co-stimulatory molecule expression (CD40L$^+$: 38.0% vs. 1.2%, 41BB: 24.7% vs. 1.9%, OX40: 46.2% vs. 1.7%, and GITR: 34.9% vs. 1.5%) (FIG. 21A). The hBCMA$_{72-80}$ CTL generated from several HLA-A2$^+$ individuals (n=3) consistently demonstrated higher levels of anti-MM activities against U266 MM cells by Tetramer-positive cells (83%, 97%, 97%; Donor A, B or C BCMA-CTL), as compared to Tetramer-negative cells (6%, 18%, 13%; Donor A, B or C BCMA-CTL) (FIG. 21B). The frequency of Tetramer-positive cells within either CD107a-positive or CD107a-negative CD8$^+$ CTL was further evaluated. It was observed a significantly higher frequency of Tetramer$^+$ cells within the degranulating CD107a-positive CTL (82%, 98%, 98%; Donor A, B or C) compared to CD107a-negative CTL (1%, 2%, 1%; Donor A, B or C BCMA-CTL) (FIG. 21C). These results therefore confirm that the specific anti-MM activities of the hBCMA$_{72-80}$ CTL are contained within the BCMA peptide specific Tetramer-positive cells, which display upregulation of CTL activation and co-stimulatory molecules.

In FIGS. 21A-21C, the heteroclitic BCMA$_{72-80}$ recognizing Tetramer-positive CTL or non-recognizing Tetramer-negative CTL were analyzed for expression of CD38, CD40L, 41BB, OX40 and GITR on CD8$^+$ T cells (FIG. 21A). Anti-tumor activities of the heteroclitic BCMA$_{72-80}$-specific CTL (N=3) were further characterized by measuring CD107 upregulation within Tetramer-positive CTL or Tetramer-negative CTL subset (FIG. 21B); and by evaluating the status of Tetramer-positivity within CD107a-positive CTL or CD107a-negative CTL (FIG. 21C).

Heteroclitic BCMA$_{72-80}$ Peptide Induces MM-Specific Memory CD8$^+$ CTL.

Figure 22A:
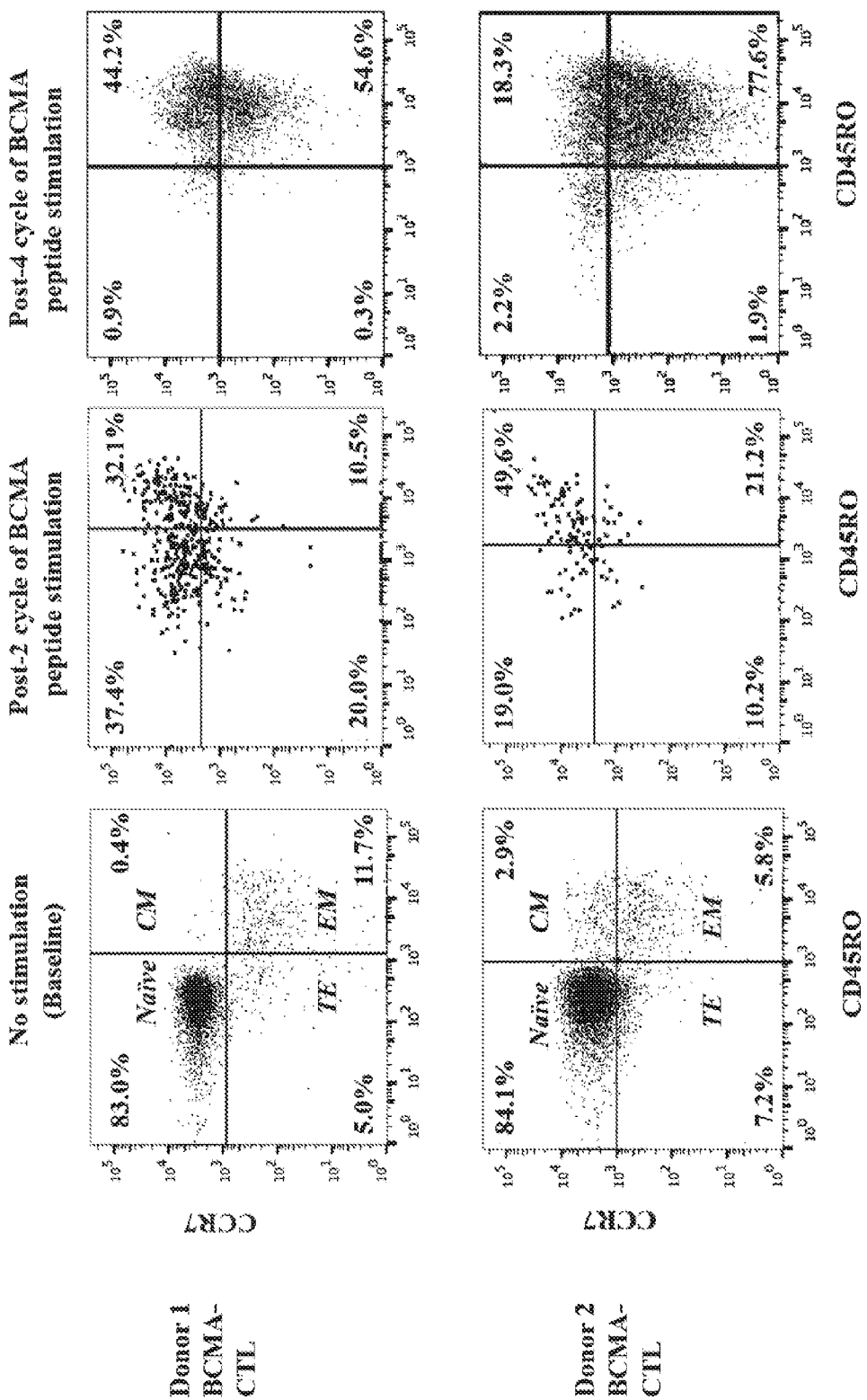
FIGS. 22A-22E. Differentiation of memory CD8$^+$ T cell of BCMA-specific CTL upon the stimulation with heteroclitic BCMA$_{72-80}$ peptide.
Figures 22B, 22C:
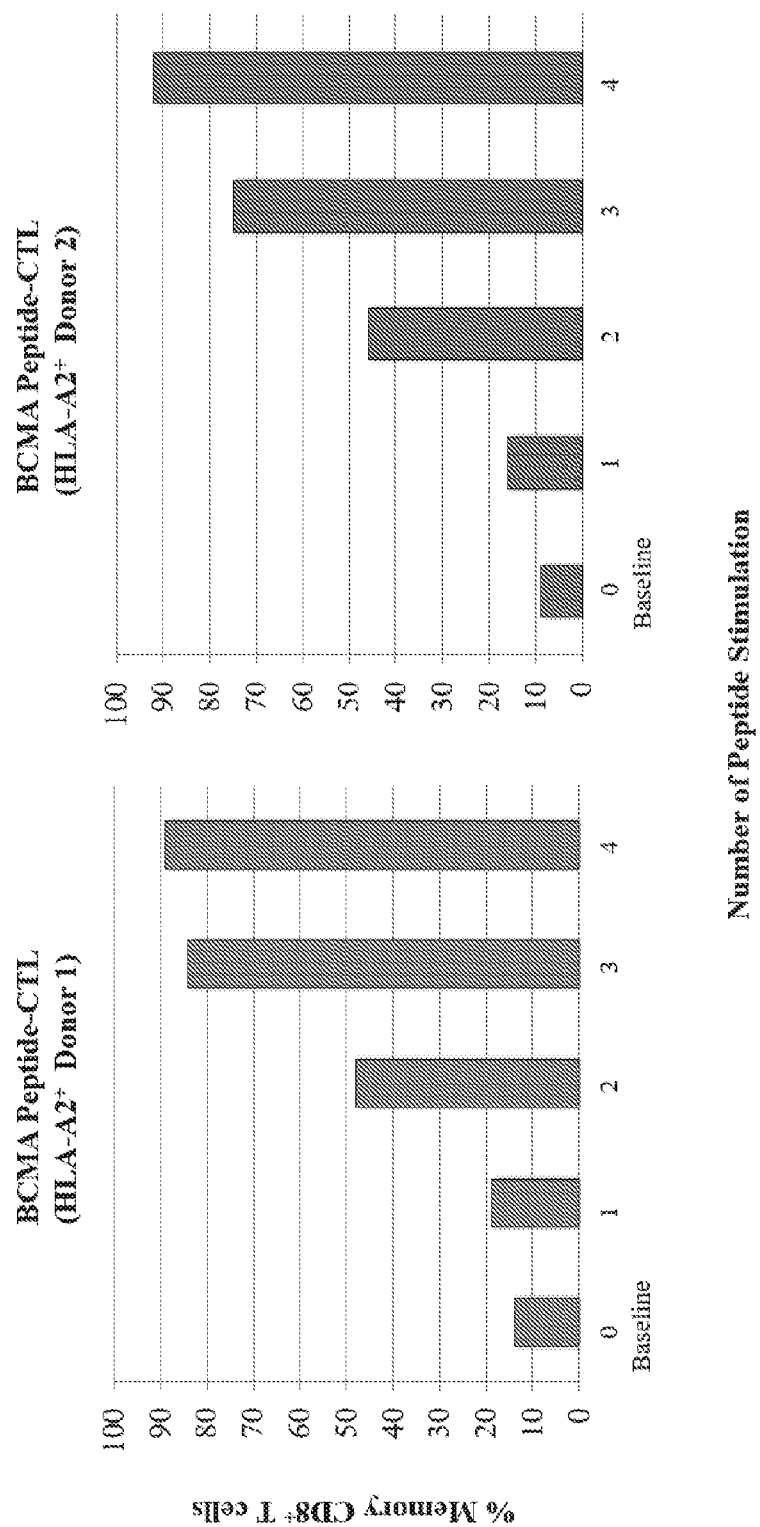
Figures 22D, 22E:
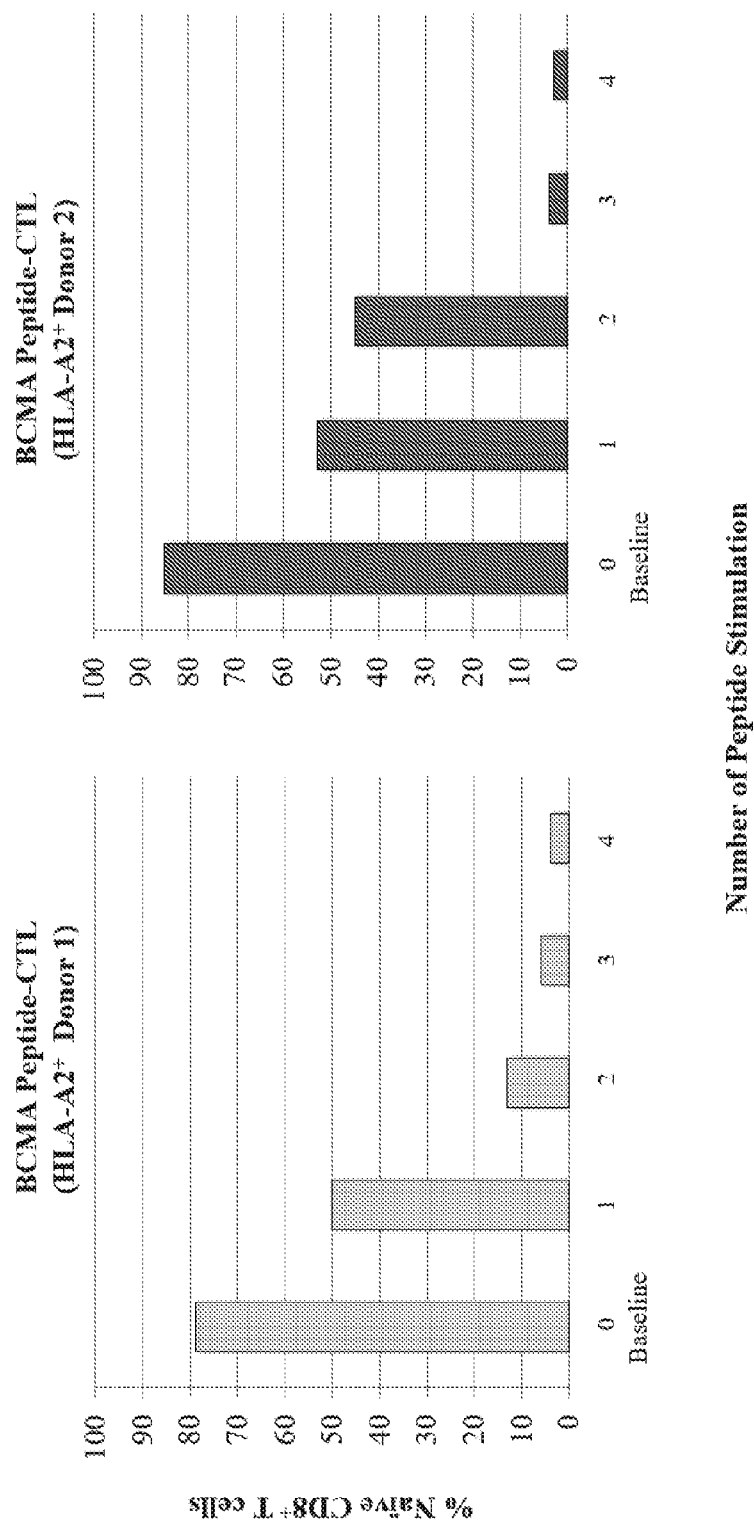

To characterize BCMA-specific CTL activities, experiments were performed to evaluate the composition of naïve: memory CTL subsets post-2 and post-4 cycles of peptide stimulation, compared to baseline. A gradual progressive phenotypic changes were detected within CD8$^+$ T cells: progressing from naïve (CD45RO$^-$CCR7$^+$) at baseline [Donor 1—Naïve: 83.0%, CM: 0.4%, Donor 2—Naïve: 84.1%]; to central memory (CM; CD45RO$^+$CCR7$^+$) after 2 cycles of peptide stimulation [Donor 1—Naïve: 37.4%, CM: 32.1%, Donor 2—Naïve: 19.0%, CM: 49.6%]; and then to effector memory (EM; CD45RO$^+$CCR7$^-$) CTL after 4 cycles of stimulation (Donor 1—CM: 44.2%, EM: 54.6%, Donor 2—CM: 18.3%, EM: 77.6%) (FIG. 22A). Overall, memory CD8$^+$ CTL development was gradually increased following each round (post-1, 2, 3, 4 cycles) of heteroclitic BCMA$_{72-80}$ peptide stimulation (FIG. 22B-22C), associated with a corresponding decrease in naïve T cells (FIG. 22D-22E). These results therefore demonstrate induction and gradual development of memory CTL upon the stimulation of T cells with heteroclitic BCMA$_{72-80}$ peptide.

In FIG. 22A-22E, the naïve: memory phenotype of heteroclitic BCMA$_{72-80}$ CTL (Donor 1, Donor 2) were analyzed at baseline (no peptide stimulation) or one week after each cycle of peptide stimulation. The pattern of phenotype changes, differentiation from naïve into memory CD8$^+$ T cells, and expansion of memory CTL were demonstrated in dot-plots (FIG. 22A) and bar graphs (FIGS. 22B-22E) after each cycle of BCMA peptide stimulation.

Central Memory hBCMA$_{72-80}$ CTL Demonstrate the Greatest Anti-MM Activities

The specific memory T cell subsets within BCMA-specific CTL generated from eight (N=8) different HLA-A2$^+$ individuals were next characterized for their anti-MM activities. Compared to CD45RO$^-$ non-memory CTL, CD45RO$^+$ memory CTL demonstrated increased CD107a degranulation in response to HLA-A2$^+$ U266 MM cells (non-memory vs. memory: 7.25% vs. 28.2%) and HLA-A2$^+$ McCAR MM cells (non-memory vs. memory: 4.14% vs. 13.2%) (FIG. 23A; Donor A BCMA-CTL). The hBCMA$_{72-80}$ specific Tetramer$^+$ cells were mainly and consistently showed the CM phenotype in BCMA-CTL generated from different individuals (% CM within Tetramer$^+$ cells—Donor B: 88.2%, Donor C: 97.4%, Donor D: 100%) (FIG. 23B). The CM CTL were also evaluated for their functional activities against U266 MM cells. Importantly, the level of CD107a degranulation was directly associated with the frequency of CM cells (% CM within CD107a$^+$ cells—Donor E: 81.0%, Donor F: 82.6%, Donor G: 67.0%, Donor H: 41.5%) (FIG. 23C). In addition, the high responders (Donor E, Donor F) showing higher anti-MM activities displayed increased frequency of BCMA peptide-specific CM CTL compared to mid level responder (Donor G) or low level responder (Donor H). These results thus further indicate the distinct peptide-specificity and anti-MM activities induced by the CM subset generated by the heteroclitic BCMA$_{72-80}$ peptide.

Figure 23A:
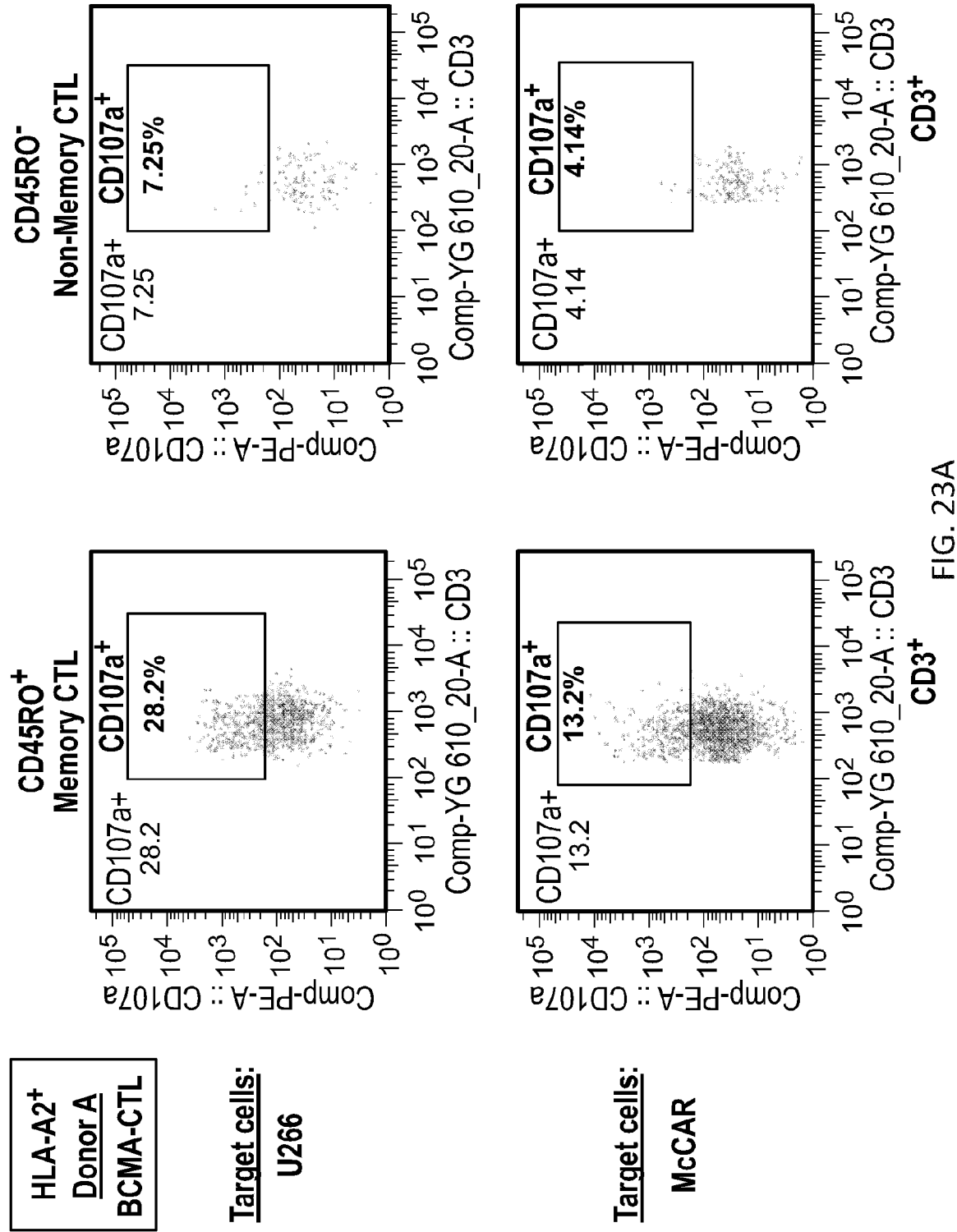
FIGS. 23A-23C. Characterization of high anti-tumor activities by BCMA specific memory CTL (FIG. 23A) and the highest levels by central memory CTL (FIG. 23B, FIG. 23C).
Figure 23B:
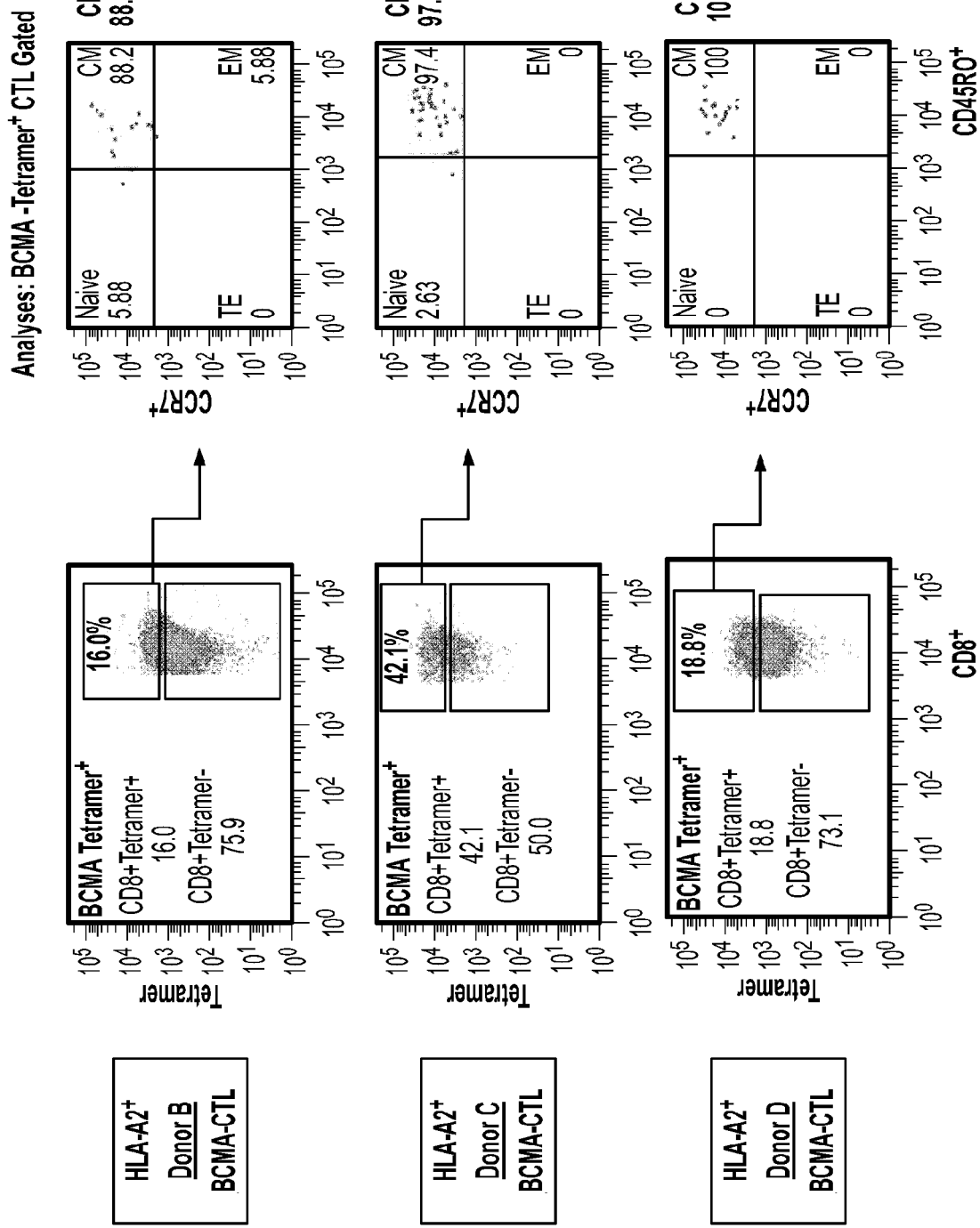
Figure 23C:
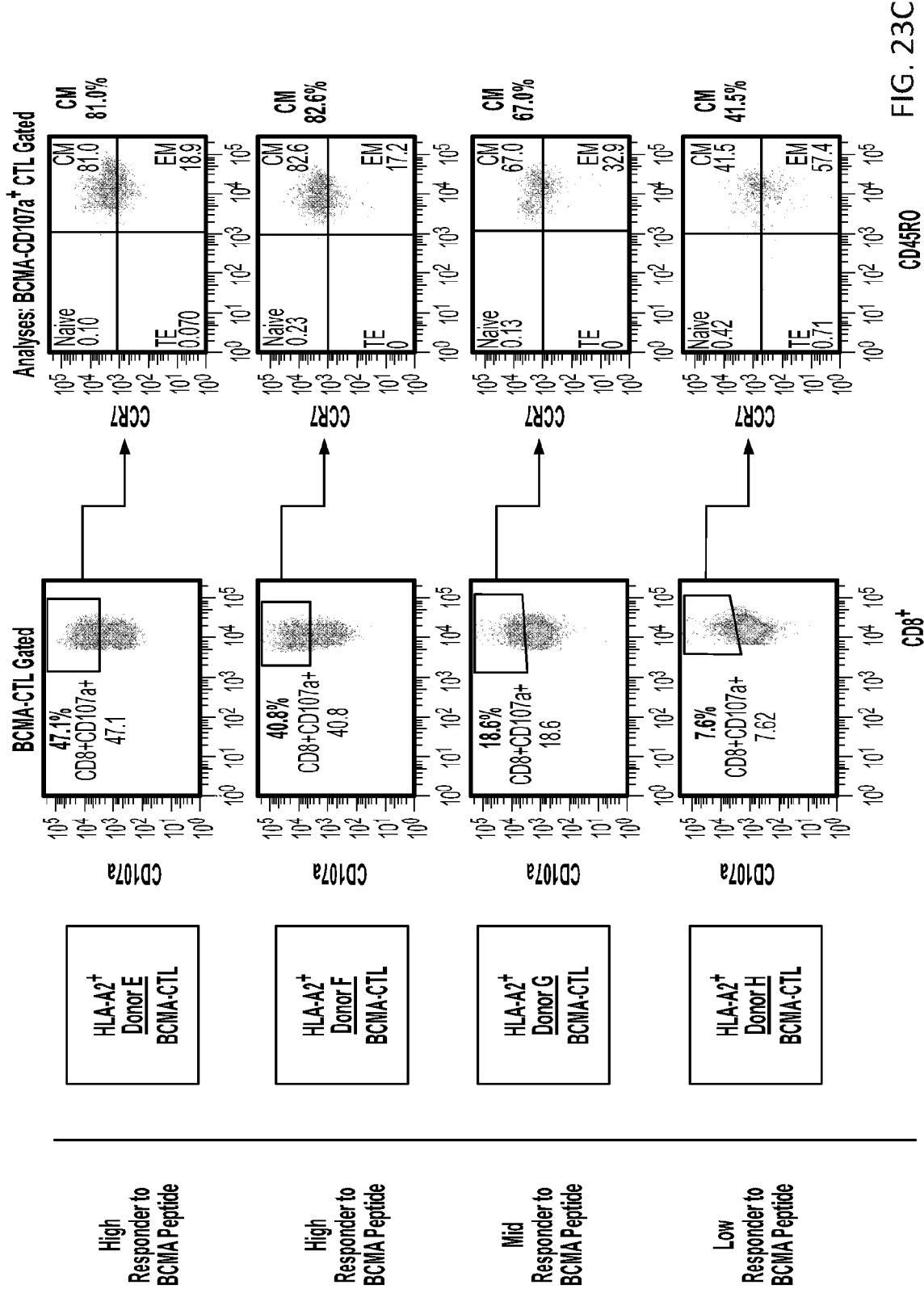

In FIGS. 23A-23C, anti-MM activity of heteroclitic BCMA$_{72-80}$ CTL was evaluated within the naïve: memory CD3$^+$CD8$^+$ T cell subsets in response to HLA-A2$^+$ MM cells (U266, McCAR; FIG. 23A). The frequency of central memory CD8$^+$ T cells was analyzed in different CTL subsets of heteroclitic BCMA$_{72-80}$ CTL (N=3); within Tetramer-positive or Tetramer-negative CTL subsets (FIG. 23B) and within CD107a-positive or CD107a-negative CTL subsets (FIG. 23C).

Inhibition of LAG3 or Stimulation of OX40 Enhances Proliferation and Anti-MM Activities of hBCMA$_{72-80}$ CTL Finally, experiments were performed to characterize the specific T cell subset of BCMA-CTL which are highly responsive to MM cells. The CD8$^+$ T cell subset was gated, demonstrating HLA-A2-restricted MM specific CTL proliferation, and their Naïve: Memory subsets were characterized. The most robust responding and highest proliferating hBCMA$_{72-80}$ CTL to U266 MM cells were mainly within the CM subset (Donor 1: 97.4%, Donor 2: 100%) (FIG. 24A), confirming the major role of CM subset within BCMA antigen-specific CTL in anti-MM activities. Next, experiments were performed to investigate the impact of a checkpoint inhibitor (anti-LAG3) or immune agonist (anti-OX40) on these memory T cells. The hBCMA$_{72-80}$ CTL treated with either anti-LAG3 or anti-OX40 demonstrated enhanced cytotoxic activity, especially by memory CTL against HLA-A2$^+$ U266 MM cells (Untreated 28.2% vs. anti-LAG3 treated 35.8% vs. anti-OX40 treated 39.5%); and against HLA-A2$^+$ McCAR MM cells (Untreated 13.2% vs. anti-LAG3 treated 14.5% vs. anti-OX40 treated 20.0%) (FIG. 24B). Interestingly, the checkpoint inhibitor and immune agonist did not induce enhance the anti-MM responses of non-memory cells within BCMA-CTL. Lastly, the beneficial effect of anti-LAG3 and anti-OX40 was further investigated within CM and EM subsets of hBCMA$_{72-80}$ CTL. Either treatment induced greater impact on BCMA-specific CM cells compared to EM cells, evidenced by higher CD107a degranulation in response to anti-LAG3 or anti-OX40 treatment (FIG. 24C). These results therefore support the utility of anti-LAG3 or anti-OX40 antibody in combination with hBCMA$_{72-80}$ peptide induced CTL to further enhance anti-MM activities within the BCMA-specific CM subset.

Figure 24A:
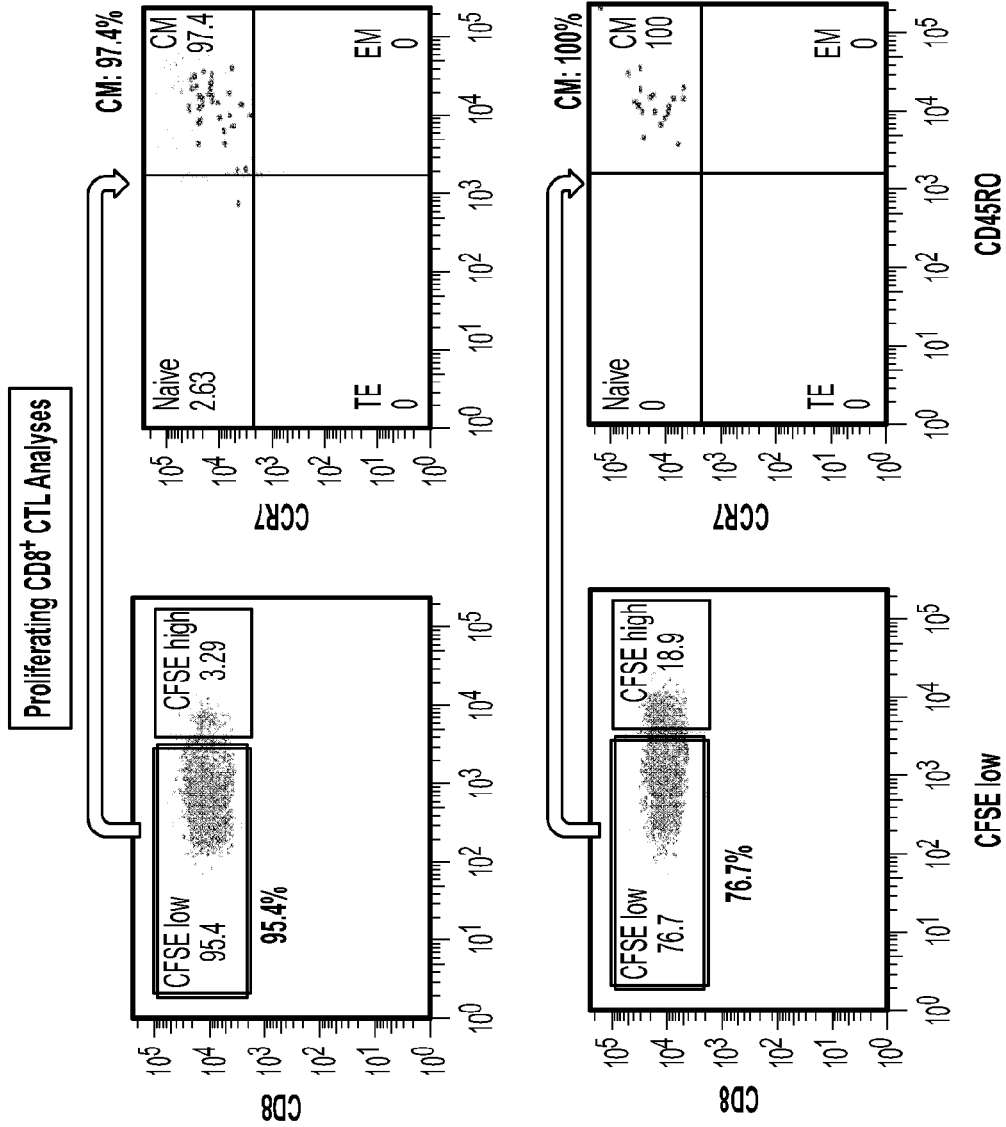
FIG. 24A. The results of BCMA peptide-specific CTL co-cultured (7 days) with 25 U266 cells.
Figure 24B:
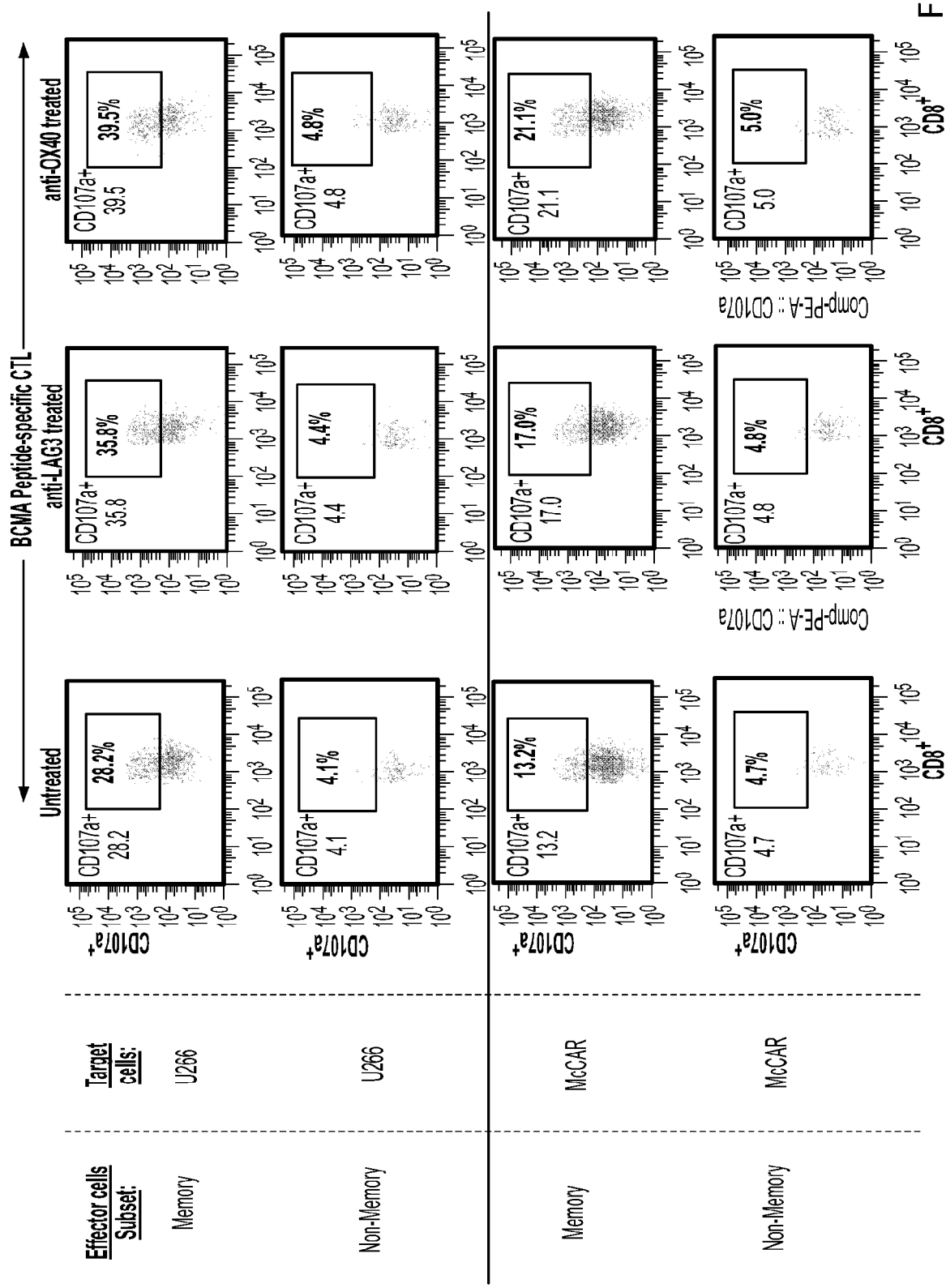
FIGS. 24B-24C. Enhanced anti-myeloma activities of memory CD8+ T cells of heteroclitic BCMA72-80 CTL [generated from one HLA-A2+ individual] in treatment with anti-LAG3 or anti-OX40.
Figure 24C:
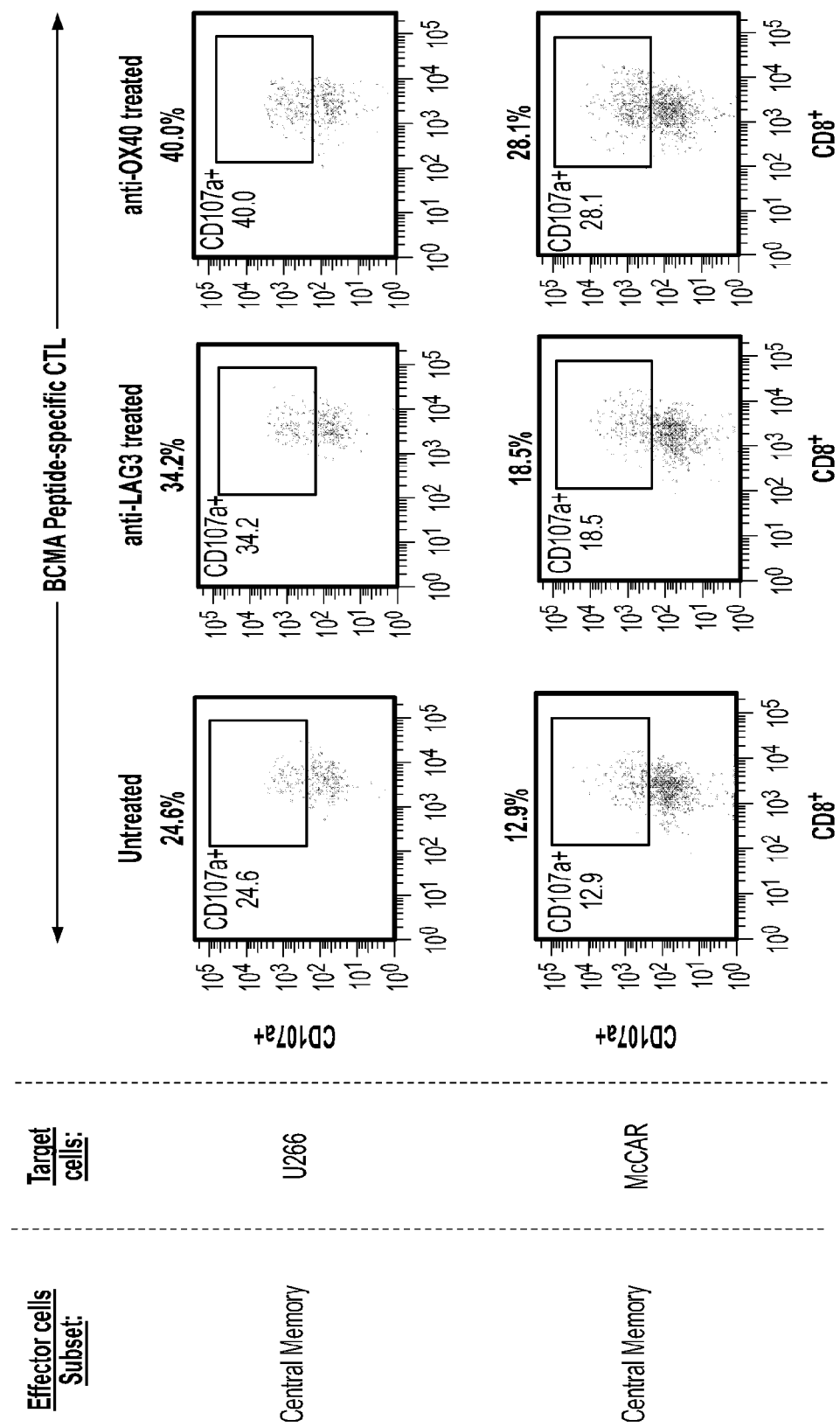
Figure 24D:
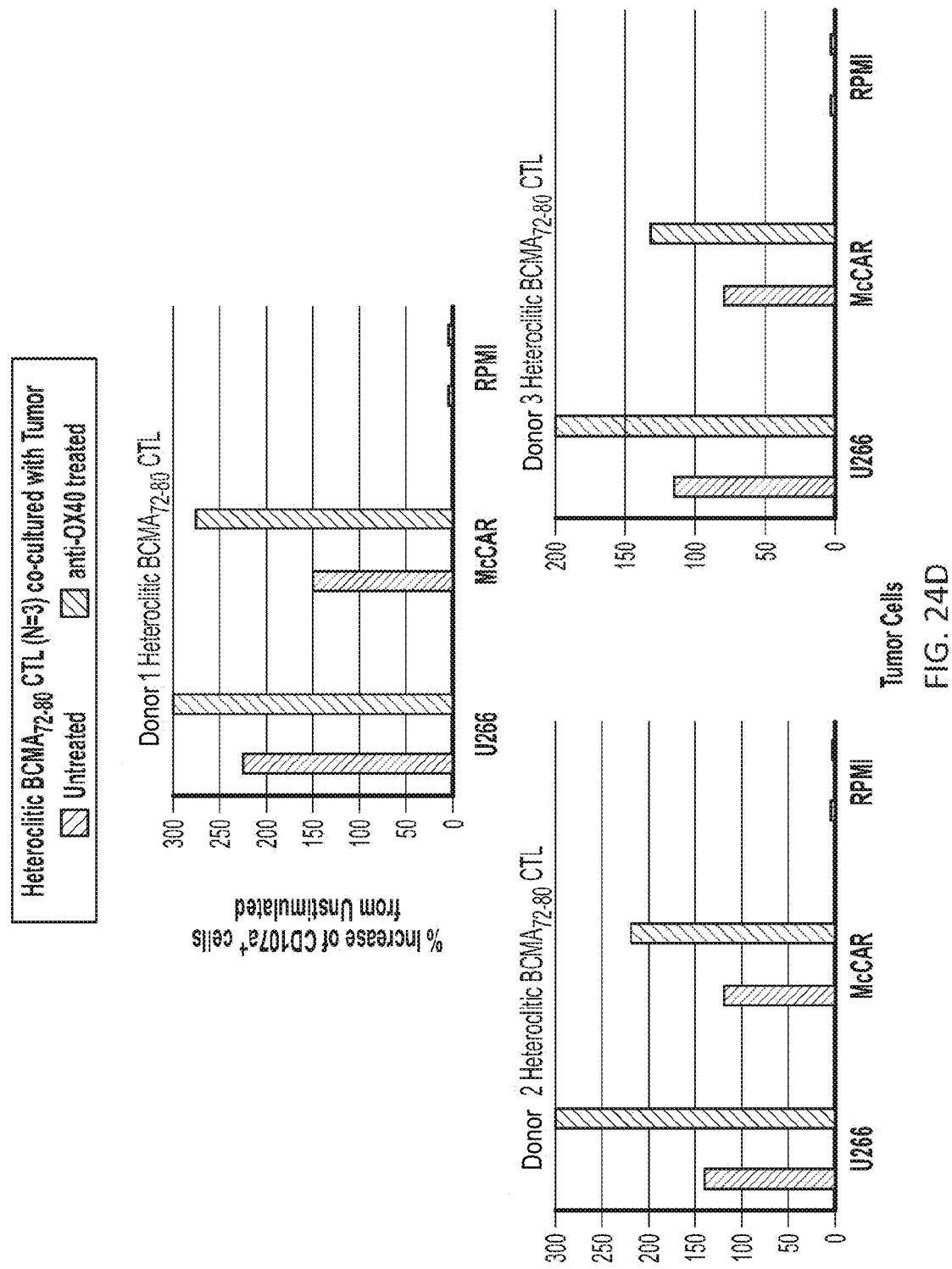
FIG. 24D. Enhanced anti-tumor activities of heteroclitic BCMA$_{72-80}$ CTL [generated from HLA-A2$^+$ Donor 1, Donor 2 or Donor 3] in treatment with anti-OX40 against myeloma cells in an HLA-A2-restricted manner.

In FIGS. 24A-24C, the specific subset inducing MM-specific CD8$^+$ T cell proliferation was identified within heteroclitic BCMA$_{72-80}$ specific CTL in response to U266 cells (FIG. 24A). Furthermore, the heteroclitic BCMA$_{72-80}$ CTL was evaluated in combination with anti-LAG3 or anti-OX40 for their modification of anti-myeloma activities by memory T cells (FIG. 24B) or central memory T cell subset (FIG. 24C).

DISCUSSION

Even in patients with refractory MINI relapsing after allotransplantation, long-lasting responses have been achieved with the infusion of donor lymphocytes (DLI). These early encouraging results of DLI have provided the framework for evaluation of active-specific immunotherapy approaches to treat MM. Cancer targeting vaccines, one such active-specific immunotherapy approach, have demonstrated the ability to induce highly effective CD8$^+$ CTL with anti-tumor activities. The success of vaccination depends on selection of the appropriate patient population, targeting antigens expressed selectively on tumor, and utilizing combination approaches to effectively induce and maintain antigen-specific memory anti-tumor immune responses. This disclosure provides immunogenic HLA-A2 and HLA-A24 specific peptides derived from XBP1, CD138 and CS1 antigens, which are highly over-expressed in MM and solid tumors including breast, pancreatic, and colon cancers, and demonstrated their ability to induce the peptides-specific CD8$^+$ CTL with anti-tumor activities against HLA-A2$^+$ or HLA-A24$^+$ tumor cells both in preclinical and clinical studies. In addition, combination studies of peptide stimulation/vaccination with immune modulatory drugs such as lenalidomide or with histone deacetylase 6 inhibitor ACY241 enhanced the peptides-specific CTL activities against tumor cells. The experiments demonstrated that combinations of peptide stimulation with either Lenalidomide or ACY241 augmented antigens-specific CD8$^+$ T cell activity associated with upregulation of transcriptional regulators such as T-bet/Eomes and with activation of AKT, which links antigen-specific CTL differentiation to FOXO, mTOR and Wnt/β-catenin signaling pathways. Importantly, these effects were confined primarily to antigen-specific CD45RO$^+$ memory CTL, with the most robust increases in IFN-γ and granzyme B production and CD8$^+$ T cell proliferation in response to tumor cells observed mainly within the specific CM subset.

Due to the encouraging preclinical results, the XBP1/CD138/CS1 multipeptide vaccine has been evaluated, alone and in combination with lenalidomide, in clinical trials to treat patients with smoldering MM (SMM), as well as in combination with anti-PD1 in clinical trials to treat patients with triple negative breast cancer. In patients with SMM, the multipeptide vaccine was well tolerated and immunogenic as a monotherapy, evidenced by enhanced frequency of Tetramer$^+$ CD8$^+$ CTL with IFN-γ production; moreover, combination with lenalidomide triggered higher mean fold increases in CD8$^+$ T cells with tetramer-positivity and IFN-γ production. Importantly, CD45RO$^+$ memory CTL specific to the XBP1/CD138/CS1 peptides were induced by the peptide vaccine, and further enhanced in combination with lenalidomide. Although stable disease and responses have been observed in SMM, randomized trials are needed to assess whether time to progression from SMM to active disease can be prolonged by the peptide vaccination.

To expand the MM-specific immunotherapy beyond XBP1/CD138/CS1 antigens, the disclosure also identified additional tumor associated antigens on CD138$^+$ tumor cells from newly diagnosed MM patients (N=616). Here the disclosure provides the identification and characterization of an immunotherapeutic strategy targeting BCMA, selectively expressed on normal and malignant plasma cells and the target of several current immune treatments in MM. The examples provide highly immunogenic engineered BCMA-specific nanopeptides, heteroclitic BCMA$_{72-80}$ (YLMFLLRKI (SEQ ID NO: 13)) and BCMA$_{54-62}$ (YILWTCLGL (SEQ ID NO: 14)) with highly improved HLA-A2 affinity/stability from their native BCMA peptides. These peptides evoke BCMA-specific CTL, increased BCMA-specific Tetramer$^+$ cells, enhanced CD107 degranulation, Th1-type cytokines (IFN-γ/IL-2/TNF-α) production, and proliferation to MM cells in an HLA-A2-restricted manner. Most importantly, the increase of BCMA-specific memory CD8$^+$ CTL, both CM and EM cells, along with the capacity of self-renewal and response to MM cells, strongly support the potential of heteroclitic BCMA peptide in novel vaccination and/or immunotherapeutic approaches in MM. Indeed, the disclosure provides clinical protocols with heteroclitic BCMA$_{72-80}$ peptide vaccination, harvest and expansion of BCMA-specific CM cells ex vivo, reinfusion of these CM cells as adoptive immunotherapy, and then vaccination with the BCMA peptide as needed thereafter to assure their persistence to effectively treat MM patients.

It has been observed that BCMA-specific memory CD8$^+$ CTL expressed key molecules modulating T cells function, both for co-stimulation and immune suppression. The highest induction of co-stimulatory and immune checkpoint molecules was detected on CM subset within hBCMA$_{72-80}$ peptide-specific CTL, which is the population demonstrated highly effective poly-functional activities against MM. Importantly, these findings indicated the potential of combination therapy of BCMA-CTL with checkpoint inhibitors or immune agonists to enhance their functional anti-MM activities. This may be particularly relevant, given the recent concerns when combining PD-1 checkpoint inhibitor with immunomodulatory drugs lenalidomide or pomalidomide or with Ab daratumumab, where toxicities have curtailed studies. Here, the examples attempted to targeting alternative inhibitory receptors and suppressive mechanisms within the MM tumor microenvironment. In particular, LAG3 (CD223) is the third inhibitory receptor to be targeted in the clinic, following CTLA and PD1/PD-L1 and was expressed on BCMA-specific CM CTLs. In parallel, immune agonists, especially the co-stimulatory tumor necrosis factor receptors targeting OX40 (CD134), 41BB (CD137) and GITR (CD357), have received considerable attention for their therapeutic utility in enhancing anti-tumor immune responses; among these, anti-OX40 mAb has recently demonstrated encouraging efficacy in induction of tumor regression by boosting effector T cell expansion and functional anti-tumor activities in several pre-clinical studies. Importantly, a clinical grade anti-LAG3 and anti-OX40 (provided by Bristol-Myers Squibb; New York, N.Y.) was used to evaluate functional activities of heteroclitic $BCMA_{72-80}$ specific CTL to MM cells. The ex vivo experiments demonstrated that both anti-LAG3 and anti-OX40 increased functional activity specifically of memory CTL within the BCMA-CTL against MM cells, without affecting the activity of non-memory CTL. The impact on BCMA-CTL generated from multiple HLA-A2$^+$ individuals' T cells was greater after treatment with anti-OX40 than anti-LAG3, and greater on CM versus EM subset within BCMA specific CTL. These studies provide the framework for scientifically-informed combination clinical trials of BCMA peptide specific immunotherapy with the immune agonist or checkpoint inhibitor.

In summary, these experiments identified and validated novel immunogenic HLA-A2-specific engineered BCMA peptides, which are capable of inducing antigen-specific CD8$^+$ CTL with functional anti-tumor activities against MM cells. These results provide the framework for therapeutic application of these highly immunogenic heteroclitic BCMA peptides in MM patients as vaccines and/or as stimuli for expansion of autologous antigen-specific memory CTL. They further support the potential utility of combinations incorporating BCMA peptide vaccine or BCMA-specific adoptive T cells immunotherapy with anti-OX40 and/or anti-LAG3 to enhance BCMA directed anti-MM responses.

Example 13. HLA-A2-Specific Immunogenic TACI Peptide for Eliciting TACI-Specific CD8+ Cytotoxic T Lymphocytes Experiments were performed to demonstrate that novel immunogenic engineered heteroclictic $TACI_{154-162}$ (YLSADQVAL (SEQ ID NO: 16)) peptide can induce antigen-specific memory CD8$^+$ CTL with robust poly-functional immune responses against MM. These results in this example provide the framework for therapeutic application of heteroclitic TACI peptides in MM patients and support the therapeutic application of TACI peptides-specific vaccine or TACI peptides-specific adoptive T cells immunotherapy to treat the patients with myeloma or other diseases expressing TACI.

The following materials and methods were used in the examples.

Materials and Methods

Cell Lines

The HLA-A2$^+$ (U266 and McCAR) and HLA-A2$^-$ (OPM2 and RPMI) MM cell lines were obtained from ATCC (Manassas, Va.). The T2 cell line, a human B and T cell hybrid expressing HLA-A2, was provided by Dr. J. Molldrem (University of Texas M. D. Anderson Cancer Center, Houston, Tex.). The cell lines were cultured in DMEM (for MM and T2 cells; Gibco-Life Technologies, Rockville, Md.) media supplemented with 10% fetal calf serum (FCS; Bio-Whittaker, Walkersville, Md.), 100 IU/ml penicillin and 100 µg/ml streptomycin (Gibco-Life Technologies).

Reagents

Fluorochrome conjugated anti-human monoclonal antibodies (mAbs) were purchased from Becton Dickinson (BD) (San Diego, Calif.), LifeSpan Bioscience (Seattle, Wash.) or BioLegend (San Diego, Calif.). Live/Dead Aqua stain kit was purchased from Molecular Probes (Grand Island, N.Y.). Recombinant human GM-CSF was obtained from Immunex (Seattle, Wash.) and human IL-2, IL-4, IFN-α and TNF-α were purchased from R&D Systems (Minneapolis, Minn.). TACI peptide-specific Tetramer-PE was synthesized by MBL International Corporation (Woburn, Mass.).

Synthetic Peptides

Native TACI peptides [$TACI_{178-186}$ (FLVAVACFL (SEQ ID NO: 7)), $TACI_{174-182}$ (VLCCFLVAV (SEQ ID NO: 8)), $TACI_{154-162}$ (KLSADQVAL (SEQ ID NO: 9)), $TACI_{166-174}$ (TLGLCLCAV (SEQ ID NO: 10)), $TACI_{161-169}$ (ALVYSTLGL (SEQ ID NO: 11)), $TACI_{155-163}$ (LSADQ-VALV (SEQ ID NO: 12))], heteroclitic TACI peptides [$TACI_{178-186}$ (YLVAVACFL (SEQ ID NO: 15)), $TACI_{154-162}$ (YLSADQVAL (SEQ ID NO: 16)), $TACI_{166-174}$ (YLGLCLCAV (SEQ ID NO: 17))] and $HIV-Gag_{77-85}$ (SLYNTVATL (SEQ ID NO: 21)) peptides (HLA-A2-specific positive control peptide) were synthesized by standard fmoc (9-fluorenylmethyl-oxycarbonyl) chemistry, purified to >95% using reverse-phase chromatography and validated by mass-spectrometry for molecular weight (Biosynthesis, Lewisville, Tex.).

HLA A2 Affinity and Stability Assays

T2 cells were pulsed overnight with various concentrations of peptide plus β2-microglobulin (3 µg/ml) (Sigma, St Louis, Mo.). Following overnight incubation, the cells were stained with HLA-A2-PE mAb and analyzed using a FACSCanto™ flow cytometer (BD). The stability of peptide/HLA-A2 complex binding was measured on peptide loaded T2 cells at 0, 2, 4, 6 and 14 hours post-brefeldin A treatment followed by staining with HLA-A2-PE mAb and flow cytometric analysis.

Generation of Dendritic Cells

Monocytes isolated from peripheral blood mononuclear cells (PBMC) were cultured for 7 days in the presence of 1,000 units/ml GM-CSF and 1,000 units/ml IL-4 in RPMI-1640 medium (Gibco-Life Technologies) supplemented with 10% FCS. Fresh media plus GM-CSF and IL-4 was added to the cultures every other day. Mature DC (mDC) were obtained on day 7, following 3 additional days incubation with 1,000 units/ml IFN-α plus 10 ng/ml TNF-α.

Induction of TACI Peptide-Specific CTL

TACI peptide-specific CTL (TACI-CTL) were generated ex vivo by repeated stimulation of enriched CD3$^+$ T cells obtained from HLA-A2$^+$ donors with peptide-pulsed antigen-presenting cells (APC). In brief, peptide (50 µg/ml)-pulsed APC were irradiated (10 Gy) and used to stimulate T cells at a 1:20 APC/peptide-to-T cell ratio. The T cell cultures were restimulated every 7 days and maintained in AIM-V medium supplemented with 10% human AB serum (BioWhittaker) in the presence of IL-2 (50 units/ml).

Phenotypic Analysis of TACI Peptide-Specific CTL or Stimulatory Tumor Cells

Phenotypic characterization was performed on the MM target cells to conform TACI expression. Phenotypic characterization was performed on the TACI-CTL after staining with Live/Dead Aqua stain kit and fluorochrome conjugated anti-human mAbs. After staining, the cells were washed, fixed in 2% paraformaldehyde, and analyzed by flow cytometry.

Cell Proliferation by Carboxy Fluorescein Succinimidyl Ester (CFSE) Tracking

TACI-CTL were labeled with CFSE (Molecular Probes) and co-incubated with irradiated (10 Gy) MM cells or peptide-pulsed APC in the presence of IL-2 (10 units/ml). On day 4, 5, 6 or 8 of co-culture, the cells were harvested and stained with Live/Dead Aqua stain kit and fluorochrome conjugated anti-human mAb specific to CD3, CD8, CD45RO and CCR7. The level of $CD3^+CD8^+$ CTL proliferation was determined as a reduction in CFSE fluorescence intensity, as measured by flow cytometry.

CD107a Degranulation and Intracellular IFN-γ/IL-2/TNF-α Cytokines Production

The functional cytolytic activity of TACI-CTL was measured by CD107a degranulation (cytotoxicity) and production of Th1 cytokines by flow cytometry. In brief, TACI-CTL were co-incubated with tumor cells or T2/peptide in the presence of CD107a mAb. After 1 hour, CD28/CD49d mAb, brefeldin A and Monensin (BD) were added for an additional 5 hours incubation. Cells were harvested, washed in PBS, and incubated with fluorochrome conjugated mAbs to key T cell markers. After surface staining, cells were fixed/permeabilized, stained with anti-IFN-γ/IL-2/TNF-α mAbs, washed with Perm/Wash solution (BD), fixed in 2% paraformaldehyde, and analyzed by flow cytometry.

Statistical Analysis

Results are presented as mean±SE. Groups were compared using unpaired Student's t-test. Differences were considered significant when p<0.05.

Results

Identification of Heteroclitic $TACI_{154-162}$ Peptide with the Highest Binding Affinity and Stability to HLA A2 Molecules The full length TACI protein sequence was evaluated to predict epitopes with HLA-A2 affinity, extended half-time disassociation rates, proteasomal C terminal cleavage and TAP transport using various search software programs including BIMAS and NetCTL. Among the six native peptides selected [$TACI_{178-186}$ (FLVAVACFL (SEQ ID NO: 7)), $TACI_{174-182}$ (VLCCFLVAV (SEQ ID NO: 8)), $TACI_{154-162}$ (KLSADQVAL (SEQ ID NO: 9)), $TACI_{166-174}$ (TLGLCLCAV (SEQ ID NO: 10)), $TACI_{161-169}$ (ALVYSTLGL (SEQ ID NO: 11)), $TACI_{155-163}$ (LSADQVALV (SEQ ID NO: 12))], all peptides excepting for $TACI_{161-169}$ displayed the HLA-A2 specificity, however the highest level of affinity was detected by $TACI_{166-174}$. In order to improve the binding and stability of the peptide to HLA-A2 molecules, three heteroclitic peptides were designed including $TACI_{178-186}$ (YLVAVACFL (SEQ ID NO: 15)), $TACI_{154-162}$ (YLSADQVAL (SEQ ID NO: 16)) and $TACI_{166-174}$ (YLGLCLCAV (SEQ ID NO: 17)) peptides, synthesized and evaluated their HLA-A2 affinity. The heteroclitic $TACI_{154-162}$ peptide displayed greatly enhanced affinity from its native form at the peptide doses of 50 μg/ml and 100 μg/ml. The HLA-A2 affinity of heteroclitic $TACI_{154-162}$ peptide was similar to the affinity of the HIV-$Gag_{77-85}$ (SLYNTVATL (SEQ ID NO: 21)), which was served as HLA-A2-specific positive control peptide. However, the engineered heteroclitic $TACI_{178-186}$ and $TACI_{166-174}$ peptides showed no significant improvement in HLA-A2 affinity as compared to their native peptides. The selected TACI peptides (50 μg/ml) were further evaluated for their affinity and stability to HLA-A2 molecule. The highest HLA-A2 binding affinity (time=0) and stability (2, 4, 6 and 18 hours) was seen with the heteroclitic $TACI_{154-162}$ as compared to its native peptide. Overall, the HLA-A2 affinity stability of heteroclitic $TACI_{154-162}$ was similar to HLA-A2 positive control HIV-$Gag_{77-85}$ peptide at the various time points. Based on the highest level of HLA-A2 affinity and stability among the TACI peptides investigated, the heteroclitic $TACI_{154-162}$ was selected for further evaluation of its immunogenic potential to induce the antigen-specific effector T cells against MM.

Anti-Tumor Activities of Heteroclitic $TACI_{154-162}$ Peptide-Specific CTL Through Development and Expansion of Antigen-Specific Memory $CD8^+$ Cells Differentiated from Naïve $CD8^+$ Cells.

Figure 29A:
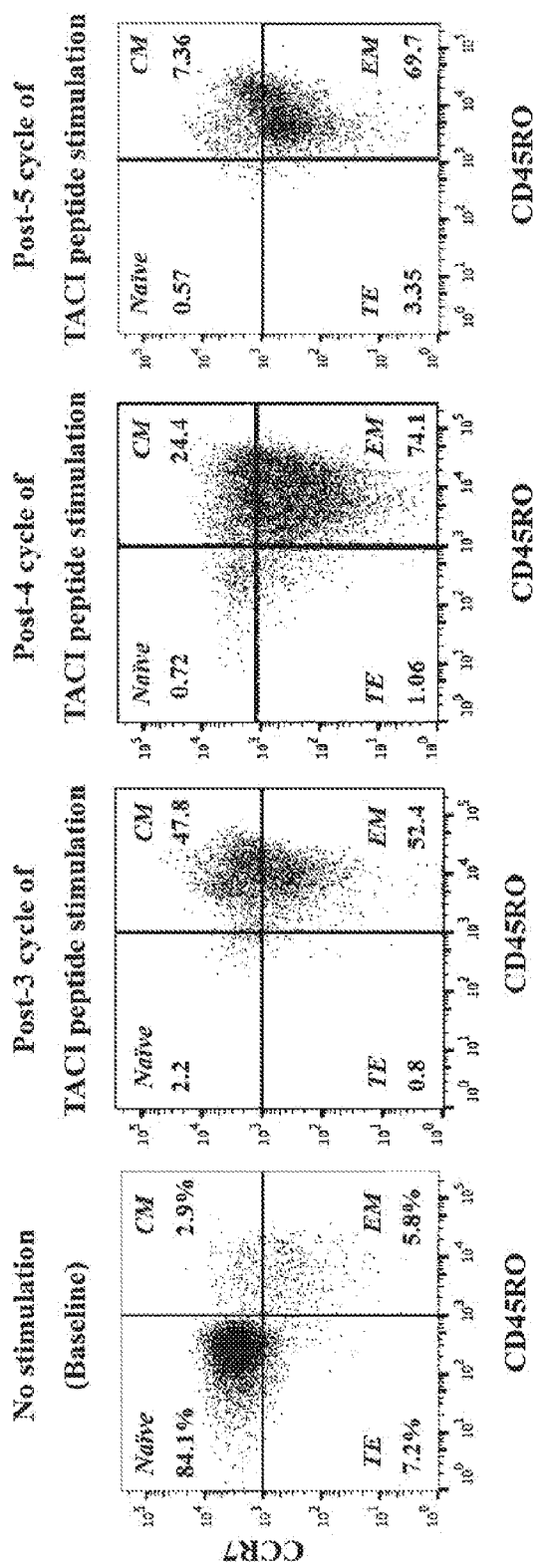
FIGS. 29A-29C show differentiation of naïve cells into memory CTL upon stimulation with heteroclitic TACI$_{154-162}$ Peptide.
Figure 29B:
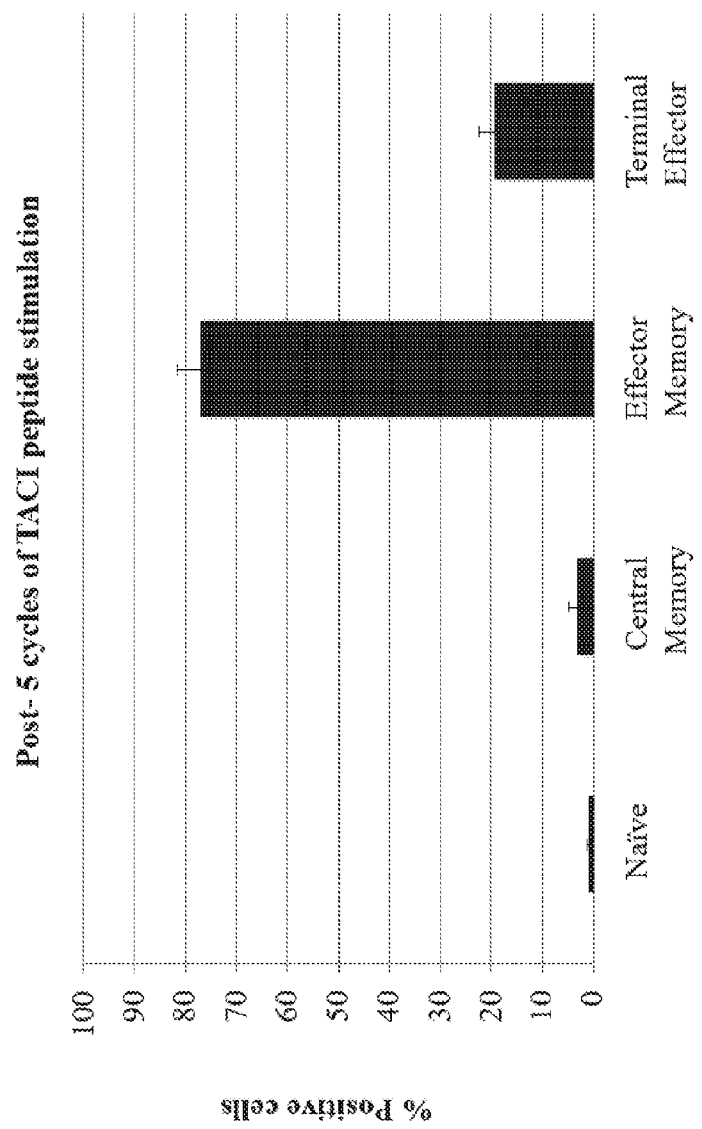

Phenotypic changes in $CD8^+$ T cell were evaluated within Naïve: Memory subsets, following weekly stimulation of enriched $CD3^+$ T cells from HLA-$A2^+$ donors with the heteroclitic $TACI_{154-162}$ (YLSADQVAL (SEQ ID NO: 16)). At baseline [prior to peptide stimulation], the majority (84.1%) of the $CD8^+$ T cells were found as Naïve ($CD45RO^-CCR7^+$) cell subset. Upon the stimulation with heteroclitic $TACI_{154-162}$ peptide, it was observed that a gradual differentiation of Naïve CTL into central memory CTL (CM; $CD45RO^+CCR7^+/CD3^+CD8^+$) and then effector memory CTL (EM; $CD45RO^+CCR7^-/CD3^+CD8^+$) within heteroclitic $TACI_{154-162}$ peptide-specific CTL (h$TACI_{154-162}$ CTL). Development of memory CTL was detected after 3 cycles of peptide stimulation [Naïve: 2.2%, CM: 47.8%, EM: 52.4%] with the heteroclitic $TACI_{154-162}$ peptide. Further differentiation was observed from naïve CTL into the memory CTL subsets after 4 cycles of peptide stimulation [Naïve: 0.72%, CM: 24.4%, EM: 74.1%] and 5 cycles of stimulation [Naïve: 0.57%, CM: 7.36%, EM: 69.7%] (FIG. 29A), supporting the potential of peptide to develop memory T cells. The immunogenicity of heteroclitic $TACI_{154-162}$ peptide was further evaluated in T cells obtained from additional HLA-$A2^+$ donors (N=3) (FIG. 29B). The gradual decrease in naïve $CD8^+$ CTL and increase in memory $CD8^+$ CTL (both central memory and effector memory CTL) were verified in all the individuals' T cells tested, following stimulation with the heteroclitic $TACI_{154-162}$ peptide. Thus, these results confirm the capacity of heteroclitic $TACI_{154-162}$ peptide to develop memory $CD8^+$ T cells.

Figure 29C:
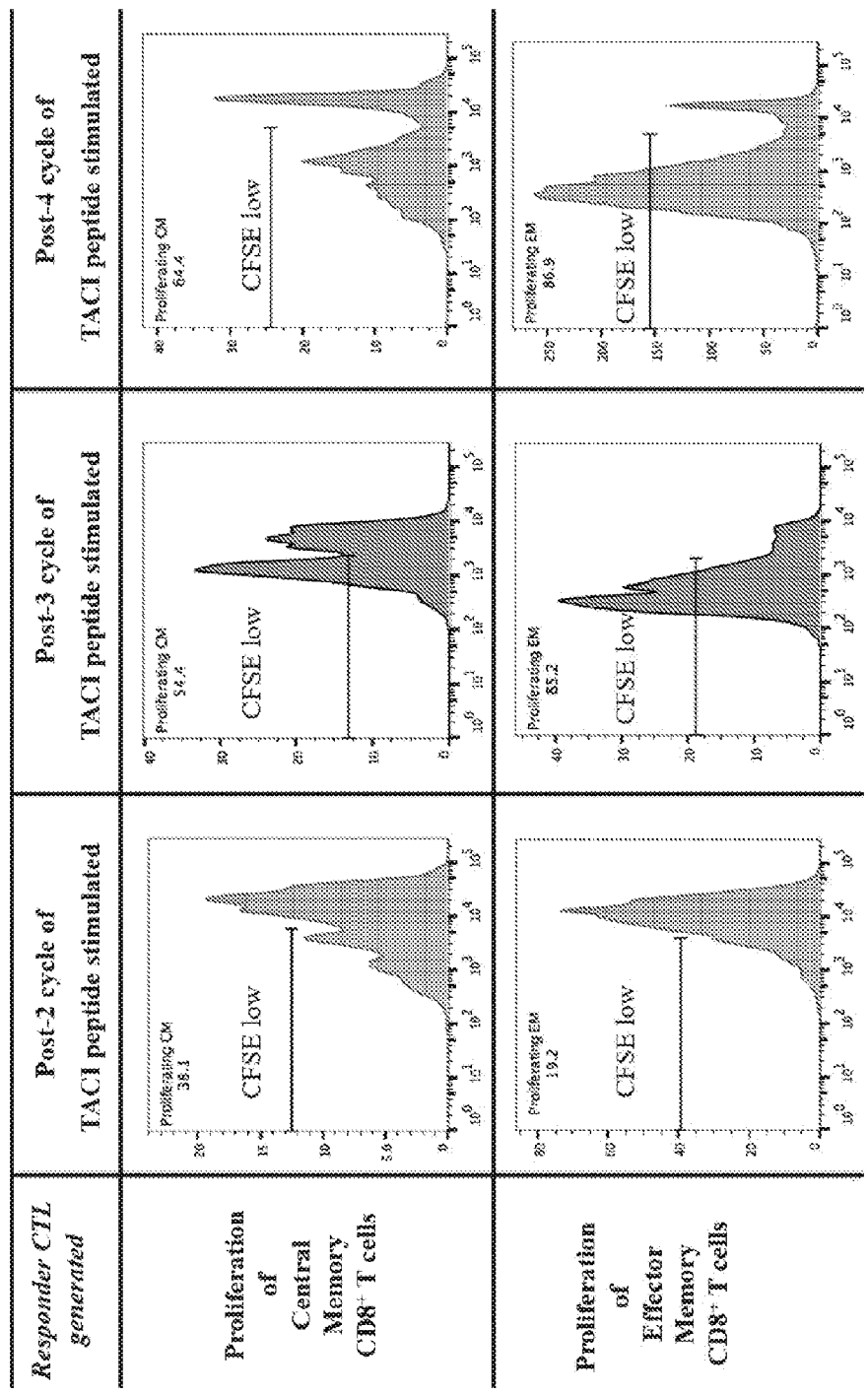

Next, experiments were performed to evaluate the immune functional capacity of the heteroclitic $TACI_{154-162}$-specific CTL in response to myeloma cells. The proliferation of $CD8^+$ CTL was detected in the heteroclitic $TACI_{154-162}$ peptide-specific CTL, especially in memory CTL including central memory and effector memory CTL subsets, upon the co-culture with HLA-$A2^+$ U266 MM cells. The proliferative capacity of the TACI-CTL continued to increase, following more cycles of $TACI_{154-162}$ peptide stimulation [2' stimulation: Proliferating CM—38.1%, Proliferating EM—19.2%; 3rd stimulation: Proliferating CM—54.4%, Proliferating EM—85.2%; 4th stimulation: Proliferating CM—64.4%, Proliferating EM—86.9%] (FIG. 29C). Thus, these results further support the immune function of heteroclitic $TACI_{154-162}$ peptide-specific CTL through development and continuous expansion of memory $CD8^+$ T cells in response to myeloma cells.

Proliferation of TACI-Specific Tetramer⁺ CTL in Heteroclitic TACI$_{154-162}$ Specific CTL Demonstrating Polyfunctional and Th1-Specific Anti-Myeloma Activities in HLA-A2-Restricted Manner.

Figure 3:
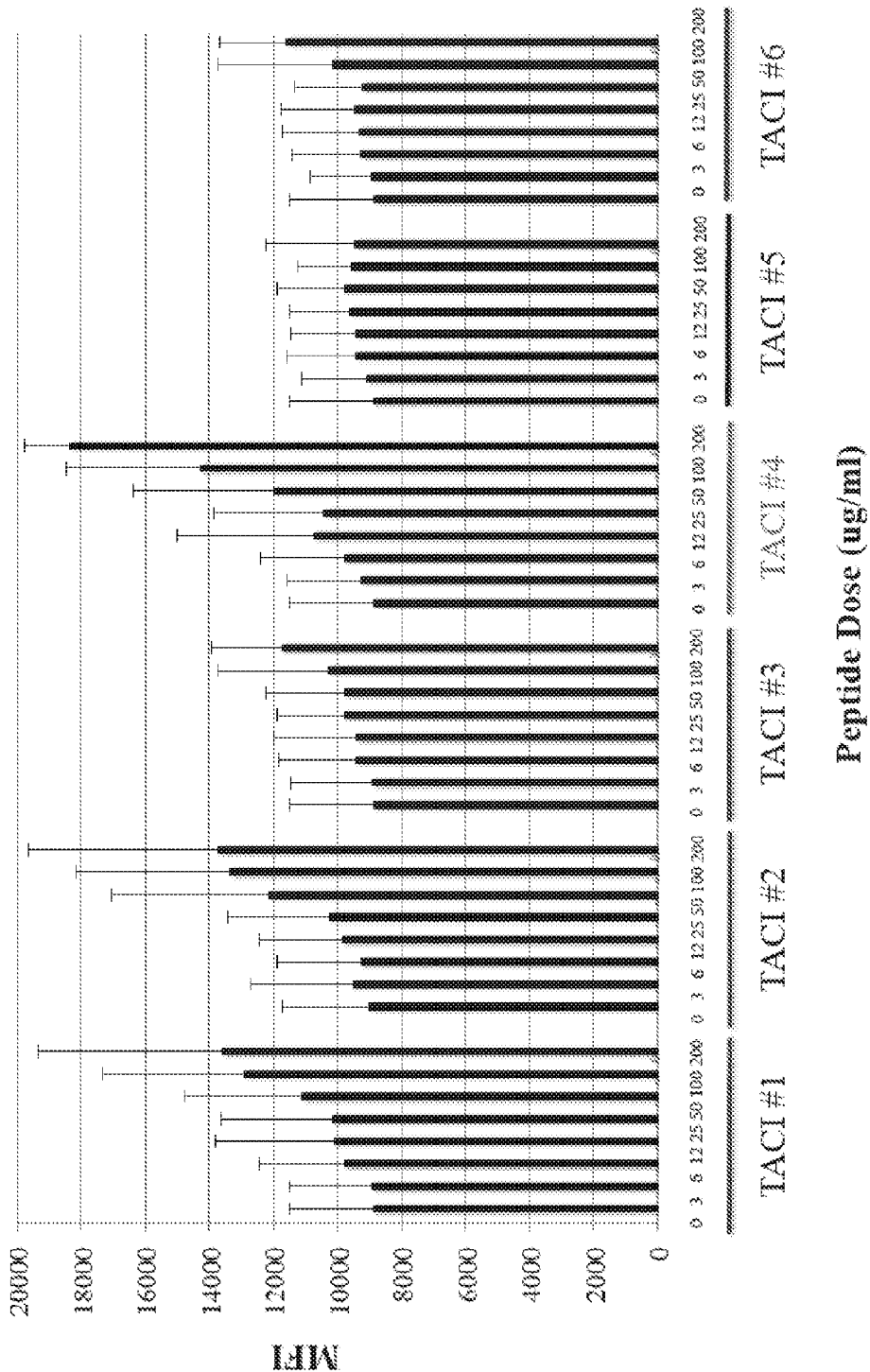
FIG. 3 shows binding affinity of native TACI peptides to HLA-A2
Figure 30A:
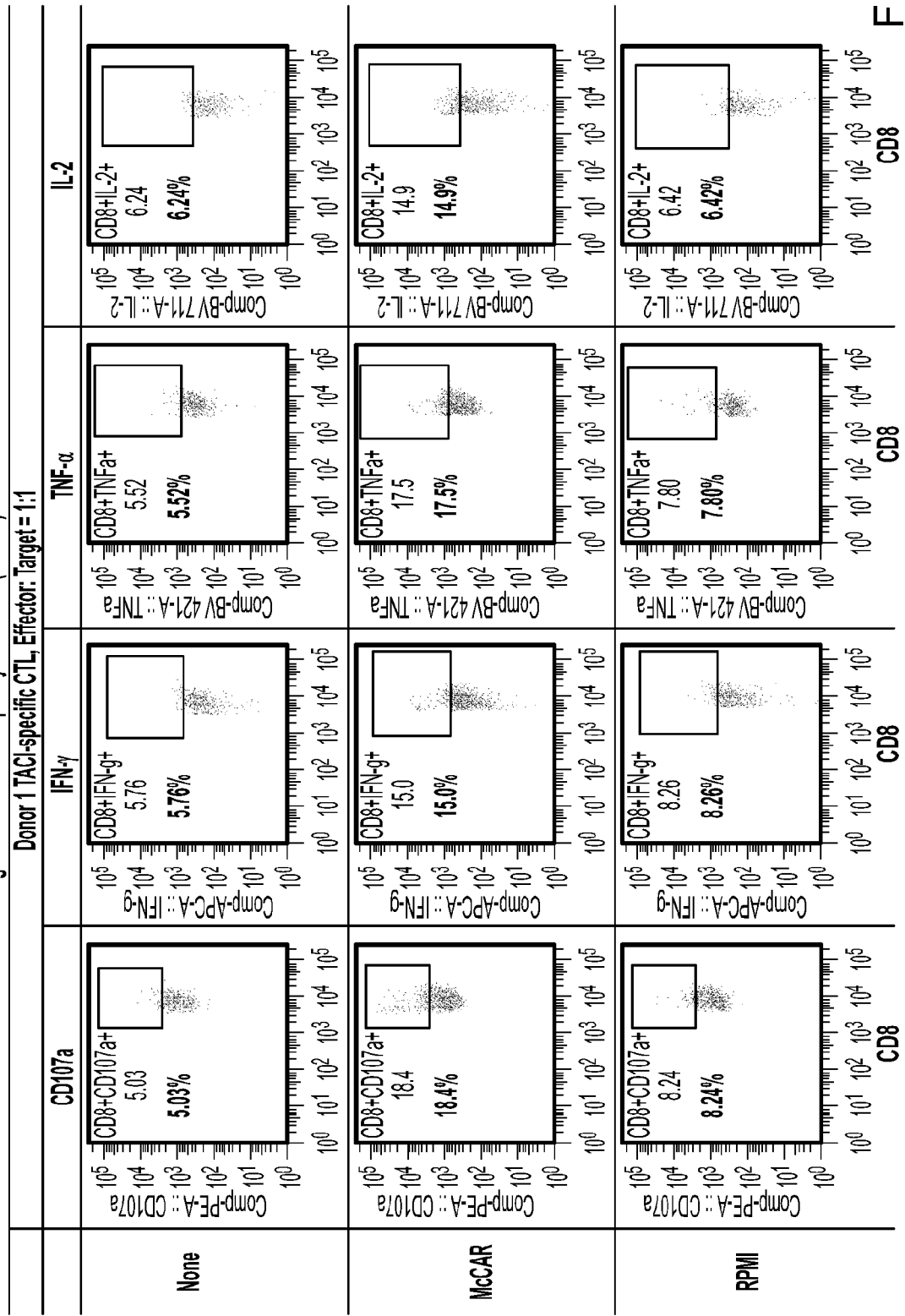
Figure 30B:
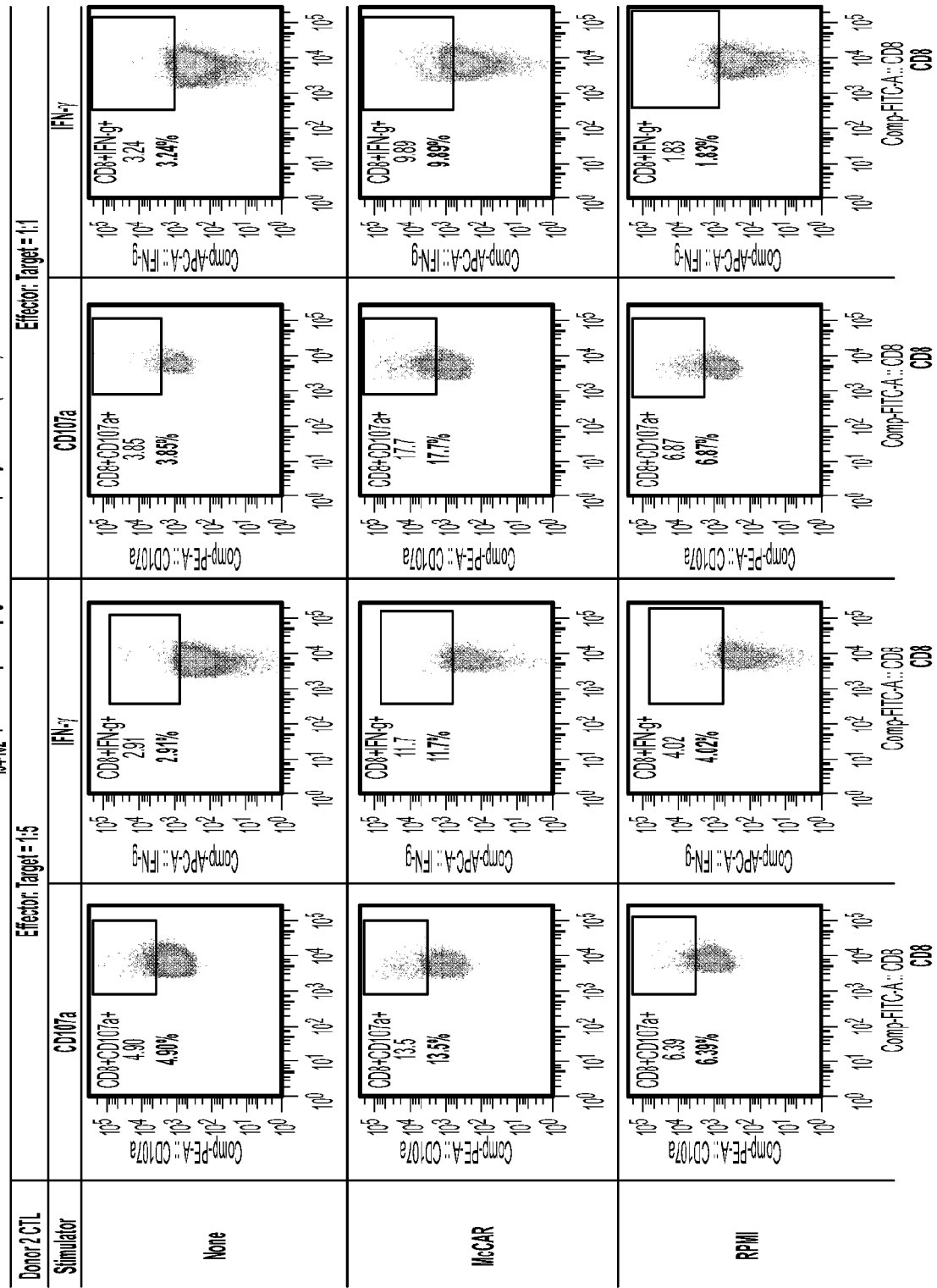
Figure 31A:
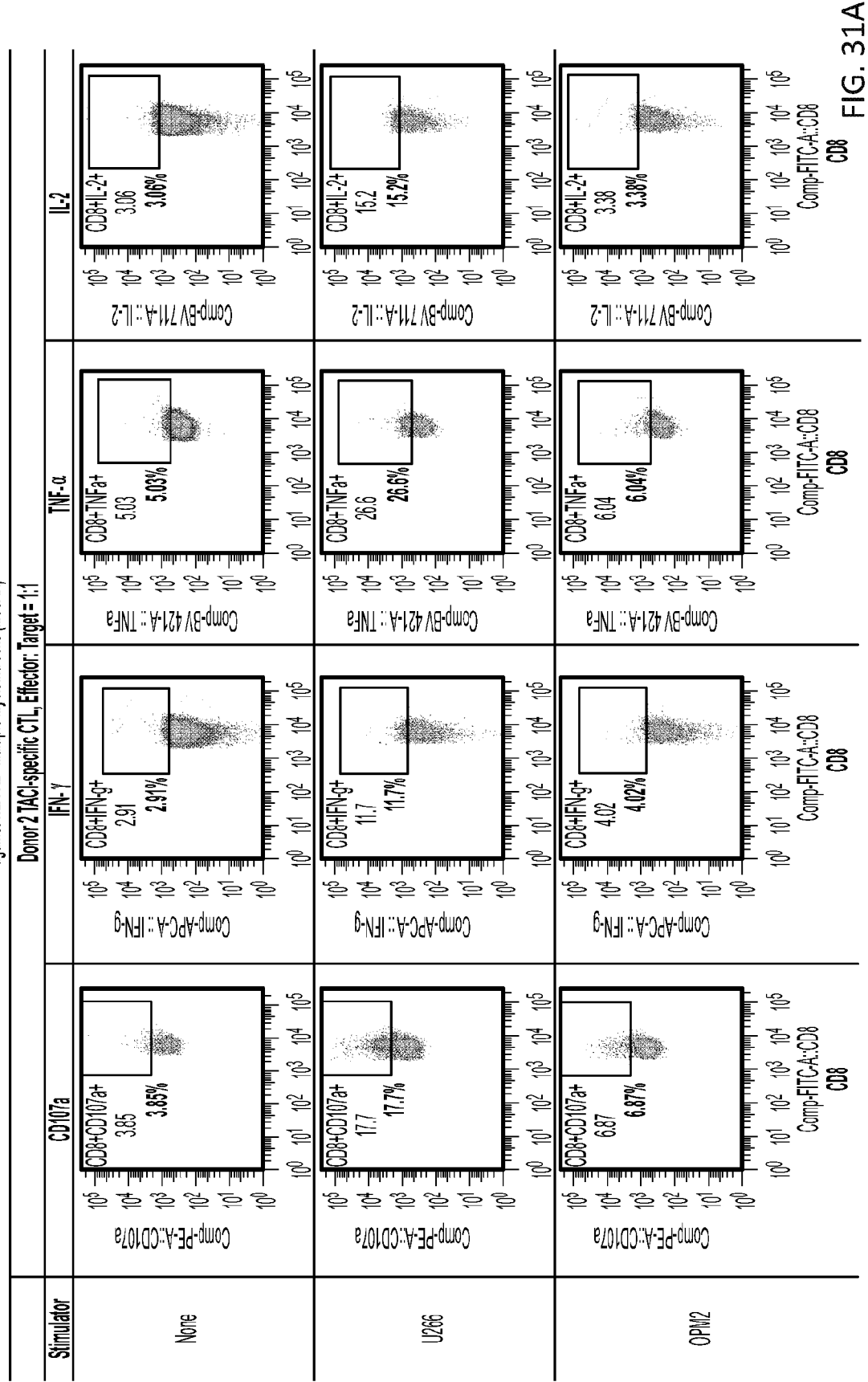
Figure 31F:
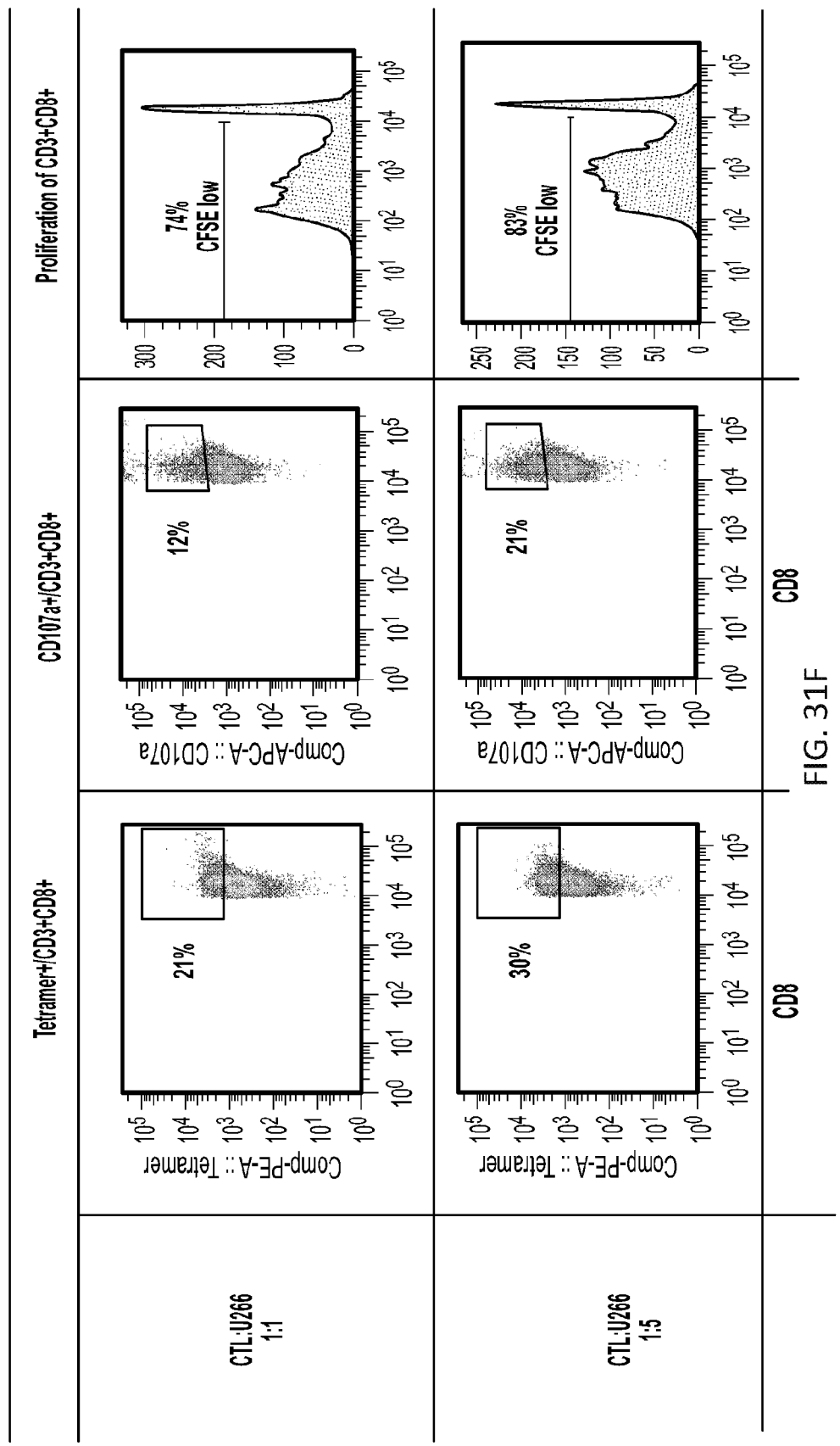
FIG. 31F shows induction of peptide-specific Tetramer+ CTL and anti-tumor activity and proliferation by heteroclitic TACI$_{154-162}$ peptide to HLA-A2+ multiple myeloma cells.

The functional activities of hTACI$_{154-162}$ CTL were examined for their polyfunctional immune responses against myeloma cells. The hTACI$_{154-162}$ CTL demonstrated HLA-A2 restricted degranulation (CD107a upregulation) against HLA-A2⁺ McCAR MM cells, which is directly associated with cytotoxic activity against tumor cells, as compared to HLA-A2⁻ RPMI (8.24%) or media alone (5.03%) (FIG. 30A). In addition, the hTACI$_{154-162}$ CTL demonstrated a higher production of Th1-type of cytokines, IFN-γ (15.0%), TNF-α (17.5%) and IL-2 (14.9%), in response to HLA-A2⁺ McCAR, as compared to HLA-A2⁻ RPMI (IFN-γ 8.26%, TNF-α 7.80%, IL-2 6.42%) or media alone (IFN-γ 5.76%, TNF-α 5.52%, IL-2 6.24%). The specific anti-MM activities, as measured by CD107a degranulation and IFN-γ production, were consistently observed in hTACI$_{154-162}$ CTL generated from different HLA-A2⁺ individuals (N=5), against HLA-A2⁺ MM cells (McCAR) as compared to the MHC mis-matched HLA-A2⁻ MM cells (RPMI) (FIG. 30B, 3C). To confirm the HLA-A2-specific anti-MM activities of heteroclitic hTACI$_{154-162}$ CTL, experiments were performed to evaluate their immune functional activities against additional myeloma cell lines including HLA-A2⁺ U266 and HLA-2⁻ OPM2 cells. The same pattern of HLA-A2-restricted functional anti-tumor activities were observed against the myeloma cells in hTACI$_{154-162}$-CTL generated from HLA-A2⁺ Donor 1 (FIG. 31A) as well as a total of five different HLA-A2⁺ individuals (FIGS. 31B-31E). Furthermore, the hTACI$_{154-162}$ CTL stained positive for TACI$_{154-162}$ peptide-specific Tetramer⁺ CTL and these Tetramer⁺ cells demonstrated a high level of CD107a degranulation and proliferation in response to HLA-A2⁺ U266 myeloma cells (FIG. 31F). Thus, these results demonstrate the HLA-A2-restricted immunogenicity of heteroclitic TACI$_{154-162}$ peptide to evoke antigen-specific CTL with poly-functional activities (cytotoxicity, Th-1 type cytokine production) against MM cells, which supporting the potential therapeutic application of the immunogenic heteroclictic TACI$_{154-162}$ (YLSADQVAL (SEQ ID NO: 16)) peptide in myeloma patients.

Example 14. BCMA Heteroclitic Peptide Encapsulated Nanoparticle Enhances Antigen Stimulatory Capacity and Tumor-Specific CD8⁺ Cytotoxic T Lymphocytes Against Multiple Myeloma B-cell Maturation Antigen (BCMA), a member of the tumor necrosis factor (TNF) receptor superfamily and the receptor for binding of B cell activating factor (BAFF) and the proliferation-inducing ligand (APRIL), is a promising therapeutic target for MM. BCMA has restricted expression pattern on MM cells and plasma cells and has a role in promoting MM cells growth, survival, and drug resistance.

The present disclosure has identified nanomedicine-based therapeutics targeting BCMA as a promising area of translational research to effectively evoke and augment anti-tumor responses in MM patients. Several nanomedicines are available and more advanced nanoparticle constructs are under development for antigen encapsulation. To this end, this example provides novel engineered peptides specific to BCMA, and used a heteroclitic BCMA$_{72-80}$ (YLMFLLRKI (SEQ ID NO: 13)) peptide encapsulated nanoparticle-based cancer vaccine to overcome the limitations of free peptide vaccines including poor peptide stability, susceptibility to enzyme degradation, and low antigen uptake and delivery. Furthermore, the nanotechnology-based cancer vaccine was developed to induce more robust BCMA-specific CD8⁺ cytotoxic T lymphocytes (CTL) activities in MM patients, with more sustained antigen release and increased bioavailability and presentation of the immunogenic peptide. Here, experiments are performed to examine the potential of a novel nanomedicine-based therapeutic delivery system specific to BCMA antigen to treat patients with MM. The purpose of this example was to design the optimal nanoparticle encapsulated BCMA antigen constructs to efficiently evoke BCMA-specific CD8⁺ CTL with functional anti-myeloma activities.

The results show that nanoparticles [liposome or poly(D,L-lactide-co-glycolide) (PLGA)] with different antigen-release kinetics demonstrated their capacity to effectively deliver heteroclitic BCMA peptide to antigen-presenting cells and evoke BCMA antigen-specific CTL with anti-MM activities. The heteroclitic BCMA peptide encapsulated nanoparticles demonstrated a higher uptake by human dendritic cells than free peptide, with the highest uptake mediated with liposome-based nanoparticles. In contrast, BCMA-specific CTL induced with PLGA-based nanoparticle demonstrated the highest functional activities and specific immune responses against MM cells. Importantly, the PLGA/BCMA peptide nanoparticle-induced BCMA-specific CTL displayed greater CD107a degranulation, antigen-specific CD8⁺ CTL proliferation, and Th-1 type cytokines (IFN-γ, IL-2, TNF-α) production in response to MM patients' tumor cells and MM cell lines than BCMA-CTL generated with free BCMA peptide or liposome/BCMA peptide nanoparticle. CD28 costimulatory molecules upregulation, Tetramer⁺ CTL generation, and peptide-specific responses within the BCMA-CTL generated by PLGA/BCMA nanoparticles were also greater than BCMA-CTL generated with free BCMA peptide or liposome/BCMA peptide nanoparticle. Furthermore, the PLGA/BCMA nanoparticles triggered a more robust induction of antigen-specific memory CD8⁺ T cells, which demonstrated significantly higher anti-tumor activities, evidenced by CD107a degranulation and IFN-γ production than non-memory CD8⁺ T cells within the BCMA-CTL. The induction of central memory CTL with anti-tumor activities by PLGA/BCMA peptide were associated with the optimal peptide release kinetics and enhanced immunogenicity.

These results therefore demonstrate that the heteroclitic BCMA peptide encapsulated nanoparticle strategy enhances peptide delivery into dendritic cells and subsequently to T cells, thereby inducing BCMA-specific central memory CTL with poly-functional activities against MM.

These results also demonstrate the utility of nanotechnology using encapsulated heteroclitic BCMA peptide to enhance the immunogenicity of BCMA peptide-specific therapeutics against MM. Importantly, the observations provide the framework for therapeutic application of PLGA nanoparticle-based heteroclitic BCMA peptide delivery to enhance the BCMA-specific memory T cell immune responses, overcome the limitations of current peptide-based cancer vaccine and adoptive immunotherapy, and improve patient outcome in MM.

The following methods and materials were used in this example.

Materials and Methods

Materials

Poly(D,L-lactide-co-glycolide) (PLGA, molecular weight 23,000, copolymer ratio 50:50) was purchased from Birmingham Polymers (Birmingham, Ala.). Polyvinyl alcohol (PVA, average molecular weight 30,000-70,000), trifluoroacetic acid, acetonitrile, lipopolysaccharide, and L-15 (Leibovitz) medium were purchased from Sigma-Aldrich (St Louis, Mo.).

Formulation and Characterization of BCMA Peptide-Loaded PLGA-NP.

Immunogenic heteroclitic hBCMA$_{72-80}$ (<u>Y</u>LMFLLRKI (SEQ ID NO: 13)) peptide was used to produce BCMA antigen-specific nanoparticle preparations for generation of BCMA-specific cytotoxic T lymphocytes (CTL). A double emulsion-solvent technique was used to formulate hBCMA$_{72-80}$ peptide with PLGA-NP, along with Poly(vinyl alcohol) (PVA) to stabilize the emulsion. Heteroclitic hBCMA$_{72-80}$ peptide with PLGA-NPs was formulated substantially as previously described, (Sahoo S K, et al. 2004). In brief, PLGA (50:50 lactide-to-glycolide ratio) and peptide or blank PLGA itself were emulsified in Dichloromethane (DCM), and the mixture was resuspended in 2% PVA to form an oil and water emulsion. The emulsification process was completed using a micro-tip probe ultra-sonicator at 55 watts for 10 minutes in an ice bucket. The emulsion was stirred for 3 hr at room temperature to allow evaporation of DCM and formation of PLGA-NPs. The peptide-loaded PLGA-NPs were recovered by ultracentrifugation at 30,000 rpm for 30 min at 4° C. to deplete PVA and free peptide, washed, and resuspended in PBS. To evaluate PLGA-NP structure, the nanoparticle formulations were lyophilized for 24 hours and visualized using a scanning electron microscope (Hitachi S-4800 microscope, Schaumburg, Ill.).

Formulation and Characterization of BCMA Peptide-Loaded Liposome-NP.

A thin film hydration method was used to synthesize the BCMA peptide-loaded liposome-NP. The liposomes lipid bilayer was made with a mixture of Cholesterol (MW=386.654), DOPC (MW=786.113), and DOTAP (MW=698.542) (Avanti Polar, Alabaster, Ala.). Briefly, a 1 ml stock solution from the mixture of 3 mM Cholesterol, 5 mM DOPC, and 5 mM DOTAP was prepared in chloroform. The solvent was evaporated using a rotary evaporator (RV 10, IKA, Wilmington, N.C.) to yield a thin lipid film at the base of the flask. The lipid film was subjected to overnight vacuum drying to remove any residual organic solvent. The next day, hBCMA$_{72-80}$ peptide dissolved in sodium phosphate (dibasic; pH 11) buffer and 1% DMSO was used to hydrate the lipid film using 10 freeze-thaw cycles (−80° C. and 37° C.), followed by 1 minute of probe sonication on ice to reduce particle sizes to the desired range. The peptide-loaded liposome-NPs were recovered by ultracentrifugation and resuspended in PBS. Blank liposomes were prepared following the same procedure except for the hydration step, where dibasic buffer with 1% DMSO was used without any peptide. Transmission electron microscopy (TEM) was used to characterize the surface morphology of the BCMA peptide-loaded liposome-NP. Uranyl acetate (2%) was used as a negative staining to visualize the BCMA peptide-loaded liposome-NP using TEM (JEM-1000, JEOL, Tokyo, Japan).

BCMA Peptide Encapsulation in PLGA-NP or Liposome-NP.

The level of peptide encapsulation on PLGA-NP or Liposome-NP was measured using the Quantitative Fluorometric Peptide Assay Kit (Thermo Fisher) per the manufacturers' suggested protocol. In brief, an equal amount of BCMA peptide in suspension, BCMA peptide loaded in PLGA-NPs (10 µl) or BCMA peptide loaded in liposome-NPs (10 µl) was loaded in triplicate to a 96-well fluorescence-compatible microplate. Blank PLGA or blank liposome were used as the negative control. Next a solution of 1:1 Acetonitrile: DMSO (70 µl) and FluoroBrite™ DMEM (20 µl) was added to each well and incubated for 5 minutes at room temperature in the dark. Acetonitrile: DMSO solution was used as a control to measure the background fluorescence. Following incubation, fluorescence was measured using a spectrophotometer at Ex/Em at 390 nm/475 nm. The peptide concentration was determined based on the standard curve (0-1,000 µg/ml) generated in a linear fit.

Generation of Monocyte-Derived Dendritic Cells

Monocyte-derived dendritic cells (DC) were generated substantially as described previously (Bae et al. 2011, Bae et al. 2012). Briefly, monocytes isolated from HLA-A2$^+$ normal donors' peripheral blood mononuclear cells (PBMC) were cultured for 7 days in the presence of 1,000 U/ml GM-CSF and 1,000 U/ml IL-4 in RPMI-1640 medium (Gibco-Life Technologies) supplemented with 10% FCS. The fresh media containing cytokines is replaced every other day. The immature dendritic cells were collected from the culture on day 7 for uptake study. Mature DC were obtained by adding 1,000 U/ml IFN-α plus 10 ng/ml TNF-α, along with fresh GM-CSF and IL-4 in 10% FCS-RPMI, upon immature dendritic cells generation on day 7, and then incubating for an additional three days. Either immature or mature DC were used as antigen-presenting cells (APC).

Binding and Uptake of BCMA Peptide-Encapsulated Nanoparticles by Dendritic Cells Immature human dendritic cells (immDC) were harvested, washed, resuspended in serum-free media (1×10$^6$ cells/ml), and aliquoted into wells of a 48-well TC-plate at a final at concentration of 5×10$^5$ cells/well. Cells were pulsed with 50 ug/ml of BCMA peptide-FITC peptide or BCMA peptide-FITC encapsulated nanoparticles in the presence of 3 µg/ml of human β2-microglobulin, and then incubated at 37° C. Peptide loading of immDC was evaluated in a time-dependent manner (0, 30 min, 1 hr, 2 hr, 6 hr, 18 hr) by flow cytometry. Additionally, BCMA peptide-FITC uptake was imaged by confocal microscopy (Nikon widefield Microscope; Tokyo, Japan) on dendritic cells after a 2 hr peptide pulse. Following incubation, the ImmDC were washed, fixed with 2% paraformaldehyde (Electron Microscopy Sciences, Hatfield, Pa.), and stained with DAPI (Sigma) at 300 nM to identify cell nuclei.

Isolation of Primary CD138+ Tumor Cells from Newly Diagnosed Multiple Myeloma Patients.

Primary CD138$^+$ cells were isolated from bone marrow mononuclear cells (BMMC) obtained from both HLA-A2$^+$ and HLA-A2$^-$ newly diagnosed multiple myeloma patients using RoboSep® CD138 positive immunomagnetic selection technology (StemCell Technologies), after appropriate informed consent.

Generation of BCMA Peptide-Specific CTL.

BCMA peptide-specific CTL (BCMA-CTL) were generated ex vivo by repeated stimulation of peripheral blood mononuclear cells isolated from HLA-A2$^+$ normal donors' with (1) HLA-A2 specific BCMA immunogenic peptide (50 ug/ml), (2) a blank nanoparticle (PLGA or liposome) without peptide, or (3) the BCMA peptide (50 ug/ml) encapsulated nanoparticle (PLGA/peptide or liposome/peptide). PBMC were cultured in DMEM medium supplemented with 10% human AB serum (BioWhittaker) and pulsed weekly with the appropriate BCMA peptide for a total of 4 or 5 cycles. IL-2 (50 U/ml) was added to the T cell cultures two days after the second stimulation.

Phenotypic Characterization of BCMA-CTL Generated by BCMA Peptide Encapsulated Nanoparticle Stimulation.

BCMA peptide-specific CD8+ CTL were evaluated for Naïve: Memory cell development and expression of CD28 co-stimulatory molecule by flow cytometry. In addition, BCMA peptide-specific CD8+ CTL were assessed within the cultures by staining with BCMA peptide-specific Tetramer-PE. Following tetramer staining at 37° C. for 30 min, cells were washed and stained with CD8-FITC and CD28-APC mAbs. After staining, cells were washed, fixed in 2% paraformaldehyde, acquired using a LSRII Fortessa™ flow cytometer, and analyzed using FACS DIVA™ v8.0 (BD) or FlowJo v10.0.7 (Tree star, Ashland, Oreg.) software. BCMA-CTL were analyzed for the presence\frequency of specific memory (central memory, effector memory)/non-memory populations within the total gated CD3+CD8+ T cell population.

Evaluation of Anti-Myeloma Specific Functional Activities of BCMA-CTL Generated with BCMA Peptide Encapsulated Nanoparticles.

BCMA-specific CTL (N=3) generated with (1) BCMA immunogenic peptide (50 µg/ml), (2) blank nanoparticle without peptide, or (3) BCMA peptide (50 µg/ml) PGLA/peptide or liposome/peptide nanoparticles, were evaluated for their proliferation response and anti-tumor activities against both HLA-A2+ and HLA-A2− myeloma cell lines or primary CD138+ tumor cells. In brief, BCMA antigen-specific CTL (5×10$^5$ cells) proliferation was measured by coculture of CFSE (Molecular Probes) labeled CTL with irradiated (10 Gy) myeloma cells. On day 3, 4, 5 or 6 of CFSE assays, cells were harvested, stained with live/dead-aqua and fluorochrome conjugated anti-CD3 and anti-CD8 mAbs, and analyzed by flow cytometry. BCMA-CTL functional CD107a degranulation (cytotoxicity) and Th1 IFN-γ/IL-2/TNF-α cytokine production were analyzed in response to myeloma cell lines or primary CD138+ tumor cells. In brief, the respective BCMA-CTL (5×10$^5$ cells) were co-incubated with target cells in the presence of fluorochrome conjugated anti-CD107a mAb. After 1 hr co-culture, a cocktail of Brefeldin A and Monensin (BD) was added and incubated for an additional 5 hours. The cells were then stained with live/dead-aqua and fluorochrome conjugated mAbs specific to various cell surface antigens, fixed and permeabilized, and stained intracellularly with mAb specific to IFN-γ, IL-2 or TNF-α. Finally, the cells were washed, fixed in 2% paraformaldehyde, acquired using a LSRII Fortessa™ flow cytometer, and analyzed using FACS DIVA™ v8.0 or FlowJo v10.0.7 software.

Results

Multiple myeloma (MM) is a B-cell malignancy characterized by the clonal proliferation and accumulation of malignant plasma cells in the bone marrow, monoclonal protein in the serum and/or urine, and development of osteolytic bone lesions. Despite recent advances in treatment using novel therapeutics, MM remains incurable. Preclinical studies show that anti-myeloma CD8+ CTL can be generated with immunogenic HLA-A2 or HLA-A24 peptides targeting various tumor-associated antigens (TAA) including XBP1, CD138, and CS1. Moreover, vaccination with these peptides can generate MM specific immune responses as detected in the clinical trials. To expand the breadth and extent of antigen-specific immunotherapy and adoptive immunotherapy in myeloma beyond these antigens, the disclosure provides additional TAA on tumor cells obtained from newly diagnosed MM patients (N=616). Here, the present disclosure provides a novel heteroclitic peptide specific to BCMA, the receptor for binding of B cell activating factor (BAFF) and a proliferation-inducing ligand (APRIL). Due to its restricted expression pattern on MM cells and plasma cells along with its critical role in promoting MM cell growth, survival and drug resistance, the BCMA antigen is currently being targeted with antibodies, immunotoxins, and CAR T; however, there remains a significant need to design novel delivery systems capable of inducing more effective myeloma-specific effector cells with a favorable therapeutic index. To facilitate BCMA peptide delivery into the bone marrow microenvironment and augment anti-tumor immune responses in the patients, an approach using nanoparticle which offers potential protection of BCMA peptide from enzymatic degradation and overcomes the limitations of free peptide vaccines by increasing peptide stability, uptake, and delivery was designed. The goal of the nanotechnology-based cancer vaccine was to elicit more robust BCMA-specific CD8+ CTL immune responses and anti-tumor activities in MM patients, through longer and better T cell stimulation via sustained antigen release and presentation of the immunogenic peptide. Experiments were performed to evaluate two different types of nanoparticles, PLGA and liposome, encapsulating the BCMA peptide. Compared to peptide alone or liposome/peptide, the PLGA/peptide evokes BCMA-specific CD8+ T cells with the greatest anti-tumor activities, associated with antigen-specific memory CTL induction. These results provide the framework for a therapeutic vaccination and/or adoptive immunotherapeutic strategy using PLGA nanovehicle, which has been approved for human use granted by the US Food and Drug Administration (FDA) with biodegradability and biocompatibility, to efficiently induce BCMA peptide specific anti-tumor activity and improve patient outcome in myeloma.

Characterization and Quantification of BCMA Peptide-Encapsulated Nanoparticles.

Figure 32A:
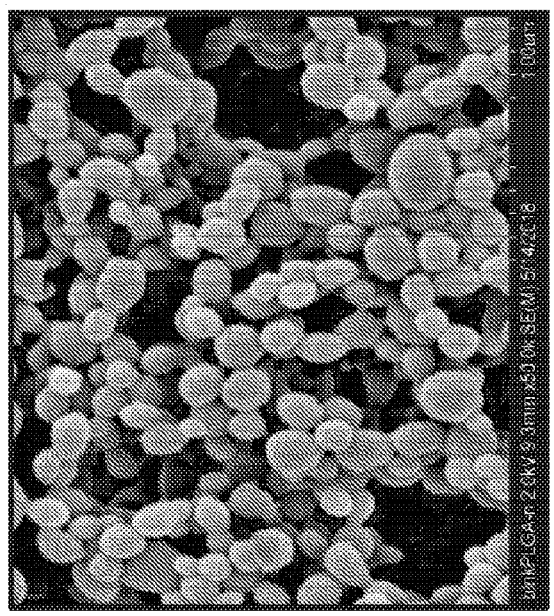
FIG. 32A shows morphology of BCMA Peptide loaded PLGA nanoparticles.
Figure 32B:
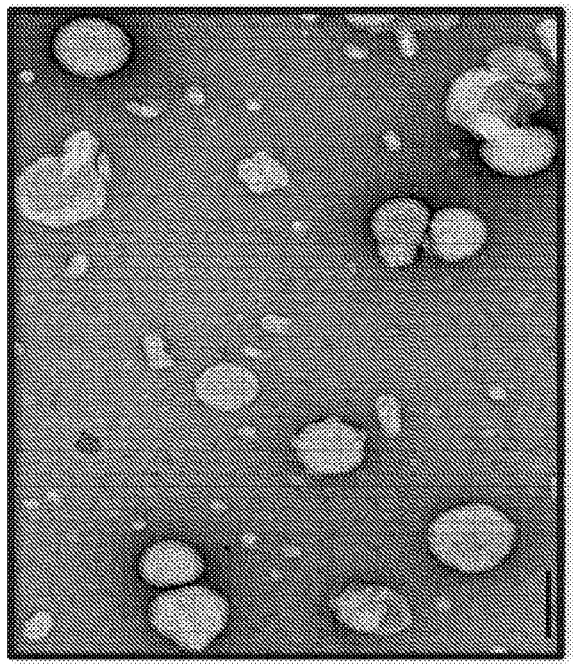
FIG. 32B shows morphology of BCMA Peptide loaded Liposome nanoparticles.
Figure 32C:
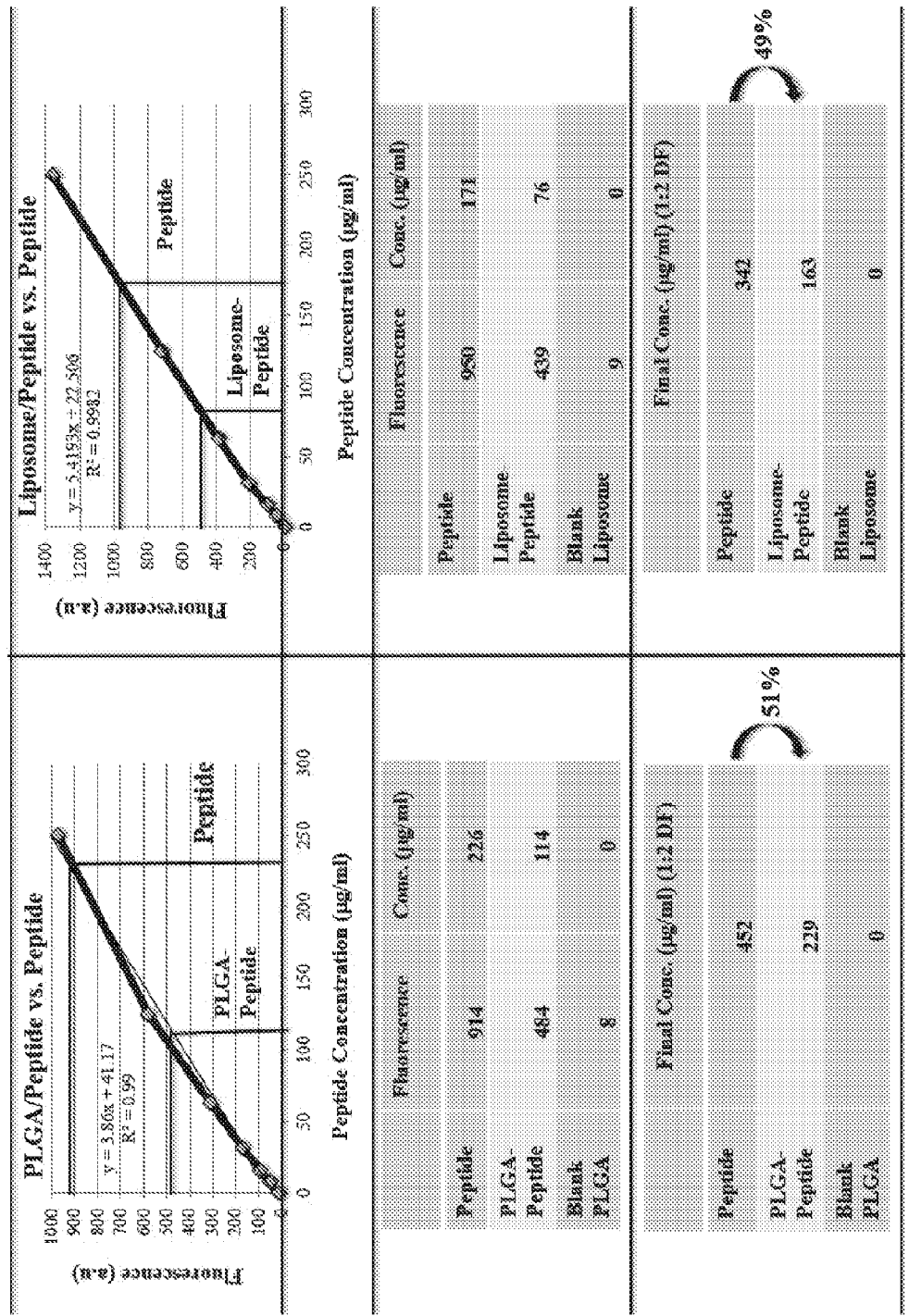
FIG. 32C shows BCMA peptide quantification.

The double emulsion-solvent technique is the most commonly used method to formulate PLGA NP to stabilize the emulsion. The lyophilized particles were resuspended in distilled water for size and zeta-potential measurements using dynamic light scattering. The blank PLGA showed a size of 309.0±4.0 nm (n=3), while peptide loaded PLGA-NP were smaller in size (257.7±11.5 nm, n=3), which could be attributed to the interaction between PLGA polymer and the peptide. The zeta-potential for both blank and PLGA-NP were −0.06 to −1.1 mV. The polydispersity index (PDI) of the PLGA-NPs was ≤0.2, indicating a uniform size distribution. Blank PLGA or BCMA peptide encapsulated PLGA-NP were sputter coated with gold/palladium and imaged using a scanning electron microscope under 20 kV at 50× to further show uniform size distribution (FIG. 32A). In parallel, liposomal formulations were synthesized using lipid DOTAP to allow interaction with the BCMA peptide. The liposomal loaded BCMA peptide nanoparticles were approximately 172±0.7 d·nm (diameter, nanometers) (n=3) in size and showed a PDI of 0.2, indicating a uniform size distribution (FIG. 32B). Negative staining with uranyl acetate was used to visualize peptide loaded liposomes using TEM, which also revealed a uniform size distribution. Peptide loading and encapsulation efficiency for both NP preparations was evaluated using Quantitative Fluorometric Peptide Assay, based on fluorescence measured at Ex/Em at 390 nm/475 nm. The peptide encapsulation efficiency (%), which indicates the percentage of peptide loaded in PLGA-NP or liposome-NP over the initial amount of loaded peptide, was 51%±1.15% (n=3) with PLGA or 49%±1.32% (n=3) with liposome (FIG. 32C). Blank PLGA and blank liposome had zero peptide loading as expected. After confirmation\normalization of peptide encapsulation, the PLGA/peptide and liposome/peptide NPs were used as the BCMA antigen source to generate antigen-specific cytotoxic T lymphocytes (CTL).

Uptake of BCMA Encapsulated Nanoparticles by Dendritic Cells.

Figure 33A:
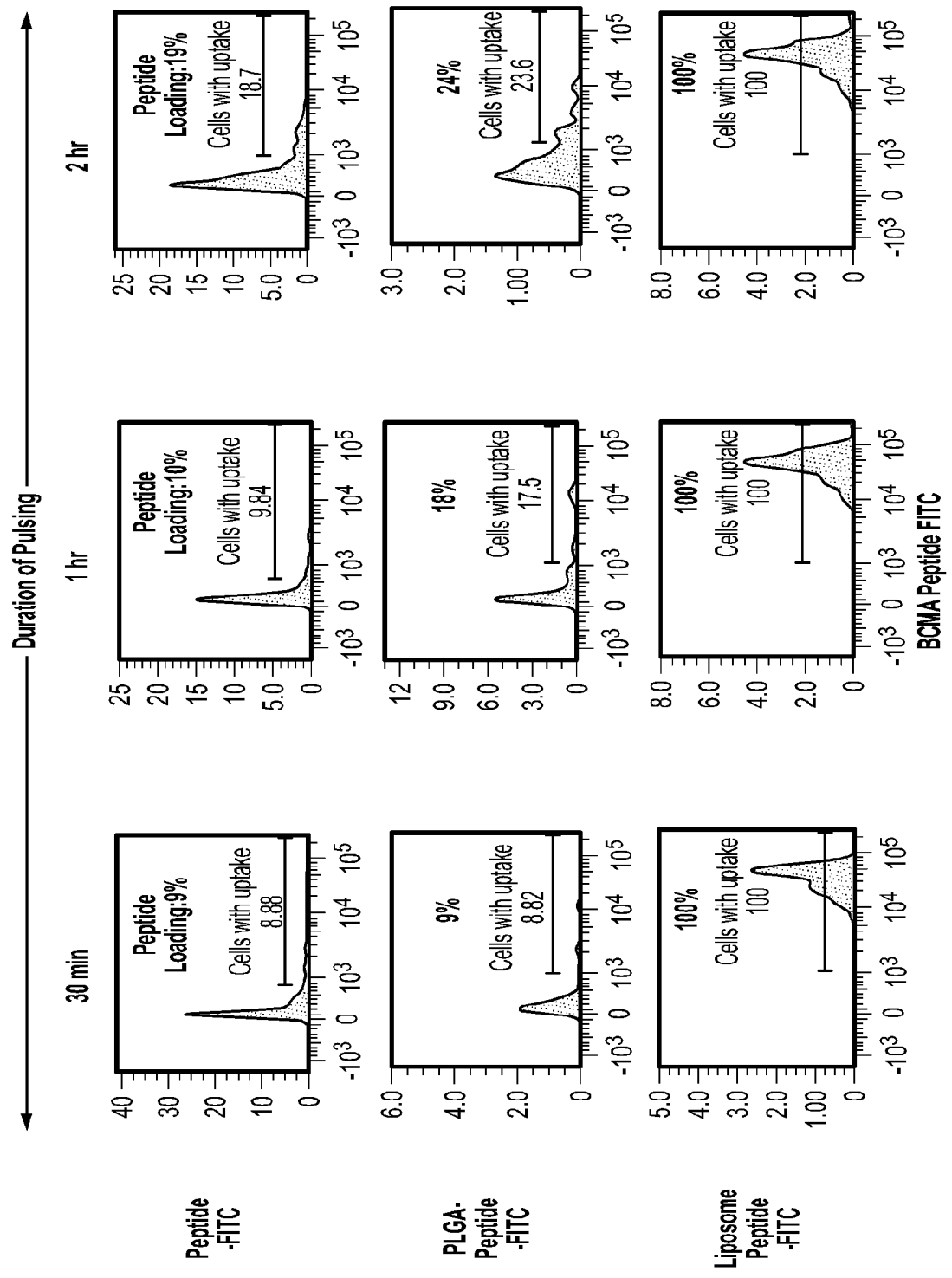
FIG. 33A shows a higher loading efficiency of BCMA peptide on dendritic cells, upon encapsulation in nanoparticle (PLGA, Liposome), in a time-dependent manner.
Figure 33B:
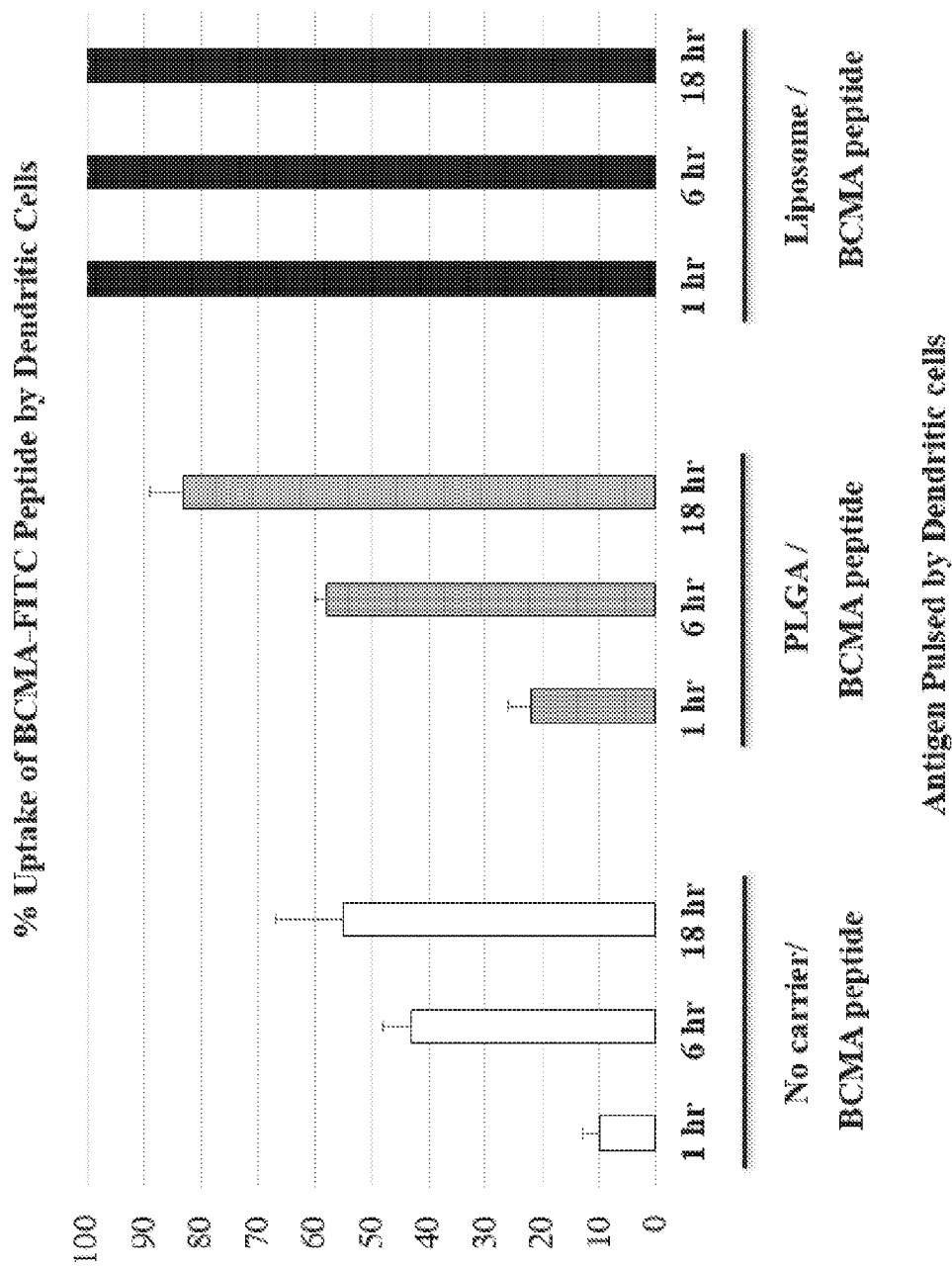
FIG. 33B shows a higher loading efficiency of BCMA peptide-FITC on dendritic cells, upon encapsulation in nanoparticle (PLGA, Liposome), in a time-dependent manner.
Figure 33C:
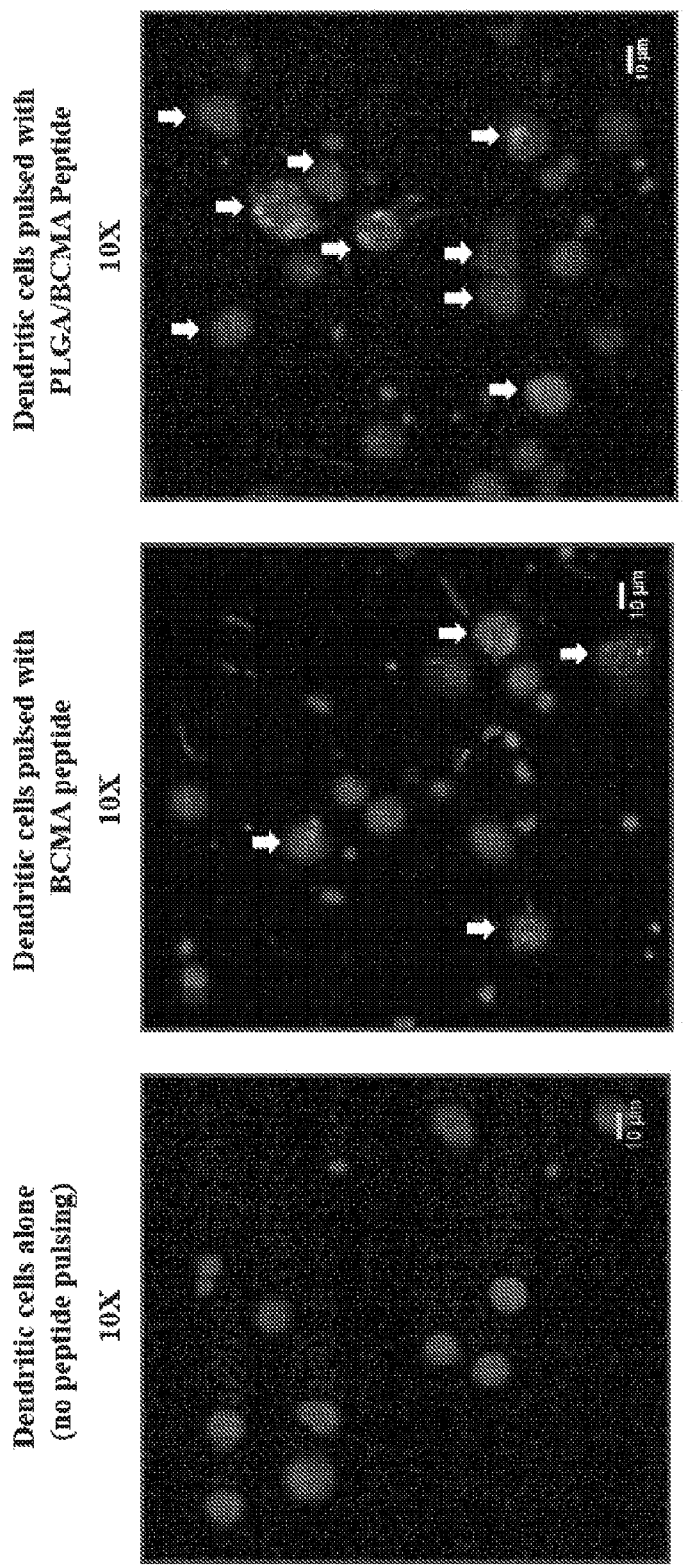
FIG. 33C shows higher PLGA/peptide uptake by dendritic cells.
Figure 33D:
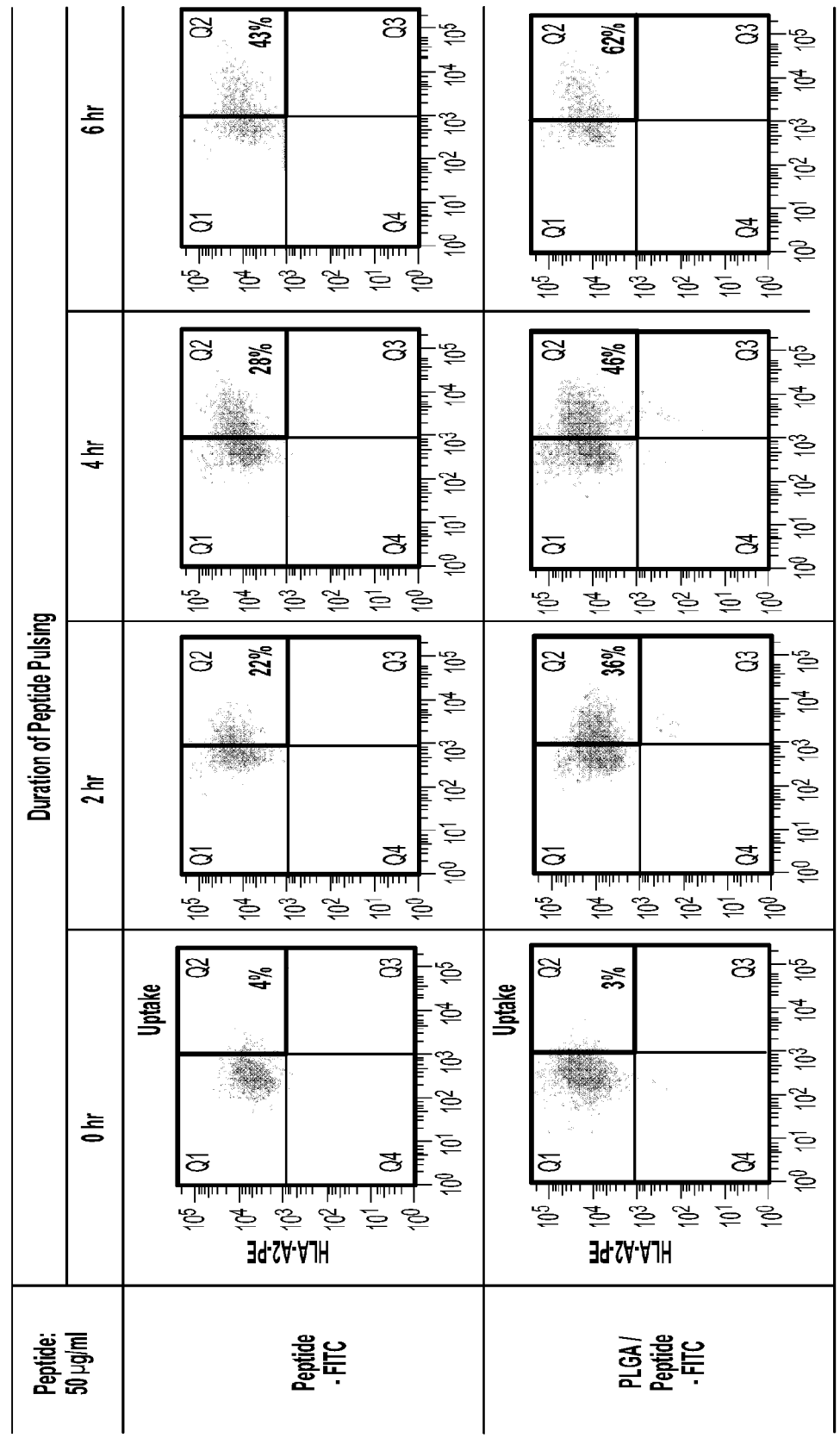
FIG. 33D shows a higher uptake of BCMA peptide-FITC by dendritic cells, upon encapsulation in PLGA, in a time-dependent manner.
Figure 33E:
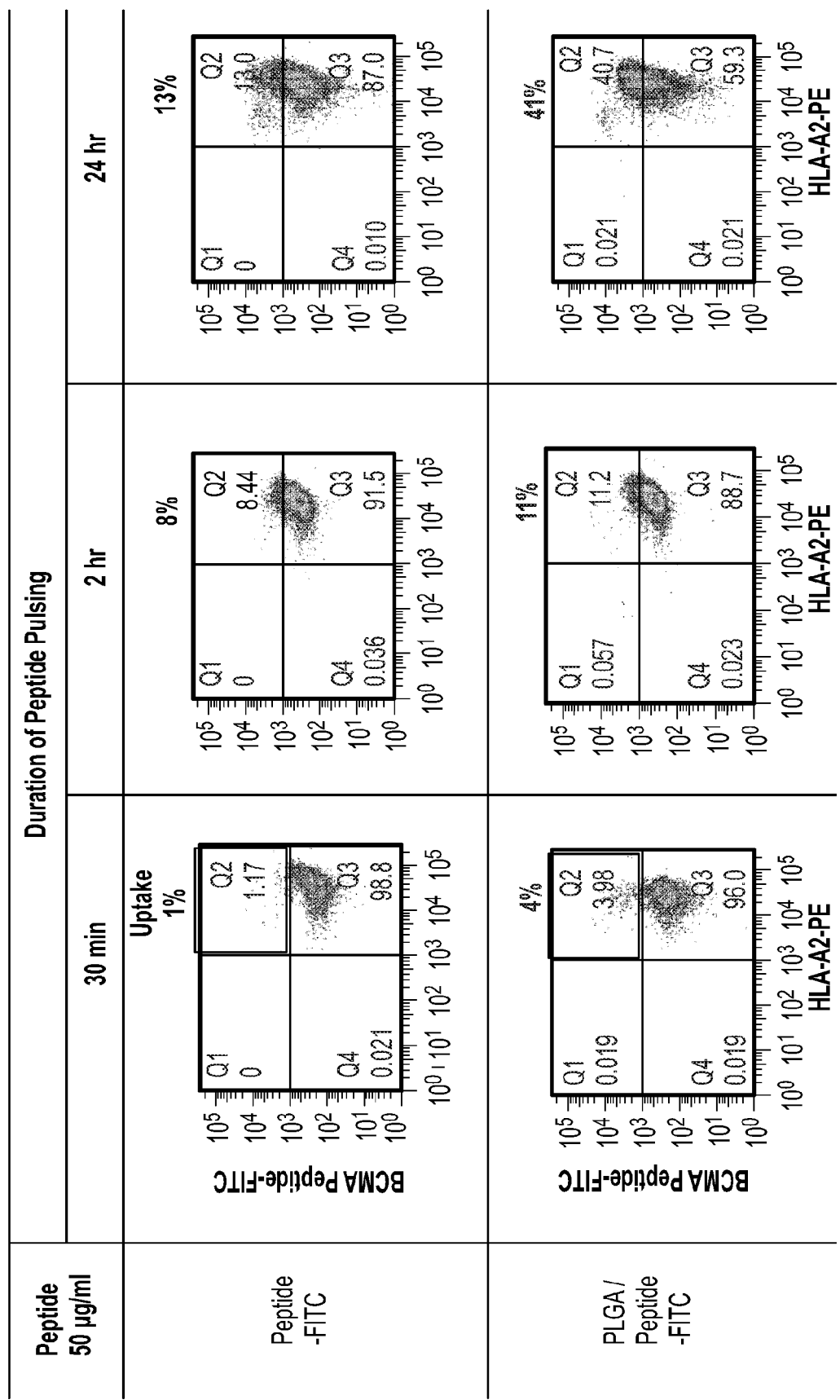
FIG. 33E shows a higher uptake of BCMA peptide-FITC by T2 cells, upon encapsulation in PLGA, in a time-dependent manner.

BCMA peptide uptake was evaluated using ImmDC generated from monocytes of HLA-A2$^+$ donors. Peptide loading efficiency to ImmDC by each BCMA-nanoparticle type or peptide alone was measured over time by flow cytometry. A higher efficiency of ImmDC peptide loading was detected with BCMA encapsulated nanoparticles as compared to peptide alone. Among the two nanoparticles evaluated, liposome/peptide displayed faster and maintained higher levels of peptide loading (100% uptake 30 minutes) over time compared to PLGA/peptide (FIG. 33A). In contrast, PLGA/peptide showed a gradual increase in peptide loading over time, being detected at 1 hr (No carrier/Peptide, PLGA/peptide vs. Liposome/Peptide: 10±4%, 22±4% vs. 100±0%), increasing at 6 hr (No carrier/Peptide, PLGA/peptide vs. Liposome/Peptide: 42±4%, 59±2% vs. 100±0%), and peaking at 18 hr (No carrier/Peptide, PLGA/peptide vs. Liposome/Peptide: 55±8%, 83±5% vs. 100±0%) (FIG. 33B). The loading efficiency of PLGA/peptide by ImmDC was further evaluated by confocal microscopy after an 18 hr pulse. Higher ImmDC BCMA peptide loading was seen with PLGA/peptide compared to peptide alone (FIG. 33C), confirming that PLGA/peptide formulation enhances BCMA peptide delivery. Further evaluation demonstrated improved ImmDC peptide loading by PLGA/peptide in a time-dependent manner, as measured by flow cytometry (No carrier/Peptide vs. PLGA/peptide: 0 hr pulse (baseline)—4% vs. 3%, 2 hr pulse—22% vs. 36%, 4 hr pulse—28% vs. 46%, 6 hr pulse—43% vs. 62%) (FIG. 33D). In addition, using T2 cells as antigen-presenting cells, the same pattern of improved APC peptide loading in a time-dependent manner was detected (No carrier/Peptide vs. PLGA/peptide: 30 min pulse—1% vs. 4%, 2 hr pulse—8% vs. 11%, 24 hr pulse—13% vs. 41%) (FIG. 33E). Between the two antigen-presenting cell types, primary ImmDC displayed a higher efficiency of peptide uptake than T2 cells. Thus, these results demonstrate the beneficial effect of both PGLA/peptide or liposome/peptide to enhance BCMA peptide loading by antigen-presenting cells.

PLGA/Peptide CTL Display the Highest Functional Immune Responses Against Multiple Myeloma Cells.

Figure 34A:
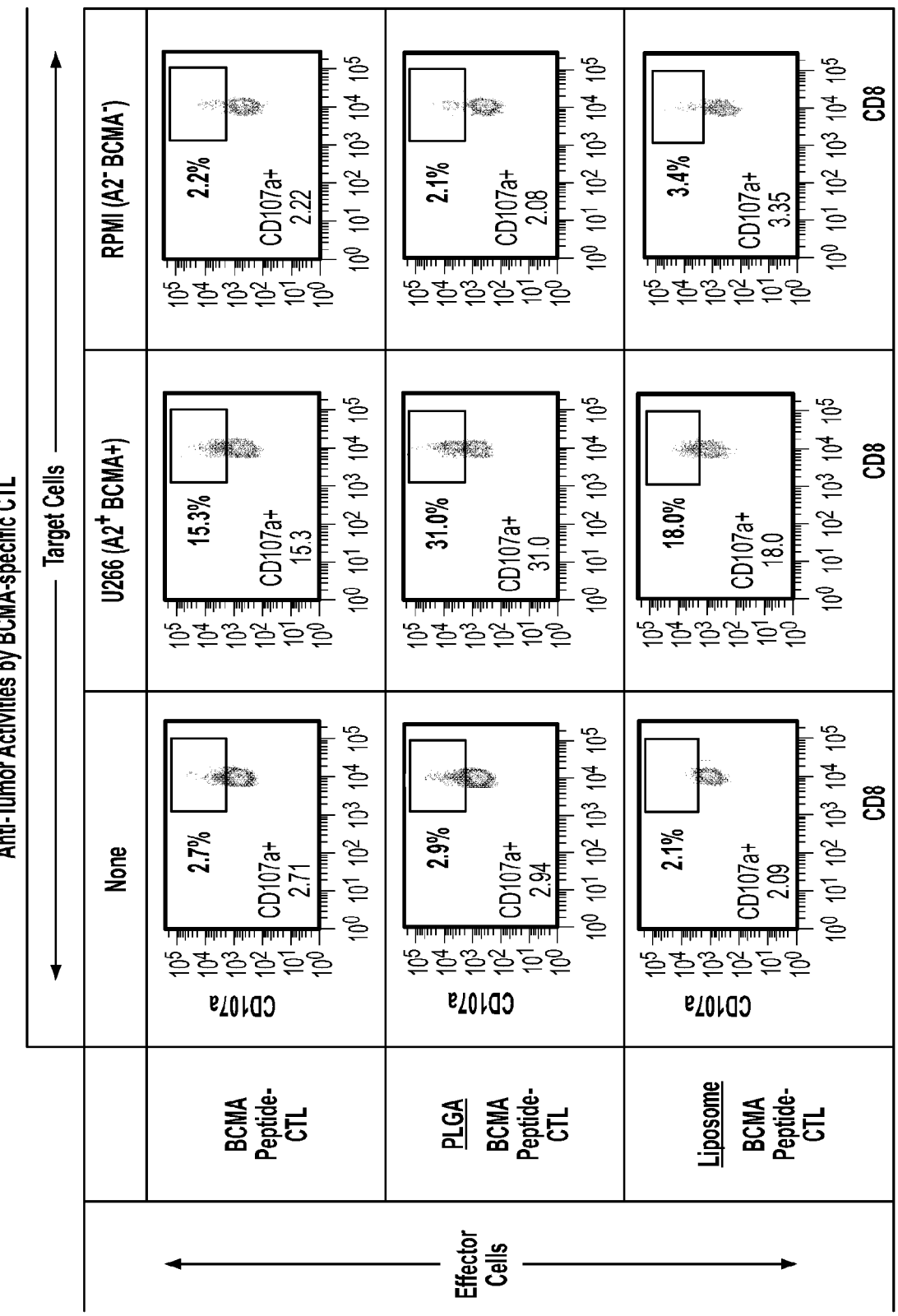
FIG. 34A shows the highest anti-MM activities by BCMA-CTL generated with PLGA/BCMA peptide against MM cell lines in an HLA-A2-restricted manner.
Figure 34B:
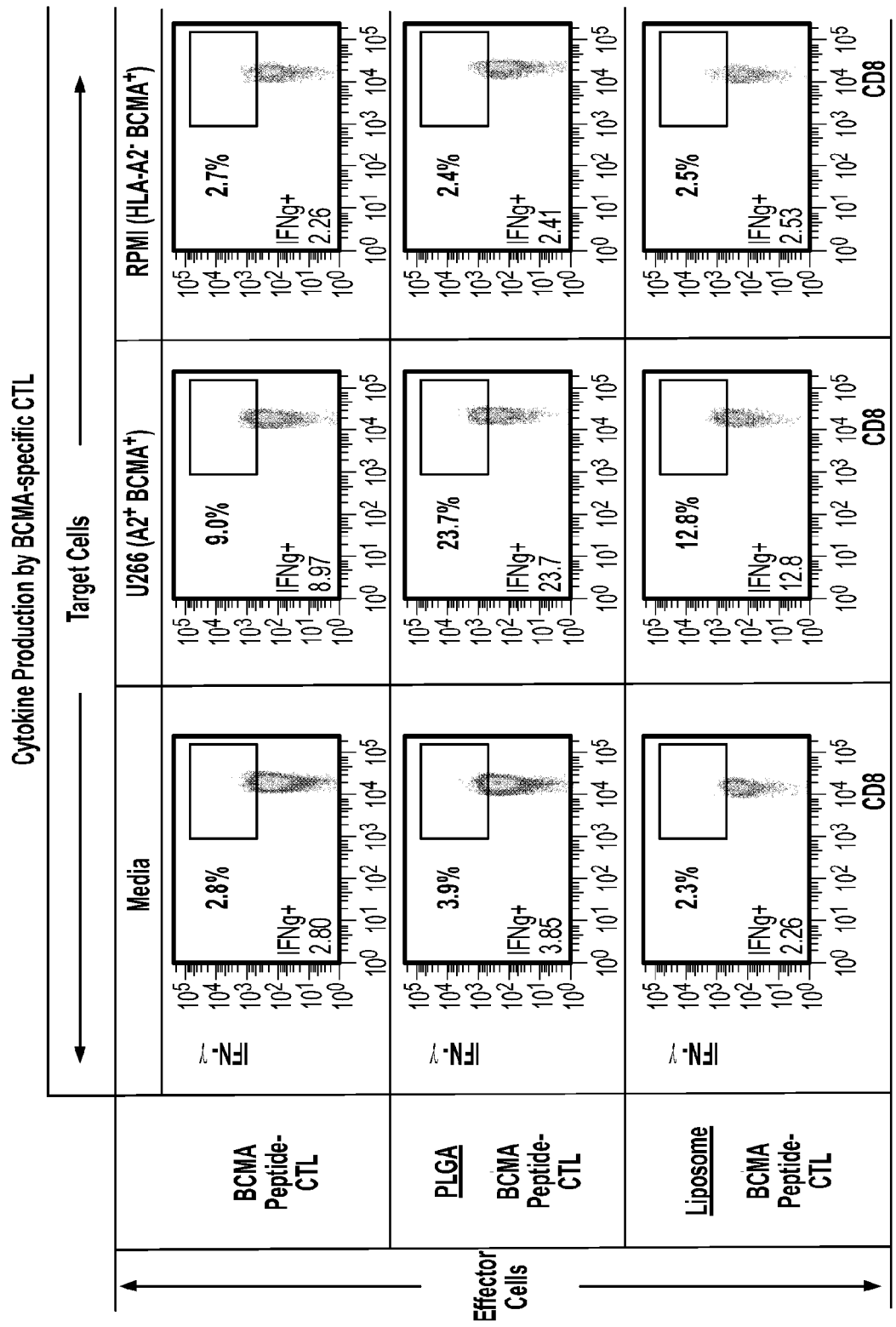
FIG. 34B shows the highest IFN-γ production by BCMA-CTL generated with PLGA/BCMA peptide against MM cell lines in an HLA-A2-restricted manner.
Figure 34C:
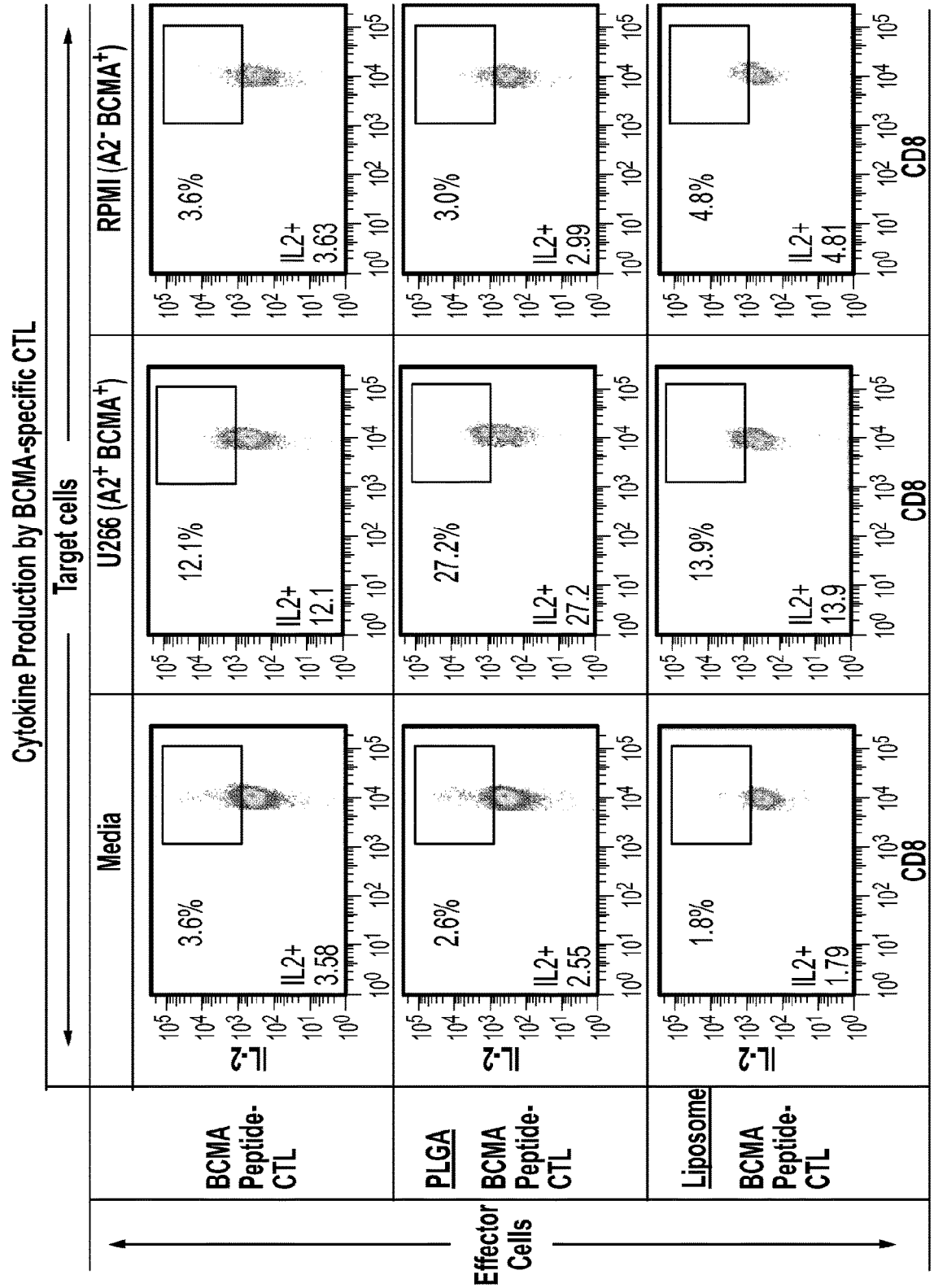
FIG. 34C shows the highest IL-2 production by BCMA-CTL generated with PLGA/BCMA peptide against MM cell lines in an HLA-A2-restricted manner.
Figure 34D:
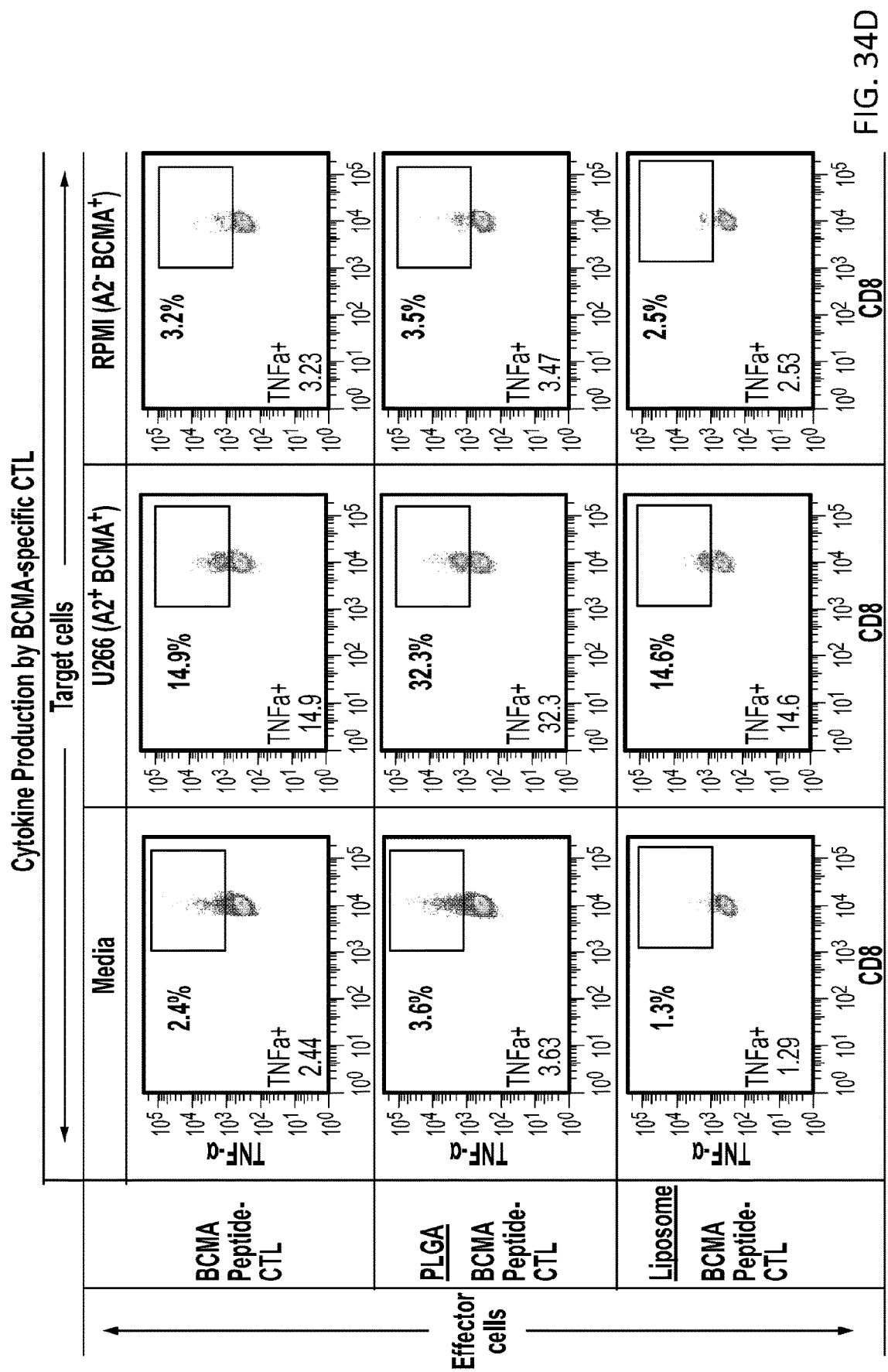
FIG. 34D shows the highest TNF-α production by BCMA-CTL generated with PLGA/BCMA peptide against MM cell lines in an HLA-A2-restricted manner.
Figure 34E:
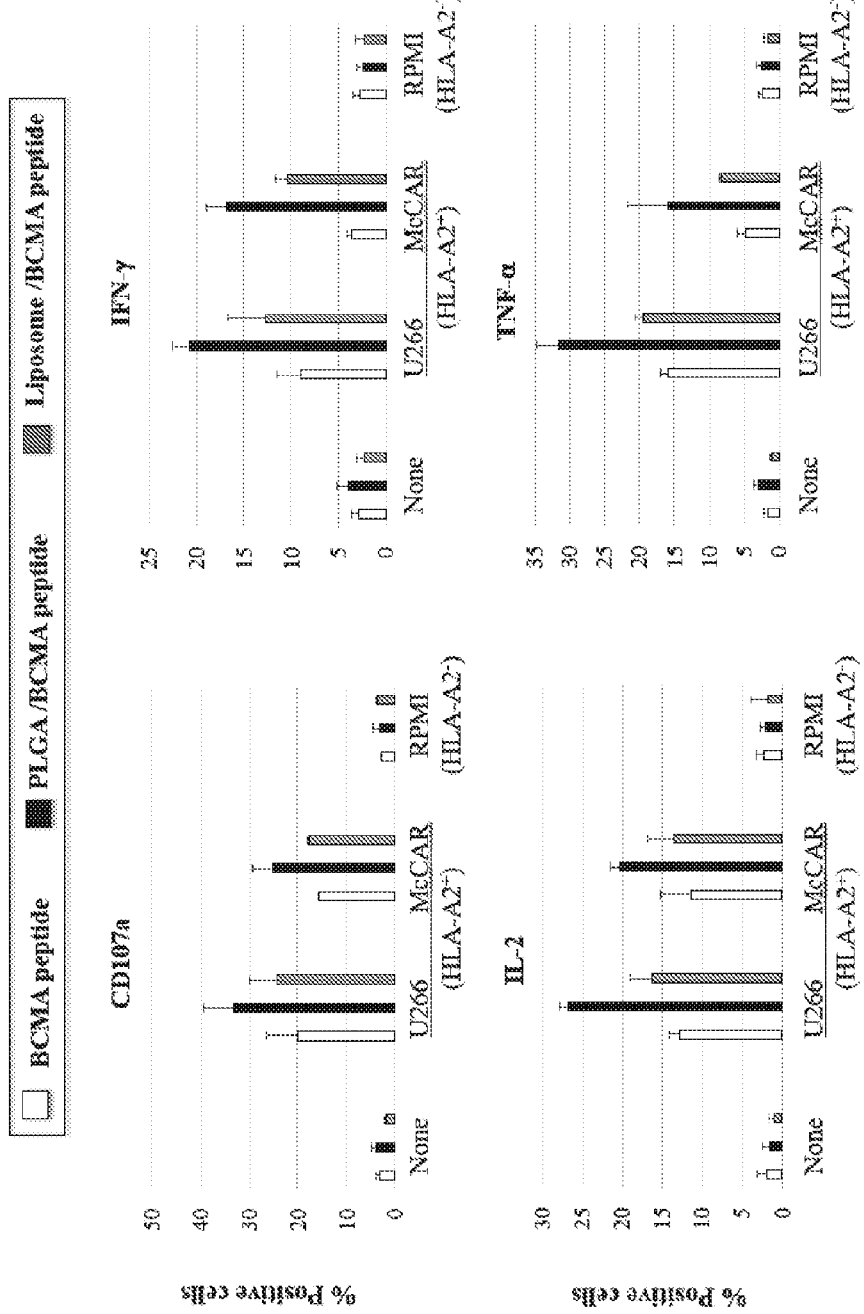
FIG. 34E shows the highest anti-MM activities and Th1 type cytokines (IFN-γ, IL-2, TNF-α) production by BCMA- CTL generated from different HLA-A2+ individuals (N=3) with PLGA/BCMA peptide against MM cell lines in an HLA-A2-restricted manner.

BCMA-specific CTL were evaluated one week after the fourth stimulation for their tumor-specific activities, following incubation with either HLA-A2$^+$ BCMA$^+$ (U266, McCAR) or HLA-A2$^-$ BCMA$^+$ (RPMI) myeloma cells. Representative flow cytometric analyses of BCMA-CTL generated by (1) BCMA peptide itself, (2) PLGA/peptide or (3) liposome/peptide demonstrated HLA-A2 restricted anti-myeloma activities including CD107a degranulation (FIG. 34A), IFN-γ production (FIG. 34B), IL-2 production (FIG. 34C), and TNF-α production (FIG. 34D), against HLA-A2$^+$ U266 myeloma cells, but not against HLA-A2$^-$ RPMI myeloma cells. Among the nanoparticle generated BCMA-CTL, PLGA/peptide induced superior antigen-specific CTL, evidenced by their higher level of anti-tumor activities [CD107a upregulation and IFN-γ/IL-2/TNF-α productions] than liposome/BCMA peptide-induced CTL. Further analyses confirmed that PLGA/peptide-CTL generated from additional HLA-A2$^+$ donors' (n=3) displayed the highest anti-myeloma activities in response to HLA-A2$^+$ BCMA$^+$ U266 and HLA-A2$^+$ BCMA$^{+(low)}$ McCAR, but not to MHC mismatched HLA-A2$^-$ BCMA$^+$ RPMI myeloma cells (FIG. 34E). In comparison, liposome/peptide-CTL had a slightly higher level of anti-MM activities compared to BCMA peptide-CTL, which were both lower than PLGA/peptide-CTL. Thus, these results indicate enhanced immunogenicity of BCMA peptide upon PLGA encapsulation, resulting in efficient induction of poly-functional CTL against multiple myeloma cells in an HLA-A2 restricted manner.

Highest Anti-MM Activities by BCMA-CTL Generated with PLGA Encapsulated BCMA Peptide Stimulation Against Primary CD138+ Tumor Cells from Myeloma Patients.

Figure 35A:
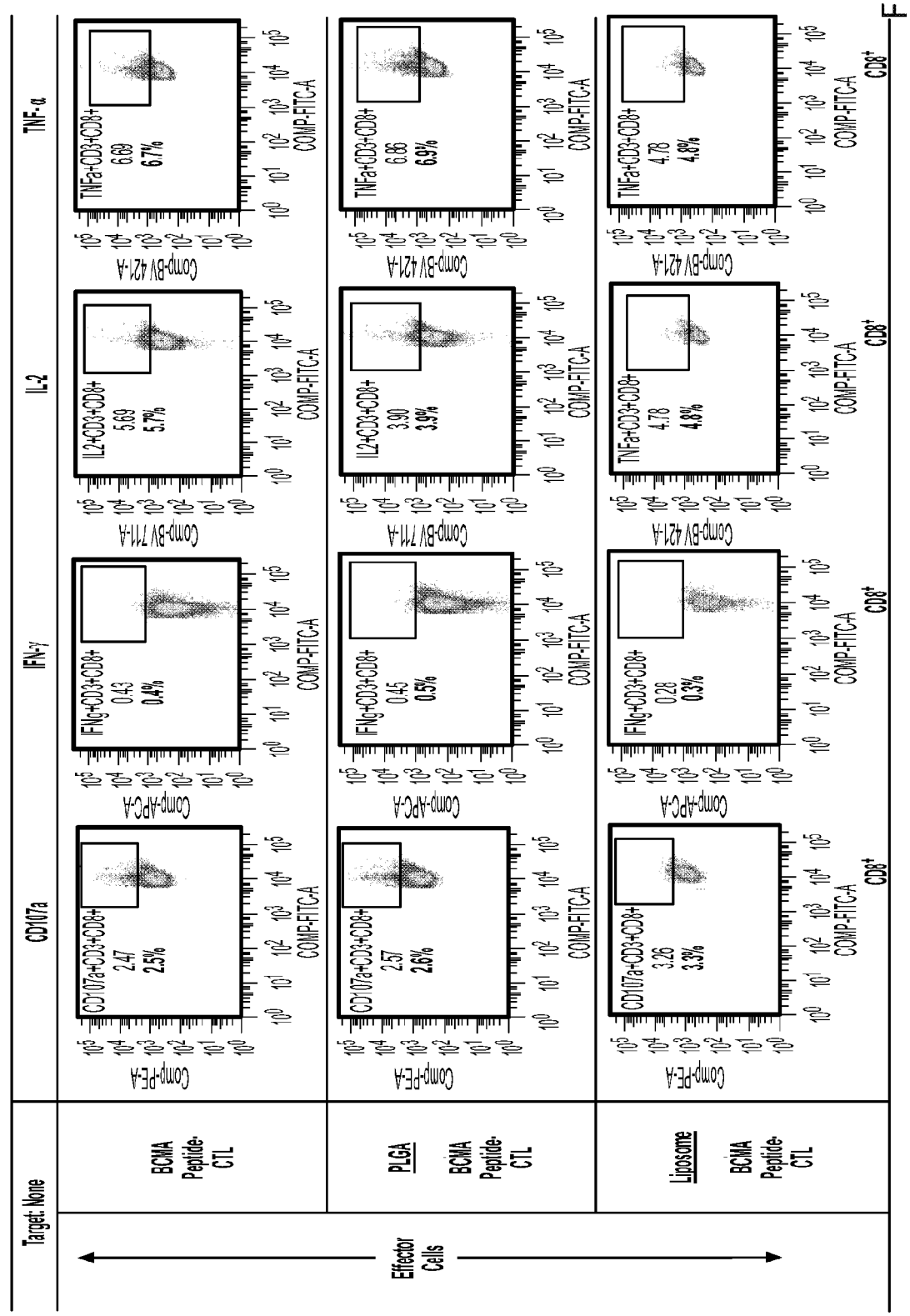
FIG. 35A shows the baseline activities of BCMA-specific CTL generated with BCMA peptide itself, PLGA/BCMA peptide or Liposome/BCMA peptide, in the absence of tumor cells.
Figure 35B:
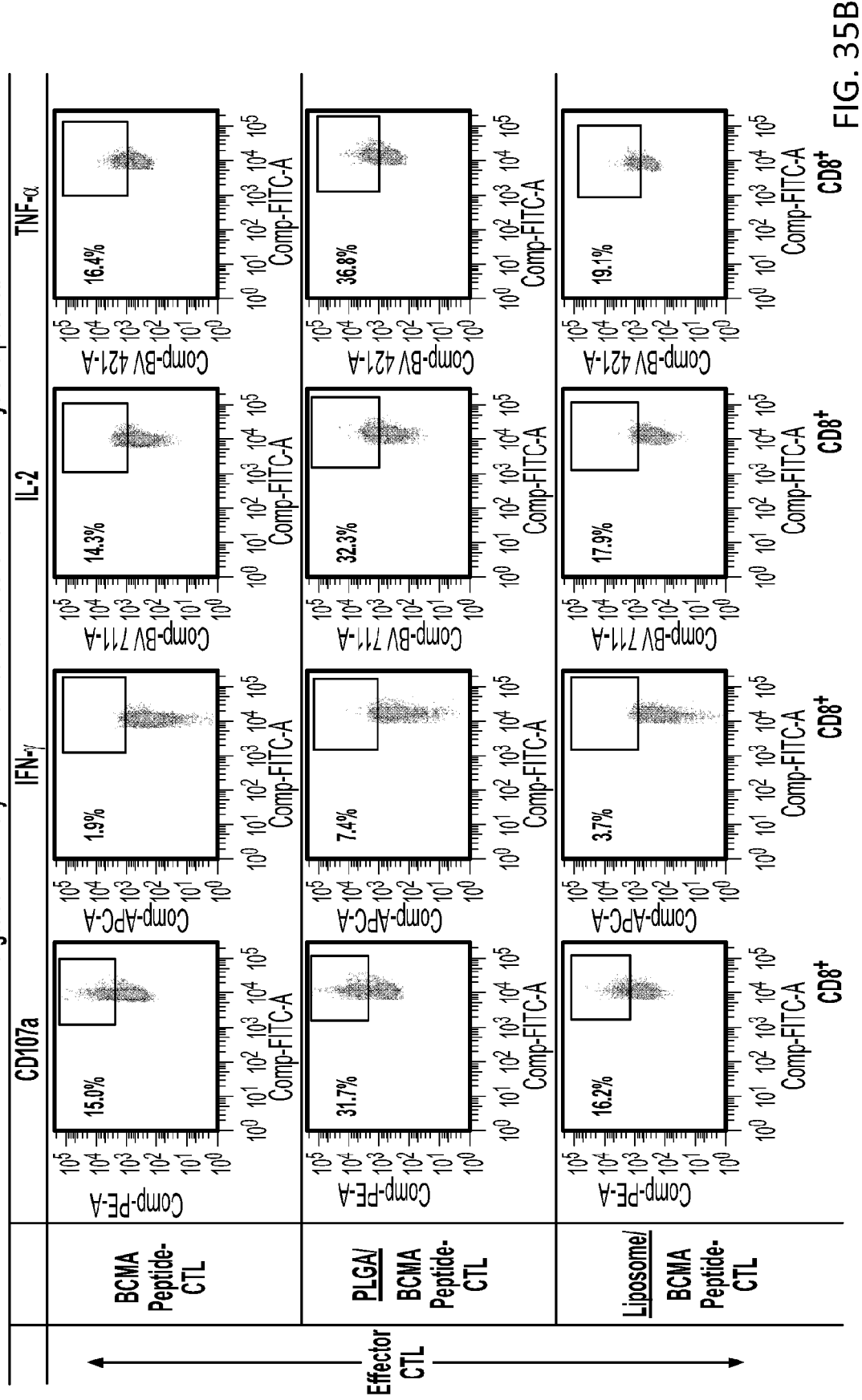
FIG. 35B shows the highest anti-MM activities by BCMA-CTL generated with PLGA/BCMA peptide in response to primary HLA-A2+ CD138+ tumor cells from HLA-A2+ myeloma patient #1.
Figure 35C:
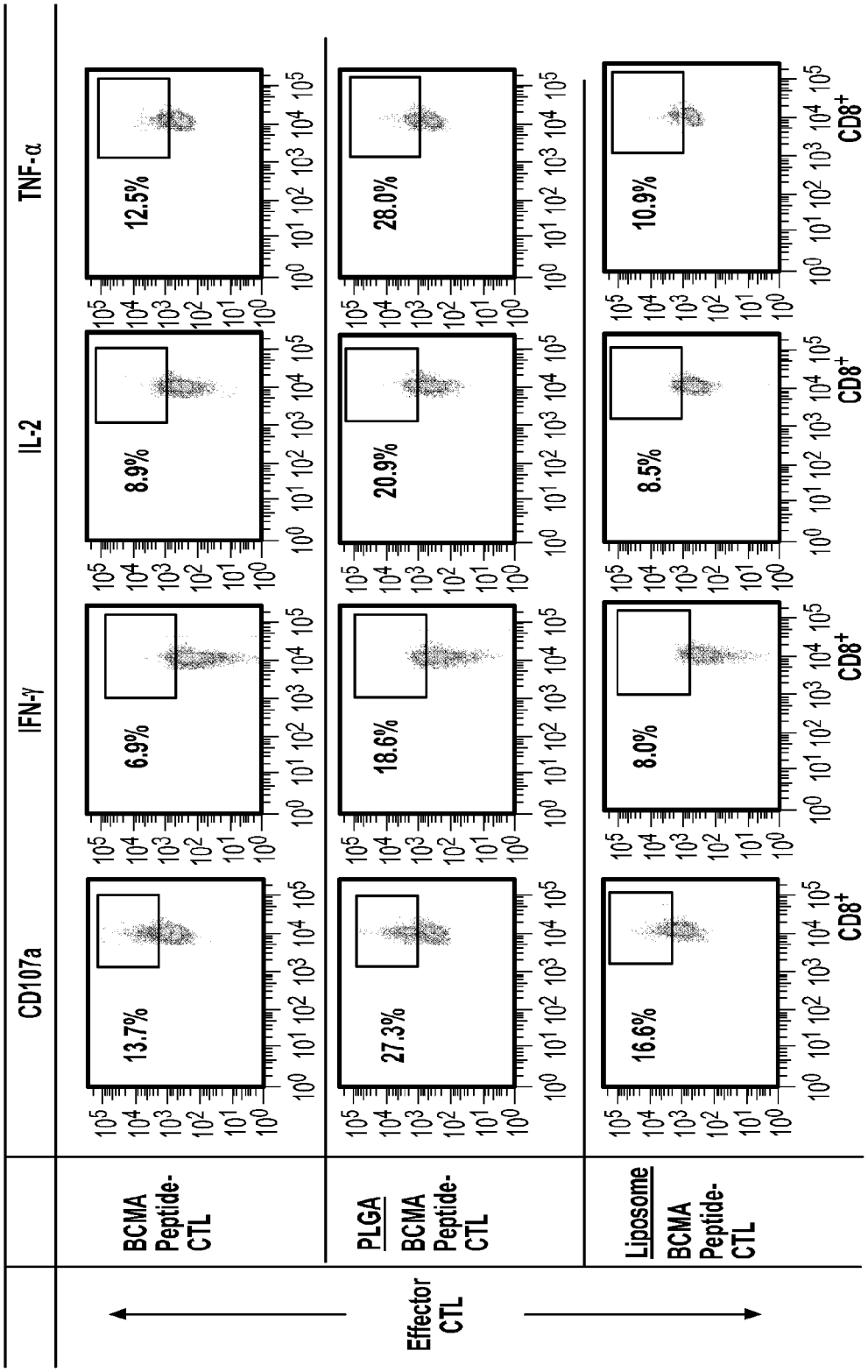
FIG. 35C shows the highest anti-MM activities by BCMA-CTL generated with PLGA/BCMA peptide in response to primary HLA-A2+ CD138+ tumor cells from HLA-A2+ myeloma patient #2.
Figure 35D:
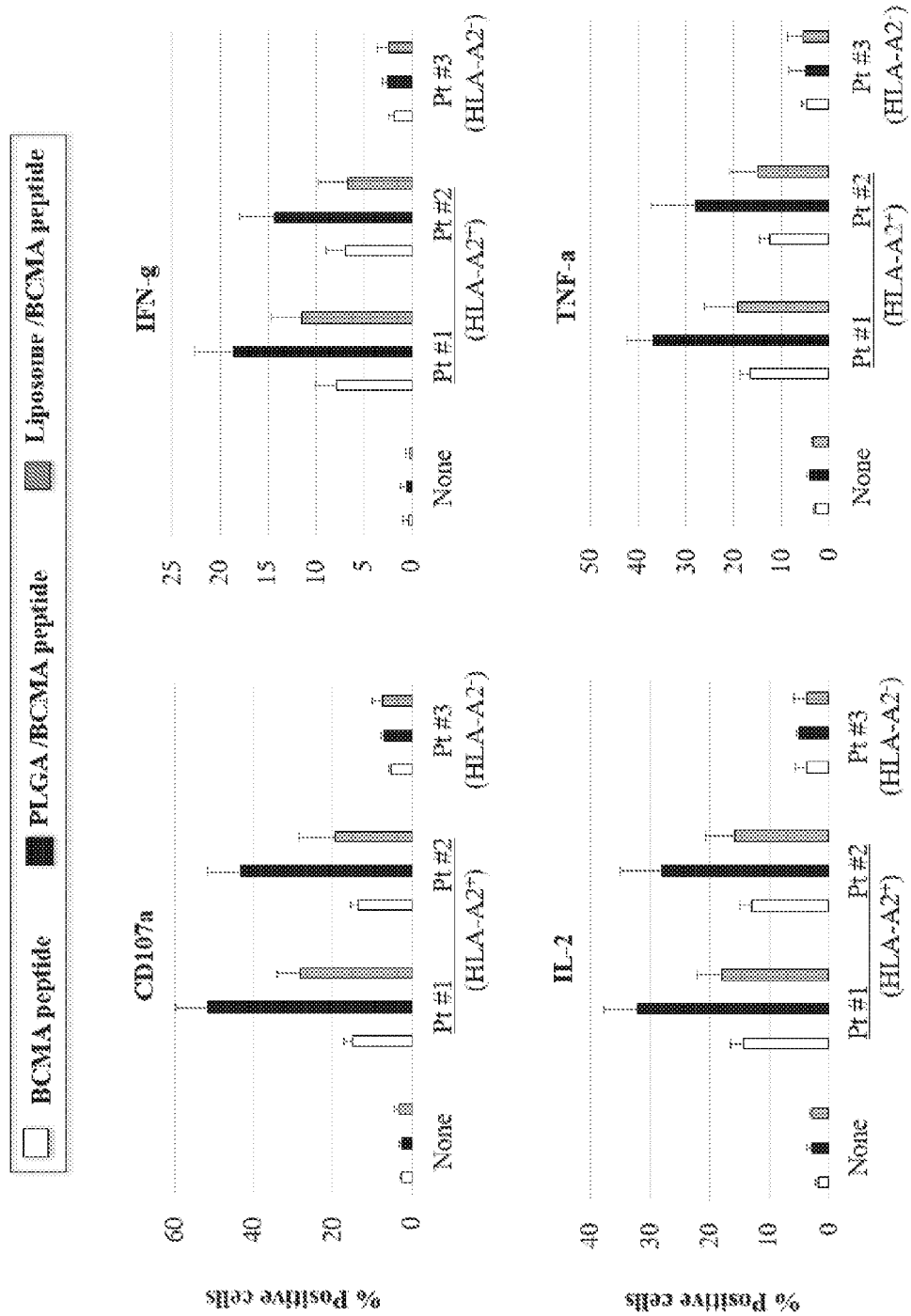
FIG. 35D shows the highest anti-MM activities and Th1 type cytokines (IFN-γ, IL-2, TNF-α) production by BCMA-CTL generated with PLGA/BCMA peptide against myeloma patients' tumor cells in an HLA-A2-restricted manner.

The myeloma-specific functional activities of BCMA-specific CTL, generated with or without NP encapsulation, were further evaluated against primary CD138$^+$ tumor cells from HLA-A2$^+$ or HLA-A2$^-$ myeloma patients. The three different effector cells generated by stimulation with BCMA peptide alone, PLGA/BCMA peptide, or liposome/BCMA peptide all showed minimal background levels pf CD107a degranulation and IFN-γ/IL-2/TNF-α production among the effector cells (FIG. 35A). Among the effector CTL, PLGA/peptide-CTL demonstrated the highest anti-MM activities against primary HLA-A2$^+$ CD138$^+$ (MM Patient 1) tumor cells [BCMA peptide-CTL vs. PLGA/peptide-CTL vs. Liposome/peptide-CTL: CD107a$^+$ CTL—15.0% vs. 31.7% vs. 16.2%, IFN-γ$^+$ CTL—1.9% vs. 7.4% vs. 3.7%, IL-2$^+$ CTL—14.3% vs. 32.3% vs. 17.9%, TNF-α$^+$ CTL—16.4% vs. 36.8% vs. 19.1%] (FIG. 35B). Despite having the highest peptide uptake by DC, the anti-MM activities of the liposome/peptide-CTL was less than PLGA/peptide-CTL against primary HLA-A2$^+$ CD138$^+$ tumor cells. A similar pattern of functional anti-MM activities was detected in the effector CTL against primary CD138$^+$ tumor cells obtained from an HLA-A2$^+$ MM patient #2, with the PLGA/peptide-CTL having the highest activities (FIG. 35C). In contrast, none of the different BCMA-CTL had anti-tumor activities against HLA-A2$^-$ CD138$^+$ tumor cells, thereby demonstrating HLA-A2-restricted immune responses (FIG. 35D). Taken together, these results indicate that the highest level of anti-myeloma activities are seen with PLGA/BCMA peptide-CTL against primary CD138$^+$ MM cells in an HLA-A2 restricted manner. The results also highlight the potential of increased anti-tumor activities through generation of BCMA-specific CTL upon the peptide encapsulation in PLGA.

Increased CD28 Costimulatory Molecule Expression and Peptide-Specific T Cells Proliferation by BCMA-CTL Generated with PLGA Encapsulation.

Figure 36A:
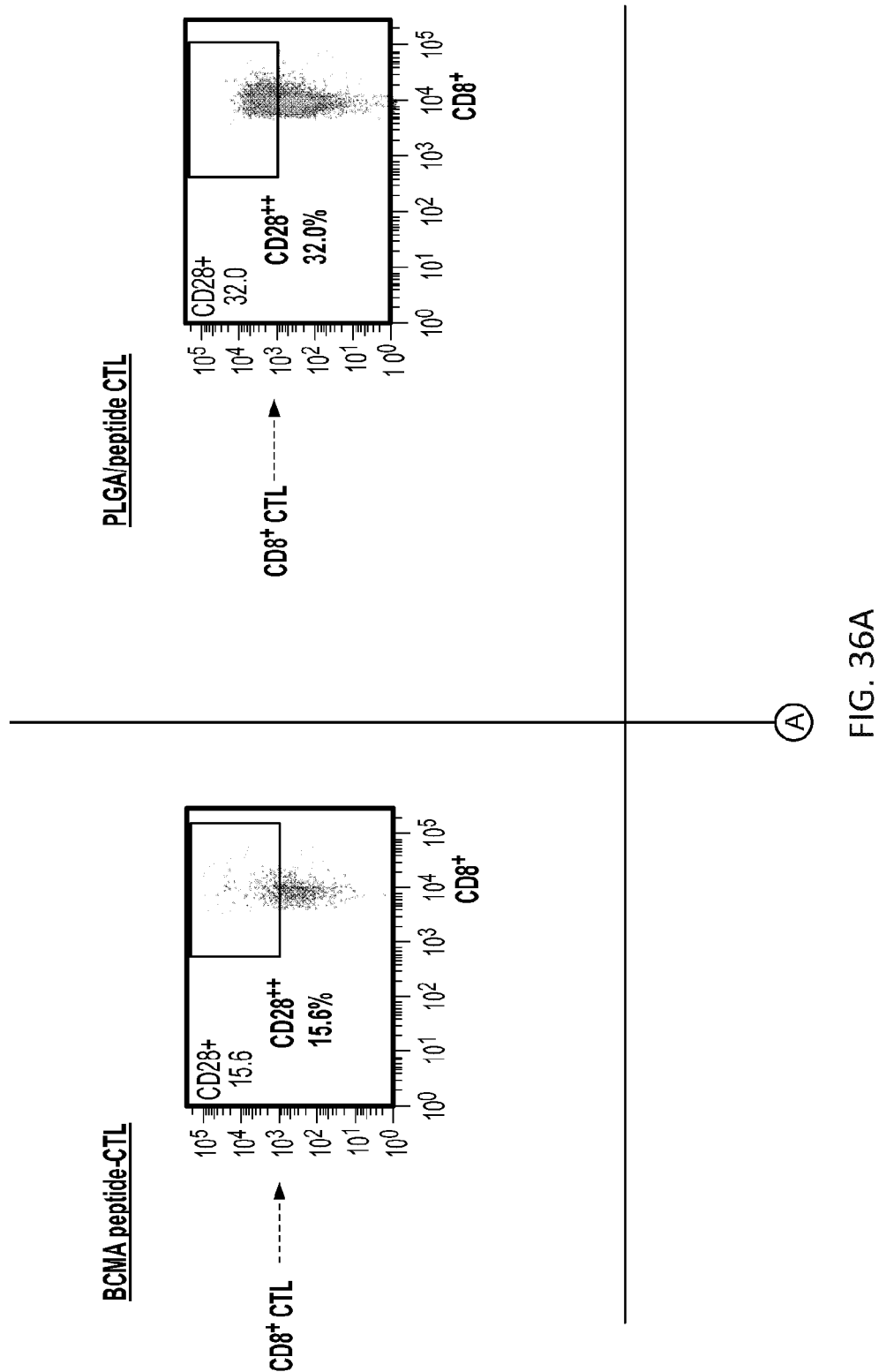
FIG. 36A shows a higher frequency of Tetramer+ CD8+ T cells and costimulatory molecule expressing (CD28+) CD8+ T cells by BCMA-CTL generated with PLGA/BCMA peptide than with BCMA peptide itself.
Figure 36A:
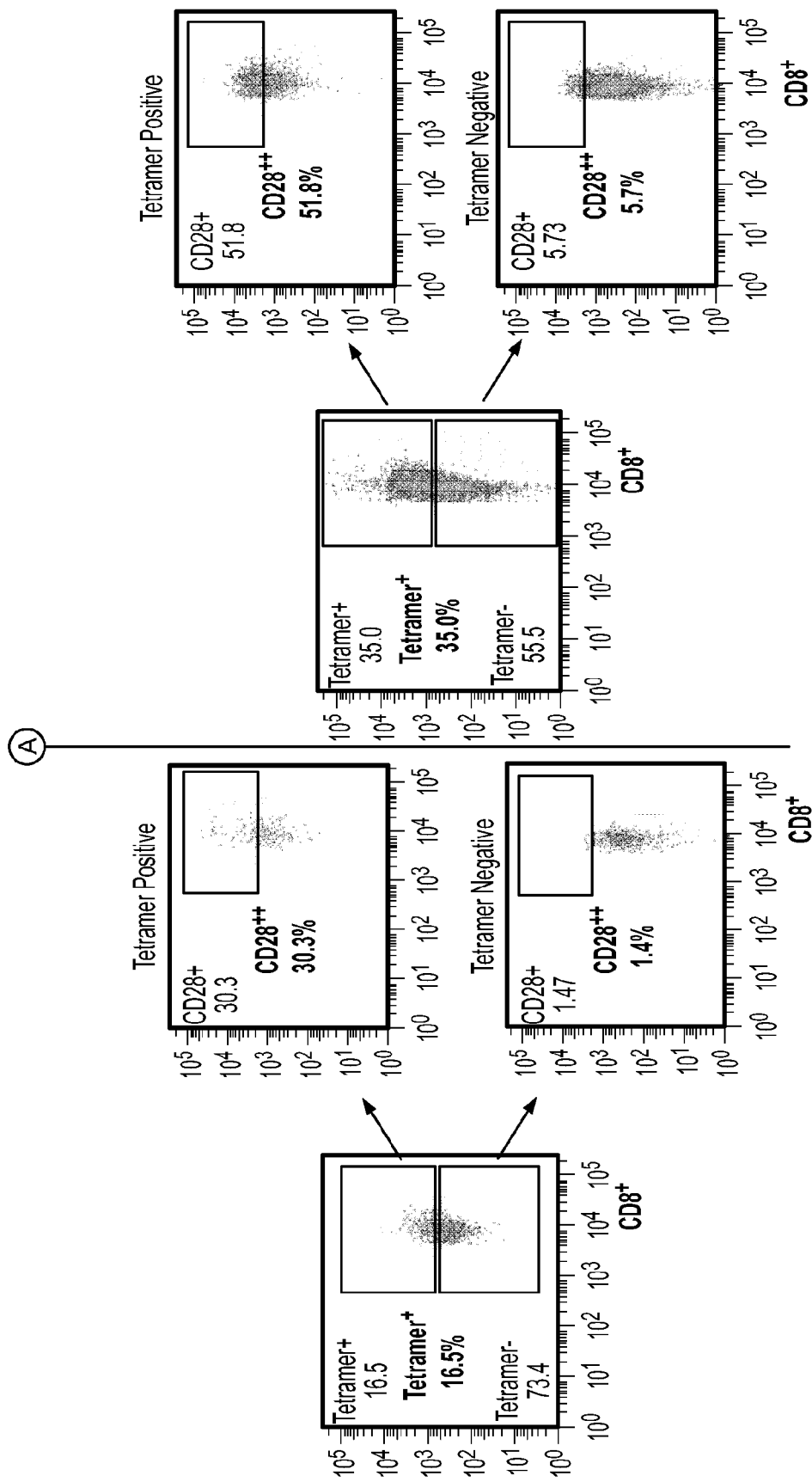
Figure 36B:
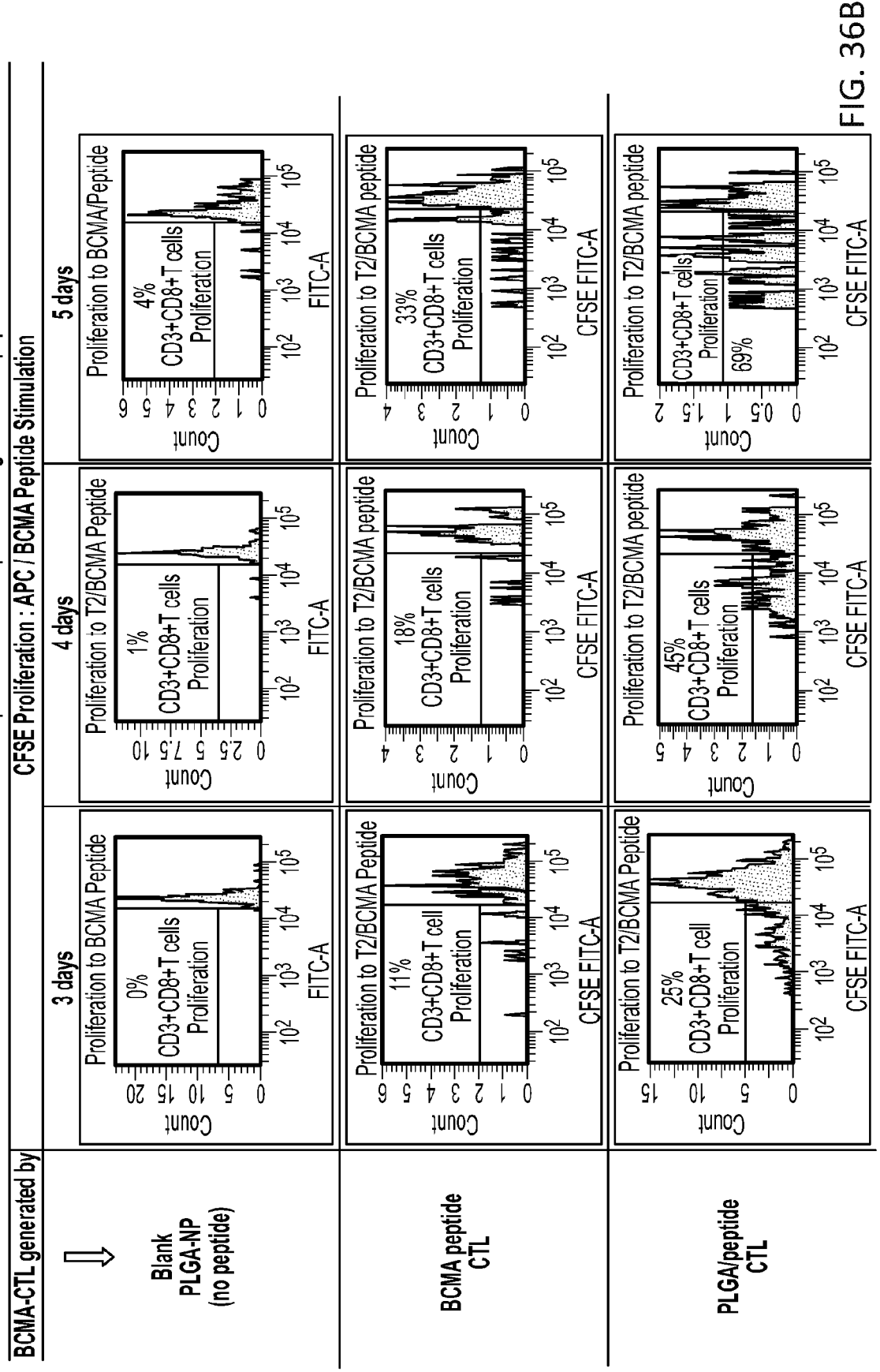
FIG. 36B shows a higher increase of peptide-specific CD8+ T cells proliferation by BCMA-CTL generated with PLGA/BCMA peptide than with BCMA peptide itself.
Figure 36C:
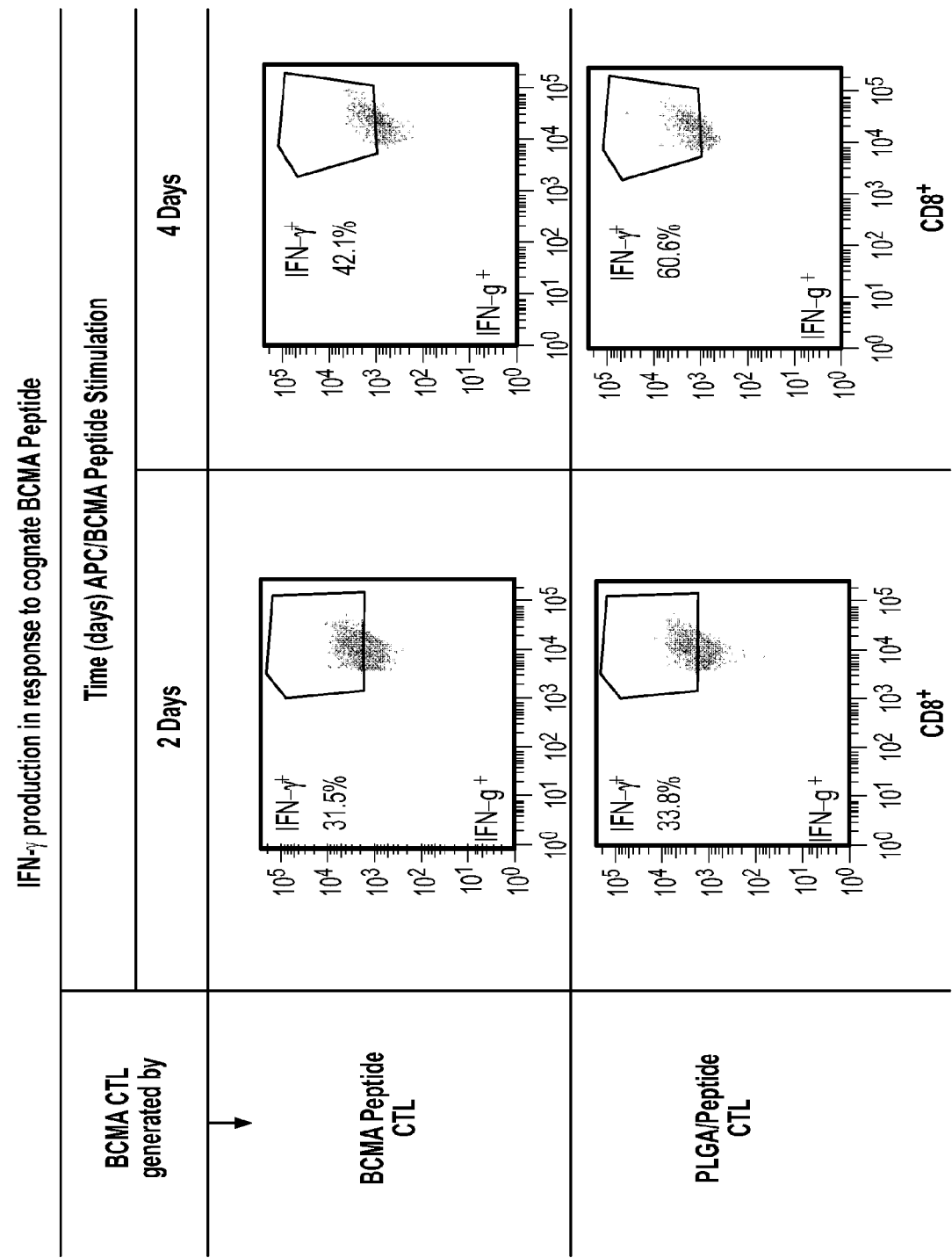
FIG. 36C shows a higher increase of peptide-specific IFN-γ production by BCMA-CTL generated with PLGA/BCMA peptide than with BCMA peptide itself.

To better understand the mechanism of high anti-tumor activities in the BCMA-specific CTL mediated by PLGA, experiments were performed to evaluate their expression of costimulatory molecule on CD8$^+$ T cells and BCMA peptide-specific Tetramer$^+$ CTL. Compared to BCMA peptide-CTL, PLGA/peptide CTL demonstrated a unique subset of cells with upregulated CD28$^{++}$ expression on the CD8$^+$ T cells (peptide-CTL vs. PLGA/peptide-CTL: 15.6% vs. 32.0%; FIG. 36A upper panel). In addition, PLGA/peptide CTL contained a higher proportion for BCMA Tetramer$^+$ peptide-specific CTL as compared to BCMA peptide CTL (peptide-CTL vs. PLGA/peptide-CTL: 16.5% vs. 35.0%; FIG. 36A lower panel). In addition, a higher frequency of bright CD28$^{++}$ cells was detected within the Tetramer-positive as compare to Tetramer-negative CD8$^+$ T cells. The PLGA/peptide Tetramer$^+$ CTL displayed a higher frequency of CD28$^{++}$ bright cells than BCMA peptide Tetramer$^+$ CTL (51.8% vs. 30.3%). Thus, these results demonstrate that PLGA/peptide induced CTL have a greater proportion of BCMA-specific Tetramer$^+$ cells having a unique population of bright CD28$^{++}$ BCMA-specific CTL. Next, experiments were performed to demonstrate proliferation of BCMA peptide CTL and PLGA/peptide CTL upon recognition of their cognate BCMA peptide presented by APC. Both BCMA peptide CTL and PLGA/peptide CTL demonstrated increased proliferation upon recognition of their cognate BCMA peptide in a time dependent manner (Day 3, Day 4 vs. Day 5:11%, 18% vs. 33%) as compared to the baseline proliferation of non-BCMA specific $CD8^+$ T cells (Day 3, Day 4 vs. Day 5: 0%, 1% vs. 4%). Importantly, proliferation occurred earlier in PLGA/peptide-CTL at all time points (Day 3, Day 4 vs. Day 5: 25%, 45% vs. 69%) (FIG. 36B), indicating an increased ability to recognize and respond to the cognate BCMA peptide. Lastly, Th1 cytokine production generated in response to cognate BCMA peptide. was measured in each effector cell population. PLGA/peptide CTL had a higher level of IFN-γ production (two days incubation—33.8%, four days incubation—60.6%), as compared to BCMA peptide CTL (two days incubation—31.5%, four days incubation—42.1%) (FIG. 36C). These results, therefore, demonstrate enhanced peptide-specific $CD8^+$ T cell immune responses, proliferation, and IFN-γ production in response to PLGA/peptide-CTL, indicating that PLGA/peptide encapsulation can increase the immunogenicity of BCMA peptide to generate CTL with higher anti-tumor activities.

Effective Generation of Memory CD8+ CTL Associated with Enhanced Anti-Myeloma Activities in Response to Stimulation with PLGA/BCMA Peptide.

Figure 37A:
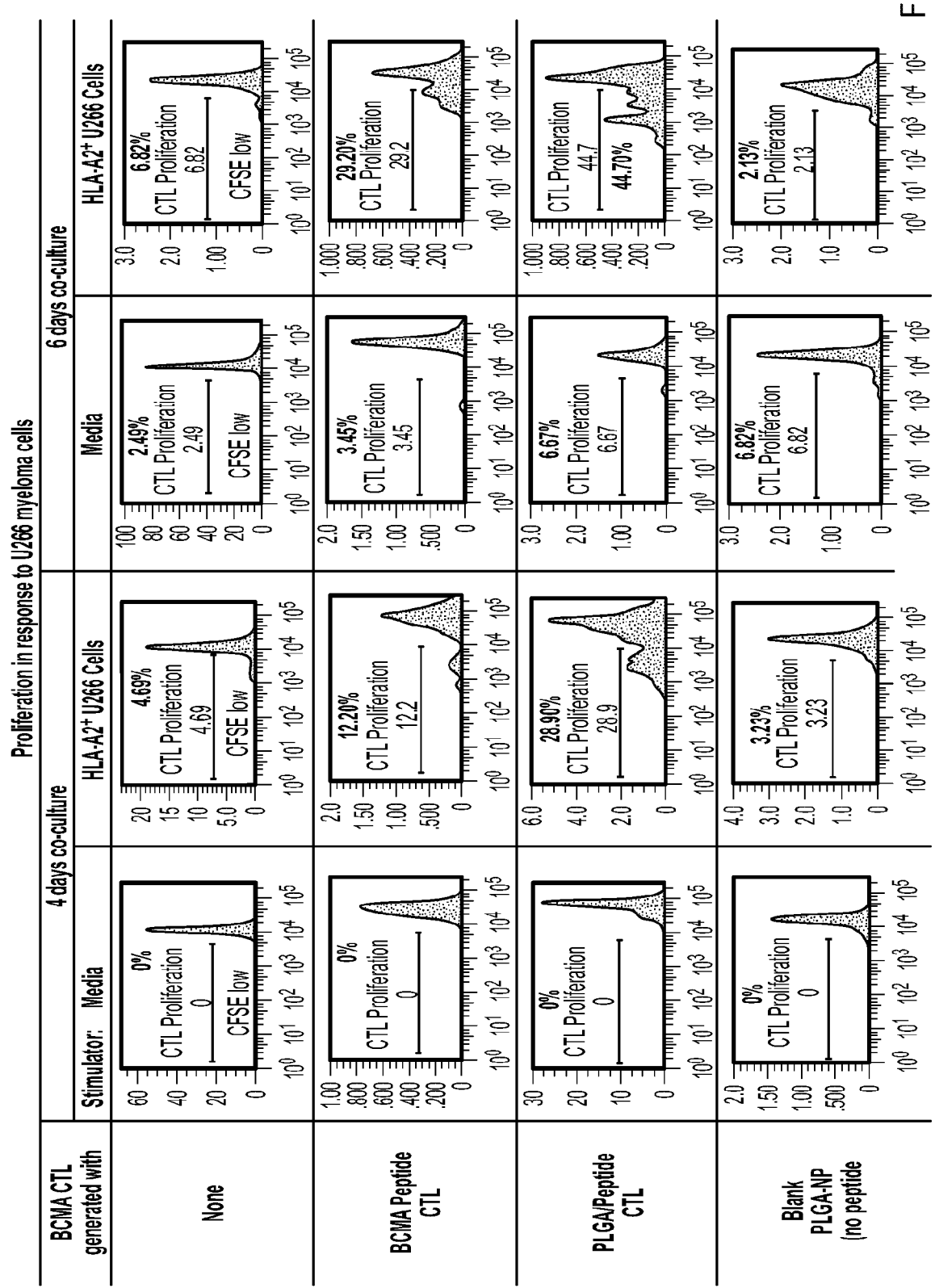
FIG. 37A shows the highest induction of myeloma-specific CD8+ T cells proliferation by BCMA-CTL generated with PLGA/BCMA peptide than with BCMA peptide itself.
Figure 37B:
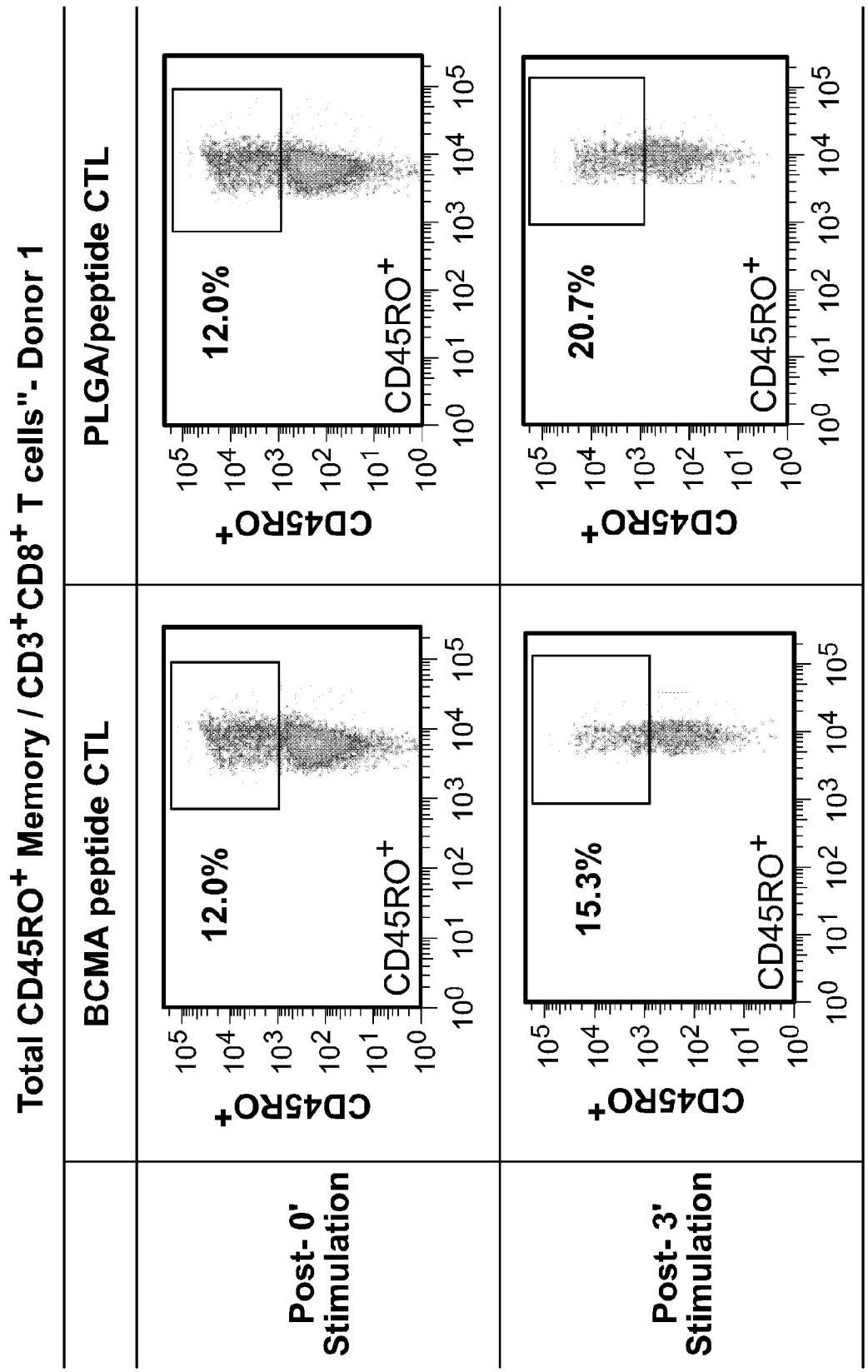
FIG. 37B shows a higher increase in CD45RO+ memory/CD3+ CD8+ T cells subset in BCMA-CTL [representative results], upon repeated stimulation with PLGA/BCMA peptide than with BCMA peptide itself.
Figure 37B:
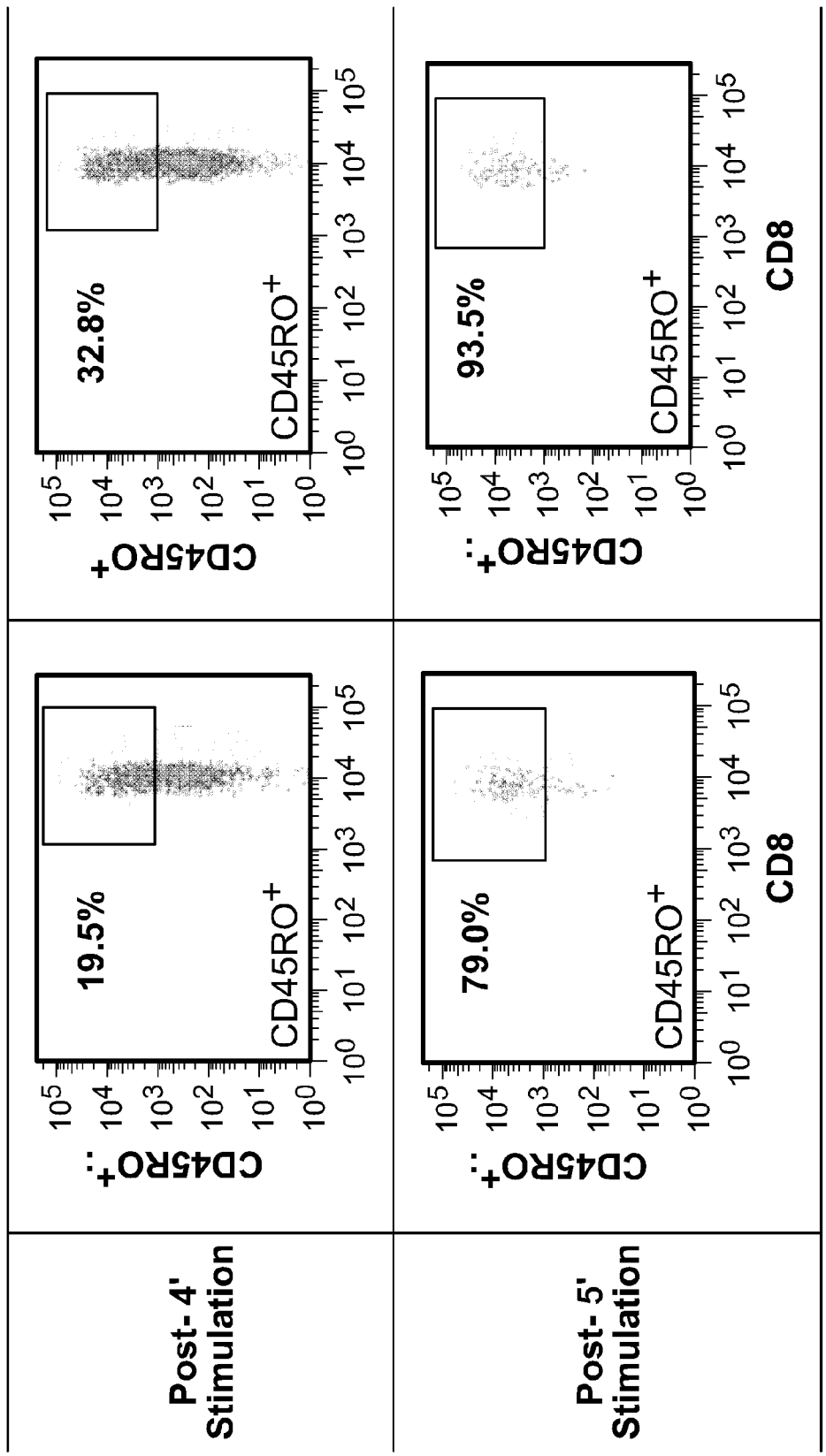
Figure 37C:
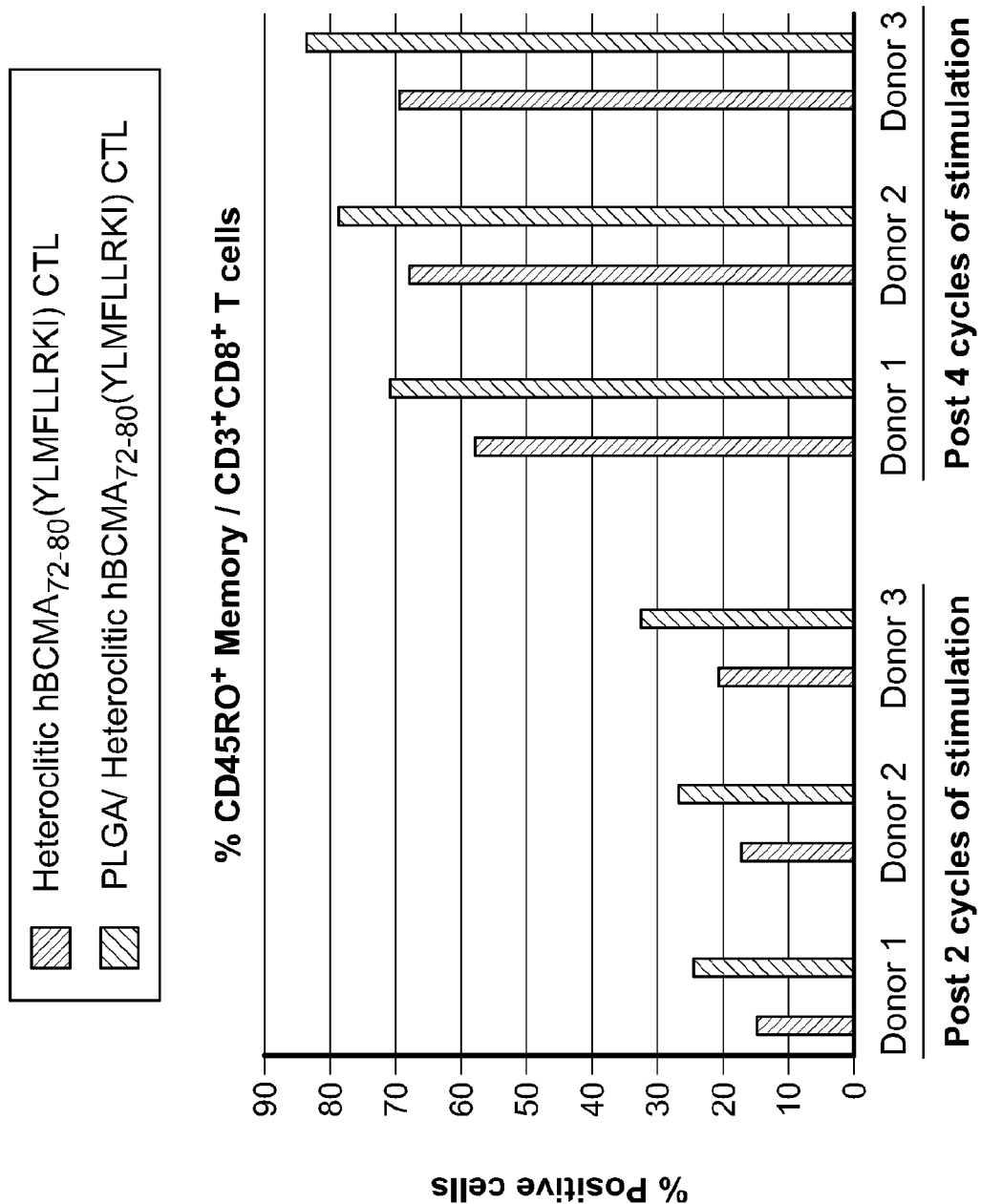
FIG. 37C shows a higher increase in CD45RO+ memory/CD3+ CD8+ T cells subset in BCMA-CTL [N=3 results], upon repeated stimulation with PLGA/BCMA peptide than with BCMA peptide itself.
Figure 37D:
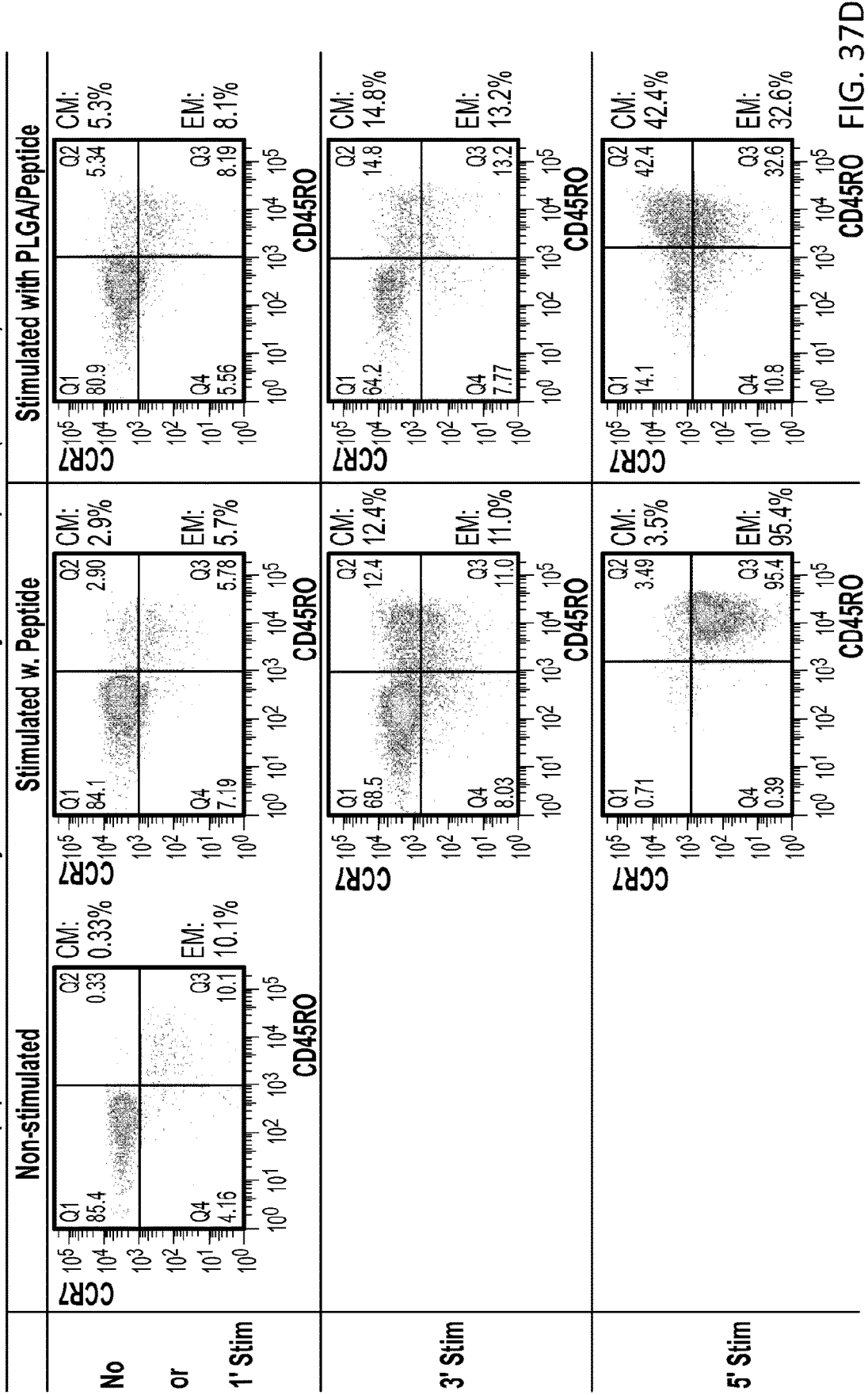
FIG. 37D shows a higher induction and maintenance of central memory/CD3+CD8+ T cells subset in BCMA-CTL, upon repeated stimulation with PLGA/BCMA peptide than with BCMA peptide itself.

Experiments were further performed to characterize and compare memory cell development and the immune functional activities of PLGA/peptide, blank PLGA (control), and peptide alone induced CTL. In CFSE assays, PLGA/peptide CTL displayed higher proliferation in response to $HLA-A2^+$ U266 cells by (Day 4: 28.90%, Day 6: 44.70%) than BCMA peptide-CTL (Day 4: 12.20%, Day 6: 29.20%) at all time points evaluated (FIG. 37A). Effector cells stimulated with PLGA itself as a vehicle displayed minimal proliferation (less than 7%) on 4 days and 6 co-culture. In addition, no proliferation was seen in the media controls, providing evidence that CTL proliferation was specific to myeloma cells. Next, experiments were performed to characterize memory cell development within BCMA peptide CTL and PLGA/peptide CTL. Overall, it was observed a gradual increase in CTL memory cell development after each round of peptide stimulation: total $CD45RO^+$ memory CTL was higher after PLGA/BCMA peptide stimulation (3' stimulation: 20.7%, 4' stimulation: 32.8%, 5' stimulation: 93.5%) compared to BCMA peptide (3' stimulation: 15.3%, 4' stimulation: 19.5%, 5' stimulation: 79.0%) (FIG. 37B). This pattern of memory cell development in the PLGA/peptide CTL and BCMA peptide CTL remained post-2 or post-4 cycles of peptide stimulation (FIG. 37C). Experiments were also performed to characterize specific central and effector memory subset development in the PLGA/peptide CTL and BCMA peptide CTL. Consistent with total $CD45RO^+$ memory development, both the central memory (CM) and effector memory (EM) CD8+ T cell subsets gradually increased after 1 cycle of stimulation (PLGA/Peptide—CM 5.3%, EM 8.1%, Peptide—CM 2.9%, EM 5.7%), and further increased after 3 cycles of stimulation (PLGA/peptide—CM 14.8%, EM 13.2%, Peptide—CM 12.4%, EM 11.0%). After the 5-cycle of peptide stimulation, a major difference in the proportion of central memory and effector memory cell development was observed (PLGA/peptide—CM 42.4%, EM 32.6%, Peptide—CM 3.5%, EM 95.4%). In addition, PLGA/peptide CTL maintained a higher proportion of central memory T cells with the highest anti-tumor activities, without further differentiation to effector memory cells (FIG. 37D).

Maintenance of Central Memory CD8+ CTL Associated with Effective Anti-Myeloma Activities by PLGA/BCMA Peptide.

Figure 38A:
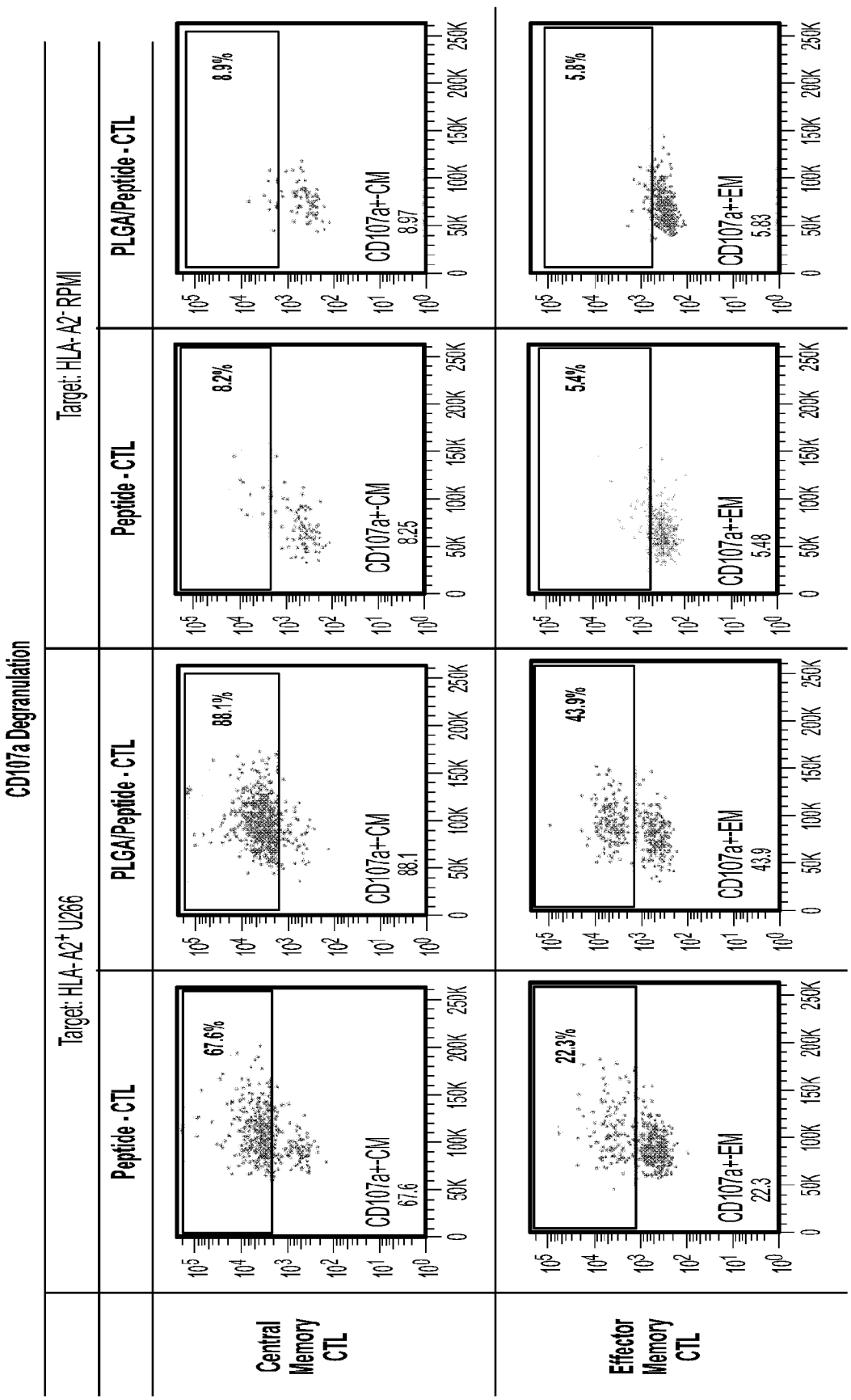
FIG. 38A shows a higher induction of central memory and effector memory CTL and their anti-MM activities against myeloma cells, in an HLA-A2-restricted manner, by BCMA-CTL generated with PLGA/BCMA peptide than with BCMA peptide itself.
Figure 38B:
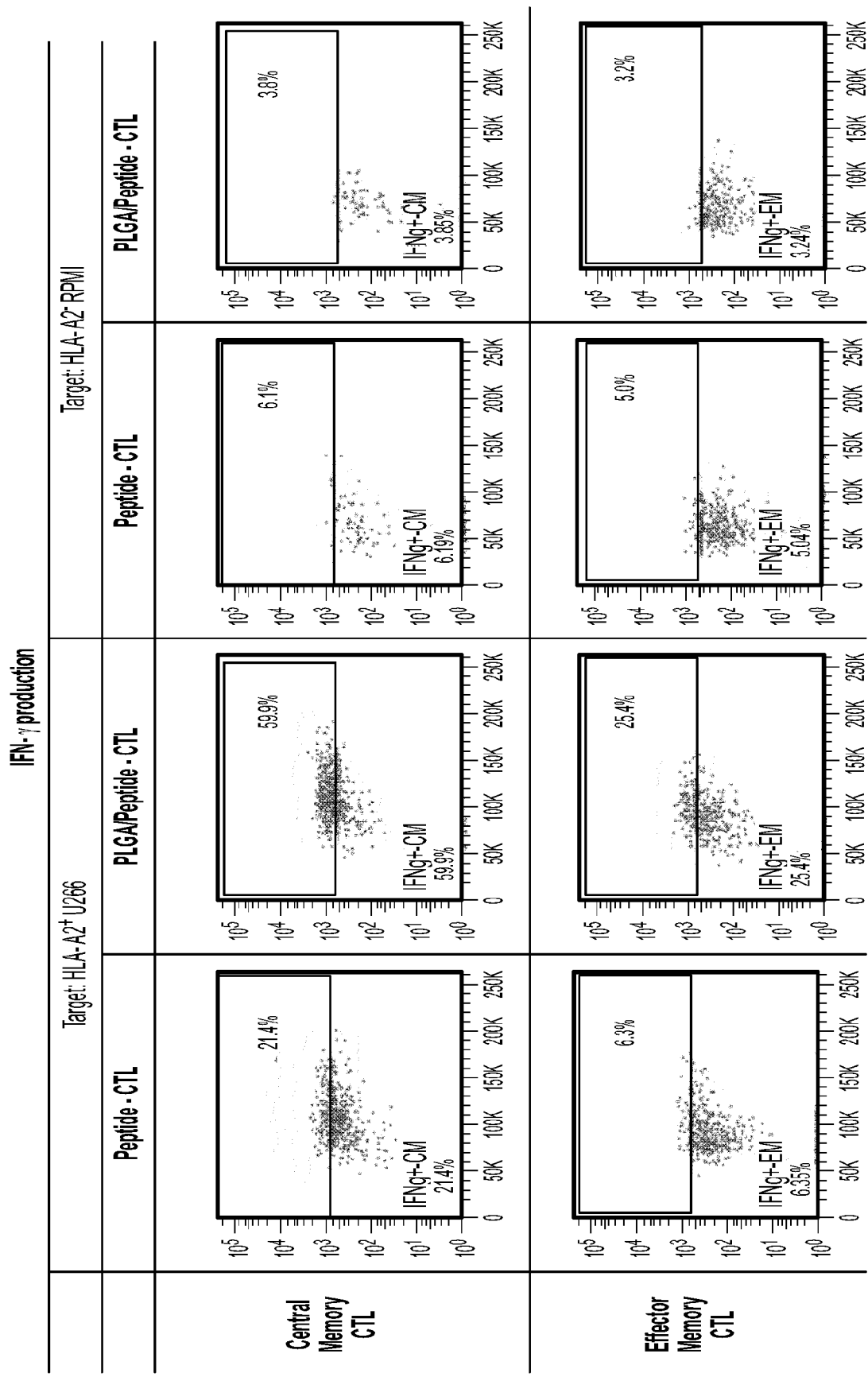
FIG. 38B shows a higher induction of central memory and effector memory CTL and their IFN-γ production against myeloma cells, in an HLA-A2-restricted manner, by BCMA-CTL generated with PLGA/BCMA peptide than with BCMA peptide itself.
Figure 38C:
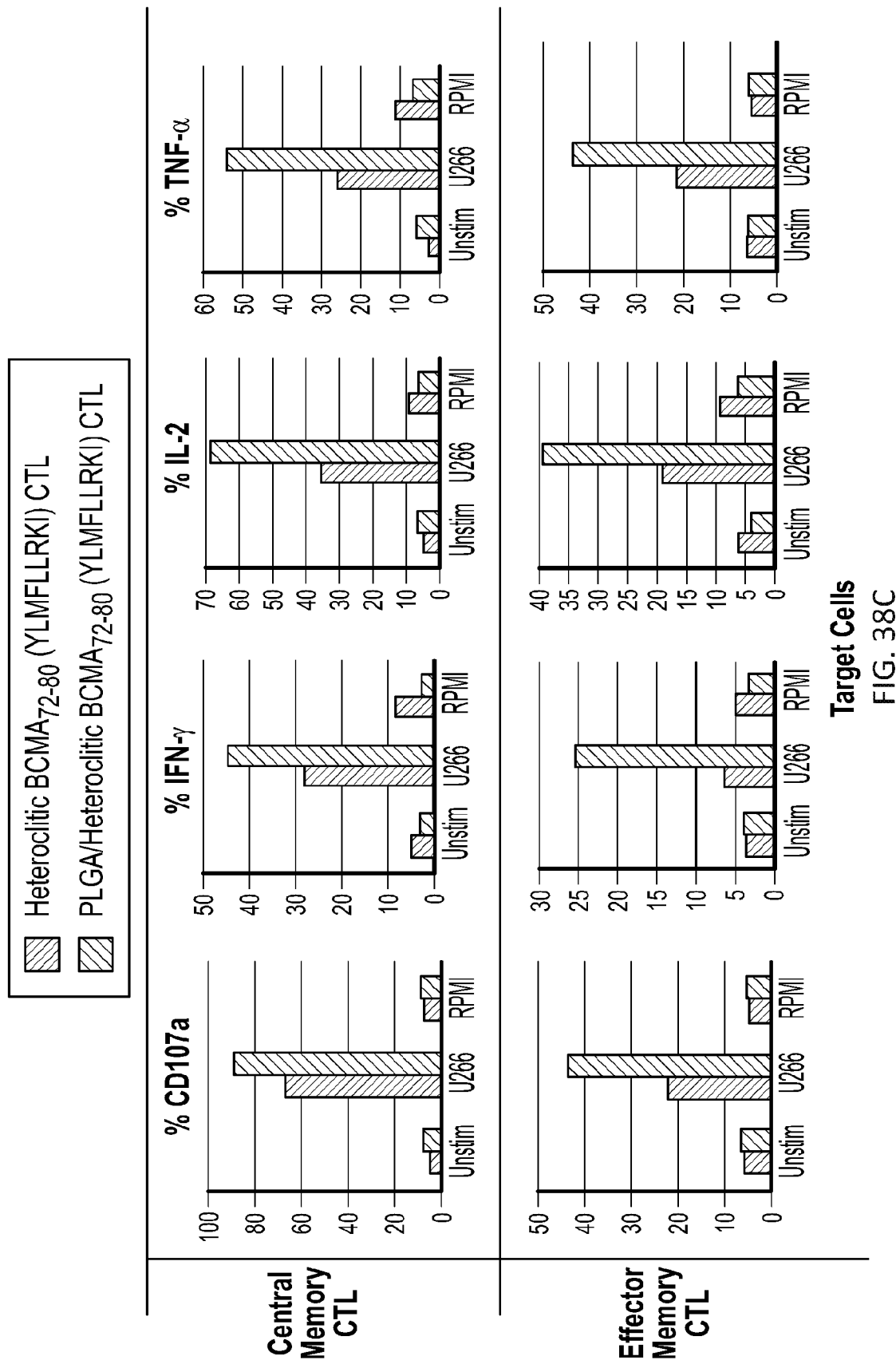
FIG. 38C shows a higher induction of central memory and effector memory CTL and their anti-MM activities and IFN-γ, IL-2, TNF-α production against myeloma cells, in an HLA-A2-restricted manner, by BCMA-CTL generated with PLGA/BCMA peptide than with BCMA peptide itself.

The specific anti-MM activities were further investigated within each memory CTL subset. Here, it was confirmed the HLA-A2-restricted anti-myeloma activities of BCMA-specific CTL generated from different HLA-A2+ individuals by stimulation with PLGA/peptide or BCMA peptide. The highest immune functional activities (CD107a upregulation and Th1-type cytokine production) in response to $HLA-A2^+$ U266 myeloma cells were consistently seen in CTL induced by PLGA/peptide (FIGS. 38A, 38B, 38C). Importantly, the highest anti-MM activities were found within the central memory as compared to the effector memory subsets, as shown by CD107a degranulation (FIGS. 38A, 38C), IFN-γ production (FIGS. 38B, 38C), and IL-2/TNF-α production (FIG. 38C). These therefore indicate that PLGA encapsulated BCMA peptide induces a more robust tumor specific CTL response than BCMA peptide, evidenced by generation and maintenance of central memory cells within the PLGA/peptide BCMA antigen-specific CTL.

These results support the use of PLGA/BCMA peptide to induce effective BCMA CTL with anti-tumor activities in novel vaccination and/or adoptive immunotherapy treatment protocols in myeloma.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A peptide comprising:
(a) an amino acid sequence set forth in any one of SEQ ID NOs: 13-17; or
(b) a first amino acid sequence consisting of an amino acid sequence set forth in any one of SEQ ID NOs: 1-17; and a second amino acid sequence that is heterologous to the first amino acid sequence; wherein the second amino acid sequence that is heterologous to the first amino acid sequence comprises: (i) a purification tag, (ii) a detectable marker, (iii) an immunoglobulin molecule or a portion thereof comprising a heavy chain constant region, (iv) a therapeutic or immune-stimulating polypeptide, (v) a carrier, or (vi) a transportation sequence.

2. A composition comprising the peptide of claim 1 and a second agent.

3. The composition of claim 2, wherein the second agent is: an immune stimulatory agent, a T helper epitope, an adjuvant, a toll like receptor-3 ligand, interferon alfa (IFNα), interferon gamma (IFNγ), an anti-OX40 antibody, an anti-glucocorticoid-induced tumor necrosis factor receptor-related protein (GITR) antibody, or Granulocyte-macrophage colony-stimulating factor (GM-CSF).

4. A pharmaceutical composition comprising the peptide of claim 1 and a pharmaceutically acceptable carrier.

5. A method of inducing an immune response against BCMA- and/or TACI-expressing cancer cells in a human subject in need thereof, the method comprising administering to the human subject the peptide of claim 1.

6. A method of treating a human subject having multiple myeloma, monoclonal gammopathy of undetermined significance (MGUS), or smoldering multiple myeloma, the method comprising administering to the human subject the peptide of claim 1.

7. A method of generating and/or proliferating BCMA-specific cytotoxic T cells, the method comprising contacting one or more cytotoxic T cells with one or more antigen presenting cells pulsed with a peptide comprising the amino acid sequence set forth in SEQ ID NO: 13 or SEQ ID NO: 14.

8. A method of generating TACI-specific cytotoxic T cells, the method comprising contacting one or more cytotoxic T cells with one or more antigen presenting cells pulsed with a peptide comprising an amino acid sequence set forth in any one of SEQ ID NOs: 15-17.

9. A method of killing a target cell, the method comprising
(a) contacting the target cell with one or more BCMA-specific cytotoxic T cells, wherein the target cell expresses or overexpresses BCMA, and expresses HLA-A, wherein the BCMA-specific cytotoxic T cells are obtained by contacting one or more cytotoxic T cells with one or more antigen presenting cells pulsed with a first peptide comprising the amino acid sequence set forth in SEQ ID NO: 13 or SEQ ID NO: 14; or
(b) contacting the target cell with one or more TACI-specific cytotoxic T cells, wherein the target cell expresses or overexpresses TACI, and expresses HLA-A, wherein the TACI-specific cytotoxic T cells are obtained by contacting one or more cytotoxic T cells with one or more antigen presenting cells pulsed with a second peptide comprising the amino acid sequence set forth in any one of SEQ ID NOs: 15-17.

10. A method of treating a human subject having multiple myeloma a cancer, the method comprising administering a plurality of BCMA-specific cytotoxic T cells or TACI-specific cytotoxic T cells to the human subject, wherein the BCMA-specific cytotoxic T cells are obtained by contacting one or more cytotoxic T cells with one or more antigen presenting cells pulsed with a first peptide comprising the amino acid sequence set forth in SEQ ID NO: 13 or SEQ ID NO: 14; wherein the TACI-specific cytotoxic T cells are obtained by contacting one or more cytotoxic T cells with one or more antigen presenting cells pulsed with a second peptide comprising the amino acid sequence set forth in any one of SEQ ID NOs: 15-17.

11. A process comprising,
(a) obtaining bone marrow derived mononuclear cells from a subject;
(b) culturing the mononuclear cells in vitro under a condition in which mononuclear cells become adherent to a culture vessel;
(c) selecting adherent mononuclear cells;
(d) culturing the adherent mononuclear cells in the presence of one or more cytokines under a condition in which the cells differentiate into antigen present cells; and
(e) contacting the antigen presenting cells with the peptide of claim 1, thereby generating antigen presenting cells that present the peptide on a major histocompatibility complex (MHC) molecule.

12. A method of identifying a T cell antigen receptor sequence for BCMA, the method comprising
(a) generating and/or proliferating BCMA-specific cytotoxic T cells, wherein the method of generating and/or proliferating BCMA-specific cytotoxic T cells comprises contacting one or more cytotoxic T cells with one or more antigen presenting cells pulsed with a peptide comprising the amino acid sequence set forth in SEQ ID NO: 13 or SEQ ID NO: 14; and
(b) determining the T cell antigen receptor sequence for BCMA in the BCMA-specific cytotoxic T cells.

13. A method of identifying a T cell antigen receptor sequence for TACI, the method comprising
(a) generating and/or proliferating TACI-specific cytotoxic T cells wherein the method of generating and/or proliferating TACI-specific cytotoxic T cells comprises contacting one or more cytotoxic T cells with one or more antigen presenting cells pulsed with a peptide comprising an amino acid sequence set forth in any one of SEQ ID NOs: 15-17; and
(b) determining the T cell antigen receptor sequence for TACI in the TACI-specific cytotoxic T cells.

14. The peptide of claim 1, which comprises the amino acid sequence set forth in any one of SEQ ID NOs:13-17.

15. The peptide of claim 1, which consists of the amino acid sequence set forth in any one of SEQ ID NOs:13-17.

16. The peptide of claim 1, which comprises the amino acid sequence set forth SEQ ID NO:13.

17. The peptide of claim 1, which comprises the amino acid sequence set forth SEQ ID NO:14.

18. The peptide of claim 1, which comprises the amino acid sequence set forth SEQ ID NO:15.

19. The peptide of claim 1, which comprises the amino acid sequence set forth SEQ ID NO:16.

20. The peptide of claim 1, which comprises the amino acid sequence set forth SEQ ID NO:17.

21. The peptide of claim 1, which comprises the first amino acid sequence consisting of an amino acid sequence set forth in any one of SEQ ID NOs: 1-17; and the second amino acid sequence that is heterologous to the first amino acid sequence; wherein the second amino acid sequence that is heterologous to the first amino acid sequence comprises: (i) a purification tag, (ii) a detectable marker, (ii) an immunoglobulin molecule or a portion thereof comprising a heavy chain constant region, (iii) a therapeutic or immune-stimulating polypeptide, (iv) a carrier protein, or (v) a transportation sequence.

22. The peptide of claim 1, which is 9 to 30 amino acids in length.

23. A pharmaceutical composition comprising the peptide of claim 15 and a pharmaceutically acceptable carrier.

24. A pharmaceutical composition comprising the peptide of claim 16 and a pharmaceutically acceptable carrier.

25. A pharmaceutical composition comprising the peptide of claim 17 and a pharmaceutically acceptable carrier.

26. A pharmaceutical composition comprising the peptide of claim 18 and a pharmaceutically acceptable carrier.

27. A pharmaceutical composition comprising the peptide of claim 19 and a pharmaceutically acceptable carrier.

28. A pharmaceutical composition comprising the peptide of claim 20 and a pharmaceutically acceptable carrier.

29. The method of claim 6, wherein the human subject has MGUS or smoldering multiple myeloma.

30. The method of claim 6, wherein the human subject has multiple myeloma.

31. A method of inducing an immune response against BCMA- and/or TACI-expressing cancer cells in a human subject in need thereof, the method comprising administering to the human subject a peptide of claim 14.

32. A method of inducing an immune response against BCMA- and/or TACI-expressing cancer cells in a human subject in need thereof, the method comprising administering to the human subject a peptide of claim 15.

33. A method of treating a human subject having multiple myeloma, MGUS, or smoldering multiple myeloma, the method comprising administering to the human subject the peptide of claim 14.

34. A method of treating a human subject having multiple myeloma, MGUS, or smoldering multiple myeloma, the method comprising administering to the human subject the peptide of claim 15.

35. The method of claim 33, wherein the human subject has MGUS or smoldering multiple myeloma.

36. The method of claim 34, the human subject has MGUS or smoldering multiple myeloma.

37. The method of claim 33, wherein the human subject has multiple myeloma.

38. The method of claim 34, wherein the human subject has multiple myeloma.

* * * * *

UNITED STATES PATENT AND TRADEMARK OFFICE
CERTIFICATE OF CORRECTION

| | |
|---|---|
| PATENT NO. | : 11,517,591 B2 |
| APPLICATION NO. | : 16/641722 |
| DATED | : December 6, 2022 |
| INVENTOR(S) | : Jooeun Bae et al. |

It is certified that error appears in the above-identified patent and that said Letters Patent is hereby corrected as shown below:

In the Claims

In Column 102, Line 59, Claim 10, delete "a cancer" between "myeloma" and "the method"

In Column 103, Line 8, Claim 11, "in vitro" should be --*in vitro*-- between "cells" and "under"

Signed and Sealed this
Seventeenth Day of October, 2023

Katherine Kelly Vidal
*Director of the United States Patent and Trademark Office*

SEQUENCE LISTING

<160> NUMBER OF SEQ ID NOS: 24

<210> SEQ ID NO 1
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 1

```
Leu Ile Ile Ser Leu Ala Val Phe Val
1               5

<210> SEQ ID NO 2
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ala Val Phe Val Leu Met Phe Leu Leu
1               5

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ser Gln Asn Glu Tyr Phe Asp Ser Leu
1               5

<210> SEQ ID NO 4
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Val Leu Met Phe Leu Leu Arg Lys Ile
1               5

<210> SEQ ID NO 5
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ala Ile Leu Trp Thr Cys Leu Gly Leu
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ile Leu Pro Arg Gly Leu Glu Tyr Thr
1               5
```

```
<210> SEQ ID NO 7
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Phe Leu Val Ala Val Ala Cys Phe Leu
1               5

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Val Leu Cys Cys Phe Leu Val Ala Val
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Lys Leu Ser Ala Asp Gln Val Ala Leu
1               5

<210> SEQ ID NO 10
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Thr Leu Gly Leu Cys Leu Cys Ala Val
1               5

<210> SEQ ID NO 11
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ala Leu Val Tyr Ser Thr Leu Gly Leu
1               5

<210> SEQ ID NO 12
<211> LENGTH: 9
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Leu Ser Ala Asp Gln Val Ala Leu Val
1               5

<210> SEQ ID NO 13
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Tyr Leu Met Phe Leu Leu Arg Lys Ile
1               5

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Tyr Ile Leu Trp Thr Cys Leu Gly Leu
1               5

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Tyr Leu Val Ala Val Ala Cys Phe Leu
1               5

<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Tyr Leu Ser Ala Asp Gln Val Ala Leu
1               5

<210> SEQ ID NO 17
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 17

Tyr Leu Gly Leu Cys Leu Cys Ala Val
1               5

<210> SEQ ID NO 18
<211> LENGTH: 184
<212> TYPE: PRT
<213> ORGANISM: Homo sapiens

<400> SEQUENCE: 18

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 19
<211> LENGTH: 293
<212> TYPE: PRT
<213> ORGANISM: Homo sapiens

<400> SEQUENCE: 19

Met Ser Gly Leu Gly Arg Ser Arg Gly Gly Arg Ser Arg Val Asp
1               5                   10                  15

Gln Glu Glu Arg Phe Pro Gln Gly Leu Trp Thr Gly Val Ala Met Arg
                20                  25                  30

Ser Cys Pro Glu Glu Gln Tyr Trp Asp Pro Leu Leu Gly Thr Cys Met
            35                  40                  45

Ser Cys Lys Thr Ile Cys Asn His Gln Ser Gln Arg Thr Cys Ala Ala
50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
            115                 120                 125

Asn Ser Asp Asn Ser Gly Arg Tyr Gln Gly Leu Glu His Arg Gly Ser
        130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290

<210> SEQ ID NO 20
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gly Leu Val Gly Leu Ile Phe Ala Val
1               5

<210> SEQ ID NO 21
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ser Leu Tyr Asn Thr Val Ala Thr Leu
1               5

<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

-continued

```
Tyr Gln Asn Glu Tyr Phe Asp Ser Leu
1               5

<210> SEQ ID NO 23
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 23

His His His His His His
1               5

<210> SEQ ID NO 24
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      KDEL sequence"

<400> SEQUENCE: 24

Lys Asp Glu Leu
1
```